(12) United States Patent
Bowdish et al.

(10) Patent No.: US 8,709,415 B2
(45) Date of Patent: Apr. 29, 2014

(54) ANTIBODIES TO OX-2/CD200 AND USES THEREOF

(75) Inventors: Katherine S. Bowdish, Del Mar, CA (US); Anke Kretz-Rommel, San Diego, CA (US); Susan Faas McKnight, Old Lyme, CT (US); Jeremy P. Springhorn, Guilford, CT (US); Dayang Wu, Cheshire, CT (US)

(73) Assignee: Alexion Pharmaceuticals, Inc., Cheshire, CT (US)

( * ) Notice: Subject to any disclaimer, the term of this patent is extended or adjusted under 35 U.S.C. 154(b) by 66 days.

(21) Appl. No.: 13/311,910

(22) Filed: Dec. 6, 2011

(65) Prior Publication Data
US 2012/0148579 A1 Jun. 14, 2012

Related U.S. Application Data

(62) Division of application No. 12/087,683, filed as application No. PCT/US2007/000711 on Jan. 11, 2007, now Pat. No. 8,075,884.

(60) Provisional application No. 60/758,426, filed on Jan. 12, 2006, provisional application No. 60/759,085, filed on Jan. 12, 2006, provisional application No. 60/801,991, filed on May 18, 2006.

(51) Int. Cl.
*A61K 39/395* (2006.01)

(52) U.S. Cl.
USPC ..................................... 424/130.1

(58) Field of Classification Search
None
See application file for complete search history.

(56) References Cited

U.S. PATENT DOCUMENTS

| | | | |
|---|---|---|---|
| 3,940,475 | A | 2/1976 | Gross |
| 4,289,747 | A | 9/1981 | Chu |
| 4,376,110 | A | 3/1983 | David et al. |
| 5,223,409 | A | 6/1993 | Ladner et al. |
| 5,225,539 | A | 7/1993 | Winter et al. |
| 5,403,484 | A | 4/1995 | Ladner et al. |
| 5,427,908 | A | 6/1995 | Dower et al. |
| 5,434,131 | A | 7/1995 | Linsley et al. |
| 5,508,717 | A | 4/1996 | Miller |
| 5,530,101 | A | 6/1996 | Queen et al. |
| 5,571,698 | A | 11/1996 | Ladner et al. |
| 5,580,717 | A | 12/1996 | Dower et al. |
| 5,780,279 | A | 7/1998 | Matthews et al. |
| 5,859,205 | A | 1/1999 | Adair et al. |
| 5,902,583 | A | 5/1999 | Buchsbaum et al. |
| 5,916,560 | A | 6/1999 | Larsen et al. |
| 6,011,138 | A | 1/2000 | Reff et al. |
| 6,040,136 | A | 3/2000 | Garrard et al. |
| 6,338,851 | B1 | 1/2002 | Gorczynski |
| 6,632,927 | B2 | 10/2003 | Adair et al. |
| 6,652,858 | B2 | 11/2003 | Gorczynski et al. |
| 6,737,056 | B1 | 5/2004 | Presta |
| 6,749,854 | B2 | 6/2004 | Gorczynski et al. |
| 6,955,811 | B2 | 10/2005 | Gorczynski et al. |
| 6,984,625 | B2 | 1/2006 | Gorczynski |
| 7,238,352 | B2 | 7/2007 | Gorczynski et al. |
| 7,368,535 | B2 | 5/2008 | Gorczynski et al. |
| 7,435,412 | B2 | 10/2008 | Bowdish et al. |
| 7,452,536 | B2 | 11/2008 | Gorczynski et al. |
| 7,887,798 | B2 | 2/2011 | Gorczynski et al. |
| 8,114,403 | B2 * | 2/2012 | Bowdish et al. ........... 424/155.1 |
| 2002/0031515 | A1 | 3/2002 | Caligiuri et al. |
| 2002/0168364 | A1 | 11/2002 | Gorczynski et al. |
| 2002/0192215 | A1 | 12/2002 | Hoek et al. |
| 2003/0017491 | A1 | 1/2003 | Shi et al. |
| 2004/0018972 | A1 | 1/2004 | Gorczynski et al. |
| 2004/0054145 | A1 | 3/2004 | Gorczynski |
| 2004/0175692 | A1 | 9/2004 | Bowdish et al. |
| 2004/0198661 | A1 | 10/2004 | Bowdish et al. |
| 2005/0048069 | A1 | 3/2005 | Gorczynski et al. |
| 2005/0129690 | A1 | 6/2005 | Bowdish et al. |
| 2005/0169870 | A1 | 8/2005 | Truitt et al. |
| 2006/0024231 | A1 | 2/2006 | Schnitzer et al. |
| 2007/0036786 | A1 | 2/2007 | Tuaillon et al. |
| 2007/0065438 | A1 | 3/2007 | Liversidge et al. |
| 2008/0131428 | A1 | 6/2008 | Young et al. |
| 2010/0249382 | A1 | 9/2010 | Desjarlais et al. |

FOREIGN PATENT DOCUMENTS

| | | |
|---|---|---|
| JP | 02-046297 | 2/1990 |
| WO | WO 84/03508 A1 | 9/1984 |
| WO | WO 85/03508 A1 | 8/1985 |
| WO | WO 88/06630 A1 | 9/1988 |
| WO | WO 92/15679 A1 | 9/1992 |
| WO | WO 94/28027 | 12/1994 |
| WO | WO 95/18825 | 7/1995 |
| WO | WO 96/27011 A1 | 9/1996 |
| WO | WO 96/38557 | 12/1996 |
| WO | WO 97/08320 A1 | 3/1997 |
| WO | WO 97/21450 | 6/1997 |
| WO | WO 98/27230 | 6/1998 |
| WO | WO 99/24565 | 5/1999 |
| WO | WO 01/87336 | 11/2001 |

(Continued)

OTHER PUBLICATIONS

Davidson, A., et. al. "Autoimmune Diseases," (editors Mackay and Rosen) New England Journal of Medicine, 345(5):340-350 (2001).
Presta, L., "Antibody engineering for therapeutics," Current Opinion in Structural Biology, 13(4):519-525 (2003).
Shields, R. L., et. al., "High Resolution Mapping of the Binding Site on Human IgG1 for Fc gamma RI, Fc gamma RII, Fc gamma RIII, and FcRn and Design of IgG1 Variants with Improved Binding to the Fc gamma R," Journal of Biological Chemistry, 276(9):6591-6604 (2001).

(Continued)

*Primary Examiner* — Ilia Ouspenski
(74) *Attorney, Agent, or Firm* — Ropes & Gray LLP

(57) ABSTRACT

This application provides methods and compositions for modulating and/or depleting CD200 positive cells.

42 Claims, 73 Drawing Sheets

(56) References Cited

FOREIGN PATENT DOCUMENTS

| WO | WO 02/11762 A2 | 2/2002 |
|---|---|---|
| WO | WO 02/42332 A2 | 5/2002 |
| WO | WO 02/46227 A2 | 6/2002 |
| WO | WO 02/059280 A2 | 8/2002 |
| WO | WO 02/095030 A2 | 11/2002 |
| WO | WO 03/025202 A2 | 3/2003 |
| WO | WO 03/074679 A2 | 9/2003 |
| WO | WO 2004/060295 A2 | 7/2004 |
| WO | WO 2004/078937 A2 | 9/2004 |
| WO | WO 2004/078938 A2 | 9/2004 |
| WO | WO 2005/007809 A2 | 1/2005 |
| WO | WO 2006/053301 A2 | 5/2006 |
| WO | WO 2007/084321 A | 7/2007 |
| WO | WO 2007/084321 A2 | 7/2007 |

OTHER PUBLICATIONS

McWhirter et al., Supplemental Materials, PNAS, vol. 103, pp. 1041-1046 (2006).
Dorai et al., "Aglycosylated Chimeric Mouse/Human IgG1 Antibody Retains Some Effector Function," Hybridoma, vol. 10(2), pp. 211-217 (1991).
Alizadeh et al., "Distinct types of diffuse large B-cell lymphoma identified by gene expression profiling," Nature, 403:503-511(2000).
Auchincloss, Jr., H., "Strategies to Induce Tolerance," Transplantation Immunology, Bach and Auchincloss, Eds., Wiley-Liss, New York, Chapter 11, pp. 211-218 (1995).
Bach, "Immunosuppressive therapy of autoimmune diseases," Immunology Today, 14(6)322-325(1993).
Banerjee, D., et al., "Blocking CD200-CD200 receptor axis augments NOS-2 expression and aggravates experimental autoimmune uveoretinitis in Lewis rats," Ocular Immunology and Inflammation, 12(2):115-125 (2004).
Barclay and Ward, "Purification and Chemical Characterisation of Membrane Glycoproteins From Rat Thymocytes and Brain, Recognised by Monoclonal Antibody MRC OX2," European J. Biochemistry, 129:447-458(1982).
Barclay et al., "CD200 and membrane protein interactions in the control of myeloid cells," Trends in Immunology, 23(6), pp. 285-290 (2002).
Barclay, A.N., "Different reticular elements in rat lymphoid tissue identified by localization of Ia, Thy-1 and MRC OX 2 antigens," Immunology, 44:727-736 (1981).
Barclay, A.N., et al., "Neuronal/Lymphoid Membrane Glycoprotein MRC OX-2 is a Member of the Immunoglobulin Superfamily with a Light-Chain-Like Structure," Biochem. Soc. Symp., 51:149-157 (1985).
Bauvois et al., Constitutive expression of CD26/dipeptidylpepidase IV on peripheral blood B lymphocytes of patients with B chronic lymphocytic leukaemia. British Journal of Cancer 1999., vol. 79. p. 1042-1048.s.
Blazer, B.R., et al., "CD28/B7 Interactions Are Required for Sustaining the Graft-Versus-Leukemia Effect of Delayed Post-Bone Marrow Transplantation Splenocyte Infusion in Murine Recipients of Myeloid or Lymphoid Leukemia Cells," J. Immunol., 159:3460-3473 (1997).
Bodey et al. "Human Cancer Detection and Immunotherapy with Conjugated and Non-Conjugated Monoclonal Antibodies" Anticancer Research 16: 661-674 (1996).
Bohen, S.P. et al., "Variation in gene expression patterns in follicular lymphoma and the response to rituximab," PNAS, 100(4):1926-1930(2003).
Boon, Thierry., "Toward a Genetic Analysis of Tumor Rejection Antigens," Advances in Cancer Res., 58:177-210(1992).
Borriello et al., "MRC OX-2 Defines a Novel T Cell Costimulatory Pathway," J. Immunol., 158:4549-4554(1997).
Borriello, F., et al., "Characterization and localization of Mox2, the gene encoding the murine homolog of the rat MRC OX-2 membrane glycoprotein," Mammalian Genome, 9(2):114-118 (1998).
Broderick et al., "Constitutive Retinal CD200 Expression Regulates Resident Microglia and Activation State of Inflammatory Cells During Experimental Autoimmune Uveoretinitis," Am. J. of Pathology, 161(5):1669-1677(2002).
Bruggemann et al., "A Matched Set of Rat/Mouse Chimeric Antibodies: Identification and Biological Properties of Rat H Chain Constant Regions μ, γ1, γ2a, γ2b, γ2c, ε, and α[1]," The Journal of Immunology, vol. 142(9), pp. 3145-3150 (1989).
Bukovsky, A., et al., "Association of lymphoid cell markers with rat ascitic malignant cells," IRCS Med. Sci., 11:866-867 (1983).
Bukovsky, A., et al., "Association of some cell surface antigens of lymphoid cells and cell surface differentiation antigens with early rat pregnancy," Immunology, 52:631-640 (1984).
Bukovsky, A., et al., "The localization of Thy-1.1, MRC OX 2 and Ia antigens in the rat ovary and fallopian tube," Immunology, 48:587-596 (1983).
Bukovsky, A., et al., "The ovarian follicle as a model for the cell-mediated control of tissue growth," Cell Tissue Res., 236:717-724 (1984).
Caldas et al., "Humanization of the anti-CD18 antibody 6.7: an unexpected effect of a framework residue in binding to antigen," Mol. Immunol. 39:941-952 (2003).
Chaouat and Clark, FAS/FAS Ligand Interaction at the Placental Interface is not Required for the Success of Allogeneic Pregnancy in Anti-Paternal MHC Preimmunized Mice, Presented at the 6th Congress of the Adria-Alps Soc. of Immunol. of Reprod., (2000) Amer. J. of Reprod. Immunol., 45:108-115(2001).
Chen, D., et al., "Discrete Monoclonal Antibodies Define Functionally Important Epitopes in the CD200 Molecule Responsible for Immunosupression Function," Transplantation, 79:282-288 (2005).
Chen, D., et al., "Synthetic peptides from the N-terminal regions of CD200 and CD200R1 modulate immunosupressive and anti-inflammatory effects of CD200-CD200R1 interaction," International Immunology, 17(3):289-296 (2005).
Chen, Z., et al., "Cloning and characterization of the murine homologue of the rat/human MRC OX-2 gene," Database Medline, Biochemica et Biophysica Acta, 1362(1):6-10 (1997).
Cherwinski, H.M., et al., "The CD200 Receptor Is a Novel and Potent Regulator of Murine and Human Mast Cell Function," J. Immunol., 174:1348-1356 (2005).
Chien et al., "Significant structural and functional change of an antigen-binding site by a distant amino acid substitution: proposal of a structural mechanism," Proc. Natl. Acad. Sci. USA 86:5532-5536 (1989).
Chitnis et al., "The Role of CD200 in Immune-Modulation and Neural Protection in EAE," Abstract, 12th International Congress of Immunology and 4th Annual Conference of FOCIS, Montreal, Jul. 21, 2004.
Chitnis, T., et al., "Elevated Neuronal Expression of CD200 Protects $Wld^S$ Mice from Inflammation-Mediated Neurodegeneration," American Journal of Pathology, 170(5):1695-1712 (2007).
Clark et al., "Fgl2 prothrombinase expression in mouse trophoblast and decidua triggers abortion but may be countered by OX-2," Mol. Human Reprod., 7:185-194(2001).
Clark et al., "Labile CD200 tolerance signal important in transfusion-related immunomodulation (TRIM) prevention of recurrent miscarriages," Amer. J. Reprod. Immunol., 45:361(2001).
Clark et al., "Procoagulants in fetus rejection: the role of the OX-2 (CD200) tolerance signal," Seminars in Immunol., 13(4)255-263(2001).
Clark et al., "The OX-2 Tolerance Signal Molecule at the Fetomaternal Interface Determines Pregnancy Outcome," Amer. Journal of Reprod Immunol., 43:326(2000). Abstract Only.
Clark et al., Amer. Soc. for Reprod. Medicine, 55th Annual Meeting (1999).
Clark, D.A., "Intralipid as Treatment for Recurrent Unexplained Abortion?", Am. J. of Reprod. Immunol., 32:290-293(1994).
Clark, M.J., et al., "MRC OX-2 antigen: a lymphoid/neuronal membrane glycoprotein with a structure like a single immunoglobulin light chain," EMBO Journal, 4(1):113-118 (1985).
Clarke, M.J., "MRC OX-2 lymphoid brain glycoprotein: S1 mapping suggests higher levels of abnormal RNA in the thymus than in the brain," Biochemical Society Transactions, 14:80-81 (1986).

(56) References Cited

OTHER PUBLICATIONS

Cochlovius et al., "Cure of Burkitt's Lymphoma in Severe Combined Immunodeficiency Mice by T Cells, Tetravalent CD3×CD19 Tandem Diabody, and CD28 Costimulation," Cancer Res. 60:4336-4341 (2000).
Cohen, P.L., "Systemic Autoimmunity," in Fundamental Immunology, Fourth edition, W.E. Paul, Editor, Lippincott-Raven Publishers, Philadelphia, Ch. 33, p. 1067-1088(1999).
DeNardo et al., "Increased Survival Associated with Radiolabeled Lym-1 Therapy for Non-Hodgkin's Lymphoma and Chronic Lymphocyctic Leukemia." Cancer Supplement (1997) vol. 80, No. 12. pp. 2706-2711.
Dennis, C., "Off by a whisker," Nature, 442,:739-741 (2006).
Dick et al., "Control of Myeloid Activity During Retinal Inflammation," J. of Leukocyte Bio., 74:161-166(2003).
Ebert et al., "Selective Immunosuppressive Action of a Factor Produced by Colon Cancer Cells," Cancer Res. 50:6158-6161 (1990).
Elgert, K. D. "Immunology : Understanding the Immune System," The Genetic Basis of Antibody Diversity, 123 (1996).
Faguet et al., "Blood Kinectics, Tissue Distribution, and Radioimaging of Anti-Common Chronic Lymphatic Leukemia Antigen (cCLLa) Monoclonal Antibody $CLL_2$ in Mice Transplanted With cCLLa-Bearing Human Leukemia Cells." Blood. vol. 75, No. 9 (1990) pp. 1853-1861.
Faisal et al., "Cell-surface Associated p43/Endothelial-monocyte-activating-polypeptide-II in Hepatocellular Carcinoma Cells Induces Apoptosis in T-lymphocytes," Asian J. of Surg. 30(1):13-22 (2007).
Fallarino, F., et al., "Murine Plasmacytoid Dendritic Cells Initiate the Immunosupressive Pathway of Tryptophan Catabolism in Response to CD200 Receptor Engagement," J. Immunol., 173:3748-3754 (2004).
Farber, U., et al., "Loss of heterozygosity on chromosome 3, bands q24-→qter, in a diploid meningioma," Cytogenet Cell Genet, 57:157-158 (1991).
Feuerstein et al., 1999, Induction of Autoimmunity in a Transgenic Model of B Cell Receptor Peripheral Tolerance: Changes in Coreceptors and B Cell Receptor-Induced Tyrosine-Phosphoproteins, J. Immunol. 163:5287-5297.
Funakoshi et al., "Antitumor Effects of Nonconjugated Murine Lym-2 and Human-Mouse Chimeric CLL-1 Monoclonal Antibodies Against Various Human Lymphoma Cell Lines In Vitro and In Vivo." Blood vol. 90, No. 8 (1997) pp. 3150-3166.
Ginaldi et al., "Levels of expression of CD52 in normal and leukemic B and T cells: correlation with in vivo therapeutic responses to Campath-1H," Leukemia Res. 22(2):185-191 (1998).
Giusti et al., "Somatic diversification of S107 from an antiphosphocholine to an anti-DNA autoantibody is due to a single base change in its heavy chain variable region," Proc. Natl. Acad. Sci. USA 84:2926-2930 (1987).
Gorczynski and Marsden, "Modulation of CD200 receptors as a novel method of immunosuppression," Expert Opin. Ther. Patents, 13(5): 711-715(2003). See also WIPO Patent No. WO02095030 assigned to Transplantation Tech, Inc.
Gorczynski et al., "Anti-CD200R Ameliorates Collagen-Induced Arthritis in Mice," J. of Immunol., 104(3):256-264(2002).
Gorczynski et al., "Does Successful Allopregnancy Mimic Transplantation Tolerance?", Graft, 4:338-345(2001).
Gorczynski et al., "Evidence of a role for CD200 in regulation of immune rejection of leukaemic tumour cells in C57BL/6 mice," Clin. Exp. Immunol., 126:220-229(2001).
Gorczynski et al., "Increased Expression of the Novel Molecule OX-2 IS Involved in Prolongation of Murine Renal Allograft Survival," Transplantation, vol. 65(8); pp. 1106-1114 (1998).
Gorczynski, "CD200 and Its Receptors as Targets for Immunoregulation Current Opinion in Investigational Drugs," Pharmapress, US, vol. 6, No. 5, May 2005, pp. 483-488. XP008051169 ISSN: 1472-4472.
Gorczynski, L., et al., "Evidence That an OX-2-Positive Cell Can Inhibit the Stimulation of Type 1 Cytokine Production by Bone Marrow-Derived B7-1 (and B7-2)-Positive Dendtritic Cells," J. Immunol., 162:774-781 (1999).
Gorczynski, R., et al., "CD200 Is a Ligand for All Members of the CD200R Family of Immunoregulatory Molecules," J. Immunol., 172:7744-7749 (2004).
Gorczynski, R., et al., "Dendritic Cells Expressing TGFBeta/IL-10, and CHO Cells With OX-2, Increase Graft Survival," Transplantation Proceedings, 33:1565-1566 (2001).
Gorczynski, R.M., "Role of Cytokines in Allograft Rejection," Current Pharmaceutical Design, 7:1039-1057 (2001).
Gorczynski, R.M., "Synergy in Induction of Increased Renal Allograft Survival after Portal Vein Infusion of Dendtritic Cells Transduced to Express TGFB and IL-10, along with Administration of CHO Cells Expressing the Regulatory Molecule OX-2," Clinical Immunology, 95(3):182-189 (2000).
Gorczynski, R.M., "Transplant tolerance modifying antibody to CD200 receptor, but not CD200, alters cytokine production profile from stimulated macrophages," Eur. J. Immunol., 31:2331-2337 (2001).
Gorczynski, R.M., et al., "A CD200FC Immunoadhesin Prolongs Rat Islet Xenograft Survival in Mice," Transplantation, 73(12):1948-1953 (2002).
Gorczynski, R.M., et al., "An Immunoadhesin Incorporating the Molecule OX-2 Is a Potent Immunosuppressant That Prolongs Allo- and Xenograft Survival," J. Immunol., 163:1654-1660(1999).
Gorczynski, R.M., et al., "Anti-Rat OX-2 Blocks Increased Small Intestinal Transplant Survival After Portal Vein Immunization," Transplantation Proceedings, 31:577-578 (1999).
Gorczynski, R.M., et al., "Augmented Induction of CD4+ CD25+ Treg using Monoclonal Antibodies to CD200R," Transplantation, 79(4):488-491 (2005).
Gorczynski, R.M., et al., "Augmented Induction of CD4+ CD25+ Treg using Monoclonal Antibodies to CD200R," Transplantation, 79(9):1180-1183 (2005).
Gorczynski, R.M., et al., "CD200 Immunoadhesin Suppresses Collagen-Induced Arthritis in Mice," Clinical Immunology, 101(3):328-334 (2001).
Gorczynski, R.M., et al., "Evidence for Persistent Expression of OX2 as a Necessary Component of Prolonged Renal Allograft Survival Following Portal Vein Immunization," Clinical Immunol., 97(1):69-78 (2000).
Gorczynski, R.M., et al., "Induction of Tolerance-Inducing Antigen-Presenting Cells in Bone Marrow Cultures In Vitor Using Monoclonal Antibodies to CD200R," Transplantation, 77(8):1138-1144 (2004).
Gorczynski, R.M., et al., "Interleukin-13, in Combination with Anti-Interleukin-12, Increases Graft Prolongation After Portal Venous Immunization with Cultured Allogeneic Bone Marrow-Derived Dentritic Cells," Transplantation, 62(11):1592-1600 (1996).
Gorczynski, R.M., et al., "Persistent expression of OX-2 is necessary for renal allograft survival," FASEB Journal, 14(6):A1069 (2000).
Gorczynski, R.M., et al., "Receptor Engagement on Cells Expressing a Ligand for the Tolerance-Inducing Molecule OX2 Induces an Immunoregulatory Population That Inhibits Alloreactivity In Vitro and In Vivo," J. Immunol., 165:4854-4860 (2000).
Gorczynski, R.M., et al., "Regulation of Gene Expression of Murine MD-1 Regulates Subsequent T Cell Activation and Cytokine Production," J. of Immunology, 165:1925-1932 (2000).
Gorczynski, R.M., et al., "Structural and Functional Heterogeneity in the CD200R Family of Immunoregulatory Molecules and their Expression at the Feto-maternal Interface," AJRI, 52:147-163 (2004).
Gorczynski, R.M., et al., "The Same Immunoregulatory Molecules Contribute to Successful Pregnancy and Transplantation," AJRI, 48:18-26 (2002).
Gorczynski,"Evidence for an Immunoregulartory Role of OX2 with its Counter Ligand (OX2L) in the Regulation of Transplant Rejection, Fetal Loss, Autoimmunity and Tumor Growth," Archibum Immunologiae et Therapiae Experimentalis, vol. 49(4) pp. 303-309 (2001).

(56) References Cited

OTHER PUBLICATIONS

Greenwood, J.D. and Clark, M., "Protein Engineering of Antibody Molecules for Prophylactic and Therapeutic Applications in Man," (ed. Clark, M.) Pub. Academic Titles, UK, pp. 4-5 (1993).
Gura, T., "Systems for Identifying New Drugs Are Often Faulty," Science, 278:1041-1042 (1997).
Gussow and Seemann, "Humanization of Monoclonal Antibodies," Meth. Enzymol. 203:99-121 (1991).
Hardy et al., "A lymphocyte-activating monoclonal antibody induces regression of human tumors in severe combined immunodeficient mice," Proc. Natl. Acad. Sci. USA 94:5756-5760 (1997).
Hart, P.H., "Modulation of Monocyte Effector Functions by Lipopolysacc-haride and Interferon-Y," Dept. of Medicine, University of Melbourne, Royal Melbourne Hospital, Parkville, Vic., 3050 (Abstract).
Heaney et al., "Severe asthma treatment: need for characterising patients," Lancet, 365:974-976(2005).
Hegen et al., "Utility of animal models for identification of potential therapeutics for rheumatoid arthritis," Ann. Rheum. Dis., vol. 67, pp. 1505-1515 (2008).
Hoek, R.M., et al., "Down-Regulation of the Macrophage Lineage Through Interaction with OX2 (CD200)," Science, 290:1768-1771 (2000).
Hoek, R.M., et al., "Macrophage regulation by the B7.1/2 homologue OX2?", FASB Journal, 14(6):A1232 (2000).
Huang, "Structural chemistry and therapeutic intervention of protein-protein interactions in immune response, human immunodeficiency virus entry, and apoptosis," Pharmacol. Therapeutics, 86:201-215(2000).
Hutchings, N.J., et al., "Interactions of Cytoplasmic Region of OX2R Are Consistent with an Inhibitory Function," Annual Congress of the British Society for Immunology, Dec. 5-8, 2000, Harrogate, UK, vol. 101, Supplement 1 (2000).
Iwanuma et al., "Antitumor Immune Response of Human Peripheral Blood Lymphocytes Coengrafted with Tumor into Severe Combined Immunodeficient Mice," Cancer Res. 57:2937-2942 (1997).
Jain, "The next frontier of molecular medicine: Delivery of therapeutics," Nature Medicine, 4(6):655-657(1998).
Jansky, L., et al., "Dynamics of Cytokine Production in Human Peripheral Blood Mononuclear Cells Stimulated by LPS or Infected by Borrelia," Physiol. Res., 52:593-598 (2003).
Jeurissen, S.H.M., et al., "Characteristics and functional aspects of nonlymphoid cells in rat germinal centers, recognized by two monoclonal antibodies ED5 and ED6," Eur. J. Immunol., 16:562-568 (1986).
Keil et al., "The Tolerance-Promoting Molecule OX-2 is Expressed in Fetal Trophoblast Cells that Cocoon the 'Fetal Allograft' and may prevent Pregnancy Loss Caused by Cytokine-Activation of FGL2 Prothrombinase," Amer. J. Reprod. Immunol., 45:343(2001) (abstract).
Kim et al., "Divergent Effects of 4-1BB Antibodies on Antitumor Immunity and on Tumor-reactive T-Cell Generation," Cancer Res., 61:2031-2037(2001).
Kjaergaard et al., "Therapeutic Efficacy of OX-40 Receptor antibody Depends on Tumor Immunogenicity and Anatomic Site of Tumor Growth," Cancer Res. 60:5514-5521(2000).
Kneitz, C., et al., "Inhibition of Tcell/B cell interaction by B-CLL cells," Leukemia, 13:98-104 (1999).
Kretz-Rommel Anke et al: "CD200 Expression on Tumor Cells Suppresses Anti-Tumor Immunity: New Approaches to Cancer Immunotherapy" Journal of Immunotherapy; vol. 29, No. 6, Nov. 2006, p. 666, xp009088616 & 21st Annual Scientific Meeting of The International-Society-For-Biological-Therapy-Of-Cancer; Los Angeles, CA, Usa; Oct. 26-29, 2006 ISSN: 1524-9557.
Kretz-Rommel, "CD200 Expression on Tumor Cells Suppresses Antitumor Immunity: New Approaches to Cancer Immunotherapy," J. Immunol. 178:5595-5605 (2007).
Kretz-Rommel, A., et al., "Immune Evasion by CD200: New Approaches to Targeted Therapies for Chronic Lymphocytic Leukemia," J. Immunother., 28(6):650 (2005).

Kretz-Rommel, A., et al., "The Immuno-Regulatory Protein CD200 Is Overexpressed in a Subset of B-Cell Chronic Lymphocytic Leukemias and Plays a Role in Down-Regulating the TH1 Immune Response," J. Immunother., 27(6):S46 (2004).
Kroese, F.G.M., et al., "Germinal centre formation and follicular antigen trapping in the spleen of lethally X-irradiated and reconstituted rats," Immunology, 57:99-104 (1986).
Kroese, F.G.M., et al., "The ontogeny of germinal centre forming capacity of neonatal rat spleen," Immunology, 60:597-602 (1987).
Liu et al., "Effect of combined T- and B-cell depletion of allogeneic HLA-mismatched bone marrow graft on the magnitude and kinetics of Epstein-Barr virus load in the peripheral blood of bone marrow transplant recipients," Clin. Transplant. 18:518-524 (2004).
Mariuzza et al., "The Structural Basis of Antigen-Antibody Recognition," Ann. Rev. Biophys. Biophys. Chem. 16:139-159 (1987).
Marsh, M.N., "Functional and Structural Aspects of the Epithelial Lymphocyte, with Implications for Coeliac Disease and Tropical Sprue," Univ. Dept. of Medicine, University of Manchester School of Medicine at Hope Hospital, Salford, Manchester UK pp. 55-75 (1985).
Matutes et al. Morphological and Immunophenotypic Features of Chronic Lymphocytic Leukemia. Rev. Clin. Exp. Hematol. vol. 4.1, Mar. 2000 p. 22-47.
McCaughan et al., "Characterization of the Human Homolog of the Rat MRC OX-2 Membrane Glycoprotein," Immunogenetics, 25:329-335(1987).
McCaughan, G.M., et al., "Identification of the human homologue of the rat lymphoid/brain antigen MRC OX-2," Australian and New Zealand Journal of Medicine 17: 142 (Abstract) (1987).
McCaughan, G.W., et al., "The Gene for MRC OX-2 Membrane Glycoprotein Is Localized on Human Chromosome 3," Immunogenetics, 25:133-135 (1987).
McMaster, W.R., et al., "Identification of Ia glycoproteins in rat thymus and purification from rat spleen," Eur. J. Immunol., 9:426-433 (1979).
McWhirter, J.R., et al., "Antibodies selected from combinatorial libraries block a tumor antigen that plays a key role in immunomodulation," PNAS, 103(4):1041-1046 (2006).
Mjaaland et al., "Modulation of immune responses with monoclonal antibodies. I. Effects on regional lymph node morphology and on anti-hapten responses to haptenized monoclonal antibodies", Eur. J. Immunol., 20:1457-1461(1990).
Mjaaland, S., et al., "The Localization of Antigen in Lymph Node Follicles of Congenitally Athymic Nude Rats," Scand. J. Immunol., 26:141-147 (1987).
Mohammad, R.M., et al., "Establishment of a human B-CLL xenograft model: utility as a preclinical therapeutic model," Leukemia, 10:130-137 (1996).
Mori et al., "Establishment of a new anti-cancer drugs-resistant cell line derived from B-chronic lymphocytic leukemia" Proceedings, Fifty-Ninth Annual Meeting of the Japanese Cancer Association, p. 583, # 3788 (Sep. 1, 2000).
Morris, R.J., et al., "Sequential Expression of OX2 and Thy-1 Glycoproteins on the Neuronal Surface during Development," Dev. Neurosci., 9:33-44 (1987).
Mueller et al., "Aglycosylated chimeric mouse/human IgG1 antibody retains some effector function," Hybridoma, vol. 10(2), pp. 211-217 (1991).
Mueller et al., "Humanized Porcine VCAM-Specific Monoclonal Antibodies With Chimeric IgG2/G4 Constant Regions Block Human Leukocyte Binding to Porcine Endothelial Cells," Molecular Immunology, vol. 34(6), pp. 441-452 (1997).
Myers et al., "Characterization of a Peptide Analog of a Determinant of Type II Collagen that Suppresses Collagen-Induced Arthritis," J. of Immunology, 3589-3595(1998).
Nagelkerken L., et al., "Accessory Cell Function of Thoracic Duct Nonlymphoid Cells, Dentritic Cells, and Splenic Adherent Cells in the Brown-Norway Rat," Cellular Immunology, 93:520-531 (1985).
Nathan and Muller, "Putting the Brakes on innate immunity: a regulatory role for CD200?", Nat Immunol., 2(1):17-19(2001).
Ni et al., "An immunoadhesin incorporating the molecule OX-2 is a potent immunosuppressant which prolongs allograft survival", FASEB Journal 13(5):A983(1999).

(56) References Cited

OTHER PUBLICATIONS

Ohno et al., "Antigen-binding specificities of antibodies are primarily determined by seven residues of $V_H$," Proc. Natl. Acad. Sci., vol. 82, pp. 2945-2949 (1985).

Pakula and Sauer, "Genetic analysis of protein stability and function," Annu. Rev. Genet., vol. 23, pp. 289-310 (1989).

Panka et al., "Variable region framework differences result in decreased or increased affinity of variant anti-digoxin antibodies," Proc, Natl. Acad. Sci. USA, vol. 85:3080-3084 (1988).

Pardoll, Drew., "Therapeutic Vaccination for Cancer," Clin. Immunol., 95(1):S44-S62(2000).

Paterson, D.J., et al., "Antigens of Activated Rat T Lymphocytes Including A Molecule of 50,000 Mr Detected Only on CD4 Positive T Blasts," Molecular Immunology, 24(12):1281-1290 (1987).

Preston et al., "The leukocyte/neuron cell surface antigen OX2 binds to a ligand on macrophages", European J. of Immunol., 27(8):1911-1918(1997).

Ragheb et al., "Preparation and functional properties of monoclonal antibodies to human, mouse and rat OX-2", Immunol. Letters, 68(2,3):311-315(1999).

Ragheb, R.F., "Exploration of OX-2 function in tolerance induction and graft acceptance using an anti-mouse OX-2 monoclonal antibody," Masters Abstracts International, 38(4):971-972 (2000).

Richards, S.J., et al., "Reported Sequence Homology Between Alzheimer Amyloid770 and the MCR OX-2 Antigen Does Not Predict Function," Brain Research Bulletin, 38(3):305-306 (1995).

Riley, "Melanoma and the Problem of Malignancy," J. Exp. Med. 204:1-9 (2004).

Rindfleisch et al., "Diagnosis and Management of Rheumatoid Arthritis," American Family Physician, vol. 72(6), pp. 1037-1047 (2005).

Rioux, P., Campath-1H (Cambridge University), IDrugs, vol. 2(2); pp. 153-167, Database Medline, abstract No. NLM16160950 (Abstract Only) (1999).

Romagnani, Sergio., "Short Analytical Review: TH1 and TH2 in Human Diseases," Clin. Immunol. Immunopathology, 80(3):225-235(1996).

Rosenblum, M.D., et al., "CD200 is a novel p53-target gene involved in apoptosis-associated immune tolerance," Blood, 103(7):2691-2698 (2004).

Rosenwald et al., "Relation of Gene Expression Phenotype to Immunoglobulin Mutation Genotype in B Cell Chronic Lymphocytic Leukemia," J. of Exp. Medicine, 194(11):1639-1647(2001).

Rudicoff et al., "Single amino acid substitution altering antigen-binding specificity," Proc. Natl. Acad. Sci. USA 79:1979-1983 (1982).

Sahin et al., "New monoclonal antibody specific for a 6.5 kDa glycoprotein which presents mainly on a B cell of chronic lymphocytic leukemia (CLL)" Immunology Letters, 2001, 76, 1-6.

Schlom, Jeffrey :Monoclonal Antibodies They're More and Less Than You Think, Molecular and Cellular Research for Future Diagnosis and Therapy, 95-134, 1991.

Schultes et al., "Immunotherapy of Human Ovarian Carcinoma with OVAREX™ MAb-B43.13 in a Human-PBL-SCID/BG Mouse Model," Hybridoma 18(1):47-55 (1999).

Sebestyen et al., Syndecan-1 (CD138) expression in human non-Hodgkin lymphomas. British Journal of Hematology. vol. 104, 1999, p. 412-419.

Sehgal, et al., "Generation of the Primary Antibody Repertoire in Rabbits: Expression of a Diverse Set of Igk-V Genes May Compensate for Limited Combinatorial Diversity at the Heavy Chain Locus," Immunogenetics 50:31-42 (1999).

Simelyte et al., "CD200-Fc, a Novel Antiarthritic Biologic Agent That Targets Proinflammatory Cytokine Expression in the Joints of Mice With Collagen-Induced Arthritis," Arthritis & Rheumatism, vol. 58(4), pp. 1038-1043 (2008).

Smith-Gill, Sandra J., "Biology of Antibody-Mediated Responses," Biologic Therapy of Cancer: Principles and Practice, Chapter 2, pp. 39-51 (1995).

Snyder et al., "Enhanced Targeting and Killing of Tumor Cells Expressing the CXC Chemokine Receptor 4 by Transducible Anticancer Peptides," Cancer Res. 65(23):10646-10650 (2005).

Srivastava, P.K., "Immunotherapy of human cancer: lessons from mice," Nature Immunology, 1(5):363-366 (2000).

Steinman, Lawrence., "Assessment of Animal Models for MS and Demyelinating Disease in the Design of Rational Therapy," Neuron, 24:511-514(1999).

Stuart et al., "Monkeying Around with Collagen Autoimmunity and Arthritis," Laboratory Investigation, vol. 54(1), pp. 1-3 (1986).

Syme, R., et al., "Comparison of CD34 and Monocyte-Derived Dendritic Cells from Mobilized Peripheral Blood from Cancer Patients," Stem Cells, 23:74-81 (2005).

Tanaka et al., "The Anti-Human Tumor Effect and Generation of Human Cytotoxic T Cells in SCID Mice Given Human Peripheral Blood Lymphocytes by the in Vivo Transfer of the Interleukin-6 Gene Using Adenovirus Vector," Cancer Res. 57:1335-1343 (1997).

Tang et al., Pathogenesis of collagen-induced arthritis: modulation of disease by arthritogenic T-Cell epitope location, J. of Immunology, 113: 384-391 (2004).

Tangri and Raghupathy, "Expression of Cytokines in Placentas of Mice Undergoing Immunologically Mediated Spontaneous Fetal Resorptions," Biology of Reprod., 49:850-856(1993).

Tao et al., "Structural Features of Human Immunoglobulin G that Determine Isotype-specific Differences in Complement Activation," J. Exp. Med., vol. 178, pp. 661-667 (1993).

Taylor, N., et al., "Enhanced Tolerance to Autoimmune Uveitis in CD200-Deficient Mice Correlates with a Pronounced Th2 Switch in Response to Antigen Challenge," J. Immunol., 174:143-154 (2005).

Thomsen et al., "Reconstitution of a human immune system in immunodeficient mice: models of human alloreaction in vivo," Tissue Antigens 66:73-82 (2005).

Toder et al., "Mouse Model for the Treatment of Immune Pregnancy Loss," Am. J. of Reprod. Immunol., 26:42-46(1991).

Webb, M., et al., "Localisation of the MRC OX-2 Glycoprotein on the Surfaces of Neurones," J. Neurochemistry, 43:1061-1067 (1984).

Wilczynski, J.R., "Immunological Analogy Between Allograft Rejection, Recurrent Abortion and Pre-Eclampsia—the Same Basic Mechanism?," Human Immunology, 67:492-511 (2006).

Wright et al., "The unusual distribution of the neuronal/lymphoid cell surface CD200 (OX2) glycoprotein is conserved in humans," Immunology 102:173-179 (2001).

Wright, G.J., et al., "Lymphoid/Neuronal Cell Surface OX2 Glycoprotein Recognizes a Novel Receptor on Macrophages Implicated in the Control of Their Function," Immunity, 13:233-242 (2000).

Wright, G.J., et al., "The lymphoid/neuronal OX-2 glycoprotein interacts with a novel protein expressed by macrophages," Tissue Antigens, 55 (Supplement 1); vol. 11 (2000).

Wright, G.J., et al., "Viral homologues of cell surface proteins OX2 and CD47 have potential to regulate macrophage function," Annual Congress of the British Society for Immunology, vol. 101 (Supplement 1): 50 Dec. 5-8, 2000.

Yamaguchi et al., "Application of monoclonal antibody for drug delivery system—Missile therapy for cancer," Nihon Rinsho, vol. 56(3), pp. 638-643 (1998).

Yamaguchi et al., "Immunomissile Therapy Using Tumor Markers: Application of tumor marker for immunotargeting therapy of cancer," Nihon Rinsho, vol. 54(6), pp. 1674-1679 (1996).

Yamaguchi et al., "Biological Response Modifier and Missile Cancer Chemotherapy," Biotherapy, vol. 10(4), pp. 605-609 (1996).

Yang, C., et al., "Functional maturation and recent thymic emigrants in the periphery: development of alloreactivity correlates with the cyclic expression of CD45RC isoforms," Eur. J. Immunol., 22:2261-2269 (1992).

(56) References Cited

OTHER PUBLICATIONS

Yu, X., et al., "The role of B7-CD28 co-stimulation in tumor rejection," International Immunology, 10(6):791-797 (1998).
Zhang, S., et al., "Molecular Mechanisms of CD200 Inhibition of Mast Cell Activation," J. Immunol., 173:6786-6793 (2004).
Zheng, P., et al., "B7-CTLA4 interaction enhances both production of antitumor cytotoxic T lymphocytes and resistance to tumor challenge," Proc. Natl. Acad. Sci. USA, 95:6284-6289 (1998).
Zhu et al., "Radioimmunotherapy of Human B-Cell Chronic Lymphocytic Leukemia in Nude Mice." Cancer Research. 54, 5111-5117 (1994).
Zips, D., et al., "New Anticancer Agents: In Vitro and In Vivo Evaluation," in vivo, 19:1-7 (2005).
Zou et al. Human Glioma-Induced Immunosuppression Involves Soluble Factor(s) That Alters Monocyte Cytokine Profile and Surface Markers. Apr. 15, 1999. vol. 162, pp. 4882-4892.

\* cited by examiner

FIG. 1

Primer C7mhHF (SEQ ID NO: 1)
TCCTCAGCCTCCACCAAGGGCC

FIG. 2

Primer Rev Age Pri (SEQ ID NO: 2)
GGGCGCCTGAGTTCCACGAC

FIG. 3
Primer C2aB7 rev (SEQ ID NO: 3)
GGCCCTTGGTGGAGGCTGAGGAAACTGTGAGAGTGGTGC

FIG. 4
lacpri (SEQ ID NO: 4)
GCTCCCGGCTCGTATGTTGTGT

FIG. 5
LeadVHpAX (SEQ ID NO: 5)
ATATGAAATATCTGCTGCCGACCG

FIG. 6A

Note: Figs. 6-15, leader sequences (AA) are underlined and constant regions are in bold.

chC2aB7-hG1
Heavy chain (introns in hG1) (SEQ ID NO. 7)
<u>MGWSCIILFLVATATGVHSL</u>EVQLQQSGPELVKPGASLKMSCKASGYSFT
DYIILWVKQNHGKSLEWIGHIDPYYGSSNYNLKFKGKATLTVDKSSSTAY
MQLNSLTSEDSAVYYCGRSKRDYFDYWGQGTTLTVSS**ASTKGPSVFPLA
PSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHT
CPPCPAPELLGGPSVFLFPPKPKDTLMISRTPEVTCVVVDVSHEDPEV
KFNWYVDGVEVHNAKTKPREEQYNSTYRVVSVLTVLHQDWLNGKE
YKCKVSNKALPAPIEKTISKAKGQPREPQVYTLPPSREEMTKNQVSLT
CLVKGFYPSDIAVEWESNGQPENNYKTTPPVLDSDGSFFLYSKLTVDK
SRWQQGNVFSCSVMHEALHNHYTQKSLSLSPGK**

FIG. 6B
(SEQ ID NO. 6) (genomic sequence hG1)
ATGGGATGGAGCTGTATCATCCTCTTCTTGGTAGCAACAGCTACAGGTGTCCACTCCCTCGAG
GTCCAGCTGCAACAGTCTGGACCTGAGCTGGTGAAGCCTGGGGCTTCACTGAAGATGTCCTGC
AAGGCTTCTGGTTATTCATTCACTGACTACATCATACTCTGGGTGAAGCAGAACCATGGAAAG
AGCCTTGAGTGGATTGGACATATTGATCCTTACTATGGTAGTTCTAACTACAATCTGAAATTCA
AGGGCAAGGCCACATTGACTGTAGACAAATCTTCCAGCACAGCCTACATGCAGCTCAACAGT
CTGACATCTGAGGACTCTGCAGTCTATTACTGTGGAAGATCTAAGAGGGACTACTTTGACTAC
TGGGGCCAAGGCACCACTCTCACAGTTTCCTCAGCCTCCACCAAGGGCCCATCGGTCTTCCCC
CTGGCACCCTCCTCCAAGAGCACCTCTGGCGGCACAGCGGCCCTGGGCTGCCTGGTCAAGGAC
TACTTCCCCGAACCGGTGACGGTGTCGTGGAACTCAGGCGCCCTGACCAGCGGCGTGCACACC
TTCCCGGCTGTCCTACAGTCCTCAGGACTCTACTCCCTCAGCAGCGTGGTGACCGTGCCCTCCA
GCAGCTTGGGCACCCAGACCTACATCTGCAACGTGAATCACAAGCCCAGCAACACCAAGGTG
GACAAGAGAGTTGGTGAGAGGCCAGCACAGGGAGGGAGGGTGTCTGCTGGAAGCCAGGCTC
AGCGCTCCTGCCTGGACGCATCCCGGCTATGCAGTCCCAGTCCAGGGCAGCAAGGCAGGCCC
CGTCTGCCTCTTCACCCGGAGGCCTCTGCCCGCCCCACTCATGCTCAGGGAGAGGGTCTTCTG
GCTTTTTCCCCAGGCTCTGGGCAGGCACAGGCTAGGTGCCCCTAACCCAGGCCCTGCACACAA
AGGGGCAGGTGCTGGGCTCAGACCTGCCAAGAGCCATATCCGGGAGGACCCTGCCCCTGACC
TAAGCCCACCCCAAAGGCCAAACTCTCCACTCCCTCAGCTCGGACACCTTCTCTCCTCCCAGA
TTCCAGTAACTCCCAATCTTCTCTCTGCAGAGCCCAAATCTTGTGACAAAACTCACACATGCCC
ACCGTGCCCAGGTAAGCCAGCCCAGGCCTCGCCCTCCAGCTCAAGGCGGGACAGGTGCCCTA
GAGTAGCCTGCATCCAGGGACAGGCCCCAGCCGGGTGCTGACACGTCCACCTCCATCTCTTCC
TCAGCACCTGAACTCCTGGGGGGACCGTCAGTCTTCCTCTTCCCCCCAAAACCCAAGGACACC
CTCATGATCTCCCGGACCCCTGAGGTCACATGCGTGGTGGTGGACGTGAGCCACGAAGACCCT
GAGGTCAAGTTCAACTGGTACGTGGACGGCGTGGAGGTGCATAATGCCAAGACAAAGCCGCG
GGAGGAGCAGTACAACAGCACGTACCGTGTGGTCAGCGTCCTCACCGTCCTGCACCAGGACT
GGCTGAATGGCAAGGAGTACAAGTGCAAGGTCTCCAACAAAGCCCTCCCAGCCCCCATCGAG
AAAACCATCTCCAAAGCCAAAGGTGGGACCCGTGGGGTGCGAGGGCCACATGGACAGAGGCC
GGCTCGGCCCACCCTCTGCCCTGAGAGTGACCGCTGTACCAACCTCTGTCCCTACAGGGCAGC
CCCGAGAACCACAGGTGTACACCCTGCCCCCATCCCGGGAGGAGATGACCAAGAACCAGGTC
AGCCTGACCTGCCTGGTCAAAGGCTTCTATCCCAGCGACATCGCCGTGGAGTGGGAGAGCAAT
GGGCAGCCGGAGAACAACTACAAGACCACGCCTCCCGTGCTGGACTCCGACGGCTCCTTCTTC
CTCTATAGCAAGCTCACCGTGGACAAGAGCAGGTGGCAGCAGGGGAACGTCTTCTCATGCTCC
GTGATGCATGAGGCTCTGCACAACCACTACACGCAGAAGAGCCTCTCCCTGTCCCCGGGTAAA
TGA A schematic representation of the heavy chain of antibody chC2aB7-hG1 (part 1).

FIG. 6C

FIG. 6E
Light Chain ( human Ck) (SEQ ID NO. 24)
MGWSCIILFLVATATGVHSRDIQMTQSPSSMYASLGERVTITCKASQDINSYL
SWFQQKPGKSPKTLIYRANRLVDGVPSRFSGSGSGQDYSLTISSLEYEDMGIY
YCLQYDEFPYTFGGGTKLEIKRTVAAPSVFIFPPSDEQLKSGTASVVCLLNN
FYPREAKVQWKVDNALQSGNSQESVTEQDSKDSTYSLSSTLTLSKADYE
KHKVYACEVTHQGLSSPVTKSFNRGEC (SEQ ID NO. 23)    FIG. 6F
ATGGGATGGAGCTGTATCATCCTCTTCTTGGTAGCAACAGCTACAGGTGT
CCACTCTAGAGACATCCAGATGACACAGTCTCCATCTTCCATGTATGCATC
TCTAGGAGAGAGAGTCACTATCACTTGCAAGGCGAGTCAGGACATTAATA
GCTATTTAAGCTGGTTCCAGCAGAAACCAGGGAAATCTCCTAAGACCCTG
ATCTATCGTGCAAACAGATTGGTAGATGGGGTTCCATCAAGGTTCAGTGG
CAGTGGATCTGGGCAAGATTATTCTCTCACCATCAGCAGCCTGGAGTATG
AAGATATGGGAATTTATTATTGTCTACAGTATGATGAGTTTCCGTACACGT
TCGGAGGGGGGACCAAGCTGGAAATAAAACGGACTGTGGCTGCACCATC
TGTCTTCATCTTCCCGCCATCTGATGAGCAGTTGAAATCTGGAACTGCCTC
TGTTGTGTGCCTGCTGAATAACTTCTATCCCAGAGAGGCCAAAGTACAGT
GGAAGGTGGATAACGCCCTCCAATCGGGTAACTCCCAGGAGAGTGTCAC
AGAGCAGGACAGCAAGGACAGCACCTACAGCCTCAGCAGCACCCTGACG
CTGAGCAAAGCAGACTACGAGAAACACAAAGTCTACGCCTGCGAAGTCA
CCCATCAGGGCCTGAGCTCGCCCGTCACAAAGAGCTTCAACAGGGGAGA
GTGTTAA hB7V4V1-hG1
Heavy chain (SEQ ID NO.9)

MGWSWIFLFLLSVTAGVHSEVQLVESGPEVKKPGASVKVSCKASGYSFID
YIILWIRQHSGKGLEWIGHIDPYYGSSNYNLKFKGRVTITADKSTRITYME
LTSLTSEDTAVYYCGRSKRDYFDYWGQGTTLTVSSASTKGPSVFPLAPSS
KSTSGGTAALGCLVKDYFPEPVTVSWNSGALTSGVHTFPAVLQSSGL
YSLSSVVTVPSSSLGTQTYICNVNHKPSNTKVDKRVEPKSCDKTHTCP
PCPAPELLGGPSVFLFPPKPKDTLMISRTPEVTCVVVDVSHEDPEVKF
NWYVDGVEVHNAKTKPREEQYNSTYRVVSVLTVLHQDWLNGKEYK
CKVSNKALPAPIEKTISKAKGQPREPQVYTLPPSREEMTKNQVSLTCL
VKGFYPSDIAVEWESNGQPENNYKTTPPVLDSDGSFFLYSKLTVDKSR
WQQGNVFSCSVMHEALHNHYTQKSLSLSPGK

FIG. 7A

FIG. 7B (SEQ ID NO. 8) (cDNA bG1)
ATGGGATGGAGCTGGATCTTTCTCTTTCTCCTGTCAGTAACTGCAGGTG
TGTTCTCTGAGGTCCAGCTGGTGGAGTCCGGACCTGAGGTGAAGAAGC
CTGGGGCTTCAGTGAAGGTGTCCTGCAAGGCTTCTGGTTATTCATTCAC
TGACTACATCATACTCTGGATCAGGCAGCATAGCGGAAAGGGCCTTGA
GTGGATTGGACATATTGATCCTTACTATGGTAGTTCTAACTACAATCTG
AAATTCAAGGGCAGGGTCACAATCACTGCAGACAAATCTACCAGGAC
AACCTACATGGAGCTCACCAGTCTGACATCTGAGGACACTGCAGTCTA
TTACTGTGGAAGATCTAAGAGGGACTACTTTGACTACTGGGGCCAAGG
CACCACTCTCACAGTTTCCTCAGCCTCCACCAAGGGCCCATCGGTCTTC
CCGCTAGCACCCTCCTCCAAGAGCACCTCTGGGGGCACAGCGGCCCTG
GGCTGCCTGGTCAAGGACTACTTCCCCGAACCGGTGACGGTGTCGTGG
AACTCAGGCGCCCTGACCAGCGGCGTGCACACCTTCCCGGCTGTCCTA
CAGTCCTCAGGACTCTACTCCCTCAGCAGCGTGGTGACCGTGCCCTCC
AGCAGCTTGGGCACCCAGACCTACATCTGCAACGTGAATCACAAGCCC
AGCAACACCAAGGTGGACAAGAGAGTTGAGCCCAAATCTTGTGACAA
AACTCACACATGCCCACCGTGCCCAGCACCTGAACTCCTGGGGGGACC
GTCAGTCTTCCTCTTCCCCCCAAAACCCAAGGACACCCTCATGATCTCC
CGGACCCCTGAGGTCACATGCGTGGTGGTGGACGTGAGCCACGAAGA
CCCTGAGGTCAAGTTCAACTGGTACGTGGACGGCGTGGAGGTGCATAA
TGCCAAGACAAAGCCGCGGGAGGAGCAGTACAACAGCACGTACCGTG
TGGTCAGCGTCCTCACCGTCCTGCACCAGGACTGGCTGAATGGCAAGG
AGTACAAGTGCAAGGTCTCCAACAAAGCCCTCCCAGCCCCCATCGAG
AAAACCATCTCCAAAGCCAAAGGGCAGCCCCGAGAACCACAGGTGTA
CACCCTGCCCCCATCCCGGGAGGAGATGACCAAGAACCAGGTCAGCC
TGACCTGCCTGGTCAAAGGCTTCTATCCCAGCGACATCGCCGTGGAGT
GGGAGAGCAATGGGCAGCCGGAGAACAACTACAAGACCACGCCTCCC
GTGCTGGACTCCGACGGCTCCTTCTTCCTCTACAGCAAGCTCACCGTG
GACAAGAGCAGGTGGCAGCAGGGGAACGTCTTCTCATGCTCCGTGAT
GCATGAGGCTCTGCACAACCACTACACGCAGAAGAGCCTCTCCCTGTC
TCCGGGTAAATGA

A schematic representation of the heavy chain of antibody hB7V4V1-hG1 (part 1).

FIG. 7C

FIG. 7E
Light chain (human Ck) (SEQ ID NO. 26)
MDMRVSAQLLGLLLLWLSGARCDIQMTQSPSSLSASIGDRVTITCKASQD
INSYLSWYQQKPGKAPKSLIYRANRLVDGVPSRFSGSGSGTDYTLTISSLQ
PEDFAVYYCLQYDEFPYTFGGGTKLEIKRTVAAPSVFIFPPSDEQLKSGT
ASVVCLLNNFYPREAKVQWKVDNALQSGNSQESVTEQDSKDSTYSLS
STLTLSKADYEKHKVYACEVTHQGLSSPVTKSFNRGEC FIG. 7F
(SEQ ID NO. 25)
ATGGACATGAGGGTCTCTGCTCAGCTCCTGGGGCTCCTGCTGCTCTGG
CTCTCAGGAGCCAGATGTGACATCCAGATGACACAGTCTCCATCTTCC
CTGTCTGCATCTATAGGAGACAGAGTCACTATCACTTGCAAGGCGAGT
CAGGACATTAATAGCTATTTAAGCTGGTACCAGCAGAAACCAGGGAA
AGCTCCTAAGTCCCTGATCTATCGTGCAAACAGATTGGTAGATGGGGT
TCCATCAAGGTTCAGTGGCAGTGGATCTGGGACAGATTATACTCTCAC
CATCAGCAGCCTGCAGCCTGAAGATTTCGCAGTTTATTATTGTCTACA
GTATGATGAGTTTCCGTACACGTTCGGAGGGGGGACCAAGCTGGAAAT
AAAACGTACGGTGGCTGCACCATCTGTCTTCATCTTCCCGCCATCTGAT
GAGCAGTTGAAATCTGGAACTGCCTCTGTTGTGTGCCTGCTGAATAAC
TTCTATCCCAGAGAGGCCAAAGTACAGTGGAAGGTGGATAACGCCCTC
CAATCGGGTAACTCCCAGGAGAGTGTCACAGAGCAGGACAGCAAGGA
CAGCACCTACAGCCTCAGCAGCACCCTGACGCTGAGCAAAGCAGACT
ACGAGAAACACAAAGTCTACGCCTGCGAAGTCACCCATCAGGGCCTG
AGCTCGCCCGTCACAAAGAGCTTCAACAGGGGAGAGTGTTAG

FIG. 7G hB7V3V1-hG1 (SEQ ID NO.11)
Heavy chain

MGWSRIFLFLLSIIAGVHCQVQLQQSGSELKKPGASVKISCKASGYSFTDY
IILWVRQNPGKGLEWIGHIDPYYGSSNYNLKFKGRVITTADQSTTAYME
LSSLRSEDTAVYYCGRSKRDYDYWGQGTTLTVSSASTKGPSVFPLAPSS
KSTSGGTAALGCLVKDYFPEPVTVSWNSGALTSGVHTFPAVLQSSGL
YSLSSVVTVPSSSLGTQTYICNVNHKPSNTKVDKRVEPKSCDKTHTCP
PCPAPELLGGPSVFLFPPKPKDTLMISRTPEVTCVVVDVSHEDPEVKF
NWYVDGVEVHNAKTKPREEQYNSTYRVVSVLTVLHQDWLNGKEYK
CKVSNKALPAPIEKTISKAKGQPREPQVYTLPPSREEMTKNQVSLTCL
VKGFYPSDIAVEWESNGQPENNYKTTPPVLDSDGSFFLYSKLTVDKSR
WQQGNVFSCSVMHEALHNHYTQKSLSLSPGK

FIG. 8A

FIG. 8B
(SEQ ID NO. 10) (cDNA hG1)
ATGGGATGGAGCCGGATCTTTCTCTTCCTCCTGTCAATAATTGCAGGTG
TCCATTGCCAGGTCCAGCTGCAACAGTCTGGATCTGAGCTGAAGAAGC
CTGGGGCTTCAGTGAAGATCTCCTGCAAGGCTTCTGGTTATTCATTCAC
TGACTACATCATACTCTGGGTGAGGCAGAACCCTGGAAAGGGCCTTGA
GTGGATTGGACATATTGATCCTTACTATGGTAGTTCTAACTACAATCTG
AAATTCAAGGGCAGAGTGACAATCACCGCCGACCAGTCTACCACCAC
AGCCTACATGGAGCTCTCCAGTCTGAGATCTGAGGACACTGCAGTCTA
TTACTGTGGAAGATCTAAGAGGGACTACTTTGACTACTGGGGCCAAGG
CACCACTCTCACAGTTTCCTCAGCCTCCACCAAGGGCCCATCGGTCTTC
CCGCTAGCACCCTCCTCCAAGAGCACCTCTGGGGGCACAGCGGCCCTG
GGCTGCCTGGTCAAGGACTACTTCCCCGAACCGGTGACGGTGTCGTGG
AACTCAGGCGCCCTGACCAGCGGCGTGCACACCTTCCCGGCTGTCCTA
CAGTCCTCAGGACTCTACTCCCTCAGCAGCGTGGTGACCGTGCCCTCC
AGCAGCTTGGGCACCCAGACCTACATCTGCAACGTGAATCACAAGCCC
AGCAACACCAAGGTGGACAAGAGAGTTGAGCCCAAATCTTGTGACAA
AACTCACACATGCCCACCGTGCCCAGCACCTGAACTCCTGGGGGGACC
GTCAGTCTTCCTCTTCCCCCCAAAACCCAAGGACACCCTCATGATCTCC
CGGACCCCTGAGGTCACATGCGTGGTGGTGGACGTGAGCCACGAAGA
CCCTGAGGTCAAGTTCAACTGGTACGTGGACGGCGTGGAGGTGCATAA
TGCCAAGACAAAGCCGCGGGAGGAGCAGTACAACAGCACGTACCGTG
TGGTCAGCGTCCTCACCGTCCTGCACCAGGACTGGCTGAATGGCAAGG
AGTACAAGTGCAAGGTCTCCAACAAAGCCCTCCCAGCCCCCATCGAG
AAAACCATCTCCAAAGCCAAAGGGCAGCCCCGAGAACCACAGGTGTA
CACCCTGCCCCCATCCCGGGAGGAGATGACCAAGAACCAGGTCAGCC
TGACCTGCCTGGTCAAAGGCTTCTATCCCAGCGACATCGCCGTGGAGT
GGGAGAGCAATGGGCAGCCGGAGAACAACTACAAGACCACGCCTCCC
GTGCTGGACTCCGACGGCTCCTTCTTCCTCTACAGCAAGCTCACCGTG
GACAAGAGCAGGTGGCAGCAGGGGAACGTCTTCTCATGCTCCGTGAT
GCATGAGGCTCTGCACAACCACTACACGCAGAAGAGCCTCTCCCTGTC
TCCGGGTAAATGA

FIG. 8C

Light chain (human Cκ) (SEQ ID NO.26)

MDMRVSAQLLGLLLLWLSGARCDIQMTQSPSSLSASIGDRVTITCKASQD
INSYLSWYQQKPGKAPKSLIYRANRLVDGVPSRFSGSGSGTDYTLTISSLQ
PEDFAVYYCLQYDEFPYTFGGGTKLEIKRTVAAPSVFIFPPSDEQLKSGT
ASVVCLLNNFYPREAKVQWKVDNALQSGNSQESVTEQDSKDSTYSLS
STLTLSKADYEKHKVYACEVTHQGLSSPVTKSFNRGEC

FIG. 8D

FIG. 8E
(SEQ ID NO. 25)
ATGGACATGAGGGTCTCTGCTCAGCTCCTGGGGCTCCTGCTGCTCTGG
CTCTCAGGAGCCAGATGTGACATCCAGATGACACAGTCTCCATCTTCC
CTGTCTGCATCTATAGGAGACAGAGTCACTATCACTTGCAAGGCGAGT
CAGGACATTAATAGCTATTTAAGCTGGTACCAGCAGAAACCAGGGAA
AGCTCCTAAGTCCCTGATCTATCGTGCAAACAGATTGGTAGATGGGGT
TCCATCAAGGTTCAGTGGCAGTGGATCTGGGACAGATTATACTCTCAC
CATCAGCAGCCTGCAGCCTGAAGATTTCGCAGTTTATTATTGTCTACA
GTATGATGAGTTTCCGTACACGTTCGGAGGGGGGACCAAGCTGGAAAT
AAAACGTACGGTGGCTGCACCATCTGTCTTCATCTTCCCGCCATCTGAT
GAGCAGTTGAAATCTGGAACTGCCTCTGTTGTGTGCCTGCTGAATAAC
TTCTATCCCAGAGAGGCCAAAGTACAGTGGAAGGTGGATAACGCCCTC
CAATCGGGTAACTCCCAGGAGAGTGTCACAGAGCAGGACAGCAAGGA
CAGCACCTACAGCCTCAGCAGCACCCTGACGCTGAGCAAAGCAGACT
ACGAGAAACACAAAGTCTACGCCTGCGAAGTCACCCATCAGGGCCTG
AGCTCGCCCGTCACAAAGAGCTTCAACAGGGGAGAGTGTTAG.

FIG. 8F hB7V3V2-hG1
Heavy chain (SEQ ID NO.11)

MGWSRIFLFLLSIIAGVHCQVQLQQSGSELKKPGASVKISCKASGYSFTDY
IILWVRQNPGKGLEWIGHIDPYYGSSNYNLFKGRVTITADQSTTTAYME
LSSLRSEDTAVYYCGRSKRDYFDYWGQGTTLTVSSASTKGPSVFPLAPSS
KSTSGGTAALGCLVKDYFPEPVTVSWNSGALTSGVHTFPAVLQSSGL
YSLSSVVTVPSSSLGTQTYICNVNHKPSNTKVDKRVEPKSCDKTHTCP
PCPAPELLGGPSVFLFPPKPKDTLMISRTPEVTCVVVDVSHEDPEVKF
NWYVDGVEVHNAKTKPREEQYNSTYRVVSVLTVLHQDWLNGKEYK
CKVSNKALPAPIEKTISKAKGQPREPQVYTLPPSREEMTKNQVSLTCL
VKGFYPSDIAVEWESNGQPENNYKTTPPVLDSDGSFFLYSKLTVDKSR
WQQGNVFSCSVMHEALHNHYTQKSLSLSPGK

FIG. 9A

FIG. 9B
(SEQ ID NO. 10) (cDNA hG1)
ATGGGATGGAGCCGGATCTTTCTCTTCCTCCTGTCAATAATTGCAGGTG
TCCATTGCCAGGTCCAGCTGCAACAGTCTGGATCTGAGCTGAAGAAGC
CTGGGGCTTCAGTGAAGATCTCCTGCAAGGCTTCTGGTTATTCATTCAC
TGACTACATCATACTCTGGGTGAGGCAGAACCCTGGAAAGGGCCTTGA
GTGGATTGGACATATTGATCCTTACTATGGTAGTTCTAACTACAATCTG
AAATTCAAGGGCAGAGTGACAATCACCGCCGACCAGTCTACCACCAC
AGCCTACATGGAGCTCTCCAGTCTGAGATCTGAGGACACTGCAGTCTA
TTACTGTGGAAGATCTAAGAGGGACTACTTTGACTACTGGGGCCAAGG
CACCACTCTCACAGTTTCCTCAGCCTCCACCAAGGGCCCATCGGTCTTC
CCGCTAGCACCCTCCTCCAAGAGCACCTCTGGGGGCACAGCGGCCCTG
GGCTGCCTGGTCAAGGACTACTTCCCCGAACCGGTGACGGTGTCGTGG
AACTCAGGCGCCCTGACCAGCGGCGTGCACACCTTCCCGGCTGTCCTA
CAGTCCTCAGGACTCTACTCCCTCAGCAGCGTGGTGACCGTGCCCTCC
AGCAGCTTGGGCACCCAGACCTACATCTGCAACGTGAATCACAAGCCC
AGCAACACCAAGGTGGACAAGAGAGTTGAGCCCAAATCTTGTGACAA
AACTCACACATGCCCACCGTGCCCAGCACCTGAACTCCTGGGGGGACC
GTCAGTCTTCCTCTTCCCCCCAAAACCCAAGGACACCCTCATGATCTCC
CGGACCCCTGAGGTCACATGCGTGGTGGTGGACGTGAGCCACGAAGA
CCCTGAGGTCAAGTTCAACTGGTACGTGGACGGCGTGGAGGTGCATAA
TGCCAAGACAAAGCCGCGGGAGGAGCAGTACAACAGCACGTACCGTG
TGGTCAGCGTCCTCACCGTCCTGCACCAGGACTGGCTGAATGGCAAGG
AGTACAAGTGCAAGGTCTCCAACAAAGCCCTCCCAGCCCCCATCGAG
AAAACCATCTCCAAAGCCAAAGGGCAGCCCCGAGAACCACAGGTGTA
CACCCTGCCCCCATCCCGGGAGGAGATGACCAAGAACCAGGTCAGCC
TGACCTGCCTGGTCAAAGGCTTCTATCCCAGCGACATCGCCGTGGAGT
GGGAGAGCAATGGGCAGCCGGAGAACAACTACAAGACCACGCCTCCC
GTGCTGGACTCCGACGGCTCCTTCTTCCTCTACAGCAAGCTCACCGTG
GACAAGAGCAGGTGGCAGCAGGGGAACGTCTTCTCATGCTCCGTGAT
GCATGAGGCTCTGCACAACCACTACACGCAGAAGAGCCTCTCCCTGTC
TCCGGGTAAATGA

A schematic representation of the light chain of antibody hB7V3V2-hG1.

FIG. 9C

Light chain (human Ck) (SEQ ID NO. 28)

MDMRVSAQLLGLLLLWLSGARCDIQMTQSPSSLSASIGDRVTITCKASQD
INSYLSWFQQKPGKAPKLLIYRANRLVDGVPSRFSGSGSGTDYTLTISSLQ
PEDFAVYYCLQYDEFPYTFGGGTKLEIKRTVAAPSVFIFPPSDEQLKSGT
ASVVCLLNNFYPREAKVQWKVDNALQSGNSQESVTEQDSKDSTYSLS
STLTLSKADYEKHKVYACEVTHQGLSSPVTKSFNRGEC

FIG. 9D

FIG. 9E
(SEQ ID NO. 27)
ATGGACATGAGGGTCTCTGCTCAGCTCCTGGGGCTCCTGCTGCTCTGG
CTCTCAGGGGCCAGGTGTGACATCCAGATGACACAGTCTCCATCTTCC
CTGTCTGCATCTATAGGAGACAGAGTCACTATCACTTGCAAGGCGAGT
CAGGACATTAATAGCTATTTAAGCTGGTTCCAGCAGAAACCAGGGAA
AGCTCCTAAGCTGCTGATCTATCGTGCAAACAGATTGGTAGATGGGGT
TCCATCAAGGTTCAGTGGCAGTGGATCTGGGACAGATTATACTCTCAC
CATCAGCAGCCTGCAGCCTGAAGATTTCGCAGTTTATTATTGTCTACA
GTATGATGAGTTTCCGTACACGTTCGGAGGGGGGACCAAGCTGGAAAT
AAAACGTACGGTGGCTGCACCATCTGTCTTCATCTTCCCGCCATCTGAT
GAGCAGTTGAAATCTGGAACTGCCTCTGTTGTGTGCCTGCTGAATAAC
TTCTATCCCAGAGAGGCCAAAGTACAGTGGAAGGTGGATAACGCCCTC
CAATCGGGTAACTCCCAGGAGAGTGTCACAGAGCAGGACAGCAAGGA
CAGCACCTACAGCCTCAGCAGCACCCTGACGCTGAGCAAAGCAGACT
ACGAGAAACACAAAGTCTACGCCTGCGAAGTCACCCATCAGGGCCTG
AGCTCGCCCGTCACAAAGAGCTTCAACAGGGGAGAGTGTTAG

FIG. 9F hB7V3V2-hG24
Heavy chain (SEQ ID NO.13)

MGWSRIFLFLLSIIAGVHCQVQLQQSGSELKKPGASVKISCKASGYSFTDY
IILWVRQNPGKGLEWIGHIDPYYGSSNYNLKFKGRVTITADQSTTTAYME
LSSLRSEDTAVYYCGRSKRDYFDYWGQGTTLTVSSASTKGPSVFPLAPC
SRSTSESTAALGCLVKDYFPEPVTVSWNSGALTSGVHTFPAVLQSSGL
YSLSSVVTVPSSNFGTQTYTCNVDHKPSNTKVDKTVERKCCVECPPCP
APPVAGPSVFLFPPKPKDTLMISRTPEVTCVVVDVSQEDPEVQFNWYV
DGVEVHNAKTKPREEQFNSTYRVVSVLTVLHQDWLNGKEYKCKVSN
KGLPSSIEKTISKAKGQPREPQVYTLPPSQEEMTKNQVSLTCLVKGFY
PSDIAVEWESNGQPENNYKTTPPVLDSDGSFFLYSRLTVDKSRWQEG
NVFSCSVMHEALHNHYTQKSLSLSLGK

FIG. 10A

FIG. 10B (SEQ ID NO. 12) (genomic sequence hG2G4)
ATGGGATGGAGCTGTATCATCCTCTTCTTGGTAGCAACAGCTACAGGTGTCCACTCCCTCGAG
GTCCAGCTGCAACAGTCTGGACCTGAGCTGGTGAAGCCTGGGGCTTCACTGAAGATGTCCTGC
AAGGCTTCTGGTTATTCATTCACTGACTACATCATACTCTGGGTGAAGCAGAACCATGGAAAG
AGCCTTGAGTGGATTGGACATATTGATCCTTACTATGGTAGTTCTAACTACAATCTGAAATTCA
AGGGCAAGGCCACATTGACTGTAGACAAATCTTCCAGCACAGCCTACATGCAGCTCAACAGT
CTGACATCTGAGGACTCTGCAGTCTATTACTGTGGAAGATCTAAGAGGGACTACTTTGACTAC
TGGGGCCAAGGCACCACTCTCACAGTTTCCTCAGCCTCCACCAAGGGCCCATCCGTCTTCCCC
CTGGCGCCCTGCTCCAGGAGCACCTCCGAGAGCACAGCCGCCCTGGGCTGCCTGGTCAAGGA
CTACTTCCCCGAACCGGTGACGGTGTCGTGGAACTCAGGCGCCCTGACCAGCGGCGTGCACAC
CTTCCCGGCTGTCCTACAGTCCTCAGGACTCTACTCCCTCAGCAGCGTGGTGACCGTGCCCTCC
AGCAACTTCGGCACCCAGACCTACACCTGCAACGTAGATCACAAGCCCAGCAACACCAAGGT
GGACAAGACAGTTGGTGAGAGGCCAGCTCAGGGAGGGAGGGTGTCTGCTGGAAGCCAGGCTC
AGCCCTCCTGCCTGGACGCACCCCGGCTGTGCAGCCCCAGCCCAGGGCAGCAAGGCAGGCCC
CATCTGTCTCCTCACCCGGAGGCCTCTGCCCGCCCACTCATGCTCAGGGAGAGGGTCTTCTG
GCTTTTTCCACCAGGCTCCAGGCAGGCACAGGCTGGGTGCCCCTACCCCAGGCCCTTCACACA
CAGGGGCAGGTGCTTGGCTCAGACCTGCCAAAAGCCATATCCGGGAGGACCCTGCCCCTGAC
CTAAGCCGACCCCAAAGGCCAAACTGTCCACTCCCTCAGCTCGGACACCTTCTCTCCTCCCAG
ATCCGAGTAACTCCCAATCTTCTCTCTGCAGAGCGCAAATGTTGTGTCGAGTGCCCACCGTGC
CCAGGTAAGCCAGCCCAGGCCTCGCCCTCCAGCTCAAGGCGGGACAGGTGCCCTAGAGTAGC
CTGCATCCAGGGACAGGCCCCAGCTGGGTGCTGACACGTCCACCTCCATCTCTTCCTCAGCAC
CACCTGTGGCAGGACCGTCAGTCTTCCTCTTCCCCCCAAAACCCAAGGACACCCTCATGATCT
CCCGGACCCCTGAGGTCACGTGCGTGGTGGTGGACGTGAGCCAGGAAGACCCCGAGGTCCAG
TTCAACTGGTACGTGGATGGCGTGGAGGTGCATAATGCCAAGACAAAGCCGCGGGAGGAGCA
GTTCAACAGCACGTACCGTGTGGTCAGCGTCCTCACCGTCCTGCACCAGGACTGGCTGAACGG
CAAGGAGTACAAGTGCAAGGTCTCCAACAAAGGCCTCCCGTCCTCCATCGAGAAAACCATCT
CCAAAGCCAAAGGTGGGACCCACGGGGTGCGAGGGCCACATGGACAGAGGTCAGCTCGGCCC
ACCCTCTGCCCTGGGAGTGACCGCTGTGCCAACCTCTGTCCCTACAGGGCAGCCCCGAGAGCC
ACAGGTGTACACCCTGCCCCCATCCCAGGAGGAGATGACCAAGAACCAGGTCAGCCTGACCT
GCCTGGTCAAAGGCTTCTACCCCAGCGACATCGCCGTGGAGTGGGAGAGCAATGGGCAGCCG
GAGAACAACTACAAGACCACGCCTCCCGTGCTGGACTCCGACGGCTCCTTCTTCCTCTACAGC
AGGCTAACCGTGGACAAGAGCAGGTGGCAGGAGGGGAATGTCTTCTCATGCTCCGTGATGCA
TGAGGCTCTGCACAACCACTACACACAGAAGAGCCTCTCCCTGTCTCTGGGTAAATGATGA A schematic representation of the heavy chain of antibody hB7V3V2-hG2G4 (part 1).

FIG. 10C

FIG. 10E
Light Chain (human Ck) (SEQ ID NO. 28)
MDMRVSAQLLGLLLLWLSGARCDIQMTQSPSSLSASIGDRVTITCKASQD
INSYLSWFQQKPGKAPKLLIYRANRLVDGVPSRFSGSGSGTDYTLTISSLQ
PEDFAVYYCLQYDEFPYTFGGGTKLEIKRTVAAPSVFIFPPSDEQLKSGT
ASVVCLLNNFYPREAKVQWKVDNALQSGNSQESVTEQDSKDSTYSLS
STLTLSKADYEKHKVYACEVTHQGLSSPVTKSFNRGEC FIG. 10F
(SEQ ID NO. 27)
ATGGACATGAGGGTCTCTGCTCAGCTCCTGGGGCTCCTGCTGCTCTGG
CTCTCAGGGGCCAGGTGTGACATCCAGATGACACAGTCTCCATCTTCC
CTGTCTGCATCTATAGGAGACAGAGTCACTATCACTTGCAAGGCGAGT
CAGGACATTAATAGCTATTTAAGCTGGTTCCAGCAGAAACCAGGGAA
AGCTCCTAAGCTGCTGATCTATCGTGCAAACAGATTGGTAGATGGGGT
TCCATCAAGGTTCAGTGGCAGTGGATCTGGGACAGATTATACTCTCAC
CATCAGCAGCCTGCAGCCTGAAGATTTCGCAGTTTATTATTGTCTACA
GTATGATGAGTTTCCGTACACGTTCGGAGGGGGGACCAAGCTGGAAAT
AAAACGTACGGTGGCTGCACCATCTGTCTTCATCTTCCCGCCATCTGAT
GAGCAGTTGAAATCTGGAACTGCCTCTGTTGTGTGCCTGCTGAATAAC
TTCTATCCCAGAGAGGCCAAAGTACAGTGGAAGGTGGATAACGCCCTC
CAATCGGGTAACTCCCAGGAGAGTGTCACAGAGCAGGACAGCAAGGA
CAGCACCTACAGCCTCAGCAGCACCCTGACGCTGAGCAAAGCAGACT
ACGAGAAACACAAAGTCTACGCCTGCGAAGTCACCCATCAGGGCCTG
AGCTCGCCCGTCACAAAGAGCTTCAACAGGGGAGAGTGTTAG

FIG. 10G chC2aB7-hG2G4
Heavy chain (SEQ ID NO.15)

MGWSCIILFLVATATGVHSZEVQLQQSGPELVKPGASLKMSCKASGYSFT
DYIILWVKQNHGKSLEWIGHIDPYYGSSNYNLKFKGKATLTVDKSSSTAY
MQLNSLTSEDSAVYYCGRSKRDYFDYWGQGTTLTVSSASTKGPSVFPLA
PCSRSTSESTAALGCLVKDYFPEPVTVSWNSGALTSGVHTFPAVLQSS
GLYSLSSVVTVPSSNFGTQTYTCNVDHKPSNTKVDKTVERKCCVECP
PCPAPPVAGPSVFLFPPKPKDTLMISRTPEVTCVVVDVSQEDPEVQFN
WYVDGVEVHNAKTKPREEQFNSTYRVVSVLTVLHQDWLNGKEYKC
KVSNKGLPSSIEKTISKAKGQPREPQVYTLPPSQEEMTKNQVSLTCLV
KGFYPSDIAVEWESNGQPENNYKTTPPVLDSDGSFFLYSRLTVDKSR
WQEGNVFSCSVMHEALHNHYTQKSLSLSLGK

FIG. 11A

FIG. 11B
(SEQ ID NO. 14) (genomic sequence hG2G4)
ATGGGATGGAGCTGTATCATCCTCTTCTTGGTAGCAACAGCTACAGGTGTCCACTCCCTCGAG
GTCCAGCTGCAACAGTCTGGACCTGAGCTGGTGAAGCCTGGGGCTTCACTGAAGATGTCCTGC
AAGGCTTCTGGTTATTCATTCACTGACTACATCATACTCTGGGTGAAGCAGAACCATGGAAAG
AGCCTTGAGTGGATTGGACATATTGATCCTTACTATGGTAGTTCTAACTACAATCTGAAATTCA
AGGGCAAGGCCACATTGACTGTAGACAAATCTTCCAGCACAGCCTACATGCAGCTCAACAGT
CTGACATCTGAGGACTCTGCAGTCTATTACTGTGGAAGATCTAAGAGGGACTACTTTGACTAC
TGGGGCCAAGGCACCACTCTCACAGTTTCCTCAGCCTCCACCAAGGGCCCATCCGTCTTCCCC
CTGGCGCCCTGCTCCAGGAGCACCTCCGAGAGCACAGCCGCCCTGGGCTGCCTGGTCAAGGA
CTACTTCCCCGAACCGGTGACGGTGTCGTGGAACTCAGGCGCCCTGACCAGCGGCGTGCACAC
CTTCCCGGCTGTCCTACAGTCCTCAGGACTCTACTCCCTCAGCAGCGTGGTGACCGTGCCCTCC
AGCAACTTCGGCACCCAGACCTACACCTGCAACGTAGATCACAAGCCCAGCAACACCAAGGT
GGACAAGACAGTTGGTGAGAGGCCAGCTCAGGGAGGGAGGGTGTCTGCTGGAAGCCAGGCTC
AGCCCTCCTGCCTGGACGCACCCCGGCTGTGCAGCCCCAGCCCAGGGCAGCAAGGCAGGCCC
CATCTGTCTCCTCACCCGGAGGCCTCTGCCCGCCCCACTCATGCTCAGGGAGAGGGTCTTCTG
GCTTTTTCCACCAGGCTCCAGGCAGGCACAGGCTGGGTGCCCCTACCCCAGGCCCTTCACACA
CAGGGGCAGGTGCTTGGCTCAGACCTGCCAAAAGCCATATCCGGGAGGACCCTGCCCCTGAC
CTAAGCCGACCCCAAAGGCCAAACTGTCCACTCCCTCAGCTCGGACACCTTCTCTCCTCCCAG
ATCCGAGTAACTCCCAATCTTCTCTCTGCAGAGCGCAAATGTTGTGTCGAGTGCCCACCGTGC
CCAGGTAAGCCAGCCCAGGCCTCGCCCTCCAGCTCAAGGCGGGACAGGTGCCCTAGAGTAGC
CTGCATCCAGGGACAGGCCCCAGCTGGGTGCTGACACGTCCACCTCCATCTCTTCCTCAGCAC
CACCTGTGGCAGGACCGTCAGTCTTCCTCTTCCCCCCAAAACCCAAGGACACCCTCATGATCT
CCCGGACCCCTGAGGTCACGTGCGTGGTGGTGGACGTGAGCCAGGAAGACCCCGAGGTCCAG
TTCAACTGGTACGTGGATGGCGTGGAGGTGCATAATGCCAAGACAAAGCCGCGGGAGGAGCA
GTTCAACAGCACGTACCGTGTGGTCAGCGTCCTCACCGTCCTGCACCAGGACTGGCTGAACGG
CAAGGAGTACAAGTGCAAGGTCTCCAACAAAGGCCTCCCGTCCTCCATCGAGAAAACCATCT
CCAAAGCCAAAGGTGGGACCCACGGGGTGCGAGGGCCACATGGACAGAGGTCAGCTCGGCCC
ACCCTCTGCCCTGGGAGTGACCGCTGTGCCAACCTCTGTCCCTACAGGGCAGCCCCGAGAGCC
ACAGGTGTACACCCTGCCCCCATCCCAGGAGGAGATGACCAAGAACCAGGTCAGCCTGACCT
GCCTGGTCAAAGGCTTCTACCCCAGCGACATCGCCGTGGAGTGGGAGAGCAATGGGCAGCCG
GAGAACAACTACAAGACCACGCCTCCCGTGCTGGACTCCGACGGCTCCTTCTTCCTCTACAGC
AGGCTAACCGTGGACAAGAGCAGGTGGCAGGAGGGGAATGTCTTCTCATGCTCCGTGATGCA
TGAGGCTCTGCACAACCACTACACACAGAAGAGCCTCTCCCTGTCTCTGGGTAAATGA A schematic representation of the heavy chain of antibody chC2aB7-hG2G4 (amino acids 1-337) (part 1).

```
GCTGACAGACTAACAGACTGTTCCTTTCCATGGGTCTTCTTCTGCAGTCACCGTCCTTGACACGAGCGGCCCACCATGGGATGGAGCTGTATCATCC  100
                                                                       Leader
                                                                    M  G  W  S  C  I  I TGTTTGTTGGTAGCAACAGCTACAGGTGTCCACTCCCTCGAGGTCCAGCTGCAACAGTCTGGACCTGAACTGGTGAAGCCTGGGGCTTCAGTGAAGATGTC  200
        Leader                | re |                                    VH
 L  F  L  V  A  T  A  T  G  V  H  S  L  E  V  Q  L  Q  Q  S  G  P  E  L  V  K  P  G  A  S  L  K  M  S CTGCAAGGCTTCTGGTTATTCACTGACTACTACATGAGCTGGGTGAAGCAGAGCCATGGAAAGAGCCTTGAGTGGATTGGACATATTGATCCTTAC  300
                                                                              VH
 C  K  A  S  G  Y  S  F  T  D  Y  Y  I  H  W  V  K  Q  N  H  G  K  S  L  E  W  I  G  H  I  D  P  Y TATGGTAGTTCTAACTACAATCTGAAATTCAAGGGCAAGGCCACAGCCTACAGTGCAACAGTCTGACAT  400
                                                                       VH
 Y  G  S  S  N  Y  N  L  K  F  K  G  K  A  T  L  T  V  D  K  S  S  S  T  A  Y  M  Q  L  N  S  L  T CTGAGGACTCTGCAGTCTATTACTGTGGAAGATCTAAGAGGACTACTTTGACTATTGGGGCCAAGGCACCACTCTCACAGTTTCCTCAGCCTCCACCAA  500
                                                                        VH                      | G2G4 CH1 |
 S  E  D  S  A  V  Y  Y  C  G  R  S  K  R  D  Y  F  D  Y  W  G  Q  G  T  L  T  V  S  S  A  S  T  K GGGCCCATCCGTCTTCCCCCTGGCGCCCTGCTCCAGGAGCACCTCCGAGAGCACAGCGGCCCTGGGCTGCCTGGTCAAGGACTACTTCCCCGAACCGGTG  600
                                                                              G2G4 CH1
 G  P  S  V  F  P  L  A  P  C  S  R  S  T  S  E  S  T  A  A  L  G  C  L  V  K  D  Y  F  P  E  P  V ACGGTGTCGTGGAACTCAGGCGCCCTGACCAGCGGCGTGCACACCTTCCCGGCTGTCCTACAGTCCTCAGGACTCTACTCCCTCAGCAGCGTGGTGACCG  700
          G2G4 CH1
 T  V  S  W  N  S  G  A  L  T  S  G  V  H  T  F  P  A  V  L  Q  S  S  G  L  Y  S  L  S  S  V  V  T
```

FIG. 11E
Light Chain (human Ck) (SEQ ID NO. 24)
MGWSCIILFLVATATGVHSRDIQMTQSPSSMYASLGERVTITCKASQDINS
YLSWFQQKPGKSPKTLIYRANRLVDGVPSRFSGSGSGQDYSLTISSLEYED
MGIYYCLQYDEFPYTFGGGTKLEIKRTVAAPSVFIFPPSDEQLKSGTASV
VCLLNNFYPREAKVQWKVDNALQSGNSQESVTEQDSKDSTYSLSSTL
TLSKADYEKHKVYACEVTHQGLSSPVTKSFNRGEC FIG. 11F
(SEQ ID NO. 23)
ATGGGATGGAGCTGTATCATCCTCTTCTTGGTAGCAACAGCTACAGGT
GTCCACTCTAGAGACATCCAGATGACACAGTCTCCATCTTCCATGTAT
GCATCTCTAGGAGAGAGAGTCACTATCACTTGCAAGGCGAGTCAGGA
CATTAATAGCTATTTAAGCTGGTTCCAGCAGAAACCAGGGAAATCTCC
TAAGACCCTGATCTATCGTGCAAACAGATTGGTAGATGGGGTTCCATC
AAGGTTCAGTGGCAGTGGATCTGGGCAAGATTATTCTCTCACCATCAG
CAGCCTGGAGTATGAAGATATGGGAATTTATTATTGTCTACAGTATGA
TGAGTTTCCGTACACGTTCGGAGGGGGGACCAAGCTGGAAATAAAAC
GGACTGTGGCTGCACCATCTGTCTTCATCTTCCCGCCATCTGATGAGCA
GTTGAAATCTGGAACTGCCTCTGTTGTGTGCCTGCTGAATAACTTCTAT
CCCAGAGAGGCCAAAGTACAGTGGAAGGTGGATAACGCCCTCCAATC
GGGTAACTCCCAGGAGAGTGTCACAGAGCAGGACAGCAAGGACAGCA
CCTACAGCCTCAGCAGCACCCTGACGCTGAGCAAAGCAGACTACGAG
AAACACAAAGTCTACGCCTGCGAAGTCACCCATCAGGGCCTGAGCTC
GCCCGTCACAAAGAGCTTCAACAGGGGAGAGTGTTAA A schematic representation of the light chain of antibody chC2aB7-hG2G4.

```
                                                                                            Xbal
AAGCTTGCCGCCACCATGGGATGGAGCTGTATCATCCTCTTCTTGTGGTAGCAACAGCTACAGGTGTCCACTCTAGAGACATCCAGATGACACAGTCTCCAT 100
         M  G  W  S  C  I  I  L  F  L  V  A  T  A  T  G  V  H  S  R  D  I  Q  M  T  Q  S  P
         |—————————leader—————————|                              |——mVL CTTCCATGTATGCATCTCTAGGAGAGAGAGTCACTATCACTTGCAAGGCGAGTCAAGGACATTAATAGCTATTTAAGCTGGTTCCAGCAGAAACCAGGGAA 200
 S  S  M  Y  A  S  L  G  E  R  V  T  I  T  C  K  A  S  Q  D  I  N  S  Y  L  S  W  F  Q  Q  K  P  G  K
                                                              mVL ATCTCCTAAGACCCTGATCTATCGTGCAAACAGATTGGTAGATGGGGTTCCATCAAGGTTCAGTGGCAGTGGATCTGGGCAAGATTATTCTCTCACCATC 300
 S  P  K  T  L  I  Y  R  A  N  R  L  V  D  G  V  P  S  R  F  S  G  S  G  S  G  Q  D  Y  S  L  T  I
                                                              mVL AGCAGCCTGGAGTATGAAGATATGGGAATTTATTATTGTCTACAGTATGATGAGTTCCCGTACACGTTCGGAGGGGGGACAAAGCTGGAAATAAAACGGA 400
 S  S  L  E  Y  E  D  M  G  I  Y  Y  C  L  Q  Y  D  E  F  P  Y  T  F  G  G  G  T  K  L  E  I  K  R
                                                              mVL CTGTGGCTGCACCATCTGTCTTCATCTTCCCGCCATCTGATGAGCAGTTGAAATCTGGAACTGCCTCTGTTGTGTGCCTGCTGAATAACTTCTATCCCAG 500
 T  V  A  A  P  S  V  F  I  F  P  P  S  D  E  Q  L  K  S  G  T  A  S  V  V  C  L  L  N  N  F  Y  P  R
                                                              hCK AGAGGCCAAAGTACAGTGGAAGGTGGATAACGCCCTCCAATCGGGTAACTCCCAGGAGAGTGTCACAGAGCAGGACAGCAAGGACAGCACCTACAGCCTC 600
 E  A  K  V  Q  W  K  V  D  N  A  L  Q  S  G  N  S  Q  E  S  V  T  E  Q  D  S  K  D  S  T  Y  S  L
                                                              hCK AGCAGCACCCTGACGCTGAGCAAAGCAGACTACGAGAAACACAAAGTCTACGCCTGCGAAGTCACCCATCAGGGCCTGAGCTCGCCCGTCACAAAGAGCT 700
 S  S  T  L  T  L  S  K  A  D  Y  E  K  H  K  V  Y  A  C  E  V  T  H  Q  G  L  S  S  P  V  T  K  S
                                                              hCK
                                    Notl
TCAACAGGGGAGAGTGTTCAGCGGCCGCAATTCATTGA 738
 F  N  R  G  E  C  S  A  A  A  I  H  .
                    |—+6 AA—|
```

FIG. 11G

FIG. 12A hB7V3V2-cG2G4
Heavy Chain (SEQ ID NO. 13)

MGWSRIFLFLLSIIAGVHCQVQLQQSGSELKKPGASVKISCKASGYSFTDY
IILWVRQNPGKGLEWIGHIDPYYGSSNYNLKFKGRVTITADQSTTTAYME
LSSLRSEDTAVYYCGRSKRDYFDYWGQGTTLTVSSASTKGPSVFPLAPC
SRSTSESTAALGCLVKDYFPEPVTVSWNSGALTSGVHTFPAVLQSSGL
YSLSSVVTVPSSNFGTQTYTCNVDHKPSNTKVDKTVERKCCVECPPCP
APPVAGPSVFLFPPKPKDTLMISRTPEVTCVVVDVSQEDPEVQFNWYV
DGVEVHNAKTKPREEQFNSTYRVVSVLTVLHQDWLNGKEYKCKVSN
KGLPSSIEKTISKAKGQPREPQVYTLPPSQEEMTKNQVSLTCLVKGFY
PSDIAVEWESNGQPENNYKTTPPVLDSDGSFFLYSRLTVDKSRWQEG
NVFSCSVMHEALHNHYTQKSLSLSLGK

FIG. 12B (SEQ ID NO. 16) (cDNA G2G4)
ATGGGATGGAGCCGGATCTTTCTCTTCCTCCTGTCAATAATTGCAGGTG
TCCATTGCCAGGTCCAGCTGCAACAGTCTGGATCTGAGCTGAAGAAGC
CTGGGGCTTCAGTGAAGATCTCCTGCAAGGCTTCTGGTTATTCATTCAC
TGACTACATCATACTCTGGGTGAGGCAGAACCCTGGAAAGGGCCTTGA
GTGGATTGGACATATTGATCCTTACTATGGTAGTTCTAACTACAATCTG
AAATTCAAGGGCAGAGTGACAATCACCGCCGACCAGTCTACCACCAC
AGCCTACATGGAGCTCTCCAGTCTGAGATCTGAGGACACTGCAGTCTA
TTACTGTGGAAGATCTAAGAGGGACTACTTTGACTACTGGGGCCAAGG
CACCACTCTCACAGTTTCCTCAGCCTCCACCAAGGGCCCATCCGTCTTC
CCCCTGGCGCCCTGCTCCAGGAGCACCTCCGAGAGCACAGCCGCCCTG
GGCTGCCTGGTCAAGGACTACTTCCCCGAACCGGTGACGGTGTCGTGG
AACTCAGGCGCCCTGACCAGCGGCGTGCACACCTTCCCGGCTGTCCTA
CAGTCCTCAGGACTCTACTCCCTCAGCAGCGTGGTGACCGTGCCCTCC
AGCAACTTCGGCACCCAGACCTACACCTGCAACGTAGATCACAAGCCC
AGCAACACCAAGGTGGACAAGACAGTTGAGCGCAAATGTTGTGTCGA
GTGCCCACCGTGCCCAGCACCACCTGTGGCAGGACCGTCAGTCTTCCT
CTTCCCCCCAAAAACCCAAGGACACCCTCATGATCTCCCGGACCCCTGA
GGTCACGTGCGTGGTGGTGGACGTGAGCCAGGAAGACCCCGAGGTCC
AGTTCAACTGGTACGTGGATGGCGTGGAGGTGCATAATGCCAAGACA
AAGCCGCGGGAGGAGCAGTTCAACAGCACGTACCGTGTGGTCAGCGT
CCTCACCGTCCTGCACCAGGACTGGCTGAACGGCAAGGAGTACAAGT
GCAAGGTCTCCAACAAAGGCCTCCCGTCCTCCATCGAGAAAACCATCT
CCAAAGCCAAAGGGCAGCCCCGAGAGCCACAGGTGTACACCCTGCCC
CCATCCCAGGAGGAGATGACCAAGAACCAGGTCAGCCTGACCTGCCT
GGTCAAAGGCTTCTACCCCAGCGACATCGCCGTGGAGTGGGAGAGCA
ATGGGCAGCCGGAGAACAACTACAAGACCACGCCTCCCGTGCTGGAC
TCCGACGGCTCCTTCTTCCTCTACAGCAGGCTAACCGTGGACAAGAGC
AGGTGGCAGGAGGGGAATGTCTTCTCATGCTCCGTGATGCATGAGGCT
CTGCACAACCACTACACACAGAAGAGCCTCTCCCTGTCTCTGGGTAAA
TGATG

FIG. 12C

FIG. 12D
Light Chain (human Cκ) (SEQ ID NO. 28)
MDMRVSAQLLGLLLLWLSGARCDIQMTQSPSSLSASIGDRVTITCKASQD
INSYLSWFQQKPGKAPKLLIYRANRLVDGVPSRFSGSGSGTDYTLTISSLQ
PEDFAVYYCLQYDEFPYTFGGGTKLEIKRTVAAPSVFIFPPSDEQLKSGT
ASVVCLLNNFYPREAKVQWKVDNALQSGNSQESVTEQDSKDSTYSLS
STLTLSKADYEKHKVYACEVTHQGLSSPVTKSFNRGEC FIG. 12E
(SEQ ID NO. 27)
ATGGACATGAGGGTCTCTGCTCAGCTCCTGGGGCTCCTGCTGCTCTGG
CTCTCAGGGGCCAGGTGTGACATCCAGATGACACAGTCTCCATCTTCC
CTGTCTGCATCTATAGGAGACAGAGTCACTATCACTTGCAAGGCGAGT
CAGGACATTAATAGCTATTTAAGCTGGTTCCAGCAGAAACCAGGGAA
AGCTCCTAAGCTGCTGATCTATCGTGCAAACAGATTGGTAGATGGGGT
TCCATCAAGGTTCAGTGGCAGTGGATCTGGGACAGATTATACTCTCAC
CATCAGCAGCCTGCAGCCTGAAGATTTCGCAGTTTATTATTGTCTACA
GTATGATGAGTTTCCGTACACGTTCGGAGGGGGGACCAAGCTGGAAAT
AAAACGTACGGTGGCTGCACCATCTGTCTTCATCTTCCCGCCATCTGAT
GAGCAGTTGAAATCTGGAACTGCCTCTGTTGTGTGCCTGCTGAATAAC
TTCTATCCCAGAGAGGCCAAAGTACAGTGGAAGGTGGATAACGCCCTC
CAATCGGGTAACTCCCAGGAGAGTGTCACAGAGCAGGACAGCAAGGA
CAGCACCTACAGCCTCAGCAGCACCCTGACGCTGAGCAAAGCAGACT
ACGAGAAACACAAAGTCTACGCCTGCGAAGTCACCCATCAGGGCCTG
AGCTCGCCCGTCACAAAGAGCTTCAACAGGGGAGAGTGTTAG A schematic representation of the light chain of antibody hB7V3V2-cG2G4.

FIG. 12F

ChC7-hG2G4
Heavy chain (genomic sequence hG2G4) (SEQ ID NO:18)

MGWSCIILFLVATATGVHSLEVQLQQSGPELEKPGASVKISCKASGYSFTG
YNMNWVKQSSGKSLEWIGNFDPYYGVITYNQKFKGKATLTVDKSSSTAY
MQLKSLTSEDSAVYYCARTATALYTMDYWGQGTSVTVSSASTKGPSVF
PLAPCSRSTSESTAALGCLVKDYFPEPVTVSWNSGALTSGVHTFPAVL
QSSGLYSLSSVVTVPSSNFGTQTYTCNVDHKPSNTKVDKTVERKCCVE
CPPCPGKPAPPVAGPSVFLFPPKPKDTLMISRTPEVTCVVVDVSQEDP
EVQFNWYVDGVEVHNAKTKPREEQFNSTYRVVSVLTVLHQDWLNG
KEYKCKVSNKGLPSSIEKTISKAKGQPREPQVYTLPPSQEEMTKNQVS
LTCLVKGFYPSDIAVEWESNGQPENNYKTTPPVLDSDGSFFLYSRLTV
DKSRWQEGNVFSCSVMHEALHNHYTQKSLSLSLGK

FIG. 13A

FIG. 13B (SEQ ID NO. 17)

ATGGGATGGAGCTGTATCATCCTCTTCTTGGTAGCAACAGCTACAGGTGTCCACTCCCTCGAG
GTCCAACTGCAGCAGTCTGGACCTGAGCTGGAGAAGCCTGGCGCTTCAGTGAAGATATCCTGC
AAGGCTTCTGGTTACTCATTCACTGGCTACAACATGAACTGGGTGAAGCAGAGCAGTGGAAA
GAGCCTTGAGTGGATTGGAAATTTTGATCCTTACTATGGTGTTATTACCTACAACCAGAAGTTC
AAGGGCAAGGCCACATTGACTGTAGACAAATCCTCCAGCACAGCCTACATGCAGCTCAAGAG
CCTGACATCTGAGGACTCTGCAGTCTATTACTGTGCAAGAACGGCTACGGCTCTCTATACTAT
GGACTACTGGGGTCAAGGAACCTCAGTCACCGTCTCCTCAGCCTCCACCAAGGGCCCATCCGT
CTTCCCCCTGGCGCCCTGCTCCAGGAGCACCTCCGAGAGCACAGCCGCCCTGGGCTGCCTGGT
CAAGGACTACTTCCCCGAACCGGTGACGGTGTCGTGGAACTCAGGCGCCCTGACCAGCGGCG
TGCACACCTTCCCGGCTGTCCTACAGTCCTCAGGACTCTACTCCCTCAGCAGCGTGGTGACCGT
GCCCTCCAGCAACTTCGGCACCCAGACCTACACCTGCAACGTAGATCACAAGCCCAGCAACA
CCAAGGTGGACAAGACAGTTGGTGAGAGGCCAGCTCAGGGAGGGAGGGTGTCTGCTGGAAGC
CAGGCTCAGCCCTCCTGCCTGGACGCACCCGGCTGTGCAGCCCCAGCCCAGGGCAGCAAGG
CAGGCCCCATCTGTCTCCTCACCCGGAGGCCTCTGCCCGCCCCACTCATGCTCAGGGAGAGGG
TCTTCTGGCTTTTTCCACCAGGCTCCAGGCAGGCACAGGCTGGGTGCCCCTACCCCAGGCCCTT
CACACACAGGGGCAGGTGCTTGGCTCAGACCTGCCAAAAGCCATATCCGGGAGGACCCTGCC
CCTGACCTAAGCCCACCCCAAAGGCCAAACTGTCCACTCCCTCAGCTCGGACACCTTCTCTCC
TCCCAGATCCGAGTAACTCCCAATCTTCTCTCTGCAGAGCGCAAATGTTGTGTCGAGTGCCCA
CCGTGCCCAGGTAAGCCAGCCCAGGCCTCGCCCTCCAGCTCAAGGCGGGACAGGTGCCCTAG
AGTAGCCTGCATCCAGGGACAGGCCCCAGCTGGGTGCTGACACGTCCACCTCCATCTCTTCCT
CAGCACCACCTGTGGCAGGACCGTCAGTCTTCCTCTTCCCCCCAAAACCCAAGGACACCCTCA
TGATCTCCCGGACCCCTGAGGTCACGTGCGTGGTGGTGGACGTGAGCCAGGAAGACCCCGAG
GTCCAGTTCAACTGGTACGTGGATGGCGTGGAGGTGCATAATGCCAAGACAAAGCCGCGGGA
GGAGCAGTTCAACAGCACGTACCGTGTGGTCAGCGTCCTCACCGTCCTGCACCAGGACTGGCT
GAACGGCAAGGAGTACAAGTGCAAGGTCTCCAACAAAGGCCTCCCGTCCTCCATCGAGAAAA
CCATCTCCAAAGCCAAAGGTGGGACCCACGGGGTGCGAGGGCCACATGGACAGAGGTCAGCT
CGGCCCACCCTCTGCCCTGGGAGTGACCGCTGTGCCAACCTCTGTCCCTACAGGGCAGCCCCG
AGAGCCACAGGTGTACACCCTGCCCCCATCCCAGGAGGAGATGACCAAGAACCAGGTCAGCC
TGACCTGCCTGGTCAAAGGCTTCTACCCCAGCGACATCGCCGTGGAGTGGGAGAGCAATGGG
CAGCCGGAGAACAACTACAAGACCACGCCTCCCGTGCTGGACTCCGACGGCTCCTTCTTCCTC
TACAGCAGGCTAACCGTGGACAAGAGCAGGTGGCAGGAGGGGAATGTCTTCTCATGCTCCGT
GATGCATGAGGCTCTGCACAACCACTACACACAGAAGAGCCTCTCCCTGTCTCTGGGTAAATG
A

FIG. 13C
Light Chain (human Ck) (SEQ ID NO. 30)
MGWSCIILFLVATATGVHSREIVLTQSPAIMSASPGEKVTMTCRASSSVSS
SYLHWYQQKSGASPKLWIYSTSNLASGVPARFSGSGSGTSYSLTISSVEAE
DAATYYCQQYSGYPLTFGSGTKLEIKRTVAAPSVFIFPPSDEQLKSGTAS
VVCLLNNFYPREAKVQWKVDNALQSGNSQESVTEQDSKDSTYSLSST
LTLSKADYEKHKVYACEVTHQGLSSPVTKSFNRGEC FIG. 13D
(SEQ ID NO. 29)
ATGGGATGGAGCTGTATCATCCTCTTCTTGGTAGCAACAGCTACAGGT
GTCCACTCTAGAGAAATTGTGCTCACCCAGTCTCCAGCAATCATGTCT
GCATCTCCAGGGGAAAAGGTCACCATGACCTGCAGGGCCAGCTCAAG
TGTAAGTTCCAGTTACTTGCACTGGTACCAGCAGAAGTCAGGTGCCTC
CCCCAAACTCTGGATTTATAGCACATCCAACTTGGCTTCTGGAGTCCCT
GCTCGCTTCAGTGGCAGTGGGTCTGGGACCTCTTACTCTCTCACAATCA
GCAGTGTGGAGGCTGAAGATGCTGCCACTTATTACTGCCAGCAGTACA
GTGGTTACCCACTCACGTTCGGCTCGGGGACAAAGTTGGAAATAAAAC
GGACTGTGGCTGCACCATCTGTCTTCATCTTCCCGCCATCCGATGAGC
AGTTGAAATCTGGAACTGCCTCTGTTGTGTGCCTGCTGAATAACTTCTA
TCCCAGAGAGGCCAAAGTACAGTGGAAGGTGGATAACGCCCTCCAAT
CGGGTAACTCCCAGGAGAGTGTCACAGAGCAGGACAGCAAGGACAGC
ACCTACAGCCTCAGCAGCACCCTGACGCTGAGCAAAGCAGACTACGA
GAAACACAAAGTCTACGCCTGCGAAGTCACCCATCAGGGCCTGAGCT
CGCCCGTCACAAAGAGCTTCAACAGGGGAGAGTGTTAA

FIG. 14A

D1B5-hC1
Heavy Chain (SEQ ID NO. 20)
MGWSCIILFLVATATGVHSLEVQLQQPGAELVRSGASVKLSCKASGFNIK
DYYIHWVKQRPEQGLEWIGWIDPEIGATKYVPKFQGKATMTTDTSSNTA
YLQLSSLTSEDTAVYYCNALYGNYDRYYAMDYWGQGTSVTVSSASTKG
PSVFPLAPSSKSTSGGTAALGCLVKDYFPEPVTVSWNSGALTSGVHTF
PAVLQSSGLYSLSSVVTVPSSSLGTQTYICNVNHKPSNTKVDKRVEPKS
CDKTHTCPPCPAPELLGGPSVFLFPPKPKDTLMISRTPEVTCVVVDVS
HEDPEVKFNWYVDGVEVHNAKTKPREEQYNSTYRVVSVLTVLHQD
WLNGKEYKCKVSNKALPAPIEKTISKAKGQPREPQVYTLPPSREEMT
KNQVSLTCLVKGFYPSDIAVEWESNGQPENNYKTTPPVLDSDGSFFLY
SKLTVDKSRWQQGNVFSCSVMHEALHNHYTQKSLSLSPGK

FIG. 14B (SEQ ID NO. 19) (genomic sequence hG1 constant region)
ATGGGATGGAGCTGTATCATCCTCTTCTTGGTAGCAACAGCTACAGGTGTCCACTCCCTCGAG
GTCCAACTGCAGCAGCCTGGGGCAGAGCTTGTGAGGTCAGGGGCCTCAGTCAAGTTGTCCTGC
AAAGCTTCTGGCTTCAACATTAAAGACTACTATATACACTGGGTGAAGCAGAGGCCTGAACA
GGGCCTGGAGTGGATTGGATGGATTGATCCTGAGATTGGTGCTACTAAATATGTCCCGAAGTT
CCAGGGCAAGGCCACTATGACTACAGACACATCCTCCAACACAGCCTACCTGCAGCTCAGCA
GCCTGACATCTGAGGACACTGCCGTCTATTACTGTAATGCCCTCTATGGTAACTACGACCGTT
ACTATGCTATGGACTACTGGGGTCAAGGAACCTCAGTCACCGTCTCCTCAGCCTCCACCAAGG
GCCCATCGGTCTTCCCCCTGGCACCCTCCTCCAAGAGCACCTCTGGCGGCACAGCGGCCCTGG
GCTGCCTGGTCAAGGACTACTTCCCCGAACCGGTGACGGTGTCGTGGAACTCAGGCGCCCTGA
CCAGCGGCGTGCACACCTTCCCGGCTGTCCTACAGTCCTCAGGACTCTACTCCCTCAGCAGCG
TGGTGACCGTGCCCTCCAGCAGCTTGGGCACCCAGACCTACATCTGCAACGTGAATCACAAGC
CCAGCAACACCAAGGTGGACAAGAGAGTTGGTGAGAGGCCAGCACAGGGAGGGAGGGTGTC
TGCTGGAAGCCAGGCTCAGCGCTCCTGCCTGGACGCATCCGGCTATGCAGTCCCAGTCCAGG
GCAGCAAGGCAGGCCCCGTCTGCCTCTTCACCCGGAGGCCTCTGCCCGCCCACTCATGCTCA
GGGAGAGGGTCTTCTGGCTTTTTCCCCAGGCTCTGGGCAGGCACAGGCTAGGTGCCCCTAACC
CAGGCCCTGCACACAAAGGGGCAGGTGCTGGGCTCAGACCTGCCAAGAGCCATATCCGGGAG
GACCCTGCCCCTGACCTAAGCCCACCCCAAAGGCCAAACTCTCCACTCCCTCAGCTCGGACAC
CTTCTCTCCTCCCAGATTCCAGTAACTCCCAATCTTCTCTCTGCAGAGCCCAAATCTTGTGACA
AAACTCACACATGCCCACCGTGCCCAGGTAAGCCAGCCCAGGCCTCGCCCTCCAGCTCAAGGC
GGGACAGGTGCCCTAGAGTAGCCTGCATCCAGGGACAGGCCCCAGCCGGGTGCTGACACGTC
CACCTCCATCTCTTCCTCAGCACCTGAACTCCTGGGGGGACCGTCAGTCTTCCTCTTCCCCCCA
AAACCCAAGGACACCCTCATGATCTCCCGGACCCCTGAGGTCACATGCGTGGTGGTGGACGTG
AGCCACGAAGACCCTGAGGTCAAGTTCAACTGGTACGTGGACGGCGTGGAGGTGCATAATGC
CAAGACAAAGCCGCGGGAGGAGCAGTACAACAGCACGTACCGTGTGGTCAGCGTCCTCACCG
TCCTGCACCAGGACTGGCTGAATGGCAAGGAGTACAAGTGCAAGGTCTCCAACAAAGCCCTC
CCAGCCCCCATCGAGAAAACCATCTCCAAAGCCAAAGGTGGGACCCGTGGGGTGCGAGGGCC
ACATGGACAGAGGCCGGCTCGGCCCACCCTCTGCCCTGAGAGTGACCGCTGTACCAACCTCTG
TCCCTACAGGGCAGCCCCGAGAACCACAGGTGTACACCCTGCCCCCATCCCGGGAGGAGATG
ACCAAGAACCAGGTCAGCCTGACCTGCCTGGTCAAAGGCTTCTATCCCAGCGACATCGCCGTG
GAGTGGGAGAGCAATGGGCAGCCGGAGAACAACTACAAGACCACGCCTCCCGTGCTGGACTC
CGACGGCTCCTTCTTCCTCTATAGCAAGCTCACCGTGGACAAGAGCAGGTGGCAGCAGGGGA
ACGTCTTCTCATGCTCCGTGATGCATGAGGCTCTGCACAACCACTACACGCAGAAGAGCCTCT
CCCTGTCCCCGGGTAAATGA A schematic representation of the heavy chain of antibody DIB5-hG1 (part 1).

FIG. 14C

A schematic representation of the heavy chain of antibody DIB5-hG1 (part 2).

FIG. 14D

Light chain (human Cκ) (SEQ ID NO. 32)

MGWSCIILFLVATATGVHSRDIVMTQSQKFMSTSVGDRVSITCKASQNVR
TAVAWYQQKPGQSPKALIYLASNRHTGVPDRFTGSGSGTDFTLTISNVQS
EDLADYFCLQHWNYPLTFGAGTKLELKRTVAAPSVFIFPPSDEQLKSGT
ASVVCLLNNFYPREAKVQWKVDNALQSGNSQESVTEQDSKDSTYSLS
NTLTLSKADYEKHKVYACEVTHQGLSSPVTKSFNRGEC

FIG. 14E (SEQ ID NO. 31)

ATGGGATGGAGCTGTATCATCCTCTTCTTGGTAGCAACAGCTACAGGT
GTCCACTCTAGAGACATTGTGATGACCCAGTCTCAAAAATTCATGTCC
ACATCAGTAGGAGACAGGGTCAGCATCACCTGCAAGGCCAGTCAGAA
TGTTCGTACTGCTGTAGCCTGGTATCAACAGAAACCAGGGCAGTCTCC
TAAAGCACTGATTTACTTGGCATCCAACCGGCACACTGGAGTCCCTGA
TCGCTTCACAGGCAGTGGATCTGGGACAGATTTCACTCTCACCATTAG
CAATGTGCAATCTGAAGACCTGGCAGATTATTTCTGTCTGCAACATTG
GAATTATCCTCTCACGTTCGGTGCTGGGACCAAGCTGGAGCTGAAACG
GACTGTGGCTGCACCATCTGTCTTCATCTTCCCGCCATCTGATGAGCAG
TTGAAATCTGGAACTGCCTCTGTTGTGTGCCTGCTGAATAACTTCTATC
CCAGAGAGGCCAAAGTACAGTGGAAGGTGATAACGCCCTCCAATCG
GGTAACTCCCAGGAGAGTGTCACAGAGCAGGACAGCAAGGACAGCAC
CTACAGCCTCAGCAACACCCTGACGCTGAGCAAAGCAGACTACGAGA
AACACAAAGTCTACGCCTGCGAAGTCACCCATCAGGGCCTGAGCTCGC
CCGTCACAAAGAGCTTCAACAGGGGAGAGTGTTAA

FIG. 14F

A schematic representation of the light chain of antibody D1B5-hG1.

```
AAGCTTGCCGCCACCATGGGATGGAGCTGTATCATCCTCTTCTTGGTAGCAACAGCTACAGGTGTCCACTCTAGAGACATTGTGATGACCCAGTCTCAAAAATTCATGTCCACATCAGTA   120
          M  G  W  S  C  I  I  L  F  L  V  A  T  A  T  G  V  H  S  R  D  I  V  M  T  Q  S  Q  K  F  M  S  T  S  V
          ——————————leader——————————  ————————————————————d1B5Vk————————————————————

GGAGACAGGGTCAGCATCACCTGCAAGGCCAGTCAGAATGTCGTAACTGCTGTAGCCTGGTATCAACAGAAACCAGGGCAGTCTCCTAAAGCACTGATTTACTTGGCATCCAACCGGCAC   240
 G  D  R  V  S  I  T  C  K  A  S  Q  N  V  V  T  A  V  A  W  Y  Q  Q  K  P  G  Q  S  P  K  A  L  I  Y  L  A  S  N  R  H
 ———————————————————————————————————————————————————d1B5Vk————————————————————————————————————————————————————————————

ACTGGAGTCCCTGATCGCTTCACAGGCAGTGGATCTGGGACAGATTTCACTCTCACCATCAGCAATGTGCAATCTGAAGACTTGGCAGATTATTTCTGCCTACAATTGGAATTATCCT    360
 T  G  V  P  D  R  F  T  G  S  G  S  G  T  D  F  T  L  T  I  S  N  V  Q  S  E  D  L  A  D  Y  F  C  L  Q  H  W  N  Y  P
                                  ————————————————————d1B5Vk————————————————————————————————————————————————————————

CTCACGTTCGGTGCTGGGACCAAGCTGGAGCTGAAACGAACTGTGGCTGCACCATCTGTCTTCATCTTCCCGCCATCTGATGAGCAGTTGAAATCTGGAACTGCCTCTGTTGTGTGCCTG   480
 L  T  F  G  A  G  T  K  L  E  L  K  R  T  V  A  A  P  S  V  F  I  F  P  P  S  D  E  Q  L  K  S  G  T  A  S  V  V  C  L
 ————————d1B5Vk————————  ——————————————————————————————————————hCk——————————————————————————————————————————

CTGAATAACTTCTATCCCAGAGAGGCCAAAGTACAGTGGAAGGTGGATAACGCCCTCCAATCGGGTAACTCCCAGGAGAGTGTCACAGAGCAGGACAGCAAGGACAGCACCTACAGCCTC   600
 L  N  N  F  Y  P  R  E  A  K  V  Q  W  K  V  D  N  A  L  Q  S  G  N  S  Q  E  S  V  T  E  Q  D  S  K  D  S  T  Y  S  L
 ———————————————————————————————————————————————————hCk————————————————————————————————————————————————————————————

AGCAACACCCTGACGCTGAGCAAAGCAGACTACGAGAAACACAAAGTCTACGCCTGCGAAGTCACCCATCAGGGCCTGAGCTCGCCCGTCACAAAGAGCTTCAACAGGGGAGAGTGTTAA   720
 S  N  T  L  T  L  S  K  A  D  Y  E  K  H  K  V  Y  A  C  E  V  T  H  Q  G  L  S  S  P  V  T  K  S  F  N  R  G  E  C  *
 ———————————————————————————————————————————hCk————————————————————————————————————————————————————
```

G2G4 63L1D
Heavy chain (SEQ ID NO. 22)
MGWSCIILFLVATATGVHSQMQLVQSGAEVKKPGSSVKVSCKASGGTFS
NYATSWVRQAPGQGLEWLGGIPVFGTANYAQKFQGRVTITADESTSTAY
MELNSLTFDDTAVYYCARGGGWGGRNYYYYYYMDVWGKGTTVTVSS
ASTKGPSVFPLAPCSRSTSESTAALGCLVKDYFPEPVTVSWNSGALTS
GVHTFPAVLQSSGLYSLSSVVTVPSSNFGTQTYTCNVDHKPSNTKVDK
TVERKCCVECPPCPAPPVAGPSVFLFPPKPKDTLMISRTPEVTCVVVD
VSQEDPEVQFNWYVDGVEVHNAKTKPREEQFNSTYRVVSVLTVLHQ
DWLNGKEYKCKVSNKGLPSSIEKTISKAKGQPREPQVYTLPPSQEEM
TKNQVSLTCLVKGFYPSDIAVEWESNGQPENNYKTTPPVLDSDGSFFL
YSRLTVDKSRWQEGNVFSCSVMHEALHNHYTQKSLSLSLGK

FIG. 15B (SEQ ID NO. 21) (genomic sequence hG2G4)
ATGGGATGGAGCTGTATCATCCTCTTCTTGGTAGCAACAGCTACAGGTGTCCACTCCCAGATG
CAGCTGGTGCAGTCTGGGGCTGAGGTGAAGAAGCCTGGGTCCTCGGTGAAGGTCTCCTGCAA
GGCCTCTGGAGGCACCTTCAGCAACTATGCTACCAGTTGGGTGCGACAGGCCCCTGGACAAG
GTCTTGAGTGGCTGGGAGGGATCATCCCCGTCTTCGGTACTGCAAACTACGCACAGAAGTTTC
AGGGCAGAGTCACCATTACCGCGGACGAGTCCACGAGCACAGCCTACATGGAGTTGAATAGT
CTGACATTTGACGACACGGCCGTCTATTACTGTGCGAGAGGGGGTGGGGGATGGGGAGGCCG
GAACTACTACTACTACTACATGGACGTCTGGGGCAAAGGGACCACTGTCACCGTCTCCTC
AGCCTCCACCAAGGGCCCATCCGTCTTCCCCCTGGCGCCCTGCTCCAGGAGCACCTCCGAGAG
CACAGCCGCCCTGGGCTGCCTGGTCAAGGACTACTTCCCCGAACCGGTGACGGTGTCGTGGAA
CTCAGGCGCCCTGACCAGCGGCGTGCACACCTTCCCGGCTGTCCTACAGTCGTCAGGACTCTA
CTCCCTCAGCAGCGTGGTGACCGTGCCCTCCAGCAACTTCGGCACCCAGACCTACACCTGCAA
CGTAGATCACAAGCCCAGCAACACCAAGGTGGACAAGACAGTTGGTGAGAGGCCAGCTCAGG
GAGGGAGGGTGTCTGCTGGAAGCCAGGCTCAGCCCTCCTGCCTGGACGCACCCCGGCTGTGC
AGCCCCAGCCCAGGGCAGCAAGGCAGGCCCCATCTGTCTCCTCACCCGGAGGCCTCTGCCCGC
CCCACTCATGCTCAGGGAGAGGGTCTTCTGGCTTTTTCCACCAGGCTCCAGGCAGGCACAGGC
TGGGTGCCCCTACCCCAGGCCCTTCACACACAGGGGCAGGTGCTTGGCTCAGACCTGCCAAAA
GCCATATCCGGGAGGACCCTGCCCCTGACCTAAGCCGACCCCAAAGGCCAAACTGTCCACTCC
CTCAGCTCGGACACCTTCTCTCCTCCCAGATCCGAGTAACTCCCAATCTTCTCTCTGCAGAGCG
CAAATGTTGTGTCGAGTGCCCACCGTGCCCAGGTAAGCCAGCCCAGGCCTCGCCCTCCAGCTC
AAGGCGGGACAGGTGCCCTAGAGTAGCCTGCATCCAGGGACAGGCCCCAGCTGGGTGCTGAC
ACGTCCACCTCCATCTCTTCCTCAGCACCACCTGTGGCAGGACGTCAGTCTTCCTCTTCCCCC
CAAAACCCAAGGACACCCTCATGATCTCCCGGACCCCTGAGGTCACGTGCGTGGTGGTGGAC
GTGAGCCAGGAAGACCCCGAGGTCCAGTTCAACTGGTACGTGGATGGCGTGGAGGTGCATAA
TGCCAAGACAAAGCCGCGGGAGGAGCAGTTCAACAGCACGTACCGTGTGGTCAGCGTCCTCA
CCGTCCTGCACCAGGACTGGCTGAACGGCAAGGAGTACAAGTGCAAGGTCTCCAACAAAGGC
CTCCCGTCCTCCATCGAGAAAACCATCTCCAAAGCCAAAGGTGGGACCCACGGGGTGCGAGG
GCCACATGGACAGAGGTCAGCTCGGCCCACCCTCTGCCCTGGGAGTGACCGCTGTGCCAACCT
CTGTCCCTACAGGGCAGCCCCGAGAGCCACAGGTGTACACCCTGCCCCCATCCCAGGAGGAG
ATGACCAAGAACCAGGTCAGCCTGACCTGCCTGGTCAAAGGCTTCTACCCCAGCGACATCGCC
GTGGAGTGGGAGAGCAATGGGCAGCCGGAGAACAACTACAAGACCACGCCTCCCGTGCTGGA
CTCCGACGGCTCCTTCTTCCTCTACAGCAGGCTAACCGTGGACAAGAGCAGGTGGCAGGAGG
GGAATGTCTTCTCATGCTCCGTGATGCATGAGGCTCTGCACAACCACTACACACAGAAGAGCC
TCTCCCTGTCTCTGGGTAAATGA FIG. 15C
Light chain (human CL) (SEQ ID NO. 34)
MGWSCIILFLVATATGVHSSYVLTQPPSESVAPGQTARISCGGSNIGSYGV
HWYQQKAGQAPVLVVHDDSDRPSGIPERFSGSNSGNTATLTISSVEAGDE
ADYYCQVWDNSAVIFGGGTKLTVLSQPKAAPSVTLFPPSSEELQANKA
TLVCLISDFYPGAVTVAWKADSSPVKAGVETTTPSKQSNNKYAASSYL
SLTPEQWKSHRSYSCQVTHEGSTVEKTVAPTECS FIG. 15D
(SEQ ID NO. 33)
ATGGGATGGAGCTGTATCATCCTCTTCTTGGTAGCAACAGCTACAGGT
GTCCACTCTTCCTATGTGCTGACTCAGCCACCCTCGGAGTCAGTGGCC
CCAGGACAGACGGCCAGGATTTCCTGTGGGGGGAGCAACATTGGAAG
TTACGGTGTGCACTGGTACCAGCAGAAGGCAGGACAGGCCCCTGTGCT
GGTCGTCCATGATGATTCCGACCGGCCCTCAGGGATTCCTGAGCGATT
CTCTGGCTCCAATTCTGGGAACACGGCCACCCTGACCATCAGCAGTGT
CGAAGCCGGCGATGAGGCCGACTATTACTGTCAGGTGTGGGATAATA
GTGCTGTGATATTCGGCGGAGGGACCAAACTAACCGTCCTAAGTCAGC
CCAAGGCTGCCCCCTCGGTCACTCTGTTCCCGCCCTCCTCTGAGGAGCT
TCAAGCCAACAAGGCCACACTGGTGTGTCTCATAAGTGACTTCTACCC
GGGAGCTGTGACAGTGGCTTGGAAAGCAGATAGCAGCCCCGTCAAGG
CGGGAGTGGAGACCACCACACCCTCCAAACAAAGCAACAACAAGTAC
GCGGCCAGCAGCTATCTGAGCCTGACGCCTGAGCAGTGGAAGTCCCA
CAGAAGCTACAGCTGCCAGGTCACGCATGAAGGGAGCACCGTGGAGA
AGACAGTGGCCCCTACAGAATGTTCATAA

5'-GACAAGCTTGCAAGGATGGAGAGGCTGGTGA-3' (SEQ ID NO: 35)

5'-GACGGATCCGCCCCTTTTCCTCCTGCTTTTCTC-3' (SEQ ID NO: 36)

Efficacy of humanized anti CD200 antibodies (C2aB7) in the RAJI_CD200/PBL model.

Comparison of mean tumor volumes in C2aB7-G1 versus C2aB7-G2G4 treated animals in the Namalwa_CD200 model.

FIG. 20

FACS analysis of CD200 expression on B-CLL cells in comparison to normal B cells.

| CLL sample | | Healthy donor | |
|---|---|---|---|
| Donor ID | B-CLL CD200 (GMFI) | Normal B CD200 (GMFI) | Ratio(CLL/normal B) |
| RC011731 | 93 | 58 | 1.6 |
| RF020934 | 659 | 185 | 3.6 |
| JA073031 | 334 | 64 | 5.2 |
| GR011846 | 156 | 64 | 2.4 |
| BB101735 | 420 | 95 | 4.4 |
| DM6988172 | 290 | 97 | 2.9 |
| MR8074020 | 403 | 97 | 4.2 |
| CB8267677 | 300 | 97 | 3.1 |
| GB1325248 | 178 | 77(7) | 2.3 |
| VN7029373 | 154 | 77(7) | 2.0 |
| DG8942820 | 146 | 77(7) | 1.9 |
| MM8451869 | 237 | 77(7) | 3.1 |
| JR4539931 | 215 | 77(7) | 2.8 |
| HS6787771 | 305 | 77(7) | 4.0 |
| VB040439 | 123 | 41 | 3.0 |
| | | | MEAN= 3.1 |
| | | | STDEV= 1.0 |

FIG. 21

| Tumor type | Cell line | CD200 staining |
|---|---|---|
| Melanoma | SK-MEL2 | - |
|  | SK-MEL28 | ++ |
|  | SK-MEL1 | + |
|  | SK-MEL5 | +/- |
|  | SK-MEL24 | +++ |
| Ovarian | OVCAR3 | ++ |
|  | SKOV3 | +/- |
| Renal | CAKI-1 | + |
|  | ACHN | - |
|  | SN12C | + |
| Neuroblastoma | IMR-32 | +++ |
|  | SK-N-SH | ++ |
| Breast cancer | MDA-MB-435 | +/- |
|  | MCF7 | - |
|  | MDA-MB-231 | - |

RTQ-PCR of primary ovarian cancer samples.

RT-QPCR: CD200 on melanoma samples

| Number | Sample | norm/#51 | sd/#51 | |
|---|---|---|---|---|
| 51 | PBL | 1.00 | 0.28 | |
| 139 | norm jejunum -1 | 2.60 | 0.15 | |
| 138 | jejunum met -1 | 8.39 | 0.24 | |
| 147 | norm jejunum -2 | 1.37 | 0.81 | |
| 146 | jejunum met -2 | 14.46 | 3.38 | |
| 143 | norm small intestine -1 | 3.57 | 1.21 | |
| 142 | small intestine met -1 | 4.61 | 0.55 | |
| 141 | norm lymph node -1 | 8.52 | 1.00 | |
| 140 | lymph node met -1 | 6.22 | 0.53 | |
| 151 | norm lymph node -2 | 4.80 | 1.40 | |
| 150 | lymph node met -2 | 12.94 | 0.51 | |
| 155 | lymph node met -3 | 0.69 | 0.21 | |
| 156 | lymph node met -4 | 2.72 | 1.72 | |
| 145 | norm lung -1 | 14.87 | 1.14 | |
| 144 | lung met -1 | 8.93 | 0.83 | |
| 149 | norm lung -2 | 4.25 | 0.64 | |
| 148 | lung met -2 | 3.65 | 1.04 | |
| 111 | norm skin -1 | 1.55 | 0.25 | |
| 152 | melanoma metastatic, skin -2 | 0.05 | 0.06 | |
| 158 | melanoma metastatic, skin -3 | 2.22 | 0.61 | |
| 159 | malign. melanoma, brain met -2 | 22.92 | 3.20 | values from 9/10/04 plate |
| 153 | malign. melanoma, lung met | 18S low | | |
| 154 | malign. melanoma, LN met | 18S low | | |
| 157 | malign. melanoma, LN met | 18S low | | |
| 160 | malign. melanoma, skin | 18S low | | |
| 160-No RT | malign. melanoma, skin | 0.00 | 0.00 | |

FIG. 23A

Immunohistochemistry staining of melanoma patient samples

Frozen Skin, Melanoma - Positive Control
Sample 1: This sample of melanoma was obtained from an 83-year-old female.

Fab Frag 1: d1B5, Malignant Cells 40X    Fab Frag 2: C2AB7, Malignant Cells 40X

FIG. 25
IL-2 production in MLR with cancer cell lines.
A. In the absence of antibody
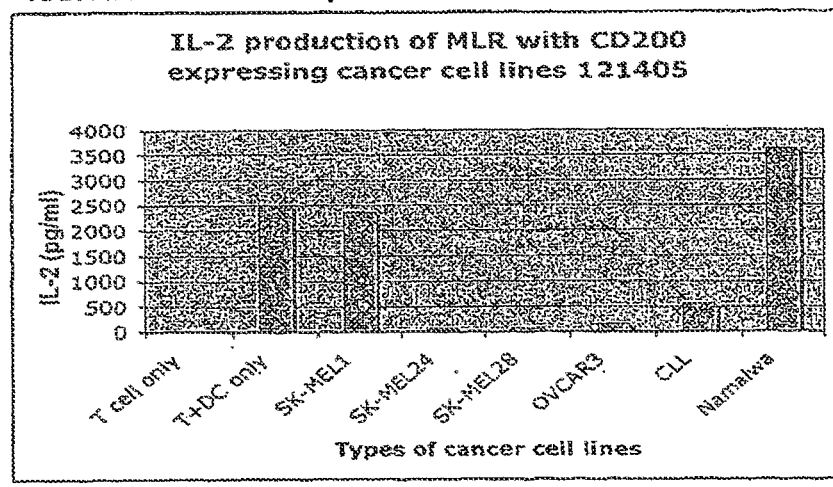
B. In the presence of antibody
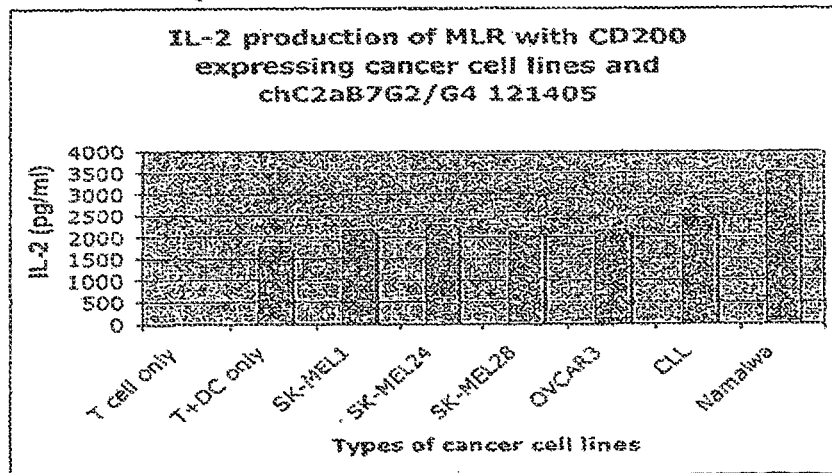

Tumor volumes in the Namalwa/PBL model (no CD200 expression) comparing anti-CD200 G1 or G2G4 construct treated groups.

FIG. 28
Human T cells activated through T cell receptor signaling serve as sensitive targets for anti-CD200 mediated ADCC.
A.
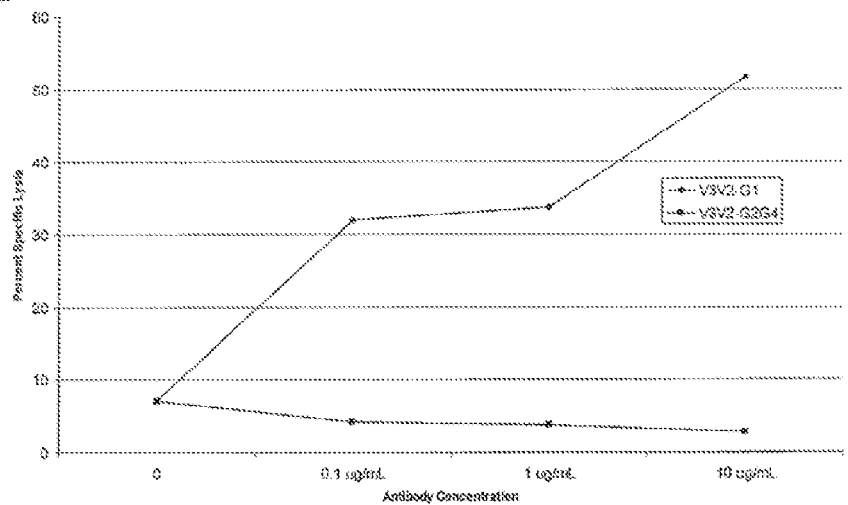
B.
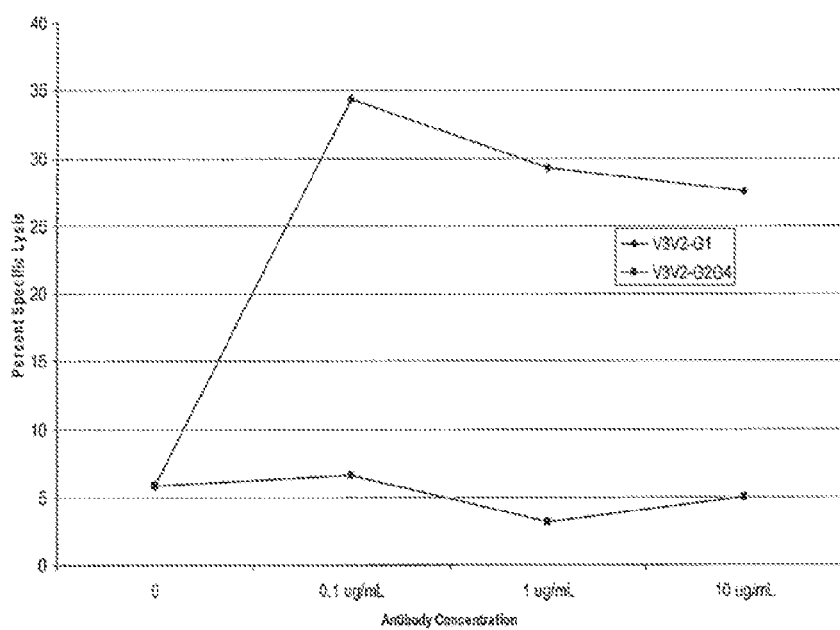

FIG. 29

| Sample | Status | Light Chain Isotype | CD200 Expression on CD38+ Bright Cells (Plasma cells) | | Current Clinical Treatment |
|---|---|---|---|---|---|
| | | | Threshold Set Through Isotype Control (Expressed as %) | Threshold Set Through Isotype Control (Expressed as Geometric Mean Intensity) | |
| 1 | Normal | Polyclonal | 48 | 6575 | NA |
| 2 | Normal | Polyclonal | 48 | 19411 | NA |
| 3 | Normal | Polyclonal | 33 | 67084 | NA |
| 4 | M Myeloma | Kappa | 12 | 4058 | Melphalan, Velcade |
| 5 | M Myeloma | Kappa | 12 | 3091 | ATO, Velcade, Aranesp, Zometa |
| 6 | M Myeloma | Negative | 14 | 2162 | Coumadin, Aranesp, DVD (Dox, Vin, Dex) |
| 7 | M Myeloma | Polyclonal | 37 | 3419 | None |
| 8 | M Myeloma | Kappa | 71 | 4024 | Zometa, Prednisone |
| 9 | M Myeloma | Kappa | 76 | 1506 | Aranesp, Zometa |
| 10 | M Myeloma | Kappa | 82 | 9056 | HTN, PCTA |
| 11 | M Myeloma | Kappa | 85 | 5388 | Prednisone, Zometa |
| 12 | M Myeloma | Kappa | 89 | 23269 | Zometa, Coumadin |
| 13 | M Myeloma | Lambda | 95 | 1535 | Zometa, IVIG, Biaxin, Medrol |

ANTIBODIES TO OX-2/CD200 AND USES THEREOF

RELATED APPLICATIONS

This application is a divisional application of U.S. application Ser. No. 12/087,683, filed Jan. 14, 2009, which is a national stage filing under 35 U.S.C. 0371 of International Application No. PCT/US2007/000711, filed Jan. 11, 2007, which claims the benefit of U.S. Provisional Application Nos. 60/758,426, filed Jan. 12, 2006, 60/759,085, filed Jan. 12, 2006, and 60/801,991, filed May 18, 2006. The specifications of each of the foregoing applications are hereby incorporated by reference in their entirety.

SEQUENCE LISTING

The instant application contains a Sequence Listing which has been submitted via EFS-Web and is hereby incorporated by reference in its entirety. Said ASCII copy, created on Nov. 17, 2011, is named ALEXP15060.txt, and is 99,201 bytes in size.

TECHNICAL FIELD

The disclosure relates to OX-2/CD200 (herein referred to as CD200) antagonists and methods of depleting or eliminating cells overexpressing CD200 in a subject with cancer or autoimmune disease. The methods of therapy for the treatment of cancer provide a combination of two mechanisms. More specifically, this disclosure relates to treating cancer using a therapy that: (1) interferes with the interaction between CD200 and its receptor to block immune suppression thereby promoting eradication of the cancer cells; and/or (2) directly kills the cancer cells either by (a) antibody-dependent cellular cytotoxicity or complement-mediated cytotoxicity or by (b) targeting cells using a fusion molecule that includes a CD200-targeting portion. The disclosure also relates to a method of treating autoimmune disorders by a therapy that increases the antibody-dependent cellular cytotoxicity and/or complement-mediated cytotoxicity of CD200-positive immune cells.

BACKGROUND

Various mechanisms play a role in the body's response to a disease state, including cancer. For example, CD4+ T helper cells play a crucial role in an effective immune response against various malignancies by providing stimulatory factors to effector cells. Cytotoxic T cells are believed to be the most effective cells to eliminate cancer cells, and T helper cells prime cytotoxic T cells by secreting Th1 cytokines such as IL-2 and IFN-γ. In various malignancies, T helper cells have been shown to have an altered phenotype compared to cells found in healthy individuals. One of the prominent altered features is decreased Th1 cytokine production and a shift to the production of Th2 cytokines. (See, e.g., Kiani, et al., *Haematologica* 88:754-761 (2003); Maggio, et al., *Ann Oncol* 13 Suppl 1:52-56 (2002); Ito, et al., *Cancer* 85:2359-2367 (1999); Podhorecka, et al., *Leuk Res* 26:657-660 (2002); Tatsumi, et al., *J Exp Med* 196:619-628 (2002); Agarwal, et al., *Immunol Invest* 32:17-30 (2003); Smyth, et al., *Ann Surg Oncol* 10:455-462 (2003); Contasta, et al., *Cancer Biother Radiopharm* 18:549-557 (2003); Lauerova, et al., *Neoplasma* 49:159-166 (2002).) Reversing that cytokine shift to a Th1 profile has been demonstrated to augment anti-tumor effects of T cells. (See Winter, et al., *Immunology* 108:409-419 (2003); Inagawa, et al., *Anticancer Res* 18:3957-3964 (1998).)

Mechanisms underlying the capacity of tumor cells to drive the cytokine expression of T helper cells from Th1 to Th2 include the secretion of cytokines such as IL-10 or TGF-β as well as the expression of surface molecules interacting with cells of the immune system. CD200, a molecule expressed on the surface of dendritic cells which possesses a high degree of homology to molecules of the immunoglobulin gene family, has been implicated in immune suppression (Gorczynski et al., *Transplantation* 65:1106-1114 (1998)). It has been shown, for example, that CD200-expressing cells can inhibit the stimulation of Th1 cytokine production.

Although immune cells can help attack and eliminate cancer cells, in certain instances, such as in autoimmune disorders, allergies, and the rejection of tissue or organ transplants, the immune system can be the cause of illness. In order to inhibit harmful immune reactions in such instances, immunosuppressive agents such as corticosteroids and cytokine antagonists may be administered to patients. However these general immunosuppressives can elicit undesirable side effects including toxicity and reduced resistance to infection. Thus alternative, and perhaps more specific, methods of treating autoimmunity are needed.

Several immunomodulatory therapies, including antibody therapies, have proven successful in the treatment of certain cancers and autoimmune disorders. However there is a clinical need for additional antibody therapies for the treatment of both cancer and autoimmune disorders. Furthermore, there is a related need for humanized or other chimeric human/mouse monoclonal antibodies. In well publicized studies, patients administered murine anti-TNF (tumor necrosis factor) monoclonal antibodies developed anti-murine antibody responses to the administered antibody. (Exley A. R., et al., *Lancet* 335:1275-1277 (1990)). This type of immune response to the treatment regimen, commonly referred to as the human anti-mouse antibody (HAMA) response (Mirick et al. *Q J Nucl Med Mol Imaging* 2004; 48: 251-7), decreases the effectiveness of the treatment and may even render the treatment completely ineffective. Humanized or chimeric human/mouse monoclonal antibodies have been shown to significantly decrease the HAMA response and to increase the therapeutic effectiveness of antibody treatments. See, for example, LoBuglio et al., *P.N.A.S.* 86:4220-4224 (June 1989). Furthermore, antibodies in which particular functionalities are either enhanced or reduced may find useful applications in the clinic.

SUMMARY

This disclosure relates to agents and methods for modulating the function of CD200. Agents that modulate the function of CD200 include agents that modulate the activity and/or expression of CD200 and/or its receptor (CD200R). In some embodiments, the agents inhibit the function or activity of CD200. Thus in certain aspects, said agents act as antagonists to CD200. Certain antagonists may bind to CD200 and inhibit or disrupt the interaction of CD200 with its receptor. Other antagonists may bind to CD200 but may not block the CD200:CD200R interaction. Thus CD200 antagonists include any agent that is capable of modulating the effects of CD200 by mechanisms that may or may not include blocking the CD200:CD200R interaction. CD200 antagonists include but are not limited to polypeptides, small molecules, organometallic compounds, oligonucleotide constructs, RNAi constructs, aptamers, spiegelmers, antisense nucleic acids, locked nucleic acid (LNA) inhibitors, peptide nucleic acid (PNA) inhibitors, immunomodulatory agents, antibodies, antigen-binding fragments, prodrugs, and/or peptidomimetic compounds.

In certain embodiments, the said antagonist is an anti-CD200 antibody. Antibodies, as referred to herein, include antigen-binding fragments, Fab, Fv, scFv, Fab' and F(ab')$_2$, monoclonal and polyclonal antibodies, engineered antibodies (including chimeric, single chain, CDR-grafted, humanized, fully human antibodies, and artificially selected antibodies), and synthetic or semi-synthetic antibodies.

In certain aspects, the present disclosure relates to chimeric, humanized, human and de-immunized anti-CD200 antibodies and antigen-binding fragments thereof. In further embodiments, an antibody of the disclosure comprises a heavy chain comprising an amino acid sequence that is at least 90% identical to an amino acid sequence selected from among SEQ ID NOS: 7, 9, 11, and 20, or fragments thereof. Included is an antibody comprising an amino acid sequence that is about 90%, 91%, 92%, 93%, 94%, 95%, 96%, 97%, 98%, 99%, or 100% identical or similar to an amino acid sequence provided in SEQ ID NOS: 7, 9, 11, and 20, or fragments thereof (including but not limited to fragments corresponding to the sequences without the leader sequences). The said antibody may additionally comprise a light chain comprising an amino acid sequence that is at least about 90% identical or similar to an amino acid sequence selected from among SEQ ID NOS: 24, 26, 28, and 32, or fragments thereof. Likewise, the aforementioned amino acid sequence may be about 90%, 91%, 92%, 93%, 94%, 95%, 96%, 97%, 98%, 99%, or 100% identical or similar to an amino acid sequence provided in SEQ ID NOS: 24, 26, 28, and 32, including fragments thereof (including but not limited to fragments corresponding to the sequences without the leader sequences).

In one embodiment, the disclosure relates to an anti-CD200 antibody comprising a heavy chain comprising an amino acid sequence that is at least about 90% identical to the amino acid sequence of SEQ ID NO: 7 and also comprising a light chain comprising an amino acid sequence that is at least about 90% identical to SEQ ID NO: 24. Also included are anti-CD200 antibodies comprising amino acid sequences that are about 90%, 91%, 92%, 93%, 94%, 95%, 96%, 97%, 98%, 99%, or 100% identical or similar to one or more amino acid sequence provided in SEQ ID NOS: 7 and 24 or fragments thereof. Fragments include, but are not limited to, sequences corresponding to the sequences set forth in SEQ ID NOS: 7 and 24 without the leader sequences. Accordingly, the disclosure relates to an anti-CD200 antibody comprising an amino acid sequence encoded by a nucleic acid sequence that hybridizes under stringent conditions to the nucleic acid sequence of SEQ ID NO: 6 (including fragments thereof and complements thereto) and also comprising an amino acid sequence encoded by a nucleic acid sequence that hybridizes under stringent conditions to the nucleic acid sequence of SEQ ID NO: 23 (including fragments thereof and complements thereto). Also included is an anti-CD200 antibody comprising an amino acid sequence encoded by a nucleic acid sequence that is at least about 80% homologous or similar to a nucleic acid sequence provided in SEQ ID NO: 6, including fragments thereof and complements thereto, and also comprising an amino acid sequence encoded by a nucleic acid sequence that is at least about 80% homologous or similar to a nucleic acid sequence provided in SEQ ID NO: 23, including fragments thereof and complements thereto. The invention also relates to anti-CD200 antibodies comprising an amino acid sequence encoded by a nucleic acid sequence that is about 80%, 85%, 90%, 91%, 92%, 93%, 94%, 95%, 96%, 97%, 98%, 99%, or 100% homologous or similar to a nucleic acid sequence provided in SEQ ID NOS: 6 or 23, including fragments thereof and complements thereto.

In another embodiment, the disclosure relates to an anti-CD200 antibody comprising a heavy chain comprising an amino acid sequence that is at least about 90% identical to the amino acid sequence of SEQ ID NO: 9 and also comprising an amino acid sequence that is at least about 90% identical to SEQ ID NO: 26. Also included are anti-CD200 antibodies comprising amino acid sequences that are about 90%, 91%, 92%, 93%, 94%, 95%, 96%, 97%, 98%, 99%, or 100% identical or similar to one or more amino acid sequence provided in SEQ ID NOS: 9 and 26 or fragments thereof. Fragments include, but are not limited to, sequences corresponding to the sequences set forth in SEQ ID NOS: 9 and 26 without the leader sequences. Accordingly, the disclosure relates to an anti-CD200 antibody comprising an amino acid sequence encoded by a nucleic acid sequence that hybridizes under stringent conditions to the nucleic acid sequence of SEQ ID NO: 8 (including fragments thereof and complements thereto) and also comprising an amino acid sequence encoded by a nucleic acid sequence that hybridizes under stringent conditions to the nucleic acid sequence of SEQ ID NO: 25 (including fragments thereof and complements thereto). Also included is an anti-CD200 antibody comprising an amino acid sequence encoded by a nucleic acid sequence that is at least about 80% homologous or similar to a nucleic acid sequence provided in SEQ ID NO: 8, including fragments thereof and complements thereto, and also comprising an amino acid sequence encoded by a nucleic acid sequence that is at least about 80% homologous or similar to a nucleic acid sequence provided in SEQ ID NO: 25, including fragments thereof and complements thereto. The invention also relates to anti-CD200 antibodies comprising an amino acid sequence encoded by a nucleic acid sequence that is about 80%, 85%, 90%, 91%, 92%, 93%, 94%, 95%, 96%, 97%, 98%, 99%, or 100% homologous or similar to a nucleic acid sequence provided in SEQ ID NOS: 8 or 25, including fragments thereof and complements thereto.

In a further embodiment, the disclosure relates to an anti-CD200 antibody comprising an amino acid sequence that is at least about 90% identical to the amino acid sequence of SEQ ID NO: 11 and also comprising an amino acid sequence that is at least about 90% identical to SEQ ID NO: 26. Also included are anti-CD200 antibodies comprising amino acid sequences that are about 90%, 91%, 92%, 93%, 94%, 95%, 96%, 97%, 98%, 99%, or 100% identical or similar to one or more amino acid sequence provided in SEQ ID NOS: 11 and 26 or fragments thereof. Fragments include, but are not limited to, sequences corresponding to the sequences set forth in SEQ ID NOS: 11 and 26 without the leader sequences. Accordingly, the disclosure relates to an anti-CD200 antibody comprising an amino acid sequence encoded by a nucleic acid sequence that hybridizes under stringent conditions to the nucleic acid sequence of SEQ ID NO: 10 (including fragments thereof and complements thereto) and also comprising an amino acid sequence encoded by a nucleic acid sequence that hybridizes under stringent conditions to the nucleic acid sequence of SEQ ID NO: 25 (including fragments thereof and complements thereto). Also included is an anti-CD200 antibody comprising an amino acid sequence encoded by a nucleic acid sequence that is at least about 80% homologous or similar to a nucleic acid sequence provided in SEQ ID NO: 10, including fragments thereof and complements thereto, and also comprising an amino acid sequence encoded by a nucleic acid sequence that is at least about 80% homologous or similar to a nucleic acid sequence provided in SEQ ID NO: 25, including fragments thereof and complements thereto. The invention also relates to anti-CD200 antibodies comprising an amino acid sequence encoded by a nucleic acid sequence that is about 80%, 85%, 90%, 91%, 92%, 93%, 94%, 95%, 96%, 97%, 98%, 99%, or 100% homologous or similar to a nucleic acid sequence provided in SEQ ID NOS: 10 or 25, including fragments thereof and complements thereto.

In an additional embodiment, the disclosure relates to an anti-CD200 antibody comprising an amino acid sequence that is at least about 90% identical to the amino acid sequence of SEQ ID NO: 11 and also comprising an amino acid sequence that is at least about 90% identical to SEQ ID NO: 28. Also included are anti-CD200 antibodies comprising amino acid sequences that are about 90%, 91%, 92%, 93%, 94%, 95%, 96%, 97%, 98%, 99%, or 100% identical or similar to one or more amino acid sequence provided in SEQ ID NOS: 11 and 28 or fragments thereof. Fragments include, but are not limited to, sequences corresponding to the sequences set forth in SEQ ID NOS: 11 and 28 without the leader sequences. Accordingly, the disclosure relates to an anti-CD200 antibody comprising an amino acid sequence encoded by a nucleic acid sequence that hybridizes under stringent conditions to the nucleic acid sequence of SEQ ID NO: 10 (including fragments thereof and complements thereto) and also comprising an amino acid sequence encoded by a nucleic acid sequence that hybridizes under stringent conditions to the nucleic acid sequence of SEQ ID NO: 27 (including fragments thereof and complements thereto). Also included is an anti-CD200 antibody comprising an amino acid sequence encoded by a nucleic acid sequence that is at least about 80% homologous or similar to a nucleic acid sequence provided in SEQ ID NO: 10, including fragments thereof and complements thereto, and also comprising an amino acid sequence encoded by a nucleic acid sequence that is at least about 80% homologous or similar to a nucleic acid sequence provided in SEQ ID NO: 27, including fragments thereof and complements thereto. The invention also relates to anti-CD200 antibodies comprising an amino acid sequence encoded by a nucleic acid sequence that is about 80%, 85%, 90%, 91%, 92%, 93%, 94%, 95%, 96%, 97%, 98%, 99%, or 100% homologous or similar to a nucleic acid sequence provided in SEQ ID NOS: 10 or 27, including fragments thereof and complements thereto.

In yet another embodiment, the disclosure relates to an anti-CD200 antibody, comprising an amino acid sequence that is at least about 90% identical to the amino acid sequence of SEQ ID NO: 20 and also comprising an amino acid sequence that is at least about 90% identical to SEQ ID NO: 32. Also included are anti-CD200 antibodies comprising amino acid sequences that are about 90%, 91%, 92%, 93%, 94%, 95%, 96%, 97%, 98%, 99%, or 100% identical or similar to one or more amino acid sequence provided in SEQ ID NOS: 20 and 32 or fragments thereof. Fragments include, but are not limited to, sequences corresponding to the sequences set forth in SEQ ID NOS: 20 and 32 without the leader sequences. Accordingly, the disclosure relates to an anti-CD200 antibody comprising an amino acid sequence encoded by a nucleic acid sequence that hybridizes under stringent conditions to the nucleic acid sequence of SEQ ID NO: 19 (including fragments thereof and complements thereto) and also comprising an amino acid sequence encoded by a nucleic acid sequence that hybridizes under stringent conditions to the nucleic acid sequence of SEQ ID NO: 31 (including fragments thereof and complements thereto). Also included is an anti-CD200 antibody comprising an amino acid sequence encoded by a nucleic acid sequence that is at least about 80% homologous or similar to a nucleic acid sequence provided in SEQ ID NO: 19, including fragments thereof and complements thereto, and also comprising an amino acid sequence encoded by a nucleic acid sequence that is at least about 80% homologous or similar to a nucleic acid sequence provided in SEQ ID NO: 31, including fragments thereof and complements thereto. Included, therefore, are anti-CD200 antibodies comprising an amino acid sequence encoded by a nucleic acid sequence that is about 80%, 85%, 90%, 91%, 92%, 93%, 94%, 95%, 96%, 97%, 98%, 99%, or 100% homologous or similar to a nucleic acid sequence provided in SEQ ID NOS: 19 or 31, including fragments thereof and complements thereto.

Anti-CD200 antibodies provided in the present disclosure include antibodies and antigen-binding fragments with altered or no effector function(s). Included are antibodies that comprise an altered constant or Fc region with either increased or decreased effector functions. The disclosure also relates to antibodies with altered or no effector functions due to increased or decreased binding affinity, which may arise from changes in the variable regions. Altered effector functions include, for example, an increased or decreased ability to bind one or more Fc receptor (FcR) or effector cell, increased or decreased antigen-dependent cytotoxicity (ADCC), and/or increased or decreased complement-dependent cytotoxicity (CDC). Variant antibodies include but are not limited to antibodies in which the constant region or Fc region contains one or more amino acid insertions, deletions, and/or substitutions. In additional embodiments, these variant antibodies comprise a constant region wherein the CH1 and hinge region are derived from human IgG2 and the CH2 and CH3 regions are derived from human IgG4. Also included are antibodies in which the constant or Fc region exhibits altered glycosylation. The aforementioned antibodies and antigen-binding fragments (including single-chain antibodies) may be murine, chimeric, humanized, fully human, or de-immunized; included are antibodies comprising the IgG1, IgG2, IgG3, IgG4, IgM, IgA1, IgA2, IgA, IgD, or IgE frameworks. Furthermore, the said antibodies, including fragments and variants thereof, may be blocking or non-blocking antibodies or fragments thereof.

In certain aspects, the disclosure provides anti-CD200 antibodies that exhibit decreased or no effector function. Antibodies with decreased or no effector function may comprise a variant or altered Fc or constant region, such as, for example, a constant region with one or more amino acid substitutions, insertions, and/or deletions, or a constant region with one or more changes in glycosylation. A variant constant region includes, for example, a region wherein one or more amino acids are substituted with alanine, such as in the Ala-Ala mutation described herein, or wherein one or more carbohydrate groups is changed, added, or removed. An alteration in the number and/or location of carbohydrate groups may be achieved by producing the said antibody in particular cell types for which post-translational modifications would be reduced, absent, or increased. In one embodiment, effector function of anti-CD200 antibodies is eliminated by swapping the IgG1 constant domain for an IgG2/4 fusion domain. Other ways of eliminating effector function can be envisioned such as, e.g., mutation of the sites known to interact with an FcR or insertion of a peptide in the hinge region, thereby eliminating critical sites required for an FcR interaction.

In certain aspects and methods of the present disclosure, anti-CD200 antibodies with altered or no effector functions comprise anti-CD200 antibodies with one or more amino acid substitutions, insertions, and/or deletions. In certain embodiments, such a variant anti-CD200 antibody exhibits reduced or no effector function. In certain embodiments, the variant constant region (of said variant antibody) possesses at least about 70% homology with the native sequence constant or Fc region and/or with a constant or Fc region of the parent antibody or fragment thereof; in other embodiments the variant constant or Fc region possesses at least about 80% homology or similarity therewith; in other embodiments at least about 90% homology or similarity therewith and in additional embodiments at least about 95% homology or similarity therewith. In particular embodiments, a variant antibody comprises a G2/G4 construct. Accordingly, the present disclosure relates to a constant or Fc region of an anti-CD200 antibody with reduced or no effector function, wherein said constant region comprises a heavy chain comprising an amino acid sequence selected from the group consisting of SEQ ID NOS: 13, 15, 18, 22, and fragments thereof. The present disclosure also relates to variant constant regions of an anti-CD200 antibody wherein an antibody comprises an amino acid sequence that is at least about 90% identical or similar to an amino acid sequence selected from among SEQ ID NOS: 13, 15, 18, 22, and fragments thereof. Also included in the disclosure are antibodies comprising an amino acid sequence that is about 90%, 91%, 92%, 93%, 94%, 95%, 96%, 97%, 98%, or 99% identical or similar to an amino acid sequence provided in SEQ ID NOS: 13, 15, 18, 22, and fragments thereof. Fragments include, but are not limited to, sequences without the leader sequences. Additionally, in some embodiments a constant region of an anti-CD200 antibody with reduced or no effector function and comprising the G2/G4 construct is encoded by a nucleic acid selected from the group consisting of SEQ ID NOS: 12, 14, 16, 17, and 21, or fragments thereof and complements thereto. In certain embodiments, an anti-CD200 antibody with reduced or no effector function is encoded by a nucleic acid comprising a nucleic acid sequence that is at least about 80% homologous or similar to a sequence selected from SEQ ID NOS: 12, 14, 16, 17, and 21, including fragments thereof and complements thereto. In other embodiments, a variant anti-CD200 antibody is encoded by a nucleic acid sequence comprising a sequence that is about 80%, 85%, 90%, 91%, 92%, 93%, 94%, 95%, 96%, 97%, 98%, 99%, or 100% homologous or similar to a nucleic acid sequence selected from the group consisting of SEQ ID NOS: 12, 14, 16, 17, and 21, including fragments thereof and complements thereto. In still other embodiments, the nucleic acid encoding a variant anti-CD200 antibody comprises a nucleic acid sequence that hybridizes under stringent conditions to a nucleic acid sequence selected from the group consisting of SEQ ID NOS: 12, 14, 16, 17, and 21, including fragments thereof and complements thereto. Included are antigen-binding fragments and both blocking and non-blocking antibodies or fragments thereof.

In one embodiment, the present disclosure relates to a variant anti-CD200 antibody comprising an amino acid sequence that is at least about 90% identical to the amino acid sequence of SEQ ID NO: 13 and also comprising an amino acid sequence that is at least about 90% identical to SEQ ID NO: 28. Also included is an anti-CD200 antibody comprising one or more amino acid sequence that is about 90%, 91%, 92%, 93%, 94%, 95%, 96%, 97%, 98%, 99%, or 100% identical to an amino acid sequence provided in SEQ ID NOS: 13 and 28 or fragments thereof. Fragments include, but are not limited to, sequences corresponding to the sequences set forth in SEQ ID NOS: 13 and 28 without the leader sequences. Accordingly, the disclosure relates to a variant anti-CD200 antibody comprising an amino acid sequence encoded by a nucleic acid sequence that hybridizes under stringent conditions to the nucleic acid sequence of SEQ ID NO: 12 (including fragments thereof and complements thereto) and also comprising an amino acid sequence encoded by a nucleic acid sequence that hybridizes under stringent conditions to the nucleic acid sequence of SEQ ID NO: 27 (including fragments thereof and complements thereto). Also included is an anti-CD200 antibody comprising an amino acid sequence encoded by a nucleic acid sequence that is at least about 80% homologous to a nucleic acid sequence provided in SEQ ID NO: 12, including fragments thereof and complements thereto, and also comprising an amino acid sequence encoded by a nucleic acid sequence that is at least about 80% homologous to a nucleic acid sequence provided in SEQ ID NO: 27, including fragments thereof and complements thereto. Included, therefore, are anti-CD200 antibodies comprising an amino acid sequence encoded by a nucleic acid sequence that is about 80%, 85%, 90%, 91%, 92%, 93%, 94%, 95%, 96%, 97%, 98%, 99%, or 100% homologous to a nucleic acid sequence provided in SEQ ID NOS: 12 or 27, including fragments thereof and complements thereto.

In another embodiment, the disclosure relates to a variant anti-CD200 antibody comprising an amino acid sequence that is at least about 90% identical to the amino acid sequence of SEQ ID NO: 15 and also comprising an amino acid sequence that is at least about 90% identical to SEQ ID NO: 24. Also included is an anti-CD200 antibody comprising an amino acid sequence that is about 90%, 91%, 92%, 93%, 94%, 95%, 96%, 97%, 98%, 99%, or 100% identical to one or more amino acid sequence provided in SEQ ID NOS: 15 and 24 or fragments thereof. Fragments include, but are not limited to, sequences corresponding to the sequences set forth in SEQ ID NOS: 15 and 24 without the leader sequences (e.g., the fragment of SEQ ID NO: 15 beginning at amino acid 20 or 21). Accordingly, the disclosure relates to a variant anti-CD200 antibody comprising an amino acid sequence encoded by a nucleic acid sequence that hybridizes under stringent conditions to the nucleic acid sequence of SEQ ID NO: 14 (including fragments thereof and complements thereto) and also comprising an amino acid sequence encoded by a nucleic acid sequence that hybridizes under stringent conditions to the nucleic acid sequence of SEQ ID NO: 23 (including fragments thereof and complements thereto). Also included is an anti-CD200 antibody comprising an amino acid sequence encoded by a nucleic acid sequence that is at least about 80% homologous to a nucleic acid sequence provided in SEQ ID NO: 14, including fragments thereof and complements thereto, and also comprising an amino acid sequence encoded by a nucleic acid sequence that is at least about 80% homologous to a nucleic acid sequence provided in SEQ ID NO: 23, including fragments thereof and complements thereto. Included, therefore, are anti-CD200 antibodies comprising an amino acid sequence encoded by a nucleic acid sequence that is about 80%, 85%, 90%, 91%, 92%, 93%, 94%, 95%, 96%, 97%, 98%, 99%, or 100% homologous to a nucleic acid sequence provided in SEQ ID NOS: 14 or 23, including fragments thereof and complements thereto.

In an additional embodiment, the disclosure relates to a variant anti-CD200 antibody comprising an amino acid sequence that is at least about 90% identical to the amino acid sequence of SEQ ID NO: 13 and also comprising an amino acid sequence that is at least 90% identical to SEQ ID NO: 28. Also included is an anti-CD200 antibody comprising one or more amino acid sequence that is about 90%, 91%, 92%, 93%, 94%, 95%, 96%, 97%, 98%, 99%, or 100% identical to an amino acid sequence provided in SEQ ID NOS: 13 and 28 or fragments thereof. Fragments include, but are not limited to, sequences corresponding to the sequences set forth in SEQ ID NOS: 13 and 28 without the leader sequences. Accordingly, the disclosure relates to a variant anti-CD200 antibody comprising an amino acid sequence encoded by a nucleic acid sequence that hybridizes under stringent conditions to the nucleic acid sequence of SEQ ID NO: 16 (including fragments thereof and complements thereto) and also comprising an amino acid sequence encoded by a nucleic acid sequence that hybridizes under stringent conditions to the nucleic acid sequence of SEQ ID NO: 27 (including fragments thereof and complements thereto). Also included is an anti-CD200 antibody comprising an amino acid sequence encoded by a nucleic acid sequence that is at least about 80% homologous to a nucleic acid sequence provided in SEQ ID NO: 16, including fragments thereof and complements thereto, and also comprising an amino acid sequence encoded by a nucleic acid sequence that is at least about 80% homologous to a nucleic acid sequence provided in SEQ ID NO: 27, including fragments thereof and complements thereto. Included, therefore, are anti-CD200 antibodies comprising an amino acid sequence encoded by a nucleic acid sequence that is about 80%, 85%, 90%, 91%, 92%, 93%, 94%, 95%, 96%, 97%, 98%, 99%, or 100% homologous to a nucleic acid sequence provided in SEQ ID NOS: 16 or 27, including fragments thereof and complements thereto.

In still another embodiment, the disclosure relates to a variant anti-CD200 antibody comprising an amino acid sequence that is at least about 90% identical to the amino acid sequence of SEQ ID NO: 18 and also comprising an amino acid sequence that is at least about 90% identical to SEQ ID NO: 30. Also included is an anti-CD200 antibody comprising an amino acid sequence that is about 90%, 91%, 92%, 93%, 94%, 95%, 96%, 97%, 98%, 99%, or 100% identical to an amino acid sequence provided in SEQ ID NOS: 18 and 30 or fragments thereof. Accordingly, the disclosure relates to a variant anti-CD200 antibody comprising an amino acid sequence encoded by a nucleic acid sequence that hybridizes under stringent conditions to the nucleic acid sequence of SEQ ID NO: 17 (including fragments thereof and complements thereto) and also comprising an amino acid sequence encoded by a nucleic acid sequence that hybridizes under stringent conditions to the nucleic acid sequence of SEQ ID NO: 29 (including fragments thereof and complements thereto). Also included is an anti-CD200 antibody comprising an amino acid sequence encoded by a nucleic acid sequence that is at least about 80% homologous to a nucleic acid sequence provided in SEQ ID NO: 17, including fragments thereof and complements thereto, and also comprising an amino acid sequence encoded by a nucleic acid sequence that is at least 80% homologous to a nucleic acid sequence provided in SEQ ID NO: 29, including fragments thereof and complements thereto. Included, therefore, are anti-CD200 antibodies comprising an amino acid sequence encoded by a nucleic acid sequence that is about 80%, 85%, 90%, 91%, 92%, 93%, 94%, 95%, 96%, 97%, 98%, 99%, or 100% homologous to a nucleic acid sequence provided in SEQ ID NOS: 17 or 29, including fragments thereof and complements thereto.

In another embodiment, the disclosure relates to a variant anti-CD200 antibody comprising an amino acid sequence that is at least about 90% identical to the amino acid sequence of SEQ ID NO: 22 and also comprising an amino acid sequence that is at least about 90% identical to SEQ ID NO. 34: Also included is an anti-CD200 antibody comprising an amino acid sequence that is about 90%, 91%, 92%, 93%, 94%, 95%, 96%, 97%, 98%, 99%, or 100% identical to an amino acid sequences provided in SEQ ID NOS: 22 and 34 or fragments thereof. Accordingly, the disclosure relates to a variant anti-CD200 antibody comprising an amino acid sequence encoded by a nucleic acid sequence that hybridizes under stringent conditions to the nucleic acid sequence of SEQ ID NO: 21 (including fragments thereof and complements thereto) and also comprising an amino acid sequence encoded by a nucleic acid sequence that hybridizes under stringent conditions to the nucleic acid sequence of SEQ ID NO: 33 (including fragments thereof and complements thereto). Also included is an anti-CD200 antibody comprising an amino acid sequence encoded by a nucleic acid sequence that is at least about 80% homologous to a nucleic acid sequence provided in SEQ ID NO: 21, including fragments thereof and complements thereto, and also comprising an amino acid sequence encoded by a nucleic acid sequence that is at least about 80% homologous to a nucleic acid sequence provided in SEQ ID NO: 33, including fragments thereof and complements thereto. Included, therefore, are anti-CD200 antibodies comprising an amino acid sequence encoded by a nucleic acid sequence that is about 80%, 85%, 90%, 91%, 92%, 93%, 94%, 95%, 96%, 97%, 98%, 99%, or 100% homologous to a nucleic acid sequence provided in SEQ ID NOS: 21 and 33, including fragments thereof and complements thereto.

Anti-CD200 antibodies with altered effector function may also exhibit increased effector function. Increased effector functions include but are not limited to increased binding to one or more Fc receptors, increased ability to elicit ADCC, and/or increased ability to elicit CDC. Anti-CD200 antibodies with increased effector function may also comprise a variant Fc or constant region as described herein. The aforementioned anti-CD200 antibodies with altered effector functions may furthermore be blocking or non-blocking antibodies. For example, an anti-CD200 antibody with increased effector function may bind to CD200 but may not block the CD200:CD200R interaction. Such an antibody may be useful when targeting an effector function (e.g., ADCC or CDC) to a CD200-expressing cell. As mentioned previously, antibodies described herein, including the aforementioned anti-CD200 antibodies with altered effector function(s), include murine, chimeric, humanized, fully human and de-immunized antibodies, all in their blocking and non-blocking forms, and fragments thereof.

In certain aspects, this disclosure provides methods and compositions for modulating or depleting CD200-positive cells. CD200-positive cells may be modulated or depleted by administering a CD200 antagonist to a subject. The said antagonist may target CD200-positive cells for effector function and/or may disrupt the CD200:CD200R interaction. In certain embodiments, the said antagonist is an anti-CD200 antibody. The said anti-CD200 antibody may be an antibody described herein, including any fragments and variants thereof. Included are antibodies and antigen-binding fragments with altered effector function(s), such as, for example, anti-CD200 antibodies with decreased or no effector function. Also included are murine, chimeric, humanized, fully human and de-immunized antibodies and antigen-binding fragments, including single-chain antibodies. The aforementioned antibodies may be non-blocking or blocking antibodies and include antibodies comprising the IgG1, IgG2, IgG3, IgG4, IgM, IgA1, IgA2, IgA, IgD, or IgE frameworks.

CD200-positive cells are implicated in certain types of cancers and certain autoimmune diseases. Accordingly, CD200-positive cells include but are not limited to immune cells (such as, e.g., B-cells and T-cells) and cancer cells (such as, e.g., cancer cells of ovarian, skin, lung, renal, breast, prostate, neuroblastoma, lymphoma, myeloma, leukemia, thyroid, and plasma cell cancers). Also included are cancer cells from any tissue or organ derived from neural crest cells. Thus the subject in need of a method of modulating or depleting CD200-positive cells may be a patient with cancer or autoimmune disease, or a patient who has received or is expected to receive an organ transplant.

In one aspect this disclosure provides methods and compositions for treating autoimmune disease. Autoimmune diseases that may be treated by the methods and compositions provided herein include but are not limited to rheumatoid arthritis, inflammatory bowel disease (including ulcerative colitis and Crohn's disease), systemic lupus erythematosus, multiple sclerosis, Hashimoto's thyroiditis, pernicious anemia, Addison's disease, type I diabetes, dermatomyositis, Sjogren's syndrome, lupus erythematosus, myasthenia gravis, Reiter's syndrome, Grave's disease, psoriasis, and autoimmune hemolytic diseases. In some embodiments, a patient with autoimmune disease is given an antagonist to CD200, and in certain embodiments, the antagonist is an anti-CD200 antibody. The anti-CD200 antibody may comprise a variant constant region as described herein. Accordingly, the anti-CD200 antibody may exhibit altered effector function(s), such as, for example, increased effector function(s). The said antibody may exhibit, for example, increased binding to one or more Fc receptors. Additionally, the said antibody may elicit increased ADCC and/or CDC. The said antibody may furthermore be either a blocking or non-blocking antibody or fragment thereof and may be either a murine, chimeric, humanized, fully human or de-immunized antibody or fragment thereof.

Cancers for which the disclosed methods may be used include but are not limited to melanoma, ovarian cancer, renal cancer, neuroblastoma, lung cancer, breast cancer, prostate cancer, lymphoma, myeloma, leukemia, and plasma cell cancers. Also included are cancers derived from neural crest cells and any cancers that express CD200. In certain embodiments, this disclosure provides a method for treating hematological malignancies, such as, for example, leukemias including chronic lymphocytic leukemia.

In a particularly useful embodiment, a cancer therapy in accordance with this disclosure comprises (1) administering an anti-CD200 antibody or antagonist that interferes with the interaction between CD200 and its receptor to block immune suppression, thereby promoting eradication of the cancer cells; and/or (2) administering a fusion molecule that includes a CD-200 targeting portion to directly kill cancer cells. Alternatively, the antibody directly kills cancer cells through complement-mediated and/or antibody-dependent cellular cytotoxicity. In various embodiments, the effector function of the anti-CD200 antibody is altered. In one particular embodiment, the anti-CD200 antibody contains a variant or altered constant region for which the effector function is decreased or eliminated; such an antibody may be useful for the methods described above in (1) and (2), for example.

In certain embodiments, the disclosure relates to fusion molecules wherein an anti-CD200 antibody or antigen-binding fragment is linked to a second molecule. The said fusion molecule may comprise, for example, a small molecule, polypeptide, peptidomimetic, heteroclitic peptide, a chemotherapeutic agent, an immunomodulatory agent, a targeting moiety, or a nucleic acid construct (e.g., antisense, RNAi, or gene-targeting construct). The disclosure also includes antigen-binding fragments to CD200 wherein the fragment is fused or otherwise linked to a polypeptide, protein domain, serum protein, albumin, PEG (polyethylene glycol), or any other molecule that will increase the half-life of the said fragment in vivo. Said antigen-binding fragments include Fab, Fv, single-chain fragments or scFv, Fab', and F(ab')$_2$, for example.

The present disclosure also relates to methods employing anti-CD200 antibodies to determine the CD200 expression status of a cell or tissue sample obtained from a patient. Such methods include but are not limited to immunohistochemical staining of tissue samples and flow cytometry analysis of CD200-stained cells from a patient. The patient may be a patient with cancer, for example.

In accordance with the methods and compositions described herein, the disclosure also relates to methods of treating a transplant or allograft patient. An anti-CD200 antibody or other CD200 antagonist of the present disclosure may be administered to a patient prior to a transplant or allograft procedure or after the procedure in order to decrease or eliminate CD200-positive immune cells that could reduce the patient's acceptance of the transplanted organ or tissue. In a particular embodiment, an anti-CD200 antibody with increased effector function is given to a transplant patient.

In further embodiments, methods are provided for combination therapies comprising anti-CD200 therapy. For example, a patient receiving a first therapy comprising a CD200 antagonist (e.g., an anti-CD200 antibody described herein) may also be given a second therapy. The CD200 antagonist may be given simultaneously with the second therapy. Alternatively, the CD200 antagonist may be given prior to or following the second therapy. Second therapies include but are not limited to chemotherapeutic agents, radiation therapy, vaccines, antibiotics and anti-viral agents, and immunomodulatory therapies.

In another embodiment of the present disclosure, methods are provided for monitoring the progress of a therapeutic treatment. The method involves administering a therapy (e.g. an immunomodulatory therapy, a chemotherapeutic therapy, etc.) and determining CD200 levels in a subject at least twice to determine the effectiveness of the therapy. Other methods to determine the effectiveness of a therapy include but are not limited to detection of cancer cells, total lymphocyte count, spleen, liver, and/or lymph node size, number of regulatory T cells, intracellular or serum cytokine profiles, or secretion of cytokines by T or B cells as measured by ELISPOT—an assay system that allows the detection of cytokines or other secreted molecules on a per cell basis.

According to the compositions and methods set forth in the present embodiments, the disclosure also relates to any pharmaceutical composition comprising an anti-CD200 antibody. Included are chimeric, humanized, human and de-immunized anti-CD200 antibodies and antigen-binding fragments, including single-chain antibodies. Also included are murine, chimeric, humanized, human and de-immunized variant anti-CD200 antibodies and antigen-binding fragments with altered effector function(s) as described herein. The aforementioned antibodies and variant antibodies may either be blocking or non-blocking antibodies or antigen-binding fragments.

In certain embodiments, patients for whom anti-CD200 therapy is useful or patients who expect to receive a therapy comprising a CD200 antagonist therapy (including, for example, an anti-CD200 antibody) may be screened for certain previously received treatments and procedures or for current medical status. In one embodiment for example, female patients may be pre-screened for pregnancy and agree to contraception, since CD200 plays an important role in protection against abortion. Accordingly, patients receiving said therapy may agree to practice one or more methods of contraception. The said patient may agree to use one or more methods of contraception for a designated period prior to starting the said therapy and/or for the duration of the said therapy. In certain embodiments, female patients receive counseling concerning the risks with respect to fetal exposure to such anti-CD200 therapy. In additional embodiments, such patients may be expected to sign informed consent forms prior to such treatment. In other aspects, physicals counseling patients regarding anti-CD200 therapy may require such patients to use contraceptive devices or formulations prior to administering the anti-CD200 therapy (see, for example, U.S. Pat. No. 6,908,432 and related patents, the contents of which are incorporated herein by reference). Similarly, in other embodiments, patients may be screened to identify patients who have previously received brain surgery and/or radiation therapy to the brain; anti-CD200 therapy would not be prescribed for such patients.

BRIEF DESCRIPTION OF THE FIGURES

FIG. 1 provides the nucleic acid sequence for the primer C7mhHF (SEQ ID NO:1) used in generating the G2/G4 construct.

FIG. 2 provides the nucleic acid sequence for the Primer Rev Age Pri (SEQ ID NO: 2) used in generating the G2/G4 construct.

FIG. 3 provides the nucleic acid sequence for the primer C2aB7 rev (SEQ ID NO: 3) used in generating the G2/G4 construct.

FIG. 4 provides the nucleic acid sequence for the lacpri (SEQ ID NO: 4) used in generating the G2/G4 construct.

FIG. 5 provides the nucleic acid sequence for LeadVHpAX (SEQ ID NO: 5).

FIGS. 6A-G depict the amino acid sequences and nucleotide sequences for the heavy and light chains of antibody chC2aB7-hG1 (SEQ ID NOS: 6, 7, 23, 24, 37, and 38). FIGS. 6C and 6D show SEQ ID NO: 37 (nucleic acid sequence) and SEQ ID NO: 7 (amino acid sequence). SEQ ID NO: 7 as shown in the schematic is contiguous but is depicted with a corresponding nucleotide sequence that includes introns. FIG. 6G shows SEQ ID NO: 38 (nucleic acid sequence) and SEQ ID NO: 24 (amino acid sequence).

Figure 7G:
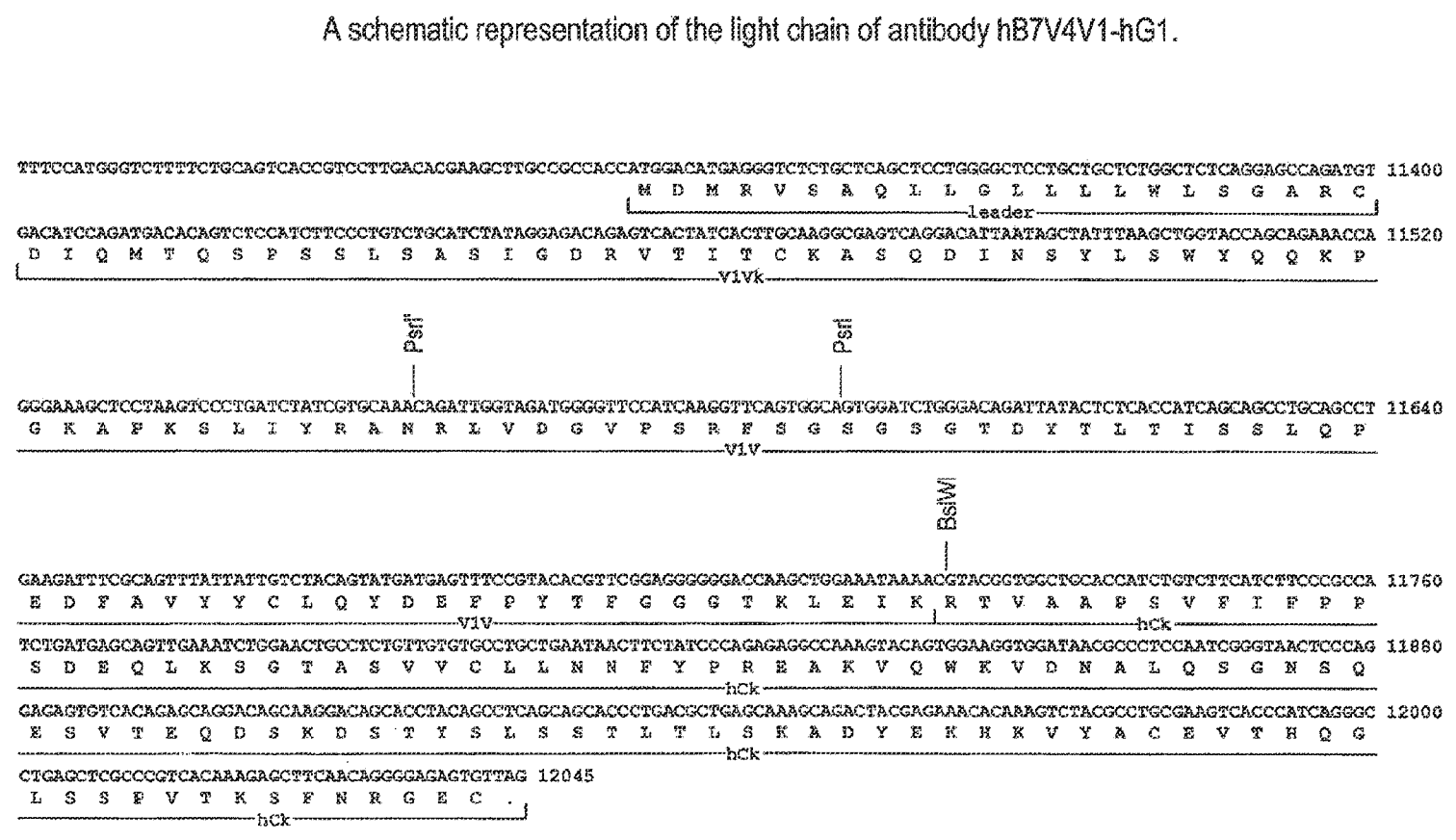

FIGS. 7A-G depict the amino acid sequences and nucleotide sequences for the heavy and light chains of antibody hB7V4V1-hG1 (SEQ ID NOS: 8, 9, 25, 26, 39, and 40). FIGS. 7C and 7D show SEQ ID NO: 39 (nucleic acid sequence) and SEQ ID NO: 9 (amino acid sequence). FIG. 7G shows SEQ ID NO: 40 (nucleic acid sequence) and SEQ ID NO: 26 (amino acid sequence).

FIGS. 8A-F depict the amino acid sequences and nucleotide sequences for the heavy and light chains of antibody hB7V3V1-hG1 (SEQ ID NOS: 10, 11, 25, 26, 40, and 41). FIG. 8C shows SEQ ID NO: 41 (nucleic acid sequence) and SEQ ID NO: 11 (amino acid sequence). FIG. 8F shows SEQ ID NO: 41 (nucleic acid sequence) and SEQ ID NO: 26 (amino acid sequence).

FIGS. 9A-F depict the amino acid sequences and nucleotide sequences for the heavy and light chains of antibody hB7V3V2-hG1 (SEQ ID NOS: 10, 11, 27, 28, 41, and 42). FIG. 9C shows SEQ ID NO: 41 (nucleic acid sequence) and SEQ ID NO: 11 (amino acid sequence). FIG. 9F shows SEQ ID NO: 42 (nucleic acid sequence) and SEQ ID NO: 28 (amino acid sequence).

Figure 10G:
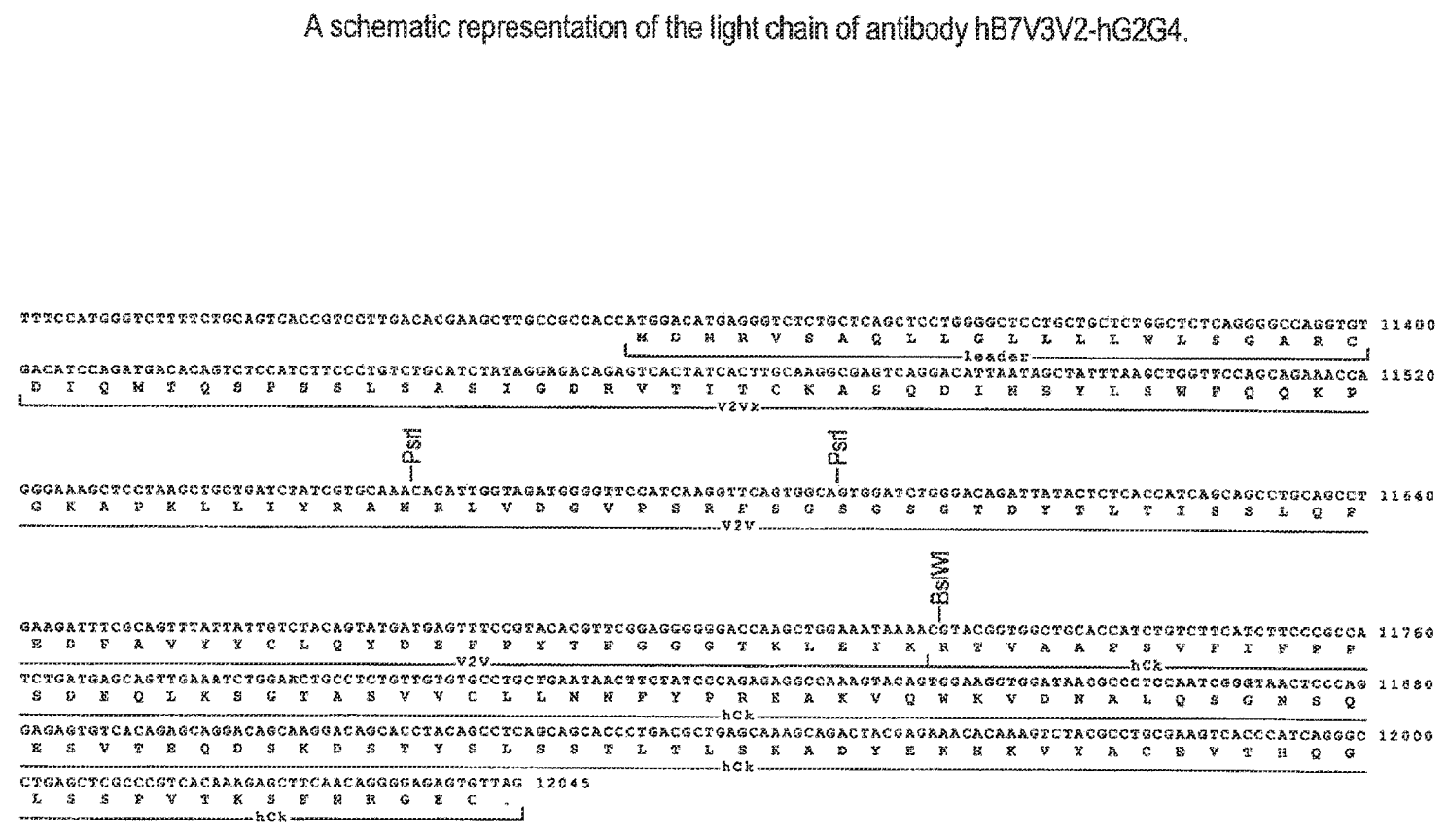

FIGS. 10A-G depict the amino acid sequences and nucleotide sequences for the heavy and light chains of antibody hB7V3V2-hG2G4 (SEQ ID NOS: 12, 13, 27, 28, 42, and 43). FIGS. 10C and 10D show SEQ ID NO: 43 (nucleic acid sequence) and SEQ ID NO: 13 (amino acid sequence). SEQ ID NO: 13 as shown in the schematic is contiguous but is depicted with a corresponding nucleotide sequence that includes introns. FIG. 10G shows SEQ ID NO: 42 (nucleic acid sequence) and SEQ ID NO: 28 (amino acid sequence).

FIGS. 11A-G depict the amino acid sequences and nucleotide sequences for the heavy and light chains of antibody chC2aB7-hG2G4 (SEQ ID NOS: 14, 15, 23, 24, 44, 45, 46, and 47). FIGS. 11C and 11D show SEQ ID NO: 44 (nucleic acid sequence) and SEQ ID NO: 45 (amino acid sequence). SEQ ID NO: 45 corresponds to amino acids 1-337 of SEQ ID NO: 15. As shown in the schematic, SEQ ID NO: 45 is contiguous but is depicted with a corresponding nucleotide sequence that includes introns. FIG. 11G shows SEQ ID NO: 46 (nucleic acid sequence) and SEQ ID NO: 47 (amino acid sequence).

FIGS. 12A-F depict the amino acid sequences and nucleotide sequences for the heavy and light chains of antibody hB7V3V2-cG2G4 (SEQ ID NOS: 13, 16, 27, 28, 48, and 49). FIG. 12C shows SEQ ID NO: 48 (nucleic acid sequence) and SEQ ID NO: 13 (amino acid sequence). FIG. 12F shows SEQ ID NO: 49 (nucleic acid sequence) and SEQ ID NO: 28 (amino acid sequence).

FIGS. 13A-D depict the amino acid sequences and nucleotide sequences for the heavy and light chains of antibody chC7-hG2G4 (SEQ ID NOS: 17, 18, 29, and 30).

FIGS. 14A-G depict the amino acid sequences and nucleotide sequences for the heavy and light chains of antibody D1B5-hG1 (SEQ ID NOS: 19, 20, 31, 32, 50, and 51). FIGS. 14C and 14D show SEQ ID NO: 50 (nucleic acid sequence) and SEQ ID NO: 20 (amino acid sequence). SEQ ID NO: 20 as shown in the schematic is contiguous but is depicted with a corresponding nucleotide sequence that includes introns. FIG. 14G shows SEQ ID NO: 51 (nucleic acid sequence) and SEQ ID NO: 32 (amino acid sequence).

FIGS. 15A-D depict the amino acid sequences and nucleotide sequences for the heavy and light chains of antibody G2G4 63L1D (SEQ ID NOS: 21, 22, 33, and 34).

FIG. 20 is a table showing the expression level of CD200 in chronic lymphocytic leukemia (CLL) patient samples compared to normal samples.

FIG. 21 depicts the relative levels of CD200 expression detected in cancer cell lines.

FIGS. 23A-B show the expression level of CD200 antigen in human melanoma patient samples relative to the expression level detected in PBL.

FIG. 25 demonstrates the effects of anti-CD200 antibody in cytokine production. The levels of IL-2 production in mixed cell population assays were measured in the absence and presence of CD200 antibody. The antibody used is a chimeric anti-CD200 antibody with no effector function.

FIG. 28 demonstrates the effects of anti-CD200 antibodies on ADCC of activated T-cells. CD3+ human T cells were stimulated with 10 μg/mL immobilized (plate-coated) mOKT3 for 72 hrs. Activated T cells were then chromated for use as targets and incubated with purified autologous CD56+ (NK) cells as effector cells. Cells were coincubated for 4 hours at 37° C. at 25:1 (A) or 10:1 (B) effector:target cell ratios in the presence or absence of a humanized anti-CD200 antibody capable of mediating effector function (V3V2-G1) or engineered to lack effector function (V3V2-G2G4). Data is represented as percent specific lysis. Anti-CD200 antibody increased ADCC of activated T-cells, whereas the anti-CD200 antibody with no effector function failed to induce ADCC.

FIG. 29 is a table showing the expression level of CD200 on plasma cells.

DETAILED DESCRIPTION OF PREFERRED EMBODIMENTS

I. CD200 Antagonists

Figure 6D:
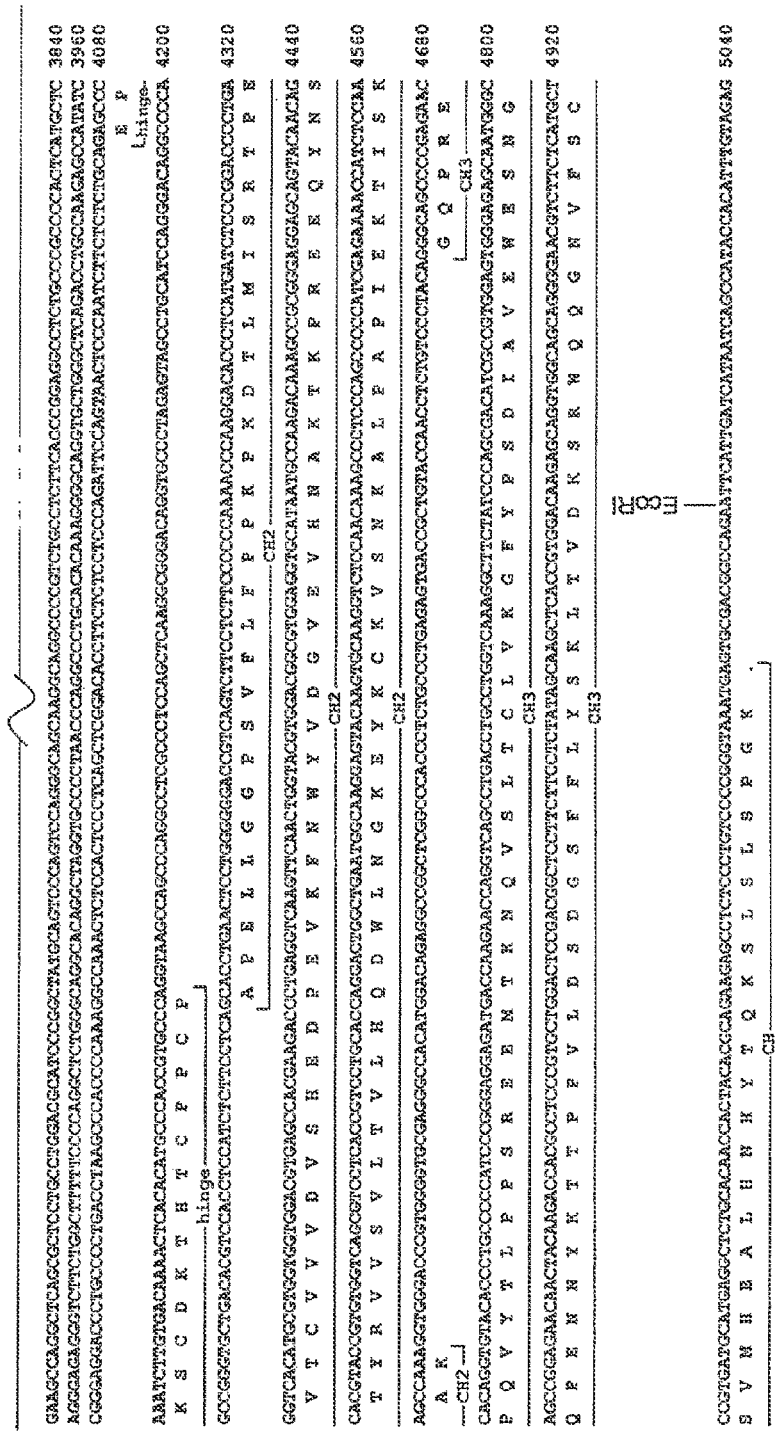
Figure 6G:
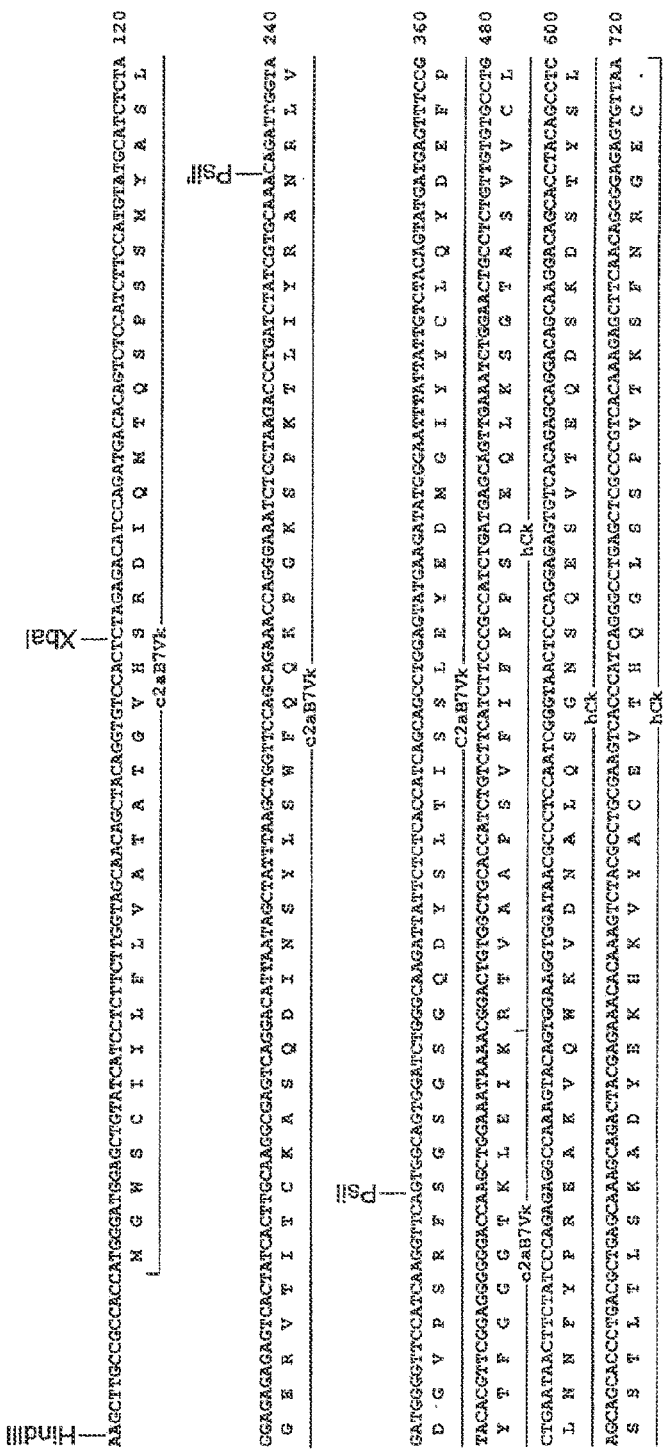
Figure 7D:
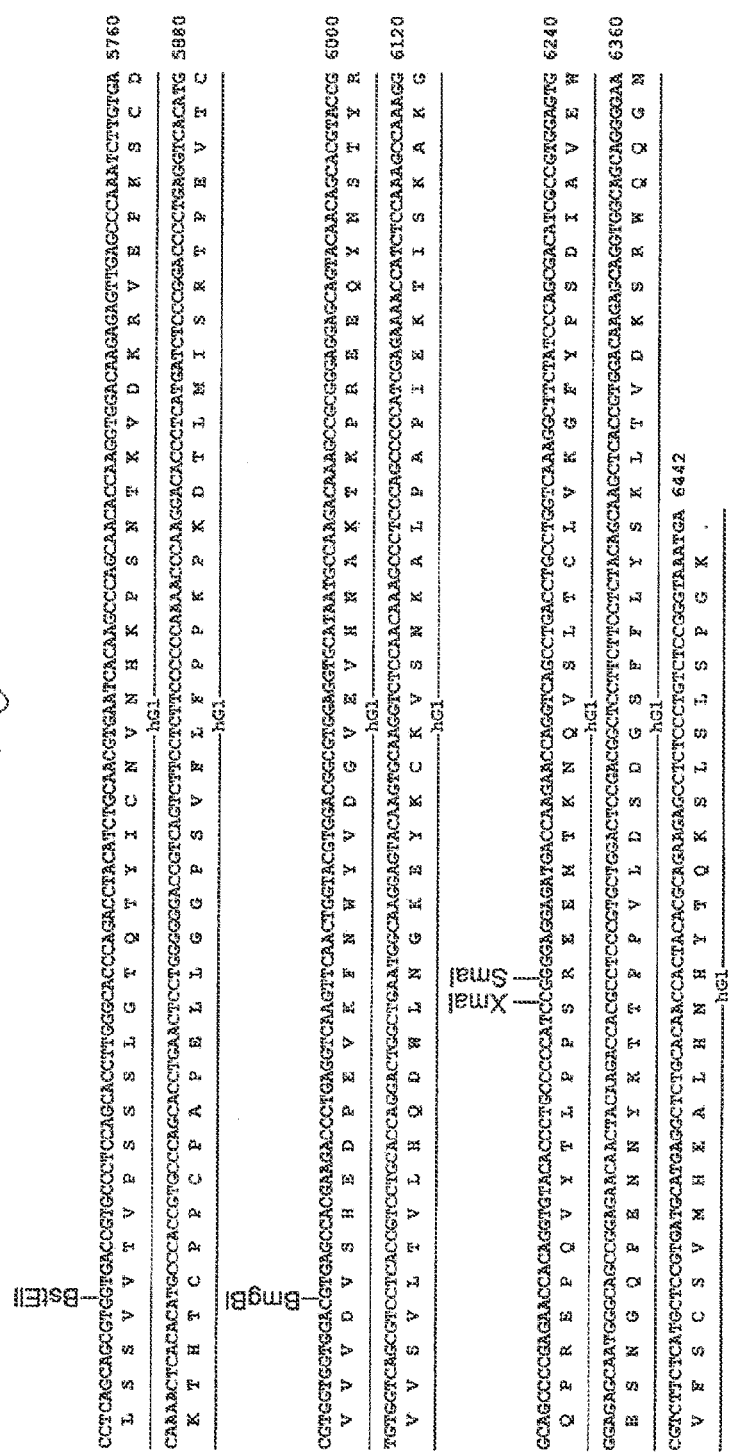
Figure 10D:
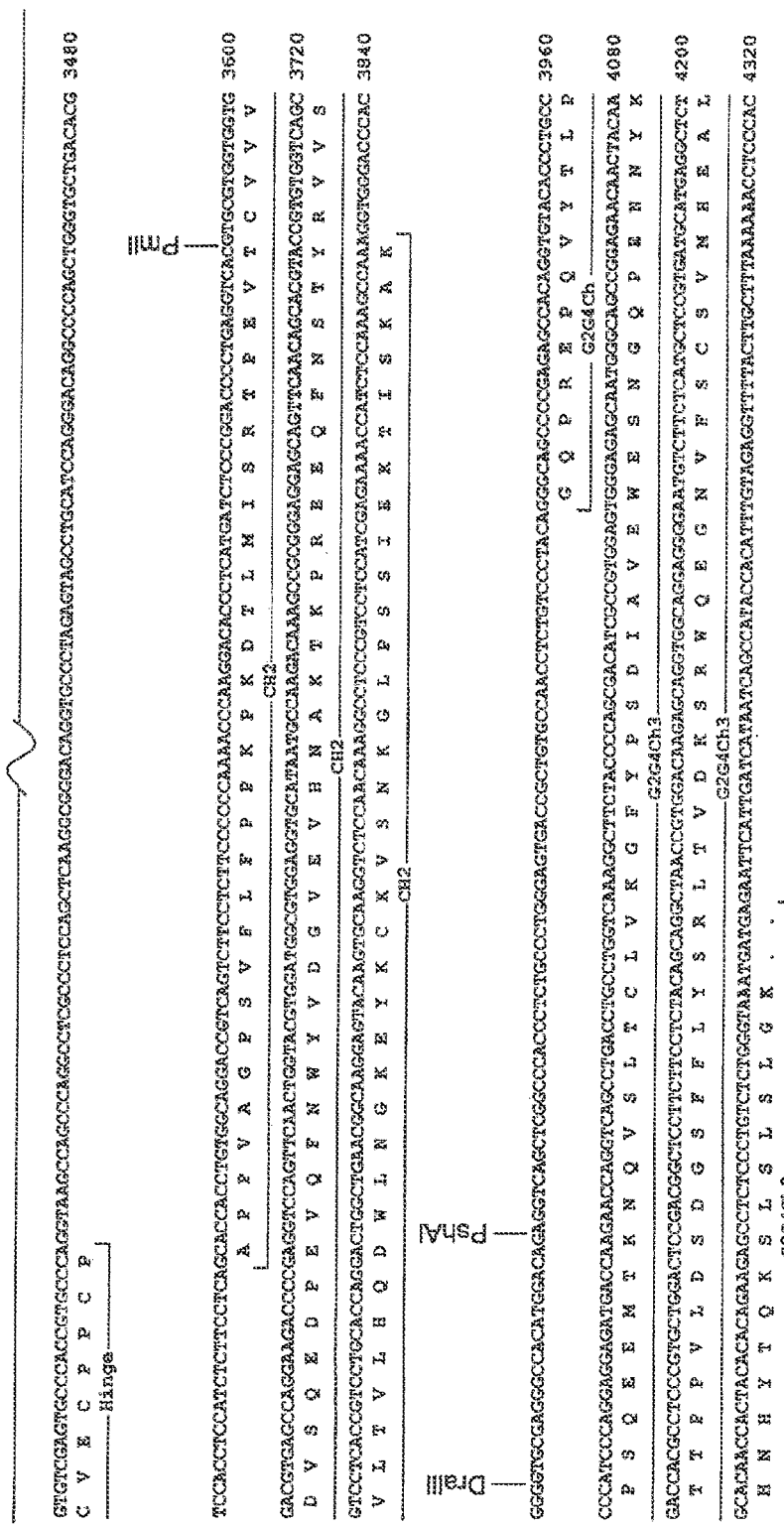

CD200 is a highly conserved type I transmembrane glycoprotein expressed on various cell types including cells of the immune system (e.g., T-cells, B-cells, and dendritic cells (Barclay et al., TRENDS Immunol. 2002: 23)) as well as certain cancer cells as shown herein. The protein interacts with its receptor CD200R on myeloid cells and sub-populations of T cells (Wright et al. J. Immunol. 2003 (171): 3034-3046 and Wright et al., Immunity 2000 (13):233-242); the CD200:CD200R interaction delivers an immunomodulatory signal to cells and induces immunosuppression including apoptosis-associated immune tolerance (Rosenblum et al. 2004 Blood (103): 2691-2698). Thus agents that interfere with the function or activity of CD200 and/or its receptor may inhibit or reverse the immunosuppressive effects of the CD200:CD200R interaction. In addition, agents that specifically bind CD200 (but that may or may not inhibit the CD200:CD200R interaction) may trigger downstream events that reverse or abolish the effects of CD200.

In certain aspects, the present disclosure relates to CD200 antagonists. As used herein, the term antagonist includes any agent that is capable of inhibiting the activity, function and/or the expression of CD200 or its receptor. Examples include but are not limited to polypeptides, antibodies, small molecules, aptamers, spiegelmers, locked nucleic acid (LNA) inhibitors, peptide nucleic acid (PNA) inhibitors, nucleic acid constructs (e.g., gene-targeting constructs, antisense constructs, RNA interference (RNAi) constructs, etc.) and peptidomimetics. In certain embodiments, the antagonist disrupts the interaction of CD200 and CD200R. In other embodiments, the CD200 antagonists are capable of decreasing the immunosuppressive effects of CD200 or are capable of targeting CD200-expressing cells for depletion or elimination.

In certain aspects, the CD200 antagonists are polypeptides. Polypeptides utilized in the present disclosure can be constructed using different techniques which are known to those skilled in the art. In one embodiment, the polypeptides are obtained by chemical synthesis. In other embodiments, the polypeptides are antibodies constructed from a fragment or several fragments of one or more antibodies. In further embodiments, the polypeptide is an anti-CD200 antibody as described herein.

Thus in certain embodiments, the CD200 antagonists are anti-CD200 antibodies. As used herein, the term "antibodies" refers to complete antibodies or antibody fragments capable of binding to CD200 or CD200R. Included are Fab, Fv, scFv, Fab' and F(ab')$_2$, monoclonal and polyclonal antibodies, engineered antibodies (including chimeric, single chain, CDR-grafted, humanized, fully human antibodies, and artificially selected antibodies), and synthetic or semi-synthetic antibodies produced using phage display or alternative techniques. Also included are antibodies engineered or produced in ways to contain variant or altered constant or Fc regions with either increased or decreased ability to bind one or more effector cell; such variant antibodies include but are not limited to antibodies in which the constant or Fc region contains altered glycosylation patterns. Small fragments, such as Fv and scFv, possess advantageous properties for diagnostic and therapeutic applications on account of their small size and consequent superior tissue distribution. Antibodies with engineered or variant constant or Fc regions can be useful in modulating effector functions, such as, for example, ADCC and CDC. Such antibodies with engineered or variant constant or Fc regions may be useful in instances where CD200 is expressed in normal tissue, for example; variant anti-CD200 antibodies without effector function in these instances may elicit the desired therapeutic response while not damaging normal tissue. Furthermore, antibodies, variant antibodies, and fragments thereof may be blocking (i.e., the said antibodies or fragments inhibit the interaction of CD200 and CD200R) or non-blocking (i.e., the said antibodies or fragments bind to CD200 but do not block its interaction with CD200R).

The disclosure also relates to anti-CD200 antibodies comprising heavy and light chains as provided herein, including heavy and light chains that are homologous or similar to the heavy and/or light chains provided herein. "Homology" or "identity" or "similarity" refers to sequence similarity between two peptides or between two nucleic acid molecules. Homology and identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. The term "homology" describes a mathematically based comparison of sequence similarities which is used to identify genes or proteins with similar functions or motifs. As used herein, "identity" means the percentage of identical nucleotide or amino acid residues at corresponding positions in two or more sequences when the sequences are aligned to maximize sequence matching, i.e., taking into account gaps and insertions. Thus methods to determine identity are designed to give the largest match between the sequences tested (see Computational Molecular Biology, Lesk, A. M., ed., Oxford University Press, New York, 1988; Biocomputing: Informatics and Genome Projects, Smith, D. W., ed., Academic Press, New York, 1993;

Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 1988, Devereux, J., et al., Nucleic Acids Research 12(1): 387 (1984), BLASTP, BLASTN, FASTA (Altschul, S. F. et al., J. Molec. Biol. 215: 403-410 (1990) and Altschul et al. Nuc. Acids Res. 25: 3389-3402 (1997)) and BLAST X (BLAST Manual, Altschul, S., et al., NCBI NLM NIH Bethesda, Md. 20894; Altschul, S., et al., J. Mol. Biol. 215: 403-410 (1990). A sequence which is "unrelated" or "non-homologous" shares less than 40% identity, though preferably less than 25% identity with a sequence of the present disclosure. In comparing two sequences, the absence of residues (amino acids or nucleic acids) or presence of extra residues also decreases the identity and homology/similarity.

Accordingly, the disclosure relates to antibodies as described herein without the leader sequences. Thus antibodies of the disclosure may comprise heavy and light chains (as described herein) in which the leader sequence is either absent or replaced by a different leader sequence. If host cells are used to produce antibodies of the present disclosure, appropriate leader sequences may therefore be selected according to the particular host cell used.

Antibodies may be produced by methods well known in the art. For example, monoclonal anti-CD200 antibodies may be generated using CD200 positive cells, CD200 polypeptide, or a fragment of CD200 polypeptide, as an immunogen, thus raising an immune response in animals from which antibody-producing cells and in turn monoclonal antibodies may be isolated. The sequence of such antibodies may be determined and the antibodies or variants thereof produced by recombinant techniques. Recombinant techniques may be used to produce chimeric, CDR-grafted, humanized and fully human antibodies based on the sequence of the monoclonal antibodies as well as polypeptides capable of binding to CD200.

Moreover, antibodies derived from recombinant libraries ("phage antibodies") may be selected using CD200-positive cells, or polypeptides derived therefrom, as bait to isolate the antibodies or polypeptides on the basis of target specificity. The production and isolation of non-human and chimeric anti-CD200 antibodies are well within the purview of the skilled artisan.

Recombinant DNA technology is used to improve the antibodies produced in non-human cells. Thus, chimeric antibodies may be constructed in order to decrease the immunogenicity thereof in diagnostic or therapeutic applications. Moreover, immunogenicity may be minimized by humanizing the antibodies by CDR grafting and, optionally, framework modification. See, U.S. Pat. No. 5,225,539, the contents of which are incorporated herein by reference.

Antibodies may be obtained from animal serum or, in the case of monoclonal antibodies or fragments thereof, produced in cell culture. Recombinant DNA technology may be used to produce the antibodies according to established procedure, including procedures in bacterial or preferably mammalian cell culture. The selected cell culture system preferably secretes the antibody product.

In another embodiment, a process for the production of an antibody disclosed herein includes culturing a host, e.g. *E. coli* or a mammalian cell, which has been transformed with a hybrid vector. The vector includes one or more expression cassettes containing a promoter operably linked to a first DNA sequence encoding a signal peptide linked in the proper reading frame to a second DNA sequence encoding the antibody protein. The antibody protein is then collected and isolated. Optionally, the expression cassette may include a promoter operably linked to polycistronic, for example bicistronic, DNA sequences encoding antibody proteins each individually operably linked to a signal peptide in the proper reading frame.

Multiplication of hybridoma cells or mammalian host cells in vitro is carried out in suitable culture media, which include the customary standard culture media (such as, for example Dulbecco's Modified Eagle Medium (DMEM) or RPMI 1640 medium), optionally replenished by a mammalian serum (e.g. fetal calf serum), or trace elements and growth sustaining supplements (e.g. feeder cells such as normal mouse peritoneal exudate cells, spleen cells, bone marrow macrophages, 2-aminoethanol, insulin, transferrin, low density lipoprotein, oleic acid, or the like). Multiplication of host cells which are bacterial cells or yeast cells is likewise carried out in suitable culture media known in the art. For example, for bacteria suitable culture media include medium LE, NZCYM, NZYM, NZM, Terrific Broth, SOB, SOC, 2×YT, or M9 Minimal Medium. For yeast, suitable culture media include medium YPD, YEPD, Minimal Medium, or Complete Minimal Dropout Medium.

In vitro production provides relatively pure antibody preparations and allows scale-up production to give large amounts of the desired antibodies. Techniques for bacterial cell, yeast, plant, or mammalian cell cultivation are known in the art and include homogeneous suspension culture (e.g. in an airlift reactor or in a continuous stirrer reactor), and immobilized or entrapped cell culture (e.g. in hollow fibres, microcapsules, on agarose microbeads or ceramic cartridges).

Large quantities of the desired antibodies can also be obtained by multiplying mammalian cells in vivo. For this purpose, hybridoma cells producing the desired antibodies are injected into histocompatible mammals to cause growth of antibody-producing tumors. Optionally, the animals are primed with a hydrocarbon, especially mineral oils such as pristane (tetramethyl-pentadecane), prior to the injection. After one to three weeks, the antibodies are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristane. After one to two weeks, ascitic fluid is taken from the animals.

The foregoing, and other, techniques are discussed in, for example, Kohler and Milstein, (1975) Nature 256:495-497; U.S. Pat. No. 4,376,110; Harlow and Lane, Antibodies: a Laboratory Manual, (1988) Cold Spring Harbor, the disclosures of which are all incorporated herein by reference. Techniques for the preparation of recombinant antibody molecules are described in the above references and also in, for example WO97/08320; U.S. Pat. No. 5,427,908; U.S. Pat. No. 5,508,717; Smith, 1985, Science, Vol. 225, pp 1315-1317; Parmley and Smith, 1988, Gene 73, pp 305-318; De La Cruz et al., 1988, Journal of Biological Chemistry, 2.63 pp 4318-4322; U.S. Pat. No. 5,403,484; U.S. Pat. No. 5,223,409; WO88/06630; WO92/15679; U.S. Pat. No. 5,780,279; U.S. Pat. No. 5,571,698; U.S. Pat. No. 6,040,136; Davis et al., 1999, Cancer Metastasis Rev., 18(4):421-5; Taylor, et al., Nucleic Acids Research 20 (1992): 6287-6295; Tomizuka et al., Proc. Natl. Academy of Sciences USA 97(2) (2000): 722-727. The contents of all these references are incorporated herein by reference.

The cell culture supernatants are screened for the desired antibodies, preferentially by immunofluorescent staining of CD200-positive cells, by immunoblotting, by an enzyme immunoassay, e.g. a sandwich assay or a dot-assay, or a radioimmunoassay.

For isolation of the antibodies, the immunoglobulins in the culture supernatants or in the ascitic fluid may be concentrated, e.g. by precipitation with ammonium sulfate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or (immuno-) affinity chromatography, e.g. affinity chromatography with one or more surface polypeptides derived from a CD200-positive cell line, or with Protein-A or -G.

Another embodiment provides a process for the preparation of a bacterial cell line secreting antibodies directed against CD200 in a suitable mammal. For example a rabbit is immunized with pooled samples from CD200-positive tissue or cells or CD200 polypeptide or fragments thereof A phage display library produced from the immunized rabbit is constructed and panned for the desired antibodies in accordance with methods well known in the art (such as, for example, the methods disclosed in the various references incorporated herein by reference).

Hybridoma cells secreting the monoclonal antibodies are also disclosed. The preferred hybridoma cells are genetically stable, secrete monoclonal antibodies described herein of the desired specificity, and can be activated from deep-frozen cultures by thawing and recloning.

In another embodiment, a process is provided for the preparation of a hybridoma cell line secreting monoclonal antibodies against CD200. In that process, a suitable mammal, for example a Balb/c mouse, is immunized with one or more polypeptides or antigenic fragments of CD200 or with one or more polypeptides or antigenic fragments derived from a CD200-positive cell, the CD200-positive cell itself, or an antigenic carrier containing a purified polypeptide as described. Antibody-producing cells of the immunized mammal are grown briefly in culture or fused with cells of a suitable myeloma cell line. The hybrid cells obtained in the fusion are cloned, and cell clones secreting the desired antibodies are selected. For example, spleen cells of Balb/c mice immunized with a CD200-positive Chronic Lymphocytic Leukemia (CLL) cell line are fused with cells of the myeloma cell line PAI or the myeloma cell line Sp2/0-Ag 14. The obtained hybrid cells are then screened for secretion of the desired antibodies and positive hybridoma cells are cloned.

Preferred is a process for the preparation of a hybridoma cell line, characterized in that Balb/c mice are immunized by injecting subcutaneously and/or intraperitoneally between $10^6$ and $10^7$ cells of a CD200-positive cell line several times, e.g. four to six times, over several months, e.g. between two and four months. Spleen cells from the immunized mice are taken two to four days after the last injection and fused with cells of the myeloma cell line PAI in the presence of a fusion promoter, preferably polyethylene glycol. Preferably, the myeloma cells are fused with a three- to twenty-fold excess of spleen cells from the immunized mice in a solution containing about 30% to about 50% polyethylene glycol of a molecular weight around 4000. After the fusion, the cells are expanded in suitable culture media as described hereinbefore, supplemented with a selection medium, for example HAT medium, at regular intervals in order to prevent normal myeloma cells from overgrowing the desired hybridoma cells.

The antibodies and fragments thereof can be "chimeric". Chimeric antibodies and antigen-binding fragments thereof comprise portions from two or more different species (e.g., mouse and human). Chimeric antibodies can be produced with mouse variable regions of desired specificity spliced into human constant domain gene segments (for example, U.S. Pat. No. 4,816,567). In this manner, non-human antibodies can be modified to make them more suitable for human clinical application.

The monoclonal antibodies of the present disclosure include "humanized" forms of the non-human (i.e., mouse) antibodies. Humanized or CDR-grafted mAbs are particularly useful as therapeutic agents for humans because they are not cleared from the circulation as rapidly as mouse antibodies and do not typically provoke an adverse immune reaction. Generally, a humanized antibody has one or more amino acid residues introduced into it from a non-human source. These non-human amino acid residues are often referred to as "import" residues, which are typically taken from an "import" variable domain. Methods of preparing humanized antibodies are generally well known in the art. For example, humanization can be essentially performed following the method of Winter and co-workers (Jones et al., Nature 321: 522-525 (1986); Reichmann et al., Nature, 332:323-327 (1988); Verheoeyen et al., Science, 239: 1534-1536 (1988)), by substituting rodent CDRs or CDR sequences for the corresponding sequences of a human antibody. Also see Staelens et al. 2006 Mol Immunol 43: 1243-1257. In particular embodiments, humanized forms of non-human (e.g., mouse) antibodies are human antibodies (recipient antibody) in which hypervariable (CDR) region residues of the recipient antibody are replaced by hypervariable region residues from a non-human species (donor antibody) such as a mouse, rat, rabbit, or non-human primate having the desired specificity, affinity, and binding capacity. In some instances, framework region residues of the human immunoglobulin are also replaced by corresponding non-human residues (so called "back mutations"). In addition, phage display libraries can be used to vary amino acids at chosen positions within the antibody sequence. The properties of a humanized antibody are also affected by the choice of the human framework. Furthermore, humanized and chimerized antibodies can be modified to comprise residues that are not found in the recipient antibody or in the donor antibody in order to further improve antibody properties, such as, for example, affinity or effector function.

Fully human antibodies are also provided in the disclosure. The term "human antibody" includes antibodies having variable and constant regions (if present) derived from human germline immunoglobulin sequences. Human antibodies can include amino acid residues not encoded by human germline immunoglobulin sequences (e.g., mutations introduced by random or site-specific mutagenesis in vitro or by somatic mutation in vivo). However, the term "human antibody" does not include antibodies in which CDR sequences derived from the germline of another mammalian species, such as a mouse, have been grafted onto human framework sequences (i.e., humanized antibodies). Fully human or human antibodies may be derived from transgenic mice carrying human antibody genes (carrying the variable (V), diversity (D), joining (J), and constant (C) exons) or from human cells. For example, it is now possible to produce transgenic animals (e.g., mice) that are capable, upon immunization, of producing a full repertoire of human antibodies in the absence of endogenous immunoglobulin production (see, e.g., Jakobovits et al., *PNAS;* 90:2551 (1993); Jakobovits et al., *Nature,* 362:255-258 (1993); Bruggermann et al., *Year in Immuno.,*

7:33 (1993); and Duchosal et al. *Nature* 355:258 (1992). Transgenic mice strain can be engineered to contain gene sequences from unrearranged human immunoglobulin genes. The human sequences may code for both the heavy and light chains of human antibodies and would function correctly in the mice, undergoing rearrangement to provide a wide antibody repertoire similar to that in humans. The transgenic mice can be immunized with the target protein (e.g., CD200, fragments thereof, or cells expressing CD200) to create a diverse array of specific antibodies and their encoding RNA. Nucleic acids encoding the antibody chain components of such antibodies may then be cloned from the animal into a display vector. Typically, separate populations of nucleic acids encoding heavy and light chain sequences are cloned, and the separate populations then recombined on insertion into the vector, such that any given copy of the vector receives a random combination of a heavy and a light chain. The vector is designed to express antibody chains so that they can be assembled and displayed on the outer surface of a display package containing the vector. For example, antibody chains can be expressed as fusion proteins with a phage coat protein from the outer surface of the phage. Thereafter, display packages can be screened for display of antibodies binding to a target.

In addition, human antibodies can be derived from phage-display libraries (Hoogenboom et al., *J. Mol. Biol.*, 227:381 (1991); Marks et al., *J. Mol. Biol.*, 222:581-597 (1991); Vaughan et al. *Nature Biotech* 14:309 (1996)). Synthetic phage libraries can be created which use randomized combinations of synthetic human antibody V-regions. By selection on antigen fully human antibodies can be made in which the V-regions are very human-like in nature. See U.S. Pat. Nos. 6,794,132, 6,680,209, 4,634,666, and Ostberg et al. (1983), *Hybridoma* 2:361-367, the contents of which are incorporated by reference.

For the generation of human antibodies, also see Mendez et al. *Nature Genetics* 15:146-156 (1997), Green and Jakobovits *J. Exp. Med.* 188:483-495 (1998), the disclosures of which are hereby incorporated by reference. Human antibodies are further discussed and delineated in U.S. Pat. Nos. 5,939,598 and 6,673,986. Also see U.S. Pat. Nos. 6,114,598, 6,075,181, and 6,162,963, all filed Jun. 5, 1995. Also see U.S. Pat. No. 6,150,584, filed Oct. 2, 1996 and U.S. Pat. Nos. 6,713,610 and 6,657,103 as well as U.S. patent application Ser. No. 10/421,011 (US 2003-0229905 A1), Ser. No. 10/455,013 (US 2004-0010810 A1), Ser. No. 10/627,250 (US 2004-0093622 A1), Ser. No. 10/656,623 (US 2006-0040363 A1), Ser. No. 10/658,521 (US 2005-0054055 A1), Ser. No. 10/917,703 (US 2005-0076395 A1) and Ser. No. 10/978,297 (US 2005-0287630 A1). See also PCT/US93/06926 filed on Jul. 23, 1993, European Patent No., EP 0 463 151 B1, grant published Jun. 12, 1996, International Patent Application No., WO 94/02602, published Feb. 3, 1994, International Patent Application No., WO 96/34096, published Oct. 31, 1996, and WO 98/24893, published Jun. 11, 1998. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661, 016, 5,770,429, 5,789,650, and 5,814,318 each to Lonberg and Kay, U.S. Pat. No. 5,591,669 to Krimpenfort and Berns, U.S. Pat. Nos. 5,612,205, 5,721,367, 5,789,215 to Berns et al., and U.S. Pat. No. 5,643,763 to Choi and Dunn, and GenPharm International. Also see U.S. Pat. Nos. 5,569,825, 5,877,397, 6,300,129, 5,874,299, 6,255,458, and 7,041,871, the disclosures of which are hereby incorporated by reference. See also European Patent No. 0 546 073 B1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884, the disclosures of which are hereby incorporated by reference in their entirety. See further Taylor et al. (1992 Nuc. Acids. Res., 20: 6287), Chen et al. (1993 Int. Immunol. 5: 647), Tuaillon et al. (1993 PNAS USA. 90: 3720-4), Choi et al., (1993 Nature Genetics 4: 117), Lonberg et al. (1994 Nature 368: 856-859), Taylor et al. (1994 International Immunology 6: 579-591), and Tuaillon et al. (1995 J. Immunol. 154: 6453-65), Fishwild et al. (1996 Nature Biotechnology 14: 845), and Tuaillon et al. (2000 Eur J. Immunol. 10: 2998-3005), the disclosures of which are hereby incorporated by reference in their entirety.

In certain embodiments, de-immunized anti-CD200 antibodies or antigen-binding fragments thereof are provided. De-immunized antibodies or antigen-binding fragments thereof may be modified so as to render the antibody or antigen-binding fragment thereof non-immunogenic, or less immunogenic, to a given species. De-immunization can be achieved by modifying the antibody or antigen-binding fragment thereof utilizing any of a variety of techniques known to those skilled in the art (see e.g., PCT Publication Nos. WO 04/108158 and WO 00/34317). For example, an antibody or antigen-binding fragment thereof may be de-immunized by identifying potential T cell epitopes and/or B cell epitopes within the amino acid sequence of the antibody or antigen-binding fragment thereof and removing one or more the potential T cell epitopes and/or B cell epitopes from the antibody or antigen-binding fragment thereof, for example, using recombinant techniques. The modified antibody or antigen-binding fragment thereof may then optionally be produced and tested to identify antibodies or antigen-binding fragments thereof that have retained one or more desired biological activities, such as, for example, binding affinity, but have reduced immunogenicity. Methods for identifying potential T cell epitopes and/or B cell epitopes may be carried out using techniques known in the art, such as, for example, computational methods (see e.g., PCT Publication No. WO 02/069232), in vitro or in silico techniques, and biological assays or physical methods (such as, for example, determination of the binding of peptides to MHC molecules, determination of the binding of peptide:MHC complexes to the T cell receptors from the species to receive the antibody or antigen-binding fragment thereof, testing of the protein or peptide parts thereof using transgenic animals with the MHC molecules of the species to receive the antibody or antigen-binding fragment thereof, or testing with transgenic animals reconstituted with immune system cells from the species to receive the antibody or antigen-binding fragment thereof, etc.). In various embodiments, the de-immunized anti-CD200 antibodies described herein include de-immunized antigen-binding fragments, Fab, Fv scFv, Fab' and F(ab')$_2$, monoclonal antibodies, murine antibodies, engineered antibodies (such as, for example, chimeric, single chain, CDR-grafted, humanized, fully human antibodies, and artificially selected antibodies), synthetic antibodies and semi-synthetic antibodies.

In a further embodiment, recombinant DNA comprising an insert coding for a heavy chain variable domain and/or for a light chain variable domain of antibodies directed to CD200 or a CD200-positive cell line are produced. The term DNA includes coding single stranded DNAs, double stranded DNAs consisting of said coding DNAs and of complementary DNAs thereto, or these complementary (single stranded) DNAs themselves.

Furthermore, DNA encoding a heavy chain variable domain and/or a light chain variable domain of antibodies directed to CD200 or the CD200-positive cell line can be enzymatically or chemically synthesized DNA having the authentic DNA sequence coding for a heavy chain variable domain and/or for the light chain variable domain, or a mutant thereof. A mutant of the authentic DNA is a DNA encoding a heavy chain variable domain and/or a light chain variable domain of the above-mentioned antibodies in which one or more amino acids are deleted, inserted, or exchanged with one or more other amino acids. Preferably said modification(s) are outside the CDRs of the heavy chain variable domain and/or of the light chain variable domain of the antibody in humanization and expression optimization applications. The term mutant DNA also embraces silent mutants wherein one or more nucleotides are replaced by other nucleotides with the new codons coding for the same amino acid(s). The term mutant sequence also includes a degenerate sequence. Degenerate sequences are degenerate within the meaning of the genetic code in that an unlimited number of nucleotides are replaced by other nucleotides without resulting in a change of the amino acid sequence originally encoded. Such degenerate sequences may be useful due to their different restriction sites and/or frequency of particular codons which are preferred by the specific host, particularly *E. coli*, to obtain an optimal expression of the heavy chain murine variable domain and/or a light chain murine variable domain.

The term mutant is intended to include a DNA mutant obtained by in vitro mutagenesis of the authentic DNA according to methods known in the art.

For the assembly of complete tetrameric immunoglobulin molecules and the expression of chimeric antibodies, the recombinant DNA inserts coding for heavy and light chain variable domains are fused with the corresponding DNAs coding for heavy and light chain constant domains, then transferred into appropriate host cells, for example after incorporation into hybrid vectors.

Recombinant DNAs including an insert coding for a heavy chain murine variable domain of an antibody directed to CD200 or a CD200-positive cell line fused to a human constant domain IgG, for example γ1, γ2, γ3 or γ4; in particular embodiments γ1 or γ4 may be used. Recombinant DNAs including an insert coding for a light chain murine variable domain of an antibody directed to the cell line disclosed herein fused to a human constant domain κ or preferably λ, are also provided.

Another embodiment pertains to recombinant DNAs coding for a recombinant polypeptide wherein the heavy chain variable domain and the light chain variable domain are linked by way of a spacer group, optionally comprising a signal sequence facilitating the processing of the antibody in the host cell and/or a DNA sequence encoding a peptide facilitating the purification of the antibody and/or a cleavage site and/or a peptide spacer and/or an agent. The DNA coding for an agent is intended to be a DNA coding for the agent useful in diagnostic or therapeutic applications. Thus, agent molecules which are toxins or enzymes, especially enzymes capable of catalyzing the activation of prodrugs, are particularly indicated. The DNA encoding such an agent has the sequence of a naturally occurring enzyme or toxin encoding DNA, or a mutant thereof, and can be prepared by methods well known in the art.

Accordingly, the monoclonal antibodies or antigen-binding fragments of the disclosure can be naked antibodies or antigen-binding fragments that are not conjugated to other agents, for example, a therapeutic agent or detectable label. Alternatively, the monoclonal antibody or antigen-binding fragment can be conjugated to an agent such as, for example, a cytotoxic agent, a small molecule, a hormone, an enzyme, a growth factor, a cytokine, a ribozyme, a peptidomimetic, a chemical, a prodrug, a nucleic acid molecule including coding sequences (such as antisense, RNAi, gene-targeting constructs, etc.), or a detectable label (e.g., an NMR or X-ray contrasting agent, fluorescent molecule, etc.). In certain embodiments, an anti-CD200 polypeptide or antigen-binding fragment (e.g., Fab, Fv, single-chain scFv, Fab' and F(ab')$_2$) is linked to a molecule that increases the half-life of the said polypeptide or antigen-binding fragment. Molecules that may be linked to said anti-CD200 polypeptide or antigen-binding fragment include but are not limited to serum proteins including albumin, polypeptides, other proteins or protein domains, and PEG.

Several possible vector systems are available for the expression of cloned heavy chain and light chain genes in mammalian cells. One class of vectors relies upon the integration of the desired gene sequences into the host cell genome. Cells which have stably integrated DNA can be selected by simultaneously introducing drug resistance genes such as *E. coli* gpt (Mulligan, R. C. and Berg, P., Proc. Natl. Acad. Sci., USA, 78: 2072 (1981)) or Tn5 neo (Southern, P. J. and Berg, P., J. Mol. Appl. Genet., 1: 327 (1982)). The selectable marker gene can be either linked to the DNA gene sequences to be expressed, or introduced into the same cell by co-transfection (Wigler, M. et al., Cell, 16: 77 (1979)). A second class of vectors utilizes DNA elements which confer autonomously replicating capabilities to an extrachromosomal plasmid. These vectors can be derived from animal viruses, such as bovine papillomavirus (Sarver, N. et al., Proc. Natl. Acad. Sci., USA, 79: 7147 (1982)), polyoma virus (Deans, R. J. et al., Proc. Natl. Acad. Sci., USA, 81: 1292 (1984)), or SV40 virus (Lusky, M. and Botchan, M., Nature, 293:79 (1981)).

Since an immunoglobulin cDNA is comprised only of sequences representing the mature mRNA encoding an antibody protein, additional gene expression elements regulating transcription of the gene and processing of the RNA are required for the synthesis of immunoglobulin mRNA. These elements may include splice signals, transcription promoters, including inducible promoters enhancers, and termination signals. cDNA expression vectors incorporating such elements include those described by Okayama, H. and Berg, P., Mol. Cell. Biol., 3: 280 (1983); Cepko, C. L. et al., Cell, 37: 1053 (1984); and Kaufman, R. J., Proc. Natl. Acad. Sci., USA, 82: 689 (1985).

In certain embodiments, an anti-CD200 antibody may be a blocking or non-blocking antibody. As used herein, a blocking antibody is one that blocks the interaction between CD200 and CD200R. A non-blocking antibody binds and/or interacts with CD200 but does not block its interaction with CD200R. Thus in certain embodiments, an anti-CD200 antibody is either a blocking or non-blocking murine, chimeric, humanized human or de-immunized antibody.

II. CD200 Antagonists with Altered Effector Functions

CD200 antagonists may be altered to elicit increased or decreased effects relative to the original or parent antagonist.

For example, an antagonist that binds CD200 may elicit secondary functions following binding to CD200 and, in some instances, inhibiting the CD200:CD200R interaction. For example, an antagonist may contain additional binding sites for other ligands, including receptors or extracellular proteins. Binding to these other ligands may trigger other events, such as the attraction or recruitment of other cells and the activation of various events including cell death. Thus in certain aspects, the present disclosure relates to CD200 antagonists that elicit altered secondary functions (or effector functions as referred to below). In certain embodiments, the CD200 antagonist with altered secondary or effector function(s) exhibits increased, decreased, or no secondary or effector function(s), and further may or may not block the CD200:CD200R interaction. In particular embodiments, the CD200 antagonist with altered secondary or effector function(s) is an anti-CD200 antibody.

A) Effector Functions

The interaction of antibodies and antibody-antigen complexes with cells of the immune system affects a variety of responses, referred to herein as effector functions. Exemplary effector functions include Fc receptor binding, phagocytosis, down-regulation of cell surface receptors (e.g. B cell receptor; BCR), etc. Other effector functions include ADCC, whereby antibodies bind Fc receptors on natural killer (NK) cells or macrophages leading to cell death, and CDC, which is cell death induced via activation of the complement cascade (reviewed in Daeron, Annu. Rev. Immunol. 15:203-234 (1997); Ward and Ghetie, Therapeutic Immunol. 2:77-94 (1995); and Ravetch and Kinet, Annu. Rev. Immunol. 9:457-492 (1991)). Such effector functions generally require the Fc region to be combined with a binding domain (e.g. an antibody variable domain) and can be assessed using various assays as herein disclosed, for example.

Several antibody effector functions, including ADCC, are mediated by Fc receptors (FcRs), which bind the Fc region of an antibody. In ADCC, NK cells or macrophages bind to the Fc region of the antibody complex and promote lysis of the target cell. The cross-linking of FcRs on NK cells triggers perforin/granzyme-mediated cytotoxicity, whereas in macrophages this cross-linking promotes the release of mediators such as nitric oxide (NO), TNF-α, and reactive oxygen species. For CD200-positive target cells, an anti-CD200 antibody binds to the target cell and the Fc region directs effector function to the target cell. The affinity of an antibody for a particular FcR, and hence the effector activity mediated by the antibody, may be modulated by altering the amino acid Sequence and/or post-translational modifications of the Fc and/or constant region of the antibody.

FcRs are defined by their specificity for immunoglobulin isotypes; Fc receptors for IgG antibodies are referred to as FcγR, for IgE as FcεR, for IgA as FcαR and so on. Three subclasses of FcγR have been identified: FcγRI (CD64), FcγRII (CD32) and FcγRIII (CD16). Because each FcγR subclass is encoded by two or three genes, and alternative RNA splicing leads to multiple transcripts, a broad diversity in FcγR isoforms exists. The three genes encoding the FcγRI subclass (FcγRIA, FcγRIB and FcγRIC) are clustered in region 1q21.1 of the long arm of chromosome I; the genes encoding FcγRII isoforms (FcγRIIA, FcγRIIB and FcγRIIC) and the two genes encoding FcγRII (FcγRIIIA and FcγRIIIB) are all clustered in region 1q22. These different FcR subtypes are expressed on different cell types (reviewed in Ravetch and Kinet, Annu. Rev. Immunol. 9:457-492 (1991)). For example, in humans, FcγRIIIB is found only on neutrophils, whereas FcγRIIIA is found on macrophages, monocytes, natural killer (NK) cells, and a subpopulation of T-cells. Notably, FcγRIIIA is the only FcR present on NK cells, one of the cell types implicated in ADCC.

FcγRI, FcγRII and FcγRIII are immunoglobulin superfamily (IgSF) receptors; FcγRI has three IgSF domains in its extracellular domain, while FcγRII and FcγRIII have only two IgSF domains in their extracellular domains. Another type of Fc receptor is the neonatal Fc receptor (FcRn). FcRn is structurally similar to major histocompatibility complex (MHC) and consists of an α-chain noncovalently bound to β2-microglobulin.

The binding site on human and murine antibodies for FcγR have been previously mapped to the so-called "lower hinge region" consisting of residues 233-239 (EU index numbering as in Kabat et al., Sequences of Proteins of Immunological Interest, 5th Ed. Public Health Service, National Institutes of Health, Bethesda, Md. (1991)). Woof et al. Molec. Immunol. 23:319-330 (1986); Duncan et al. Nature 332:563 (1988); Canfield and Morrison, J. Exp. Med. 173:1483-1491 (1991); Chappel et al., Proc. Natl. Acad. Sci. USA 88:9036-9040 (1991). Of residues 233-239, P238 and S239 have been cited as possibly being involved in binding.

Other previously cited areas possibly involved in binding to FcγR are: G316-K338 (human IgG) for human FcγRI (by sequence comparison only; no substitution mutants were evaluated) (Woof et al. Molec Immunol. 23:319-330 (1986)); K274-R301 (human IgG1) for human FcγRIII (based on peptides) (Sarmay et al. Molec. Immunol. 21:43-51 (1984)); Y407-R416 (human IgG) for human FcγRIII (based on peptides) (Gergely et al. Biochem. Soc. Trans. 12:739-743 (1984)); as well as N297 and E318 (murine IgG2b) for murine FcγRII (Lund et al., Molec. Immunol., 29:53-59 (1992)).

Human effector cells are leukocytes which express one or more FcRs and perform effector functions. In certain embodiments, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils. Effector cells may be isolated from a native source thereof, e.g. from blood or PBMCs.

In CDC, the antibody-antigen complex binds complement, resulting in the activation of the complement cascade and generation of the membrane attack complex. Activation of the classical complement pathway is initiated by the binding of the first component of the complement system (C1q) to antibodies (of the appropriate subclass) which are bound to their cognate antigen; thus the activation of the complement cascade is regulated in part by the binding affinity of the immunoglobulin to C1q protein. C1q and two serine proteases, C1r and C1s, form the complex C1, the first component of the CDC pathway. C1q is a hexavalent molecule with a molecular weight of approximately 460,000 and a structure in which six collagenous "stalks" are connected to six globular head regions. Burton and Woof, Advances in Immunol. 51:1-84 (1992). To activate the complement cascade, it is necessary for C1q to bind to at least two molecules of IgG1, IgG2, or IgG3, but only one molecule of IgM, attached to the antigenic target (Ward and Ghetie, Therapeutic Immunology 2:77-94 (1995) p. 80). To assess complement activation, a CDC assay, e.g. as described in Gazzano-Santoro et al., J. Immunol. Methods 202:163 (1996), may be performed.

It has been proposed that various residues of the IgG molecule are involved in binding to C1q including the Glu318, Lys320 and Lys322 residues on the CH2 domain, amino acid residue 331 located on a turn in close proximity to the same beta strand, the Lys235 and Gly237 residues located in the lower hinge region, and residues 231 to 238 located in the N-terminal region of the CH2 domain (see e.g., Xu et al., J. Immunol. 150:152A (Abstract) (1993), WO94/29351; Tao et al, J. Exp. Med., 178:661-667 (1993); Brekke et al., Eur. J. Immunol, 24:2542-47 (1994); Burton et al; Nature, 288:338-344 (1980); Duncan and Winter, Nature 332:738-40 (1988); U.S. Pat. No. 5,648,260, and U.S. Pat. No. 5,624,821). It has further been proposed that the ability of IgG to bind C1q and activate the complement cascade also depends on the presence, absence or modification of the carbohydrate moiety positioned between the two CH2 domains (which is normally anchored at Asn297) (Ward and Ghetie, Therapeutic Immunology 2:77-94 (1995). In certain embodiments, one or more of these residues may be modified, substituted, or removed or one or more amino acid residues may be inserted so as to enhance or decrease CDC activity of the anti-CD200 antibodies provided herein.

B) Anti-CD200 Antibodies with Modulated Effector Function(s)

Effector functions involving the constant region of the target-specific antibody may be modulated by altering properties of the constant or Fc region. Altered effector functions include, for example, a modulation in one or more of the following activities: ADCC, CDC, apoptosis, binding to one or more Fc-receptors, and pro-inflammatory responses. Modulation refers to an increase, decrease, or elimination of an activity compared to the activity of a second antibody. In certain embodiments, the second antibody is an antibody with effector function. The second antibody may be an engineered antibody or a naturally occurring antibody and may be referred to as a non-variant, native, or parent antibody. In particular embodiments, modulation includes situations in which an activity is abolished or completely absent. Further, in some instances, a non-variant antibody may exhibit effector function activity similar or equivalent to the activity of the chC2aB7-hG1 or the hB7V3V2-hG1 antibodies disclosed herein. Likewise, a functional or non-variant constant or Fc region may possess an effector function of a native constant or Fc domain; in some instances, the constant or Fc region of chC2aB7-hG1 or hB7V3V2-hG1 may represent the non-variant domains. For present purposes, chC2aB7-hG1 and hB7V3V2-hG1 are the standards against which the activities of other antibodies are compared, with hB7V3V2-hG1 being the preferred standard.

A polypeptide variant with altered FcR binding affinity and/or ADCC activity and/or altered CDC activity is a polypeptide which has either enhanced or diminished FcR binding activity and/or ADCC activity and/or CDC activity compared to the native or parent polypeptide or to a polypeptide comprising a native sequence Fc or constant region. A polypeptide variant which displays increased binding to an FcR binds at least one FcR with greater affinity than the parent polypeptide. A polypeptide variant which displays decreased binding to an FcR binds at least one FcR with lower affinity than a parent polypeptide. Such variants which display decreased binding to an FcR may possess little or no appreciable binding to an FcR, e.g., 0-20% binding to the FcR compared to the level of binding of a native sequence immunoglobulin constant or Fc region to the FcR. Similarly a polypeptide variant which displays altered ADCC and/or CDC activity may exhibit either increased or reduced ADCC and/or CDC activity compared to the native or parent polypeptide. A polypeptide variant which displays reduced ADCC and/or CDC may exhibit reduced or no ADCC or CDC activity as shown herein by example. In certain embodiments, the parent or native polypeptide and its variant are antibodies or antigen-binding fragments. In particular embodiments, the said antibody or antigen-binding fragment binds CD200 and may or may not block the CD200:CD200R interaction.

A native sequence Fc or constant region comprises an amino acid sequence identical to the amino acid sequence of a Fc or constant chain region found in nature. A variant or altered Fc or constant region comprises an amino acid sequence which differs from that of a native sequence heavy chain region by virtue of at least one amino acid modification, insertion, or deletion, for example. In certain embodiments, the variant or altered constant region has at least one amino acid substitution, insertion, and/or deletion, compared to a native sequence constant region or to the constant region of a parent polypeptide, e.g. from about one to about one hundred amino acid substitutions, insertions, and/or deletions in a native sequence constant region or in the constant region of the parent polypeptide. In some embodiments, the variant or altered constant region herein will possess at least about 70% homology (similarity) or identity with a native sequence constant region and/or with a constant region of a parent polypeptide, and in some instances at least about 75% and in other instances at least about 80% homology or identity therewith, and in other embodiments at least about 85%, 90% or 95% homology or identity therewith. The variant or altered constant region may also contain one or more amino acid deletions or insertions. Additionally, the variant constant region may contain one or more amino acid substitutions, deletions, or insertions that results in altered post-translational modifications, including, for example, an altered glycosylation pattern.

Variant anti-CD200 antibodies as presently disclosed may be encoded by a nucleic acid sequence that encodes a polypeptide with one or more amino acid insertions, deletions, or substitutions relative to the native or parent polypeptide sequence. Furthermore, variant antibodies may be encoded by nucleic acid sequences that hybridize under stringent conditions to a nucleic acid sequence encoding a variant anti-CD200 antibody. A variety of conditions may be used to detect hybridization, and the stringency is determined primarily by the wash stage of the hybridization assay. Generally high temperatures and low salt concentrations give high stringency, while low temperatures and high salt concentrations give low stringency. Low stringency hybridization is achieved by washing in, for example, about 2.0×SSC at 50° C., and high stringency is achieved with about 0.2×SSC at 50° C.

Antibodies or antigen-binding fragments thereof with altered or no effector functions may be generated by engineering or producing antibodies with variant constant, Fc, or heavy chain regions; recombinant DNA technology and/or cell culture and expression conditions may be used to produce antibodies with altered function and/or activity. For example, recombinant DNA technology may be used to engineer one or more amino acid substitutions, deletions, or insertions in regions (such as, for example, Fc or constant regions) that affect antibody function including effector functions. Alternatively, changes in post-translational modifications, such as, e.g. glycosylation patterns, may be achieved by manipulating the cell culture and expression conditions by which the antibody is produced.

Accordingly, certain aspects and methods of the present disclosure relate to anti-CD200 antibodies with altered effector functions that comprise one or more amino acid substitutions, insertions, and/or deletions. In certain embodiments, such a variant anti-CD200 antibody exhibits reduced or no effector function. In particular embodiments, a variant antibody comprises a G2/G4 construct in place of the G1 domain (see FIGS. 10, 11, 12, 13, and 15, for example).

In addition to swapping the G1 domain with a G2/G4 construct as presented herein, anti-CD200 antibodies with reduced effector function may be produced by introducing other types of changes in the amino acid sequence of certain regions of the antibody. Such amino acid sequence changes include but are not limited to the Ala-Ala mutation described by Bluestone et al. (see WO 94/28027 and WO 98/47531; also see Xu et al. 2000 Cell Immunol 200; 16-26). Thus in certain embodiments, anti-CD200 antibodies with mutations within the constant region including the Ala-Ala mutation may be used to reduce or abolish effector function. According to these embodiments, the constant region of an anti-CD200 antibody comprises a mutation to an alanine at position 234 or a mutation to an alanine at position 235. Additionally, the constant region may contain a double mutation: a mutation to an alanine at position 234 and a second mutation to an alanine at position 235. In one embodiment, the anti-CD200 antibody comprises an IgG4 framework, wherein the Ala-Ala mutation would describe a mutation(s) from phenylalanine to alanine at position 234 and/or a mutation from leucine to alanine at position 235. In another embodiment, the anti-CD200 antibody comprises an IgG1 framework, wherein the Ala-Ala mutation would describe a mutation(s) from leucine to alanine at position 234 and/or a mutation from leucine to alanine at position 235. An anti-CD200 antibody may alternatively or additionally carry other mutations, including the point mutation K322A in the CH2 domain (Hezareh et al. 2001 J Virol. 75: 12161-8). An antibody with said mutation(s) in the constant region may furthermore be a blocking or non-blocking antibody.

Changes within the hinge region also affect effector functions. For example, deletion of the hinge region may reduce affinity for Fc receptors and may reduce complement activation (Klein et al. 1981 PNAS USA 78: 524-528). The present disclosure therefore also relates to antibodies with alterations in the hinge region.

In particular embodiments, anti-CD200 antibodies may be modified to either enhance or inhibit complement dependent cytotoxicity (CDC). Modulated CDC activity may be achieved by introducing one or more amino acid substitutions, insertions, or deletions in an Fc region of the antibody (see, e.g., U.S. Pat. No. 6,194,551). Alternatively or additionally, cysteine residue(s) may be introduced in the Fc region, thereby allowing interchain disulfide bond formation in this region. The homodimeric antibody thus generated may have improved or reduced internalization capability and/or increased or decreased complement-mediated cell killing. See Caron et al., 3. Exp Med. 176:1191-1195 (1992) and Shopes, B. J. Immunol. 148:2918-2922 (1992), WO99/51642, Duncan & Winter Nature 322: 738-40 (1988); U.S. Pat. No. 5,648,260; U.S. Pat. No. 5,624,821; and WO94/29351. Homodimeric antibodies with enhanced anti-tumor activity may also be prepared using heterobifunctional cross-linkers as described in Wolff et al. Cancer Research 53:2560-2565 (1993). Alternatively, an antibody can be engineered which has dual Fc regions and may thereby have enhanced complement lysis and ADCC capabilities. See Stevenson et al. Anti-Cancer Drug Design 3:219-230 (1989).

Another potential means of modulating effector function of antibodies includes changes in glycosylation. This topic has been recently reviewed by Raju who summarized the proposed importance of the oligosaccharides found on human IgGs with their degree of effector function (Raju, T S. Bio-Process International April 2003. 44-53). According to Wright and Morrison, the microheterogeneity of human IgG oligosaccharides can affect biological functions such as CDC and ADCC, binding to various Fc receptors, and binding to C1q protein (Wright A. & Morrison S L. TIBTECH 1997, 15 26-32). It is well documented that glycosylation patterns of antibodies can differ depending on the producing cell and the cell culture conditions (Raju, T S. BioProcess International April 2003. 44-53). Such differences can lead to changes in both effector function and pharmacokinetics (Israel et al. Immunology. 1996; 89(4):573-578; Newkirk et al. P. Clin. Exp. 1996; 106(2):259-64). Differences in effector function may be related to the IgGs ability to bind to the Fcγ receptors (FcγRs) on the effector cells. Shields, et al., have shown that IgG, with variants in amino acid sequence that have improved binding to FcγR, can exhibit up to 100% enhanced ADCC using human effector cells (Shields et al. J Biol. Chem. 2001 276(9):6591-604). While these variants include changes in amino acids not found at the binding interface, both the nature of the sugar component as well as its structural pattern may also contribute to the differences observed. In addition, the presence or absence of fucose in the oligosaccharide component of an IgG can improve binding and ADCC (Shields et al. J Biol. Chem. 2002; 277(30):26733-40). An IgG that lacked a fucosylated carbohydrate linked to $Asn^{297}$ exhibited normal receptor binding to the Fcγ receptor. In contrast, binding to the FcγRIIA receptor was improved 50% and accompanied by enhanced ADCC, especially at lower antibody concentrations.

Work by Shinkawa, et al., demonstrated that an antibody to the human IL-5 receptor produced in a rat hybridoma showed more than 50% higher ADCC when compared to the antibody produced in Chinese hamster ovary cells (CHO) (Shinkawa et al. J Biol Chem. 2003 278(5):3466-73). Monosaccharide composition and oligosaccharide profiling showed that the rat hybridoma-produced IgG had a lower content of fucose than the CHO-produced protein. The authors concluded that the lack of fucosylation of an IgG1 has a critical role in enhancement of ADCC activity.

A different approach was taken by Umana, et al., who changed the glycosylation pattern of chCE7, a chimeric IgG1 anti-neuroblastoma antibody (Umana et al. Nat. Biotechnol. 1999 February; 17(2): 176-80). Using tetracycline, they regulated the activity of a glycosyltransferase enzyme (GrmII) which bisects oligosaccharides that have been implicated in ADCC activity. The ADCC activity of the parent antibody was barely above background level. Measurement of ADCC activity of the chCE7 produced at different tetracycline levels showed an optimal range of GnTIH expression for maximal chCE7 in vitro ADCC activity. This activity correlated with the level of constant region-associated, bisected complex oligosaccharide. Newly optimized variants exhibited substantial ADCC activity. Similarly, Wright and Morrison produced antibodies in a CHO cell line deficient in glycosylation (1994 J Exp Med 180: 1087-1096) and showed that antibodies produced in this cell line were incapable of complement-mediated cytolysis. Thus as known alterations that affect effector function include modifications in the glycosylation pattern or a change in the number of glycosylated residues, the present disclosure relates to a CD200 antibody wherein glycosylation is altered to either enhance or decrease effector function(s) including ADCC and CDC. Altered glycosylation includes a decrease or increase in the number of glycosylated residues as well as a change in the pattern or location of glycosylated residues.

Still other approaches exist for the altering effector function of antibodies. For example, antibody-producing cells can be hypermutagenic, thereby generating antibodies with randomly altered nucleotide and polypeptide residues throughout an entire antibody molecule (see WO 2005/011735). Hypermutagenic host cells include cells deficient in DNA mismatch repair. Antibodies produced in this manner may be less antigenic and/or have beneficial pharmacokinetic properties. Additionally, such antibodies may be selected for properties such as enhanced or decreased effector function(s).

It is further understood that effector function may vary according to the binding affinity of the antibody. For example, antibodies with high affinity may be more efficient in activating the complement system compared to antibodies with relatively lower affinity (Marzocchi-Machado et al. 1999 Immunol invest 28: 89-101). Accordingly, an antibody may be altered such that the binding affinity for its antigen is reduced (e.g., by changing the variable regions of the antibody by methods such as substitution, addition, or deletion of one or more amino acid residues). An anti-CD200 antibody with reduced binding affinity may exhibit reduced effector functions, including, for example, reduced ADCC and/or CDC.

III. Methods of Depleting or Eliminating Cells Overexpressing CD200

In accordance with the present disclosure, methods are provided for depleting cells that express CD200 in a subject by administering to the subject a therapy comprising a CD200 antagonist. As mentioned above, CD200 is expressed on certain immune cells; and as demonstrated in the present disclosure, CD200 is also expressed on certain malignant cells. The disparate expression of CD200 provides an avenue by which to target cancer cells (i.e., CD200-positive cells) for therapy. Likewise, CD200-positive immune cells may be targeted for depletion in methods of treating autoimmune disorders.

CD200, through its interaction with CD200R on myeloid cells, modulates immunosuppression by delivering an inhibitory signal for myeloid activity and/or migration. CD200-knockout mice, for example, demonstrate a more active immune response following immunogenic stimuli (Hoek et al. *Science* 2000), and CD200-expressing cells elicit immunosuppression by inducing a shift in the cytokine profile of stimulated immune cells (see data shown herein). Specifically, CD200-positive cells are capable of inducing a shift from Th1 to Th2 cytokine production in mixed cell population assays. While CD200-positive cells are capable of suppressing the immune response, CD200-positive cancer cells, accordingly, may be capable of escaping immune cell attack. However expression of CD200 on the membrane of cancer cells as well as immune cells can be exploited to target these cells in therapy. For example, an anti-CD200 antagonist can specifically target CD200-positive cells and disrupt the CD200:CD200R interaction, thereby inhibiting immune suppression, as well as target CD200-positive cells to immune effector cells. The embodiments of this disclosure, therefore, relate to methods of targeting CD200-positive cells for depletion comprising an antagonist that binds to CD200 and, in some instances, disrupts the CD200:CD200R interaction.

In certain embodiments, the present disclosure relates to methods of enhancing the immune response. Such methods include administering a therapy comprising a CD200 antagonist, and in particular embodiments the antagonist is an anti-CD200 antibody or antigen-binding fragment as set forth herein. While not wishing to be bound by any particular mechanism(s), a blocking anti-CD200 antibody, antigen-binding fragment, polypeptide, or other antagonist may eliminate CD200-positive cells by blocking immune suppression, thereby allowing immune cells to attack and eliminate CD200-positive cells. Alternatively or in combination with the aforementioned mechanism, an anti-CD200 antibody (either blocking or non-blocking) or other antagonist may recruit effector cells or other ligands (e.g., complement component) to the CD200-positive cell to which the antibody or antagonist is bound and target the CD200-positive cell for effector-mediated cell death.

In one aspect, the present disclosure relates to methods of modulating ADCC and/or CDC of CD200-positive target cells by administering a murine, chimeric, humanized, or human anti-CD200 antibody to a subject in need thereof. The disclosure relates to variant anti-CD200 antibodies that elicit increased ADCC and/or CDC and to variant anti-CD200 antibodies that exhibit reduced or no ADCC and/or CDC activity.

In one embodiment, the variant anti-CD200 antibody comprises a variant or altered Fc or constant region, wherein the variant Fc or constant region exhibits increased effector function. Such said variant region may contain one or more amino acid substitutions, insertions, or deletions. Alternatively or additionally, the variant or altered Fc or constant region may comprise altered post-translational modifications, including, for example, an altered glycosylation pattern. An altered glycosylation pattern includes an increase or decrease in the number of glycosydic bonds and/or a modification in the location (i.e., amino acid residue number) of one or more glycosydic bonds.

In another embodiment, the disclosure relates to methods of depleting or eliminating CD200-positive cells comprising variant anti-CD200 antibodies that exhibit reduced or no ADCC and/or CDC activity. In one embodiment, the variant anti-CD200 antibody comprises a variant or altered Fc or constant region, wherein the variant Fc or constant region exhibits decreased or no effector function. Such said variant or altered Fc or constant region may contain one or more amino acid substitutions, insertions, or deletions. Alternatively or additionally, the variant Fc or constant region may comprise altered post-translational modifications, including but not limited to an altered glycosylation pattern. Examples of altered glycosylation patterns are described above.

In a further embodiment, a murine, chimeric, humanized, human or de-immunized anti-CD200 antibody administered to a patient is a non-blocking antibody. The non-blocking anti-CD200 antibody may be a variant antibody as described above and may consequently exhibit modulated effector function(s). For example, a variant anti-CD200 antibody may not block the CD200:CD200R interaction and may also comprise a variant constant region that elicits increased effector function, such as, e.g., increased ADCC.

A) Methods of Treating Patients with Autoimmune Disorders

In certain aspects, the disclosure relates to treating patients with autoimmune disorders with a therapy comprising a CD200 antagonist. In certain embodiments, the antagonist is an anti-CD200 antibody or antigen-binding fragment thereof. In other embodiments, the anti-CD200 antibody or fragment thereof is a variant anti-CD200 antibody that exhibits modulated effector activity. For example, the variant antibody may comprise a variant or altered constant region capable of eliciting increased or enhanced effector function, such as, for example, ADCC. Additionally, the said antibody may be a non-blocking antibody and may be a murine, chimeric, humanized, human or de-immunized anti-CD200 antibody. Thus, methods of treating patients with autoimmune disorders may comprise any of the CD200 antagonists and antibodies as set forth in the present disclosure.

In certain embodiments, anti-CD200 antibodies or CD200 antagonists may be used for depleting any type of cell that expresses CD200 on its surface, including, for example, immune cells such as T-cells, B-cells, and dendritic cells. In one embodiment, anti-CD200 antibodies may be useful for targeted destruction of immune cells involved in an unwanted immune response, such as, for example, immune responses associated with an autoimmune disorder, transplants, allergies, or inflammatory disorders. Exemplary autoimmune diseases and disorders that may be treated with the anti-CD200 antibodies provided herein include, for example, inflammatory responses such as inflammatory skin diseases including psoriasis and dermatitis (e.g. atopic dermatitis); dermatomyositis; systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e.g. Type I diabetes mellitus or insulin dependent diabetes mellitis); multiple sclerosis; Reynaud's syndrome; autoimmune thyroiditis; allergic encephalomyelitis; Sjogren's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Bechet disease; giant cell arteritis; immune complex nephritis; IgA nephropathy; IgM polyneuropathies; immune thrombocytopenic purpura (ITP) or autoimmune thrombocytopenia and autoimmune hemolytic diseases, Hashimoto's thyroiditis, etc.

In accordance with the methods and compositions described herein, the disclosure also relates to methods of treating a transplant or allograft patient. An anti-CD200 antibody or other CD200 antagonist of the present disclosure may be administered to a patient prior to a transplant or allograft procedure or after the procedure in order to decrease or eliminate CD200-positive immune cells that could reduce the patient's acceptance of the transplanted organ or tissue. In a particular embodiment, an anti-CD200 antibody with increased effector function is given to a transplant patient. In addition, an anti-CD200 antibody is a non-blocking antibody.

Therapies comprising CD200 antagonists or antibodies may be administered to patients in combination therapies. Accordingly, targeted killing of certain populations of immune cells for treating or preventing autoimmune disorders, enhancing or extending transplant survival, treating or preventing allergies, or treating or preventing inflammatory disorders, may be administered as part of a combination therapy. For example, a patient receiving a first therapy comprising a CD200 antagonist (e.g., an anti-CD200 antibody described herein) may also be given a second therapy. The CD200 antagonist may be given simultaneously with the second therapy. Alternatively, the CD200 antagonist may be given prior to or following the second therapy. Second therapies include but are not limited to anti-inflammatory agents, immunosuppressive agents, and/or anti-infective agents.

Combination therapies of the present disclosure include, for example, a CD200 antagonist as described herein administered concurrently or sequentially in series with steroids, anti-malarials, aspirin, non-steroidal anti-inflammatory drugs, immunosuppressants, or cytotoxic drugs. Included are corticosteroids (e.g. prednisone, dexamethasone, and prednisolone), methotrexatem, methylprednisolone, macrolide immunosuppressants (e.g. sirolimus and tacrolimus), mitotic inhibitors (e.g. azathioprine, cyclophosphamide, and methotrexate), fungal metabolites that inhibit the activity of T lymphocytes (e.g. cyclosporine), mycophenolate mofetil, glatiramer acetate, and cytotoxic and DNA-damaging agents (e.g. chlorambucil). For autoimmune disorders and allograft or transplant patients, anti-CD200 therapy may be combined with antibody treatments including daclizumab, a genetically engineered human IgG1 monoclonal antibody that binds specifically to the α-chain of the interleukin-2 receptor, as well as various other antibodies targeting immune cells or other cells. Such combination therapies may be useful in the treatment of type 1 diabetes, rheumatoid arthritis, lupus, and idiopathic thrombocytopenic purpura, and other autoimmune indications. The disclosure also relates to therapies for autoimmune disorders and for transplant patients comprising a CD200 antagonist (such as, for example, the antibodies and variants thereof described in the present disclosure) conjugated to one or more agent.

B) Methods of Treating Patients with Cancer

In one aspect, the disclosure provides a method of treating cancer in which an agent that disrupts or inhibits the interaction of CD200 with its receptor is administered to a subject. Disruption of the CD200:CD200R interaction subsequently reverses or inhibits immune suppression, thus enhancing the immune response. Possible agents for the disruption of the CD200:CD200R interaction include, for example, small molecules, chemicals, polypeptides, inorganic molecules, and organometallic compounds. The CD200:CD200R interaction may also be inhibited by reducing the expression of either the membrane protein or its receptor via antisense, RNAi, or gene therapy. Additionally, a polypeptide specific for CD200 or CD200R, such as an anti-CD200- or anti-CD200R-specific antibody or fragments thereof, may inhibit the immunosuppressive effects of the CD200:CD200R interaction.

Cancer cells that may be treated by a CD200 antagonist include any cancer cells that exhibit CD200 expression or CD200 up-regulation. Cancers for which anti-CD200 therapy may be used include, for example, ovarian, melanoma, myeloma, neuroblastoma, renal, breast, prostate, hematological malignancies (e.g., lymphomas and leukemias), and plasma cell cancer. Also included are any cancer cells derived from neural crest cells. In some embodiments, the CD200 antagonist is an anti-CD200 antibody. Such antibodies used as anti-cancer therapeutics are capable of interfering with the interaction of CD200 and its receptors. This interference can block the immune-suppressing effect of CD200. By improving the immune response in this manner, such antibodies can promote the eradication of cancer cells. Anti-CD200 antibodies may also target cancer cells for effector-mediated cell death.

In one embodiment, a variant anti-CD200 antibody that exhibits modulated ADCC and/or CDC activity may be administered to a subject with CD200-positive cancer cells. For example, a variant anti-CD200 antibody used in cancer therapy may exhibit enhanced effector activity compared to the parent or native antibody. In another embodiment, the variant anti-CD200 antibody exhibits reduced effector function, including reduced ADCC, relative to the native antibody. The said antibody may be a murine, chimeric, humanized, human or de-immunized antibody. Cancers for which the variant anti-CD200 antibody may be used in treatment include but are not limited to neural crest cell cancers. Also included are plasma cell cancer, ovarian cancer, skin cancer, lung cancer, renal cancer, breast cancer, prostate cancer, neuroblastoma, lymphoma, myeloma, and leukemia.

The present antibodies can be administered as a therapeutic to cancer patients, especially, but not limited to, patients with CLL, plasma cell cancer, ovarian cancer, skin cancer, lung cancer, renal cancer, breast cancer, prostate cancer, neuroblastoma, lymphoma, myeloma, leukemia, and any cancer derived from neural crest cells. In a particularly useful embodiment, a cancer therapy in accordance with this disclosure comprises (1) administering an anti-CD200 antibody or antagonist that interferes with the interaction between CD200 and its receptor to block immune suppression, thereby promoting eradication of the cancer cells; and/or (2) administering a fusion molecule that includes a CD-200 targeting portion to directly kill cancer cells. Alternatively, the antibody directly kills the cancer cells through complement-mediated or antibody-dependent cellular cytotoxicity. Since CD200 is also expressed on normal cells such as endothelial cells, albeit at lower levels than on cancer cells, it could also be advantageous to administer an anti-CD200 antibody with a constant region modified to reduce or eliminate ADCC or CDC to limit damage to normal cells. For example, if CD200 expression is upregulated on some activated normal cells (e.g., activated T cells), rendering such cells vulnerable to killing by an anti-CD200 antibody with effector function, it may therefore also be advantageous to use an anti-CD200 antibody lacking effector function to avoid depletion of these cells which aid in destroying cancer cells.

In a particular embodiment, effector function of anti-CD200 antibodies is eliminated by swapping the IgG1 constant domain for an IgG2/4 fusion domain. Other ways of eliminating effector function can be envisioned such as, e.g., mutation of the sites known to interact with FcR or insertion of a peptide in the hinge region, thereby eliminating critical sites required for FcR interaction. Variant anti-CD200 antibodies with reduced or no effector function also include variants as described previously herein.

The aforementioned agents for the inhibition or prevention of the CD200:CD200R interaction may be used in combination with other therapies or with other agents. Other agents include but are not limited to polypeptides, small molecules, chemicals, metals, organometallic compounds, inorganic compounds, nucleic acid molecules, oligonucleotides, aptamers, spiegelmers, antisense nucleic acids, locked nucleic acid (LNA) inhibitors, peptide nucleic acid (PNA) inhibitors, immunomodulatory agents, antigen-binding fragments, prodrugs, and peptidomimetic compounds.

In certain aspects, the present disclosure relates to combination treatments comprising a CD200 antagonist including the antibodies described herein and immunomodulatory compounds, vaccines or chemotherapy. Illustrative examples of suitable immunomodulatory agents that may be used in such combination therapies include agents that block negative regulation of T cells or antigen presenting cells (e.g., anti-CTLA4 antibodies, anti-PD-L1 antibodies, anti-PDL-2 antibodies, anti-PD-1 antibodies and the like) or agents that enhance positive co-stimulation of T cells (e.g., anti-CD40 antibodies or anti 4-IBB antibodies) or agents that increase NK cell number or T-cell activity (e.g., anti-CD200 antibodies alone or in combination with inhibitors such as IMiDs, thalidomide, or thalidomide analogs). Furthermore, immunomodulatory therapy could include cancer vaccines such as dendritic cells loaded with tumor cells, proteins, peptides, RNA, or DNA derived from such cells, patient derived heat-shocked proteins (hsp's) or general adjuvants stimulating the immune system at various levels such as CpG, Luivac, Biostim, Ribominyl, Imudon, Bronchovaxom or any other compound or other adjuvant activating receptors of the innate immune system (e.g., toll like receptor agonist, anti-CTLA-4 antibodies, etc.). Also, immunomodulatory therapy could include treatment with cytokines such as IL-2, GM-CSF and IFN-gamma.

In additional embodiments, elimination of existing regulatory T cells with reagents such as anti-CD25, fludarabine, or cyclophosphamide is achieved before starting anti-CD200 treatment. Also, therapeutic efficacy of myeloablative therapies followed by bone marrow transplantation or adoptive transfer of T cells reactive with CLL cells is enhanced by anti-CD200 therapy. In yet other embodiments, efficacy of anti-CD200 treatment is improved by blocking immunosuppressive mechanisms with agents such as anti-PDL1 and/or 2 antibodies, anti-IL-10 antibodies, anti-IL-6 antibodies, and the like. Furthermore, it could be advantageous to eliminate plasmacytoid dendritic cells, shown to be immunosuppressive in the cancer environment. In these embodiments in which delivery of an anti-CD200 antibody is intended to augment an immune response by blocking immune suppression, for example, a variant anti-CD200 antibody lacking effector function may also be used.

In particularly useful embodiments, the therapy that enhances immune response is the administration of a polypeptide that binds to CD200, alone or in combination with one of the previously mentioned immunomodulatory therapies. Accordingly, a CD200 antagonist (including an anti-CD200 antibody as described herein) may be used in combination with a monoclonal antibody (e.g., rituximab, trastuzumab, alemtuzumab, cetuximab, or bevacizumab), including a conjugated monoclonal antibody (e.g., gemtuzumab ozogamicin, ibritumomab tiuxetan, or tositumomab).

Furthermore, combination of anti-CD200 therapy with chemotherapeutics could be particularly useful to reduce overall tumor burden, to limit angiogenesis, to enhance tumor accessibility, to enhance susceptibility to ADCC, to result in increased immune function by providing more tumor antigen, or to increase the expression of the T cell attractant LIGHT. When anti-CD200 therapy is administered to a subject in combination with another conventional anti-neoplastic agent, either concomitantly or sequentially, anti-CD200 therapy may be shown to enhance the therapeutic effect of either agent alone. Pharmaceutical compounds that may be used for combinatory anti-tumor therapy include, merely to illustrate: aminoglutethimide, amsacrine, anastrozole, asparaginase, bcg, bicalutamide, bleomycin, buserelin, busulfan, camptothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic anti-tumor compounds may be categorized by their mechanism of action into groups, including, for example, the following classes of agents: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristine, vinblastine, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, mechlorethamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); immunomodulatory agents (thalidomide and analogs thereof such as lenalidomide (Revlimid, CC-5013) and CC-4047 (Actimid)), cyclophosphamide; anti-angiogenic compounds (TNP-470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylprednisolone, prednisone, and prenisolone); growth factor signal transduction kinase inhibitors; mitochondrial dysfunction inducers and caspase activators; and chromatin disruptors.

In certain embodiments, pharmaceutical compounds that may be used for combinatory anti-angiogenesis therapy include: (1) inhibitors of release of "angiogenic molecules," such as bFGF (basic fibroblast growth factor); (2) neutralizers of angiogenic molecules, such as anti-βbFGF antibodies; and (3) inhibitors of endothelial cell response to angiogenic stimuli, including collagenase inhibitor, basement membrane turnover inhibitors, angiostatic steroids, fungal-derived angiogenesis inhibitors, platelet factor 4, thrombospondin, arthritis drugs such as D-penicillamine and gold thiomalate, vitamin $D_3$ analogs, alpha-interferon, and the like. For additional proposed inhibitors of angiogenesis, see Blood et al., Biochim. Biophys. Acta, 1032:89-118 (1990), Moses et al., Science, 248:1408-1410 (1990), Ingber et al., Lab. Invest., 59:44-51 (1988), and U.S. Pat. Nos. 5,092,885, 5,112,946, 5,192,744, 5,202,352, and 6,573,256. In addition, there are a wide variety of compounds that can be used to inhibit angiogenesis, for example, peptides or agents that block the VEGF-mediated angiogenesis pathway, endostatin protein or derivatives, lysine binding fragments of angiostatin, melanin or melanin-promoting compounds, plasminogen fragments (e.g., Kringles 1-3 of plasminogen), troponin subunits, antagonists of vitronectin $\alpha_v\beta_3$, peptides derived from Saposin B, antibiotics or analogs (e.g., tetracycline, or neomycin), dienogest-containing compositions, compounds comprising a MetAP-2 inhibitory core coupled to a peptide, the compound EM-138, chalcone and its analogs, and naaladase inhibitors. See, for example, U.S. Pat. Nos. 6,395,718, 6,462,075, 6,465,431, 6,475,784, 6,482,802, 6,482,810, 6,500,431, 6,500,924, 6,518,298, 6,521,439, 6,525,019, 6,538,103, 6,544,758, 6,544,947, 6,548,477, 6,559,126, and 6,569,845.

Depending on the nature of the combinatory therapy, administration of the anti-CD200 antibody may be continued while the other therapy is being administered and/or thereafter. Administration of the antibody may be made in a single dose, or in multiple doses. In some instances, administration of the anti-CD200 antibody is commenced at least several days prior to the conventional therapy, while in other instances, administration is begun either immediately before or at the time of the administration of the conventional therapy. In some cases, the anti-CD200 antibody will be administered after other therapies, or it could be administered alternating with other therapies.

The present antibodies can be utilized to directly kill or ablate cancerous cells in vivo. Direct killing involves administering the antibodies (which are optionally fused to a cytotoxic drug) to a subject requiring such treatment. Since the antibodies recognize CD200 on cancer cells, any such cells to which the antibodies bind are destroyed. Where the antibodies are used alone to kill or ablate cancer cells, such killing or ablation can be effected by initiating endogenous host immune functions, such as CDC and/or ADCC. Assays for determining whether an antibody kills cells in this manner are within the purview of those skilled in the art.

Accordingly in one embodiment, the antibodies of the present disclosure may be used to deliver a variety of cytotoxic compounds. Any cytotoxic compound can be fused to the present antibodies. The fusion can be achieved chemically or genetically (e.g., via expression as a single, fused molecule). The cytotoxic compound can be a biological, such as a polypeptide, or a small molecule. As those skilled in the art will appreciate, for small molecules, chemical fusion is used, while for biological compounds, either chemical or genetic fusion can be employed.

Non-limiting examples of cytotoxic compounds include therapeutic drugs, a compound emitting radiation, molecules of plants, fungal, or bacterial origin, biological proteins, and mixtures thereof. The cytotoxic drugs can be intracellularly acting cytotoxic drugs, such as short-range radiation emitters, including, for example, short-range, high-energy α-emitters. Enzymatically active toxins and fragments thereof are exemplified by diphtheria toxin A fragment, nonbinding active fragments of diphtheria toxin, exotoxin A (from *Pseudomo-* nas aeruginosa), ricin A chain, abrin A chain, modeccin A chain, alpha-sacrin, certain Aleurites fordii proteins, certain Dianthin proteins, *Phytolacca americana* proteins (PAP, PAPII and PAP-S), Morodica charantia inhibitor, curcin, crotin, *Saponaria officinalis* inhibitor, gelonin, mitogillin, restrictocin, phenomycin, and enomycin, for example. Procedures for preparing enzymatically active polypeptides of the immunotoxins are described in WO84/03508 and WO85/03508, which are hereby incorporated by reference. Certain cytotoxic moieties are derived from adriamycin, chlorambucil, daunomycin, methotrexate, neocarzinostatin, and platinum, for example.

Procedures for conjugating the antibodies with the cytotoxic agents have been previously described and are within the purview of one skilled in the art.

Alternatively, the antibody can be coupled to high energy radiation emitters, for example, a radioisotope, such as $^{131}$I, a γ-emitter, which, when localized at the tumor site, results in a killing of several cell diameters. See, e.g., S. E. Order, "Analysis, Results, and Future Prospective of the Therapeutic Use of Radiolabeled Antibody in Cancer Therapy", Monoclonal Antibodies for Cancer Detection and Therapy, R. W. Baldwin et al. (eds.), pp 303-316 (Academic Press 1985), which is hereby incorporated by reference. Other suitable radioisotopes include α-emitters, such as $^{212}$Bi, $^{213}$Bi, and $^{211}$At, and β-emitters, such as $^{186}$Re and $^{90}$Y.

In some embodiments, present CD200 binding antibodies provide the benefit of blocking immune suppression in CLL by targeting the leukemic cells directly through CD200. Specifically, stimulating the immune system can allow the eradication of CLL cells from the spleen and lymph nodes. Applicants are unaware of any successful eradication of CLL cells from these microenvironments having been achieved with agents that simply target B cells (such as alemtuzumab). In contrast, CLL reactive T cells can have better access to these organs than antibodies. In other embodiments, direct cell killing is achieved by tagging the CLL cells with anti-CD200 Abs.

According to the compositions and methods of the present disclosure, in particularly useful embodiments, the combination of direct cell killing and driving the immune response towards a Th1 profile provides a particularly powerful approach to cancer treatment. Thus, in one embodiment, a cancer treatment is provided wherein an antibody or antibody fragment, which binds to CD200 and both a) blocks the interaction between CD200 and its receptor and b) directly kills the cancer cells expressing CD200, is administered to a cancer patient. The mechanism by which the cancer cells are killed can include, but are not limited to ADCC and/or CDC; fusion with a toxin; fusion with a radiolabel; fusion with a biological agent involved in cell killing, such as granzyme B or perforin; fusion with a cytotoxic virus; fusion with a cytokine such as TNF-α or IFN-α. In an alternative embodiment, a cancer treatment involves administering an antibody that both a) blocks the interaction between CD200 and its receptor and b) enhances cytotoxic T cell or NK cell activity against the tumor. Such enhancement of the cytotoxic T cell or NK cell activity may, for example, be combined by fusing the antibody with cytokines such as e.g. IL-2, IL-12, IL-18, IL-13, and IL-5. In addition, such enhancement may be achieved by administration of an anti-CD200 antibody in combination with inhibitors such as IMiDs, thalidomide, or thalidomide analogs.

In yet another embodiment, the cancer treatment involves administering an antibody that both (1) blocks the interaction between CD200 and its receptor and (2) attracts T cells to the tumor cells. T cell attraction can be achieved by fusing the Ab with chemokines such as MIG, IP-10, I-TAC, CCL21, CCL5 or LIGHT. Also, treatment with chemotherapeutics can result in the desired upregulation of LIGHT. The combined action of blocking immune suppression and killing directly through antibody targeting of the tumor cells is a unique approach that provides increased efficacy.

Anti-CD200 antibodies in accordance with the present disclosure can also be used as a diagnostic tool. Biopsies or cancer cell tissue samples may be tested for CD200 expression prior to treatment in order to predict the efficacy of anti-CD200 therapy, alone or in combination with other agents or methods (such as chemotherapeutic agents, radiation therapy, immunomodulatory therapy, etc.). For example, using blood obtained from patients with hematopoietic cancers, expression of CD200 can be evaluated on cancer cells by FACS analysis using anti-CD200 antibodies in combination with the appropriate cancer cell markers such as, e.g., CD38 and CD19 on CLL cells. Patients with CD200 levels at least 1.4-fold above the levels found on normal B cells can be selected for treatment with anti-CD200 antibodies. As another example, tissue samples from a patient may be stained with anti-CD200 antibody to determine the expression of CD200 in the patient's malignant and normal cells.

In another example of using the present anti-CD200 antibodies as a diagnostic or prognostic tool, biopsies from patients with malignancies are obtained and expression of CD200 is determined by FACS analysis using anti-CD200 antibodies or by immunohistochemistry using anti-CD200. If tumor cells express CD200 at levels that are at least 1.4-fold higher compared to corresponding normal tissue, cancer patients are selected for immunomodulatory therapy (including but not limited to a therapy comprising anti-CD200 therapy). For cancer derived from cells that normally do not express CD200, any detectable CD200 on cancer biopsies indicates potential usefulness of anti-CD200 therapy. Immunomodulatory therapy can be anti-CD200 therapy, but can also be any other therapy affecting the patient's immune system. Examples of suitable immunomodulatory therapies include the administration of agents that block negative regulation of T cells or antigen presenting cells (e.g., anti-CTLA4, anti-PD-L1, anti-PDL-2, anti-PD-1) or the administration of agents that enhance positive co-stimulation of T cells (e.g., anti-CD40 or anti 4-1138). Furthermore, immunomodulatory therapy could be cancer vaccines such as heteroclitic peptides or tumor cell peptides that generate cytotoxic T cells or dendritic cells loaded with tumor cells, or the administration of agents that increase NK cell number or T-cell activity (e.g., anti-CD200 antibodies alone or in combination with inhibitors such as IMiDs, thalidomide, or thalidomide analogs), or the administration of agents that deplete regulatory T cells (e.g. anti-CD200 antibodies alone or in combination with ONTAK), or plasmacytoid dendritic cells. Combination with agents increasing T cell or dendritic cell migration is also advantageous, such as e.g. any agent blocking SPARC. Furthermore, immunomodulatory therapy could be cancer vaccines such as dendritic cells loaded with tumor cells, patient derived exosomes tumor RNA or tumor DNA, tumor protein or tumor peptides, patient derived heat-shocked proteins (hsp's), hsp's loaded with tumor antigens or general adjuvants stimulating the immune system at various levels such as CpG, Luivac, Biostim, Ribominyl, Imudon, Bronchovaxom or any other compound activating receptors of the innate immune system (e.g., toll like receptors). Also, therapy could include treatment with cytokines such as IL-2, GM-CSF and IFN-gamma. Combination with agents restoring compromised activity of dendritic cells in the tumor environment such as e.g. MAP kinase inhibitors are also contemplated.

In one embodiment, the present antibodies also may be utilized to detect cancerous cells in vivo. Detection in vivo is achieved by labeling the antibody, administering the labeled antibody to a subject, and then imaging the subject. Examples of labels useful for diagnostic imaging in accordance with the present disclosure are radiolabels such as $^{131}$I, $^{111}$In, $^{123}$I, $^{99m}$Tc, $^{32}$P, $^{125}$I, $^{3}$H, $^{14}$C, and $^{188}$Rh, fluorescent labels such as fluorescein and rhodamine, nuclear magnetic resonance active labels, positron emitting isotopes detectable by a positron emission tomography ("PET") scanner, chemiluminescers such as luciferin, and enzymatic markers such as peroxidase or phosphatase. Short-range radiation emitters, such as isotopes detectable by short-range detector probes, such as a transrectal probe, can also be employed. The antibody can be labeled with such reagents using techniques known in the art. For example, see Wensel and Meares, Radioimmunoimaging and Radioimmunotherapy, Elsevier, N.Y. (1983), which is hereby incorporated by reference, for techniques relating to the radiolabeling of antibodies. See also, D. Colcher et al., "Use of Monoclonal Antibodies as Radiopharmaceuticals for the Localization of Human Carcinoma Xenografts in Athymic Mice", Meth. Enzymol. 121: 802-816 (1986), which is hereby incorporated by reference.

A radiolabeled antibody in accordance with this disclosure can be used for in vitro diagnostic tests. The specific activity of an antibody, binding portion thereof, probe, or ligand, depends upon the half-life, the isotopic purity of the radioactive label, and how the label is incorporated into the biological agent. In immunoassay tests, the higher the specific activity, in general, the better the sensitivity. Procedures for labeling antibodies with the radioactive isotopes are generally known in the art.

The radiolabeled antibody can be administered to a patient where it is localized to cancer cells bearing the antigen with which the antibody reacts, and is detected or "imaged" in vivo using known techniques such as radionuclear scanning using e.g., a gamma camera or emission tomography. See e.g., A. R. Bradwell et al., "Developments in Antibody Imaging", Monoclonal Antibodies for Cancer Detection and Therapy, R. W. Baldwin et al., (eds.), pp. 65-85 (Academic Press 1985), which is hereby incorporated by reference. Alternatively, a positron emission transaxial tomography scanner, such as designated Pet VI located at Brookhaven National Laboratory, can be used where the radiolabel emits positrons (e.g., $^{11}$C, $^{18}$F, $^{15}$O, and $^{13}$N).

Fluorophore and chromophore labeled biological agents can be prepared from standard moieties known in the art. Since antibodies and other proteins absorb light having wavelengths up to about 310 nm, the fluorescent moieties should be selected to have substantial absorption at wavelengths above 310 nm and preferably above 400 nm. A variety of suitable fluorescers and chromophores are described by Stryer, Science, 162:526 (1968) and Brand, L. et al., Annual Review of Biochemistry, 41:843-868 (1972), which are hereby incorporated by reference. The antibodies can be labeled with fluorescent chromophore groups by conventional procedures such as those disclosed in U.S. Pat. Nos. 3,940,475, 4,289,747, and 4,376,110, which are hereby incorporated by reference.

In another embodiment in accordance with the present disclosure, methods are provided for monitoring the progress and/or effectiveness of a therapeutic treatment. The method involves administering an immunomodulatory therapy and determining CD200 levels in a subject at least twice to determine the effectiveness of the therapy. For example, pre-treatment levels of CD200 can be ascertained and, after at least one administration of the therapy, levels of CD200 can again be determined. A decrease in CD200 levels is indicative of an effective treatment. Measurement of CD200 levels can be used by the practitioner as a guide for increasing dosage amount or frequency of the therapy. It should of course be understood that CD200 levels can be directly monitored or, alternatively, any marker that correlates with CD200 can be monitored. Other methods to determine the effectiveness of this therapy include but are not limited to detection of cancer cells, total lymphocyte count, lymph node size, number of regulatory T cells, cytokine profiles in the serum or intracellular, or secretion of cytokines by T or B cells as measured by ELISPOT.

C. Other CD200 Antagonists

The CD200 antagonists and polypeptides and/or antibodies utilized in the present disclosure are especially indicated for diagnostic and therapeutic applications as described herein. Accordingly CD200 antagonists and anti-CD200 antibodies and variants thereof may be used in therapies, including combination therapies, in the diagnosis and prognosis of disease, as well as in the monitoring of disease progression.

In the therapeutic embodiments of the present disclosure, bispecific antibodies are contemplated. Bispecific antibodies are monoclonal, preferably human or humanized, antibodies that have binding specificities for at least two different antigens. In the present case, one of the binding specificities is for the CD200 antigen on a cell (such as, e.g., a cancer cell or immune cell), the other one is for any other antigen, and preferably for a cell-surface protein or receptor or receptor subunit.

Methods for making bispecific antibodies are within the purview of those skilled in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Antibody variable domains with the desired binding specificities (antibody-antigen combining sites) can be fused to immunoglobulin constant domain sequences. The fusion preferably is with an immunoglobulin heavy-chain constant domain, including at least part of the hinge, CH2, and CH3 regions. DNAs encoding the immunoglobulin heavy-chain fusions and, if desired, the immunoglobulin light chain, are inserted into separate expression vectors, and are co-transfected into a suitable host organism. For further details of illustrative currently known methods for generating bispecific antibodies see, for example, Suresh et al., Methods in Enzymology, 121:210 (1986); WO 96/27011; Brennan et al., Science 229:81 (1985); Shalaby et al., J. Exp. Med. 175:217-225 (1992); Kostelny et al., J. Immunol. 148(5):1547-1553 (1992); Hollinger et al., Proc. Natl. Acad. Sci. USA 90:6444-6448 (1993); and Gruber et al., J. Immunol. 152:5368 (1994); and Tutt et al., J. Immunol. 147:60 (1991). Bispecific antibodies also include cross-linked or heteroconjugate antibodies. Heteroconjugate antibodies may be made using any convenient cross-linking methods. Suitable cross-linking agents are well known in the art, and are disclosed in U.S. Pat. No. 4,676,980, along with a number of cross-linking techniques.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins may be linked to the Fab' portions of two different antibodies by gene fusion. The antibody homodimers may be reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (scFv) dimers has also been reported. See Gruber et al., J. Immunol., 152:5368 (1994). Alternatively, the antibodies can be "linear antibodies" as described in Zapata et al. Protein Eng. 8(10):1057-1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

D. Modes of Administration and Formulations

The route of antibody administration of the antibodies of the present disclosure (whether the pure antibody, a labeled antibody, an antibody fused to a toxin, etc.) is in accord with known methods, e.g., injection or infusion by intravenous, intraperitoneal, intracerebral, intramuscular, subcutaneous, intraocular, intraarterial, intrathecal, inhalation or intralesional routes, or by sustained release systems. The antibody is preferably administered continuously by infusion or by bolus injection. One may administer the antibodies in a local or systemic manner.

The present antibodies may be prepared in a mixture with a pharmaceutically acceptable carrier. Techniques for formulation and administration of the compounds of the instant application may be found in "Remington's Pharmaceutical Sciences," Mack Publishing Co., Easton, Pa., latest edition. This therapeutic composition can be administered intravenously or through the nose or lung, preferably as a liquid or powder aerosol (lyophilized). The composition may also be administered parenterally or subcutaneously as desired. When administered systemically, the therapeutic composition should be sterile, substantially pyrogen-free and in a parenterally acceptable solution having due regard for pH, isotonicity, and stability. For example, a pharmaceutical preparation is substantially free of pyrogenic materials so as to be suitable for administration as a human therapeutic. These conditions are known to those skilled in the art.

Pharmaceutical compositions suitable for use include compositions wherein one or more of the present antibodies are contained in an amount effective to achieve their intended purpose. More specifically, a therapeutically effective amount means an amount of antibody effective to prevent, alleviate or ameliorate symptoms of disease or prolong the survival of the subject being treated. Determination of a therapeutically effective amount is well within the capability of those skilled in the art, especially in light of the detailed disclosure provided herein. Therapeutically effective dosages may be determined by using in vitro and in vivo methods.

While the above disclosure has been directed to antibodies, in some embodiments polypeptides derived from such antibodies can be utilized in accordance with the present disclosure.

EXEMPLIFICATION

Mouse Model and CD200+ Cell Construction
Raji/PBL Model

NOD.CB17-Prkdc<scid> mice (Jackson Laboratory) were injected with 200 µl RPMI containing $4 \times 10^6$ RAH cells (ATCC) s.c. along with 0, 1, 5 or 10 million PBLs. Nine or ten mice were included per group. PBLs were isolated from 250 ml whole blood on a histopaque gradient followed by red blood cell lysis using 0.9% ammonium chloride. Tumor growth was monitored three times a week by measuring length and width with a caliper. Tumor volume was calculated based on length×width×width/2.

Differences between the groups that were injected with PBLs compared to the group that received tumor cells only were analyzed by 2-tailed unpaired Student's t-test. Significant differences were observed in the groups that received 5 or 10 million PBLs, but not in the group that received 1 million PBLs from Day 32 on.

Namalwa PBL Model

NOD.C817-Prkdc<scid> mice (Jackson Laboratory, Bar Harbor, Me.) were injected with 200 µl RPMI containing $4 \times 10^6$ Namalwa cells (ATCC) s.c. along with 0, 2 or 10 million PBLs. 9-10 mice were included per group. PBLs were isolated from 250 ml whole blood on a histopaque gradient followed by red blood cell lysis using 0.9% ammonium chloride. Tumor growth was monitored three times a week by measuring length and width with a caliper. Tumor volume was calculated based on length×width×width/2.

Creation of Stable CD200-Expressing Cell Lines

Stable CD200-expressing Raji and Namalwa cell lines were generated using the Virapower Lentiviral Expression System (Invitrogen, Carlsbad, Calif.). A CD200 cDNA was isolated from primary CLL cells by RT-PCR using forward primer 5'-GACAAGCTTGCAAGGATGGAGAGGCTG-GTGA-3' (SEQ ID NO: 34) and reverse primer 5'-GACG-GATCCGCCCCTTTTCCTCCTGCTTTTCTC-3' (SEQ ID NO: 35). The PCR product was cloned into the Gateway entry vector pCR8/GW/TOPO-TA and individual clones were sequenced. Clones with the correct sequence were recombined in both the sense and antisense orientations into the lentiviral vectors pLenti6/V5/DEST and pLenti6/UbC/V5/DEST using Gateway technology (Invitrogen, Carlsbad, Calif.). The primary difference between these two vectors is the promoter used to drive CD200 expression: pLenti6/V5/DEST contains the human CMV immediate early promoter, whereas pLenti6/UbC/V5/DEST contains the human ubiquitin C promoter.

High-titer, VSV-G pseudotyped lentiviral stocks were produced by transient cotransfection of 293-FT cells as recommended by the manufacturer. Raji or Namalwa cells were transduced by resuspending $10^6$ cells in 1 ml of growth medium containing 12 µg/ml Polybrene and adding 1 ml of lentiviral stock. After incubating the cells overnight at 37° C., the medium containing virus was removed and replaced with 4 ml of fresh medium. Two days later, the infected cells were analyzed for CD200 expression by flow cytometry. In all experiments, >70% of the cells were CD200+, whereas CD200 was undetectable in the parental cell lines and in cells transduced with the negative control (antisense CD200) viruses.

To isolate clonal cell lines that overexpress CD200, the infected cells were selected with blasticidin for 13 days. The concentrations of blasticidin used were 6 μg/ml for Raji cells or 2 μg/ml for Namalwa cells. Stable clones were then isolated by limiting dilution of the blasticidin-resistant cells into 96-well plates. Clones were screened in 96-well format by flow cytometry using PE-conjugated Mouse Anti-Human CD200 (clone MRC OX10[4], Serotec) and a BD FACSCalibur equipped with a High Throughput Sampler. After screening a total of 2000 Raji and 2000 Namalwa clones, those clones with the highest CD200 expression were expanded for further characterization using conventional techniques.

Example 1

Efficacy of Humanized Versions of C2aB7 in the RAJI_CD200/PBL Model

A) To evaluate whether humanized versions of C2aB7 retain their efficacy in in vivo tumor models, chimeric C2aB7 (see U.S. patent application publication number 2005/0129690) and 3 humanized versions (C2aB7V4V1, C2aB7V3V1 and C2aB7V3V2) as well as the negative control antibody alxn4100 were tested in the RAJI-CD200/PBL model. RAJI cells transduced with CD200 were injected s.c. into NOD.CB17-Prkdc<scid> mice, and the ability of PBLs to reduce tumor growth in the presence or absence of chimeric or humanized C2aB7 antibodies or control antibody alxn4100 (which does not bind tumor cells) was assessed. Antibodies at concentrations indicated below were administered initially with the tumor cells, and then twice/week i.v. The following groups were set up with 10 mice each:
Group 1: $4\times10^6$ RAJI_CD200 s.c.
Group 2: $4\times10^6$ RAJI_CD200 s.c.+$6\times10^6$ PBL
Group 3: $4\times10^6$ RAJI_CD200 s.c.+$6\times10^6$ PBL+5 mg/kg C2aB7
Group 4: $4\times10^6$ RAJI_CD200 s.c.+$6\times10^6$ PBL+20 mg/kg C2aB7V4V1
Group 5: $4\times10^6$ RAJI_CD200 s.c.+$6\times10^6$ PBL+5 mg/kg C2aB7V4V1
Group 6: $4\times10^6$ RAJI_CD200 s.c.+$6\times10^6$ PBL+20 mg/kg C2aB7V3V1
Group 7: $4\times10^6$ RAJI_CD200 s.c.+$6\times10^6$ PBL+5 mg/kg C2aB7V3V1
Group 8: $4\times10^6$ RAJI_CD200 s.c.+$6\times10^6$ PBL+5 mg/kg C2aB7V3V2
Group 9: $4\times10^6$ RAJI_CD200 s.c.+$6\times10^6$ PBL+20 mg/kg alxn4100

Figures 16, 17, 18:
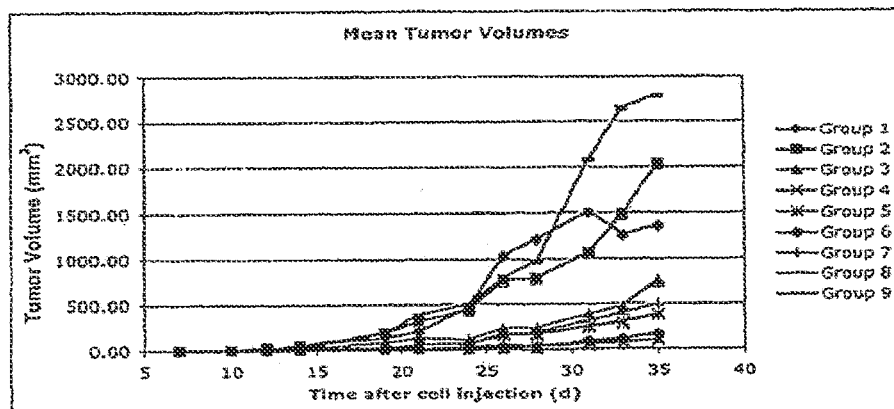
FIG. 16 provides the nucleic acid sequence for the forward primer for cloning CD200 cDNA (SEQ ID NO: 35).
FIG. 17 provides the nucleic acid sequence for the reverse primer for cloning CD200 cDNA (SEQ ID NO: 36).
FIG. 18 shows the effects of administering humanized CD200 antibodies in the RAJI-CD200/PBL model. Humanized anti-CD200 antibodies resulted in an inhibition of tumor growth.

Tumor length and width were measured 3 times a week, and the tumor volume was calculated by tumor length*width*width/2. FIG. 18 shows that, as expected, CD200 expression on the tumor cells prevented the immune cells from reducing tumor growth. All humanized versions of C2aB7 blocked tumor growth by up to 97% at doses of 20 mg/kg. The control antibody alxn4100 did not affect tumor growth. These data demonstrate that all the humanized antibodies are highly efficacious in blocking tumor growth.

B) Immune Evasion by CD200

Although the human immune system is capable of raising an immune response against many cancer types, that response is insufficient to eradicate the cancer in most patients, possibly due to immune evasion through negative regulation of the immune system by the tumor. We identified the immune-suppressive molecule CD200 to be upregulated 1.5-5.4-fold on chronic lymphocytic leukemia (CLL) cells in all patients examined (n=80). Interaction of CD200 with its receptor is known to alter cytokine profiles from Th1 to Th2 in mixed lymphocyte reactions, and to result in the induction of regulatory T cells, which are thought to hamper tumor-specific effector T cell immunity. In the present study we addressed whether CD200 expression on tumor cells plays a role in immune evasion, thereby preventing elimination of tumor cells by the immune system in a xenograft hu/SCID mouse model, and whether treatment with an antagonistic anti-CD200 antibody affects tumor growth in this model.

The human non-Hodgkin's lymphoma cell lines RAJI and Namalwa were transduced with human CD200 and were injected subcutaneously together with human peripheral blood lymphocytes (PBMC) into NOD/SCID mice. Tumor growth in mice that received CD200 expressing tumor cells was compared to tumor growth in mice that received tumor cells not expressing CD200 over time. In subsequent experiments, mice were treated with chimeric or humanized anti-CD200 antibodies (dose range 1 mg/kg to 20 mg/kg) by intravenous injection. Treatment was either started immediately or 7 days after tumor cell injection.

PBMCs reduced RAJI or Namalwa tumor growth by up to 75% in the absence of CD200 expression. In contrast, growth of RAJI or Namalwa tumors expressing CD200 at levels comparable to CLL was not reduced by PBMCs. Administration of anti-CD200 antibodies at 5 mg/kg resulted in nearly complete tumor growth inhibition (1/10 mice developed a small tumor) over the course of the study even when treatment was started 7 days after tumor cell injection.

The presence of human CD200 on tumor cells inhibits the ability of human lymphocytes to eradicate tumor cells. Treatment of CD200-expressing tumors with antagonistic anti-CD200 antibodies inhibits tumor growth, indicating the potential for anti-CD200 therapy as a promising approach for CLL.

C) Efficacy of C2aB7G1 Versus C2aB7G2/G4 Constructs

To evaluate whether anti-CD200 antibodies without effector function (G2/G4 fusion constructs of C2aB7 as described below) are equally or more efficacious than the G1 constructs, G1 and G2/G4 versions as well as the humanized version of C2aB7 (alxn5200) were tested in the Raji_CD200/PBL model. RAJI cells transduced with CD200 as described above were injected s.c. into NOD.CB17-Prkdc<scid> mice, and the ability of PBLs to reduce tumor growth in the presence or absence of chimeric anti-CD200 antibodies c2aB7G1 (c2aB7), c2aB7G2/G4 or the humanized versions hC2aB7V3V1G1 (V3V1), or hC2aB7V3V2G1 (V3V2) or control antibody alxn4100 was assessed. Antibodies at concentrations indicated below were administered initially with the tumor cells and then twice/week i.v. The following groups were set up with 10 mice each:
Group 1: $4\times10^6$ RAJI_CD200 s.c.
Group 2: $4\times10^6$ RAJI_CD200 s.c.+$6\times10^6$ PBL
Group 3: $4\times10^6$ RAJI_CD200 s.c.+$6\times10^6$ PBL+20 mg/kg hV3V2-G1
Group 4: $4\times10^6$ RAJI_CD200 s.c.+$6\times10^6$ PBL+5 mg/kg alxn 5200
Group 5: $4\times10^6$ RAJI_CD200 s.c.+$6\times10^6$ PBL+2.5 mg/kg alxn 5200
Group 6: $4\times10^6$ RAJI_CD200 s.c.+$6\times10^6$ PBL+1 mg/kg alxn 5200
Group 7: $4\times10^6$ RAJI_CD200 s.c.+$6\times10^6$ PBL+20 mg/kg chC2aB7G2/G4
Group 8: $4\times10^6$ RAJI_CD200 s.c.+$6\times10^6$ PBL+5 mg/kg chC2aB7G2/G4
Group 9: $4\times10^6$ RAJI_CD200 s.c.+$6\times10^6$ PBL+2.5 mg/kg chC2aB7G2/G4
Group 10: $4\times10^6$ RAJI_CD200 s.c.+$6\times10^6$ PBL+1 mg/kg chC2aB7G2/G4

Group 11: 4×10⁶ RAJI_CD200 s.c.+6×10⁶ PBL+20 mg/kg alxn4100

Figure 19:
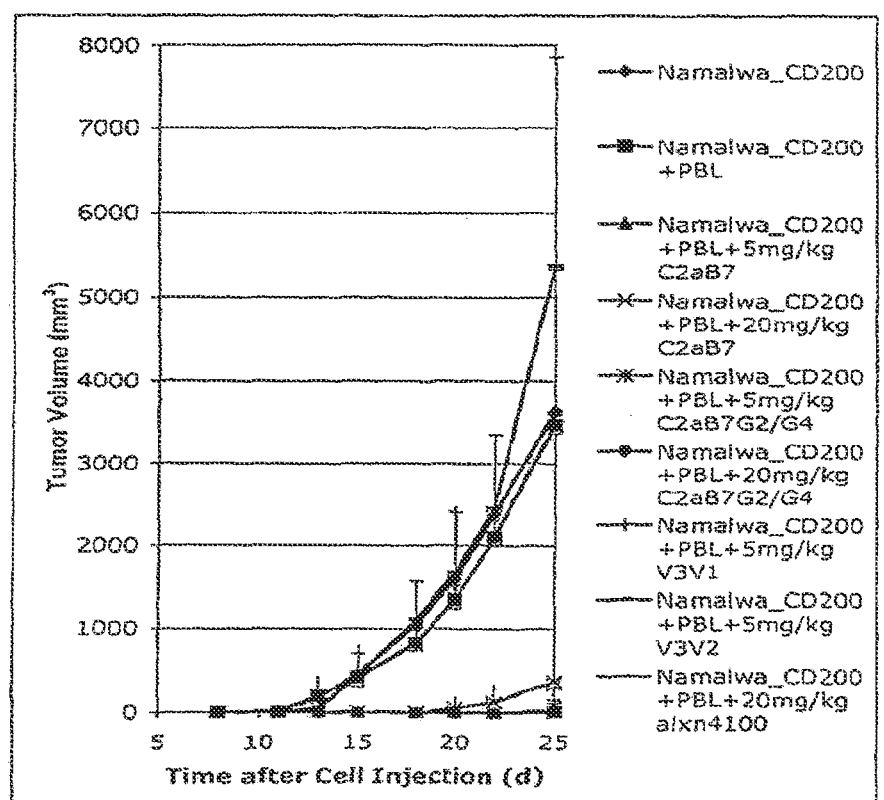
FIG. 19 demonstrates the effects of administering humanized CD200 antibodies with and without effector function in the Namalwa_CD200 animal model. Antibodies without effector function exhibited efficacy in inhibiting tumor growth.

Tumor length and width were measured three times a week, and the tumor volume was calculated by tumor length*width*width/2. FIG. 19 shows that, as expected, CD200 expression on the tumor cells prevented the immune cells from reducing tumor growth. However, addition of anti-CD200 antibodies reduced the tumor volume by up to 100%. While 20 mg/kg C2aB7G1 resulted in growth of small tumors in 6/10 mice, only 1 mouse grew tumors in the group treated with 20 mg/kg C2aB7G2/G4, suggesting that the G2/G4 version might result in better or at least equal efficacy as the G1 version. All anti-CD200 antibodies, including the humanized versions, completely blocked tumor growth at 5 mg/kg. Treatment with the control antibody did not reduce the tumor growth. These data prove that the G2/G4 version of C2aB7 is highly efficacious in blocking tumor growth of CD200 expressing tumors. These data further confirm that the humanized versions of C2aB7 are highly efficacious in blocking tumor growth in this model.

D) Generation of G2/G4 Construct

Plasmids were altered in two steps, first replacing the IgG1 region from an Age I site in the human CH1 region through the stop codon to a BamH I site located after the SV40 poly A signal. C2aB7-6 and cC7 G2G4 (L-SIGN antibody) were digested with Age I and BamH I, and C2aB7-6 was treated with CIP. A 10,315 bp fragment from C2AB7-6 and a 1752 bp fragment from cC7 G2G4 were purified by electrophoresis and gel extraction. These fragments were ligated, electroporated into XLI Blue *E. coli*, and plated on LB/carb/gluc plates. Colonies were grown in solution and DNA was isolated using Qiagen miniprep columns. The presence of the IgG2G4 Age I/BamH I fragment, as opposed to the IgG1 fragment, was determined by Pvu II digestion which results in the presence of two bands of 267 and 1152 bp as opposed to one band of 1419 bp. Clone 21 was selected for further use.

The remainder of the CH1 region from the end of the variable region to the Age I site was generated in an IgG2/G4 format by using overlap PCR. The PCR fragment containing the beginning of the CH1 region through the Age I site had previously been generated in the production of plasmid cC7 G2G4. Primers C7 mhHF (TCCTCAGCCTCCAC-CAAGGGCC, SEQ ID NO:1) and Rev Age Pri (GGGCGC-CTGAGTTCCACGAC, SEQ ID NO: 2) were used in a PCR reaction with G204 63L1D as template to generate a 142 bp fragment. Primers C2aB7 rev (GGCCCTTGGTGGAGGCT-GAGGAAACTGTGAGAGTGGTGC, SEQ ID NO: 3) and lacpri (GCTCCCGGCTCGTATGTTGTGT, SEQ ID NO: 4) were used with Fab C2aB7 as template to generate the murine heavy chain variable region (and upstream material) in a fragment of about 1250 bp. These fragments were purified by electrophoresis and gel extraction and were used in overlap PCR with the primers Rev Age Pri (GGGCGCCTGAGTTC-CACGAC, SEQ ID NO: 2) and LeadVHpAX (ATAT-GAAATATCTGCTGCCGACCG, SEQ ID NO: 5) to generate a 558 bp fragment that was purified on a PCR purification column. This 558 bp fragment and clone 21 were digested with Xho I and Age I to generate a 458 bp fragment that was purified by electrophoresis and gel extraction. Clone 21 was also digested with Xho I and Age I, treated with CIP, and an 11.6 kb fragment was purified by electrophoresis and gel extraction. These fragments were ligated and electroporated into XL1 Blue *E. coli* and plated on LB/carb/gluc plates. Clone C2aB7G2G4.11 was seen to have the expected restriction fragments when digested with Pvu II.

The final construct C2AB7G2G4.11 was sequenced. It was discovered that the TAA stop codon of the light chain had been mutated to the sequence TCA such that an additional 6 amino acids would be added to the carboxy terminus of the light chain. It was found to have been present in the IgG1 version clone C2AB7-6 that was the parent for C2AB7G2G4.11. Antibodies containing the 0204 construct are depicted in FIGS. 10, 11, 12, 13, and 15.

Example 2

CD200 Expression on Cancer Cells

A. Determination of CD200 Upregulation in CLL Patients

Lymphocytes from 15 CLL patients were stained with FITC-conjugated anti-CD5 (e-bioscience), APC-conjugated anti-CD 19 (e-bioscience) and PE-conjugated anti-CD200 (Serotec). Lymphocytes from healthy donors were stained accordingly. CD200 expression on CD5+CD19+ cells was determined. As shown in FIG. 20, although the level of CD200 expression varied among CLL patient samples, all CLL samples showed elevated levels (1.6-4-fold range) higher CD200 expression compared to CD200 expression on normal B cells. The CLL patients showing elevated levels of CD200 expression are selected for anti-CD200 treatment in accordance with the methods described herein.

B. FACS Analysis on Cancer Cell Lines

CD200 expression was evaluated by FACS analysis using a panel of NCI60 cell lines from melanoma cancer patients, prostate cancer patients, glioblastoma patients, astrocytoma patients, neuroblastoma patients, ovarian cancer patients, lung cancer patients and renal cancer patients. C2aB7 was labeled with Zenon-Alexa488 according to the manufacturer's instructions (Invitrogen). One half million to 1 million cells were stained with 1 μg of the labeled antibody for 20 min, followed by a PBS wash. Cell staining was assessed using a FACSCalibur (Becton Dickinson). Staining of antibody-labeled cells was compared with samples that remained unlabeled and the ratio of stained/unstained was determined. In FIG. 21, a ratio greater than 1 but smaller than 2 is indicated as +/−, a ratio between 2 and 3 is +, between 3 and 10 is ++, >10 is +++. None of the cell lines tested for glioblastoma, astrocytoma, prostate or lung cancer expressed CD200, and are not listed below. Four out of 5 tested melanoma cell lines, 2/3 ovarian cancer cell lines, 2/3 renal cell lines, 2/2 neuroblastoma cell lines and 1/3 breast cancer cell lines expressed CD200 at detectable levels on the cell surface, suggesting that solid tumors might use CD200 as an immune escape mechanism as well.

C. RT-QPCR on Patient Samples

Figure 22:
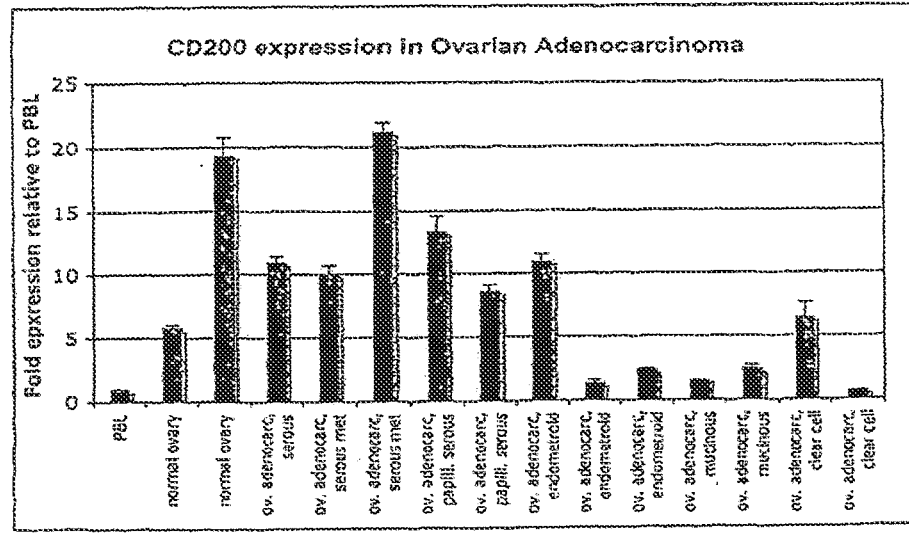
FIG. 22 shows the expression level of CD200 antigen in human ovarian cancer samples relative to the expression level detected in human peripheral blood lymphocytes (PBL).

To verify whether CD200 is upregulated not only on cell lines, but also on primary patient samples, RT-QPCR and immunohistochemistry (IHC) were performed on primary patient samples. RNA samples from ovarian and melanoma patients were obtained from Cytomix. cDNA was prepared and samples were diluted 1:100 and 1:1000 in 10 ng/ml yeast RNA. Samples were run for QPCR with CD200 assay Hs00245978_m1 as provided by ABI. For 18S normalization, 18S assay (ABI) was run with samples diluted 1:10,000. Each dilution was run in duplicate. Ovarian and melanoma patient samples, along with CLL patient samples were normalized to 18S, then fold expression relative to normal PBL was determined. FIG. 22 shows CD200 expression on ovarian cancer samples. Serous/serous metastatic/papillary serous appeared to have the highest expression of CD200 at approximately 10- to 20-fold higher than normal PBL. CD200 expression was relatively low in endometroid, mucinous, and clear cell samples, all at or below normal ovary expression levels (1-5 fold higher than normal PBL).

Figure 23B:
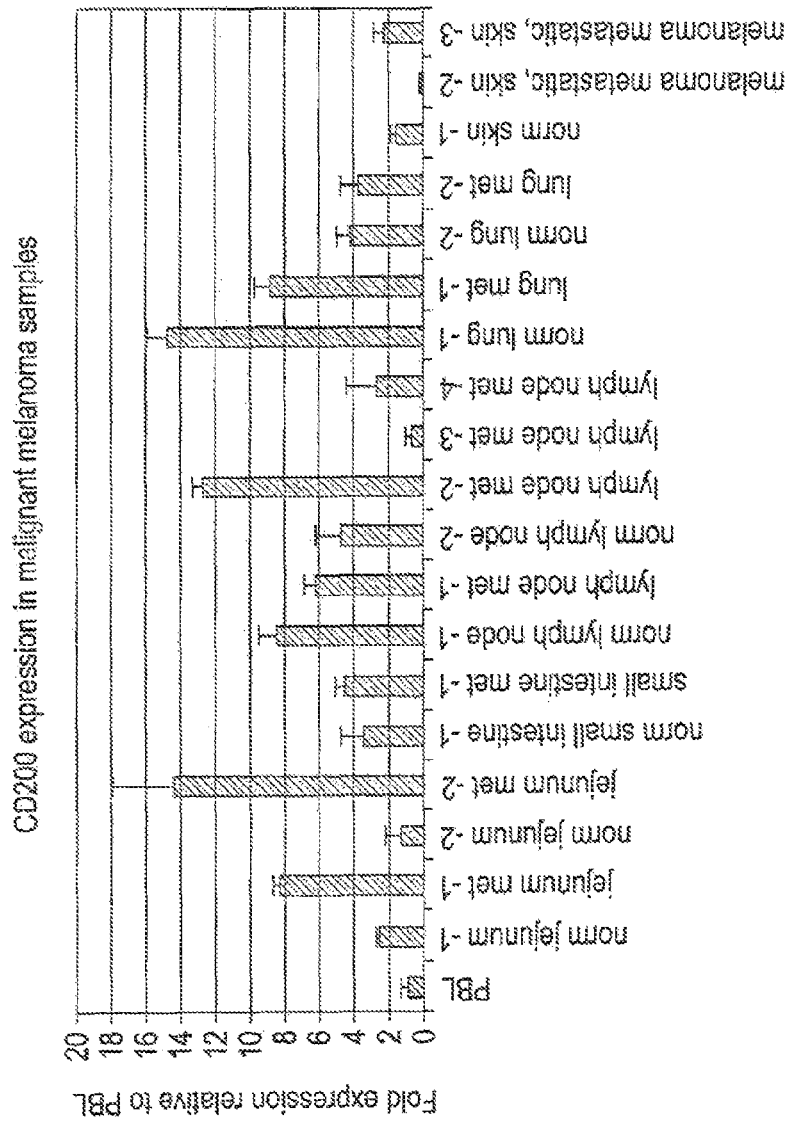

FIG. 23 shows the CD200 expression levels of several melanoma metastases samples: jejunum, small intestine, lymph node, lung, skin, and brain). Several of these samples are matched normal/tumor, indicated by the number (−1 pair or −2 pair). Other additional samples without matched normals were also run for comparison. Jejunum samples showed significantly higher CD200 expression levels than the normal organ, with the metastatic samples about 4-7-fold higher than normal jejunum.

D. Immunohistochemistry on Primary Patient Samples

IHC was performed on 2 frozen melanoma patient samples (LifeSpan). D1B5 and C2aB7 Fab fragments were used for staining. An IgG1 antibody was used as isotype control. Binding of the primary antibodies was detected with an anti-mouse secondary antibody and DAB chromagen.

Figure 24:
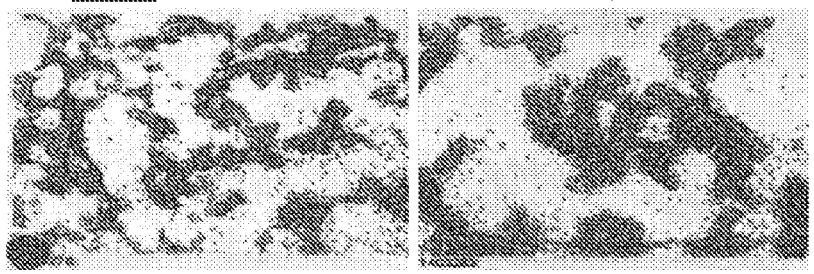
FIG. 24 shows immunohistochemical staining of CD200 of melanoma patient samples.

As shown in FIG. 24, both melanoma samples tested showed strong membrane staining with the anti-CD200 antibodies, but no staining with the isotype control. Normal skin tissue did not show CD200 staining. These data demonstrate that CD200 is not only upregulated on melanoma and ovarian cancer cell lines, but also on primary patient samples.

E. Immune Evasion of Melanoma and Ovarian Tumor Cells Through Upregulation of The Immunosuppressive Molecule CD200

Immune escape is a critical feature of cancer progression. Tumors can evade the immune system by multiple mechanisms, each a significant barrier to immunotherapy. Implementing new and more effective forms of immunotherapy will require understanding of these processes as well as their similarities and differences across cancers. We previously identified the immunosuppressive molecule CD200 to be upregulated on chronic lymphocytic leukemia cells. Presence of CD200 downregulates Th1 cytokine production required for an effective cytotoxic T cell response. We demonstrated in animal models that CD200 expression by human tumor cells prevents human lymphocytes from rejecting the tumor, and treatment with an antagonistic anti-CD200 antibody inhibited tumor growth. In this study, we evaluated whether CD200 upregulation is found on other cancers, and whether CD200 expression on these cancer cells affects the immune response.

Relative CD200 message levels were quantitated by RT-QPCR in ovarian adenocarcinoma (serous/serous metastatic/papillary serous, endometroid, mucinous, clear cell) and malignant melanoma metastatic patient samples.

Cell surface expression of CD200 was evaluated by IHC in two melanoma and three ovarian carcinoma (serous) patient frozen tissue samples in comparison with normal skin and normal ovaries. CD200 expression on the cell surface of the melanoma cancer cell lines SK-MEL-5, SK-MEL-24 and SK-MEL-28 and the ovarian cancer cell line OV-CAR-3 was assessed by FACS analysis using a PE-labeled anti-CD200 antibody. The effect of the CD200-expressing cancer cell lines on cytokine profile mixed in lymphocyte reactions were assessed by adding the cells to a culture of human monocyte-derived dendritic cells with allogeneic human T cells. Cytokine production (IL-2 and IFN-γ for Th1, IL4 and IL10 for Th2) was detected in the supernatant by ELISA.

Quantitative PCR showed CD200 expression levels in serous ovarian adenocarcinoma samples at up to 20 fold higher than normal PBL, and equal to or up to 4-fold higher than normal ovary. CD200 expression was at or below normal ovary levels in endometroid, mucinous, and clear cell ovarian adenocarcinoma samples. In malignant melanoma metastases to the jejunum, CD200 expression levels appeared to be significantly higher than normal samples. In malignant melanoma lung metastases, ⅔ showed higher CD200 expression than normal samples.

IHC showed strong, specific, membrane-associated CD200 staining on malignant cells of both melanoma patients. The normal skin sample showed faint staining of endothelial cells. Among three ovarian cancer patients, one showed strong CD200 staining, one was moderately positive, and one showed subsets of faintly stained tumor cells. In all three cases, the stroma showed strong staining.

CD200 was highly expressed on the cell surface of the melanoma cancer cell lines SK-MEL-24 and SK-MEL-28 as well as on the ovarian cancer cell line OV-CAR-3, and moderately expressed on the melanoma cell line SK-MEL-5. Addition of any of these cell lines to a mixed lymphocyte reaction downregulated the production of Th1 cytokines, while cell lines not expressing CD200 did not, demonstrating a direct correlation. Inclusion of an antagonistic anti-CD200 antibody during the culture abrogated the effect.

Melanoma and ovarian tumor cells can upregulate CD200, thereby potentially suppressing an effective immune response. Therapy with an antagonistic anti-CD200 might allow the immune system to mount an effective cytotoxic response against the tumor cells.

F. Effect of CD200-Expressing Cancer Cell Lines on Cytokine Profiles in Mixed Lymphocyte Reactions The capability of cells overexpressing CD200 to shift the cytokine response from a TH1 response (IL-2, IFN-γ) to a Th2 response (IL-4, IL-10) was assessed in a mixed lymphocyte reaction. As a source of CD200-expressing cells, either CD200 transfected cells or cells from CD200 positive cancer cell lines were used.

Mixed lymphocyte reactions were set up in 24 well plates using 250,000 dendritic cells matured from human peripheral monocytes using IL-4, GM-CSF and IFN-γ and $1 \times 10^6$ responder cells. Responder cells were T cell enriched lymphocytes purified from peripheral blood using Ficoll. T cells were enriched by incubating the cells for 1 hour in tissue culture flasks and taking the non-adherent cell fraction. 500,000 cells from the melanoma cancer cell lines SK-MEL-1, SK-MEL-24, SK-MEL-28, the ovarian cancer cell line OVCAR3 and the non-Hodgkin's lymphoma cell line Namalwa or primary CLL cells as positive control were added to the dendritic cells in the presence or absence of 30 μg/ml anti-CD200 antibody. Supernatants were collected after 48 and 68 hours and analyzed for the presence of cytokines Cytokines such as IL-2, IFN-γ, and IL-10 found in the tissue culture supernatant were quantified using ELISA. Matched capture and detection antibody pairs for each cytokine were obtained from R+D Systems (Minneapolis, Minn.), and a standard curve for each cytokine was produced using recombinant human cytokine. Anti-cytokine capture antibody was coated on the plate in PBS at the optimum concentration. After overnight incubation, the plates were washed and blocked for 1 hour with PBS containing 1% BSA and 5% sucrose. After 3 washes with PBS containing 0.05% Tween, supernatants were added at dilutions of two-fold or ten-fold in PBS containing 1% BSA. Captured cytokines were detected with the appropriate biotinylated anti-cytokine antibody followed by the addition of alkaline phosphatase conjugated streptavidin and SigmaS substrate. Color development was assessed with an ELISA plate reader (Molecular Devices).

As shown in FIG. 25A, the presence of cell lines with high CD200 expression (MEL-24, MEL-28, OVCAR-3) resulted in down-regulation of Th1 cytokines such as IL-2 and IFN-γ. In contrast, addition of MEL-1 (low CD200 expression) or Namalwa (no CD200 expression) did not affect the cytokine profile. Addition of the anti-CD200 antibody hB7VH3VL2 at 50 μg/ml fully restored the Th1 response (FIG. 25B), indicating that anti-CD200 antibody treatment of melanoma or ovarian cancer patients might be therapeutically beneficial.

Example 3

Elimination of Activated T Cells by C2aB7-G1 and its Derivatives

To evaluate whether anti-CD200 treatment has an effect in a cancer model using tumor cells not expressing CD200, Namalwa cells and human PBLs were injected into NOD/SCID mice, and mice were treated as outlined below. In this model, CD200 is only present on immune cells naturally expressing CD200 such as B cells and follicular T-helper cells.
Group Design:
10 animals/group
Group 1: $4\times10^6$ Namalwa s.c.
Group 2: $4\times10^6$ Namalwa s.c.+$8\times10^6$ PBL
Group 3: $4\times10^6$ Namalwa s.c.+$8\times10^6$ PBL+20 mg/kg hV3V2-G1
Group 4: $4\times10^6$ Namalwa s.c.+$8\times10^6$ PBL+5 mg/kg hV3V2-G1
Group 5: $4\times10^6$ Namalwa s.c.+$8\times10^6$ PBL+2.5 mg/kg hV3V2-G1
Group 6: $4\times10^6$ Namalwa s.c.+$4\times10^6$ PBL
Group 7: $4\times10^6$ Namalwa s.c.+$8\times10^6$ PBL+20 mg/kg chC2aB7-G2G4
Group 8: $4\times10^6$ Namalwa s.c.+$8\times10^6$ PBL+5 mg/kg chC2aB7-G2G4
Group 9: $4\times10^6$ Namalwa s.c.+$8\times10^6$ PBL+2.5 mg/kg chC2aB7-G2G4
Group 10: $4\times10^6$ Namalwa s.c.+$4\times10^6$ PBL+20 mg/kg chC2aB7-G2G4
Group 11: $4\times10^6$ Namalwa s.c.+$8\times10^6$ PBL+20 mg/kg alxn4100
$1;10^{th}$ of the dose was included in the injection mixture. Subsequent dosing was 2x/week i.v. for 3 weeks.

Figure 26:
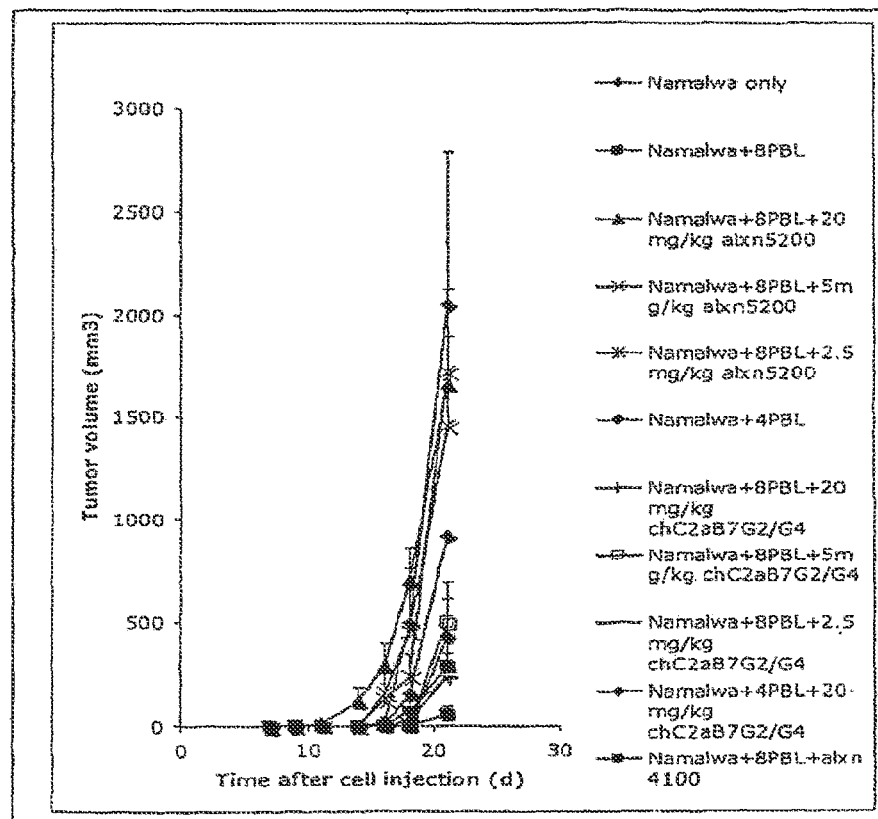
FIG. 26 shows the effects of administering anti-CD200 antibodies, with or without effector function, in the Namalwa/PBL model in which the tumors do not express CD200.
Figure 27A:
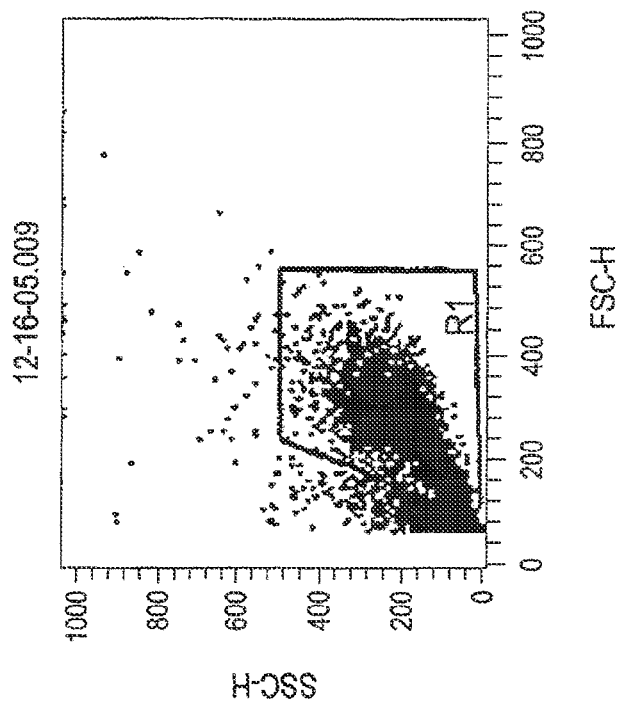
FIGS. 27A-F show flow cytometric analysis of CD200 expression on activated T-cells. CD3+ cells were activated with mOKT3, harvested, washed and subjected to staining with the indicated conjugated antibodies specific for human CD25, CD200, CD5, CD4 and CD8. Cells were washed and analyzed for immunofluorescence on a FacsCaliber flow cytometer using CellQuest software.
Figure 27B:
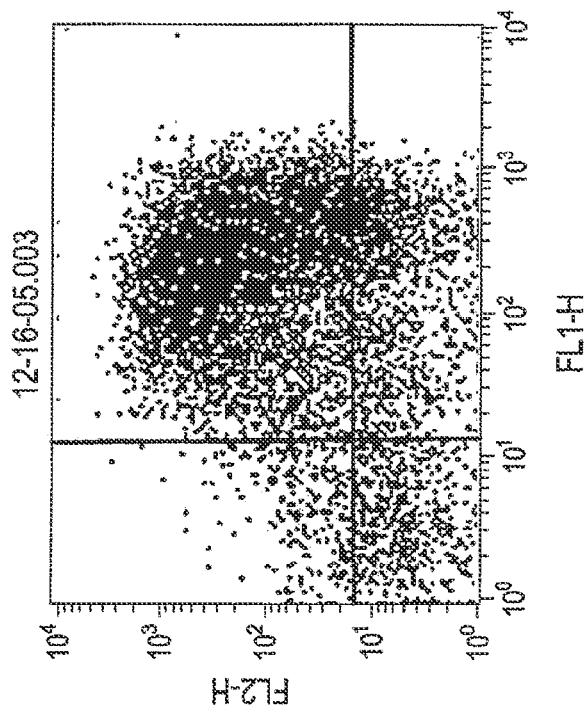
Figure 27C:
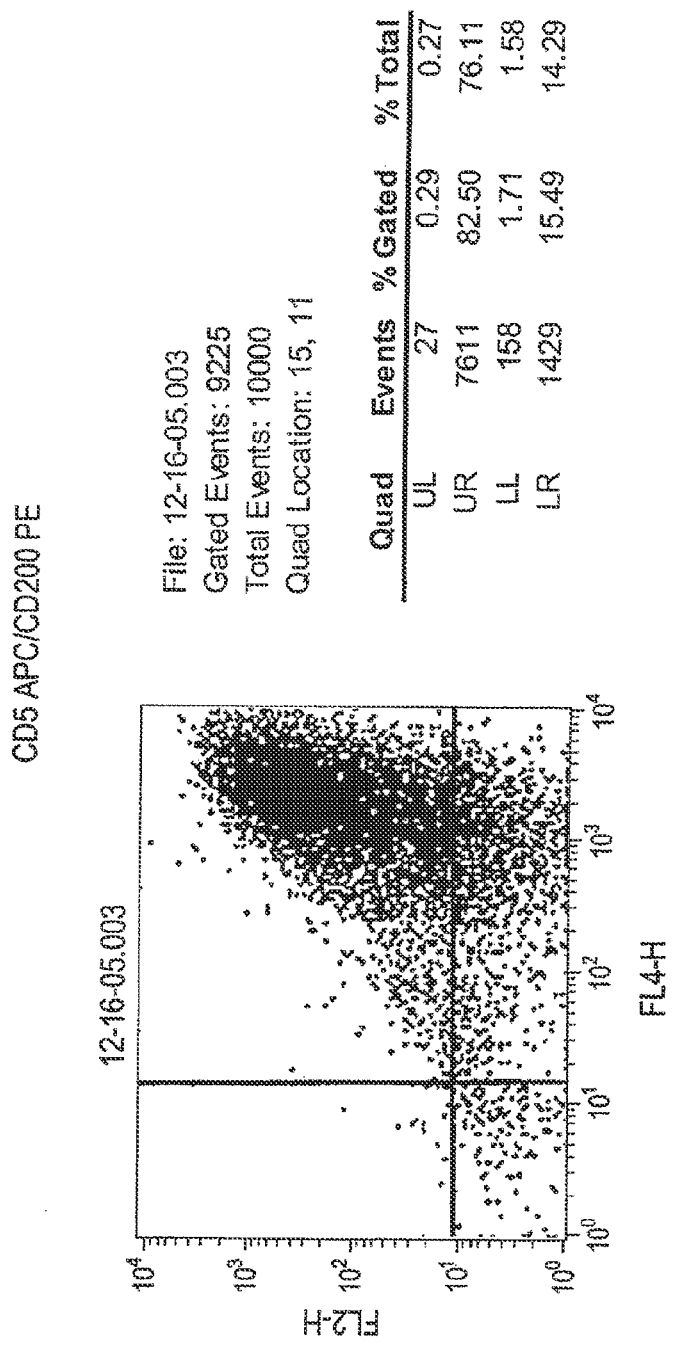
Figure 27D:
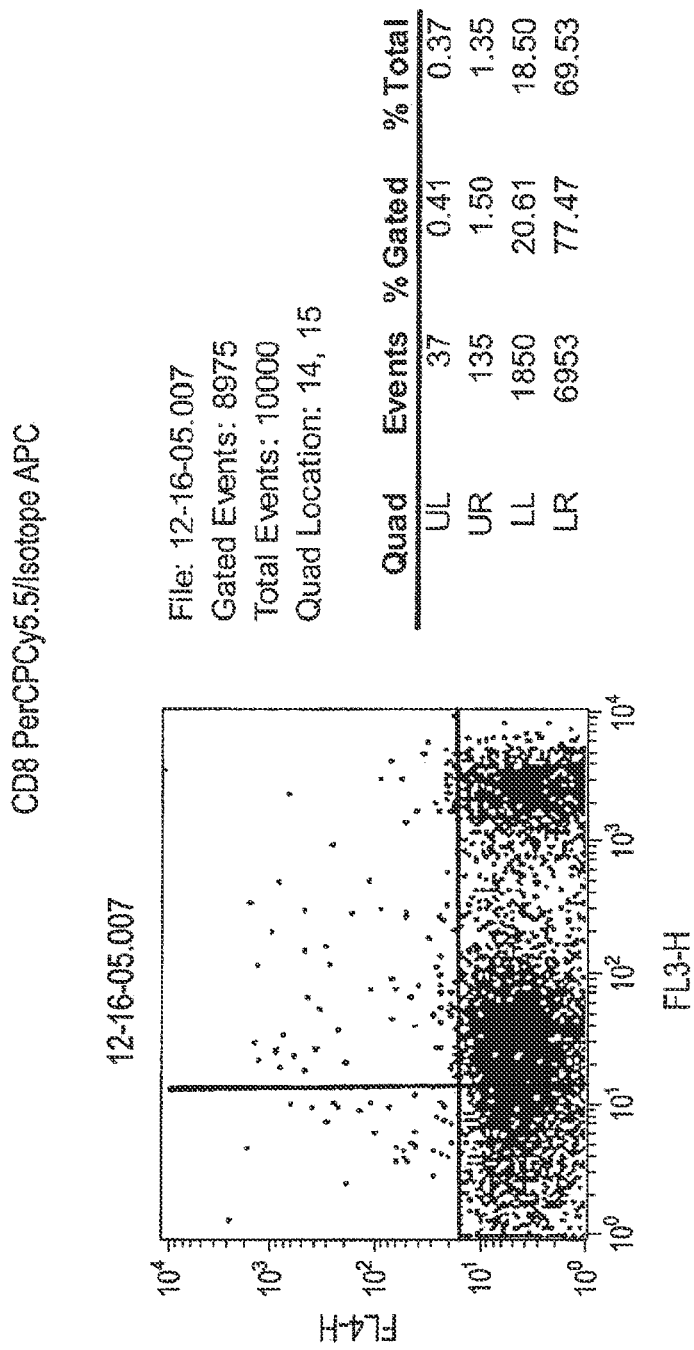
Figure 27E:
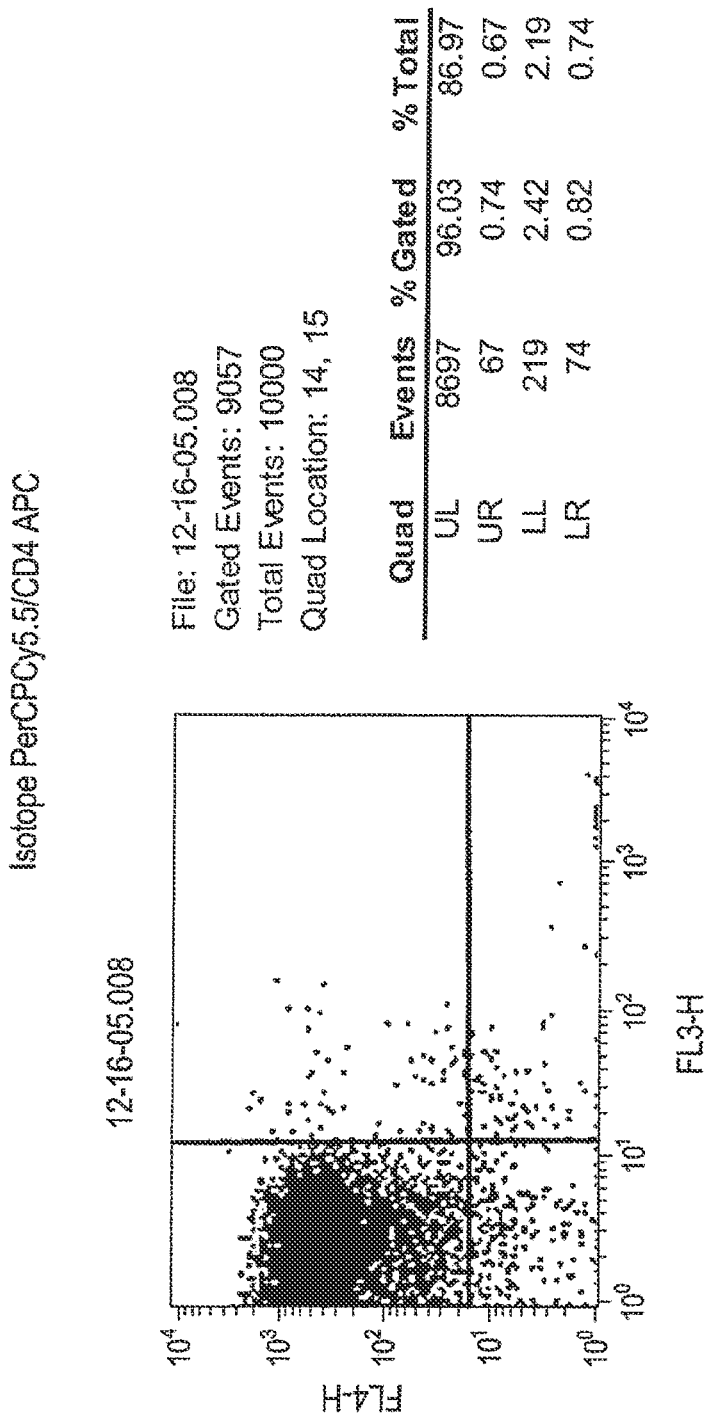
Figure 27F:
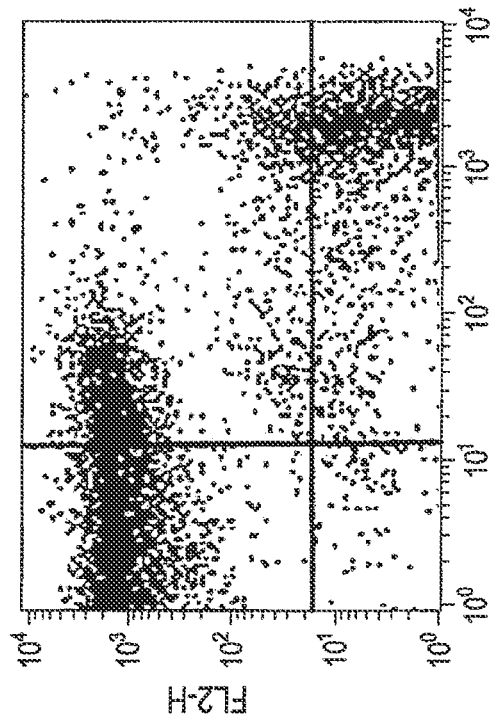

Tumor length (L) and width (W) were measured 3 times/week and tumor volumes were calculated by L*W*W/2. FIG. 26 shows that as previously established, simultaneous injection of human PBLs with Namalwa cells inhibits tumor growth. No effect of chC2aB7-G2G4 on PBL-mediated tumor growth inhibition was observed. In contrast, administration of ALXN5200 (hB7VH3VL2-G1) blocked PBL mediated tumor growth inhibition. In the absence of CD200 on tumor cells, it appears that anti-CD200 antibody treatment with an antibody that mediates effector function such as G1 constructs, critical effector cells in the PBL population are eliminated. These data suggest that anti-CD200 cancer therapy is less effective when an antibody with effector function is being used as compared to using the antibody without effector function. However, anti-CD200 treatment using a construct with effector function could be therapeutically beneficial in situations where elimination of immune cells is desirable such as in the transplantation setting or autoimmune diseases.

Example 4

T Cell Killing by HB7VH3VL2

To evaluate whether incubation of activated T cells with anti-CD200 antibodies containing a constant region mediating effector function (e.g. G1) results in the killing of the T cells, T cells were activated and killing assays were set up as described below.

A). CD3+ T Cell Isolation

Human peripheral blood lymphocytes (PBLs) were obtained from normal healthy volunteers by density gradient centrifugation of heparinized whole blood using the Accuspin™ System. Fifteen ml of Histopaque-1077 (Sigma, St. Louis, Mo.; cat#H8889) was added to each Accuspin tube (Sigma, St. Louis, Mo.; ca A2055) which was then centrifuged at 1500 rpm for 2 minutes so that the Histopaque was allowed to pass through the frit. Thirty ml of whole blood was layered over the frit and the tubes were centrifuged for 15 minutes at 2000 rpm at room temperature with no brake. The PBL interface was collected and mononuclear cells were washed twice in PBS with 2% heat-inactivated fetal bovine serum (FBS) (Atlas Biologicals, Ft. Collins, Colo.; cat#F-0500-D) with 1200 rpm centrifugation for 10 minutes. CD3+ T cells were isolated by passage over a HTCC-5 column (R&D Systems) according to the manufacturer's instructions. Eluted cells were washed, counted and resuspended in RPMI 1640 containing 5% heat-inactivated single donor serum, 2 mM L-glutamine, 10 mM Hepes and penicillin/streptomycin.

B. Activation with plate-bound mOKT3

Wells of 12-well plates (Falcon) were coated by overnight incubation at 4° C. with 10 µg/mL mOKT3 (Orthoclone) diluted in PBS. Residual antibody was removed and the plates gently rinsed with PBS. Purified CD3+ T cells, isolated as described above, were added to the plates at a final concentration of $2\times10^6$/well in RPMI 1640 containing 5% heat-inactivated single donor serum, 2 mM L-glutamine, 10 mM Hepes and penicillin/streptomycin. Cells were maintained for 72 hours at 37° C. in a humidified incubator containing 5% $CO_2$.

C. $^{51}$Chromium Labeling of mOKT3-Activated CD3+ Target Cells

At the end of the culture period, mOKT3-activated CD3+ cells were harvested, washed and resuspended at $10^7$ cells/mL in RPMI 1640 without serum. Cells were chromated by the addition of 125 of $^{51}$Chromium (Perkin Elmer, Billerica, Mass.)/$10^6$ cells for 2 hours at 37° C. Labeled cells were harvested, washed in RPMI containing 5% heat-inactivated single donor serum and resuspended at a final concentration of $2\times10^5$ cells/mL in the same medium.

D. Preparation of Autologous NK Effector Cells

Human peripheral blood lymphocytes (PBLs) from the same individual were obtained as described above by density gradient centrifugation. The PBL interface was collected and mononuclear cells were washed twice in PBS with 2% heat-inactivated fetal bovine serum (FBS) (Atlas Biologicals, Ft. Collins, Colo.; cat#F-0500-D) with 1200 rpm centrifugation for 10 minutes. CD56+ cells were isolated by positive selection over anti-CD56-conjugated magnetic beads (Miltenyi Biotec, Auburn, Calif., Cat #120-000-307) according to the manufacturer's instructions. Eluted cells were washed, counted and resuspended at $1.3\times10^6$ cells/mL in RPMI 1640 containing 5% heat-inactivated single donor serum, 2 mM L-glutamine, 10 mM Hepes and penicillin/streptomycin. Cells were incubated overnight at 37° C. in a humidified incubator containing 5% $CO_2$ at a final concentration of $4\times10^6$ cells/well in 3 mL of the same medium. At the end of the culture period, the cells were harvested, washed, counted and resuspended in serum-free RPMI containing 2 mM L-glutamine, 10 mM Hepes, $2\times10^{-5}$M 2-mercaptoethanol and penicillin/streptomycin.

E. ADCC Assay $^{51}$Cr-labelled mOKT3-activated CD3+ target cells prepared as described above were distributed in wells of a 96-well plate at $10^4$ cells/well in 50 µL. CD56+ effector cells were harvested, washed, counted and resuspended at either 2.5×10⁶ cells/mL (for an effector:target cell ratio of 25:1) or 10⁶ cells/mL (for an effector:target cell ratio of 10:1) and were distributed (100 µL/well) to wells containing the target cells. Ten-fold dilutions of anti-CD200 antibodies (V3V2-G1 or V3V2-G2/G4) were added to the effectors and targets at final concentrations of 10, 1, 0.1 and 0.01 µg/mL. Assay controls included the following: 1) effectors and targets in the absence of antibody (0 Ab); 2) target cells in the absence of effectors (spontaneous lysis) and 3) effectors and targets incubated with 0.2% Tween-80 (maximum release). All cell culture conditions were performed in triplicate. Cells were incubated at 37° C. for 4 hours in a humidified incubator containing 5% $CO_2$. At the end of the culture period, the plates were centrifuged to pellet the cells and 150 µL of cell supernatant was transferred to scintillation vials and counted in a gamma scintillation counter (Wallac). The results are expressed as percent specific lysis according to the following formula:

(Mean sample counts per minute (cpm)−mean spontaneous lysis)×100 (mean maximum lysis−mean spontaneous lysis)

F. Flow Cytometry

One hundred µl of cell suspensions (mOKT3-activated CD3+ cells or purified CD56+ NK cells) prepared as described above were distributed to wells of a 96-well round bottom plate (Falcon, Franklin Lakes N.J.; cat#353077). Cells were incubated for 30 minutes at 4° C. with the indicated combinations of the following fluorescein isothiocyanate (FITC)-, Phycoerythrin (PE)-, PerCP-Cy5.5-, or allophycocyanin (APC)-conjugated antibodies (all from Becton-Dickinson, San Jose, Calif.); anti-human CD25-FITC (cat#555431); anti-human CD3-APC (cat#555335); anti-human CD200-PE (cat #552475); anti-human CD8-PerCP-Cy5.5 (cat#341051); anti-human CD4-APC (cat#555349); anti-human CD5-APC (cat#555355) and anti-human CD56-APC (cat#341025). Isotype controls for each labeled antibody were also included. After washing cells twice with FACS buffer (1800 rpm centrifugation for 3 minutes), cells were resuspended in 300 µl of PBS (Mediatech, Herndon, Va.; cat#21-031-CV) and analyzed by flow cytometry using a FacsCaliber machine and CellQuest Software (Becton Dickinson, San Jose, Calif.).

As shown in FIG. 27, activated T cells show high CD200 expression on their surface. Activated T cells are efficiently killed in the presence of VH3VL2-G1 but not VH3VL2-G2G4 when NK cells are used as effector cells (FIG. 28). These data demonstrate that anti-CD200 antibodies with effector function can eliminate activated T cells. Such an antibody could be of therapeutic use in the transplantation setting or for the treatment of autoimmune diseases.

In addition to regulatory T cells, plasmacytoid dendritic cells have been shown to play a negative immunoregulatory role in human cancer (Wei S, Kryczek 1, Zou L, Daniel B, Cheng P, Mottram P, Curiel T, Lange A, Zou W Plasmacytoid dendritic cells induce CD8+ regulatory T cells in human ovarian carcinoma. Cancer Res. 2005 Jun. 15; 65(12):5020-6). Combination of a therapy eliminating plasmacytoid dendritic cells with anti-CD200 therapy could therefore be advantageous.

Example 5

CD200 on Plasma Cells

Bone marrow cells from 10 multiple myeloma patients and 3 normal donors were prepared by first lysing red blood cells using ammonium chloride. Cells were resuspended in FACS buffer and labeled with the following antibody cocktails:
Kappa-FITC/CD38-PE/CD138-PerCP-Cy5.5
Lambda-FITC/CD38-PE/CD 138-PerCP-Cy5.5
Isotype Control-FITC/CD38-PE
CD200-FITC/CD38-PE Data were collected using a BD FACS Canto and analyzed using BD DiVA software. Expression of CD200 on CD38 bright cells (plasma cells) was analyzed. As shown in FIG. 29, a portion of plasma cells expresses CD200 at high intensity in normal donors. In multiple myeloma patients, the majority of plasma cells express CD200.

In the multiple myeloma setting, similar to CLL or other cancers expressing CD200, CD200 expression by the tumor cells might prevent the immune system from eradicating the tumor cells. Antagonistic anti-CD200 therapy might subsequently allow the immune system to eliminate cancer cells. Ablative anti-CD200 therapy targeting plasma cells could be therapeutically beneficial in the autoimmune or transplantation setting.

Example 6

CD200 on Viruses

CD200 is also expressed on a number of viruses such as myxoma virus M141R or human herpesvirus 8. Similar to expression of CD200 on tumor cells, CD200 on viruses might prevent the immune system from effectively clearing the virus. Treatment with an antagonistic anti-CD200 antibody could be therapeutically beneficial in an infection with a CD200 expressing virus, allowing the immune system to eradicate the virus. Alternatively, an ablative anti-CD200 antibody could be used.

It will be understood that various modifications may be made to the embodiments disclosed herein. For example, as those skilled in the art will appreciate, the specific sequences described herein can be altered slightly without necessarily adversely affecting the functionality of the polypeptide, antibody or antibody fragment used in binding OX-2/CD200. For instance, substitutions of single or multiple amino acids in the antibody sequence can frequently be made without destroying the functionality of the antibody or fragment. Thus, it should be understood that polypeptides or antibodies having a degree of identity greater than 70% to the specific antibodies described herein are within the scope of this disclosure. In particularly useful embodiments, antibodies having an identity greater than about 80% to the specific antibodies described herein are contemplated. In other useful embodiments, antibodies having an identity greater than about 90% to the specific antibodies described herein are contemplated. Therefore, the above description should not be construed as limiting, but merely as exemplifications of preferred embodiments. Those skilled in the art will envision other modifications within the scope and spirit of this disclosure.

REFERENCES

The following references are incorporated herein by reference to more fully describe the state of the art to which the present invention pertains. Any inconsistency between these publications below or those incorporated by reference above and the present disclosure shall be resolved in favor of the present disclosure.

1) Agarwal, et al., (2003). Disregulated expression of the Th2 cytokine gene in patients with intraoral squamous cell carcinoma. Immunol Invest 32:17-30.

2) Almasri, N M et al. (1992). Am J Hemato 140 259-263.
3) Contasta, et al., (2003). Passage from normal mucosa to adenoma and colon cancer: alteration of normal sCD30 mechanisms regulating TH1/TH2 cell functions. Cancer Biother Radiopharm 18:549-557.
4) Gorczynski, et al., (1998). Increased expression of the novel molecule OX-2 is involved in prolongation of murine renal allograft survival. Transplantation 65:1106-1114.
5) Gorczynski, et al., (2001). Evidence of a role for CD200 in regulation of immune rejection of leukaemic tumour cells in CS7BL/6 mice. Clin Exp Immunol 126:220-229.
6) Hainsworth, J D (2000). Oncologist 2000; 5(5):376-84.
7) Inagawa, et al., (1998). Mechanisms by which chemotherapeutic agents augment the antitumor effects of tumor necrosis factor: involvement of the pattern shift of cytokines from Th2 to Th1 in tumor lesions. Anticancer Res 18:3957-3964.
8) Ito, et al., (1999). Lung carcinoma: analysis of T helper type 1 and 2 cells and T cytotoxic type 1 and 2 cells by intracellular cytokine detection with flow cytometry. Cancer 85:2359-2367.
9) Kiani, et al., (2003). Normal intrinsic Th1/Th2 balance in patients with chronic phase chronic myeloid leukemia not treated with interferon-alpha or imatinib. Haematologica 88:754-761.
10) Lauerova, et al., (2002). Malignant melanoma associates with Th1/Th2 imbalance that coincides with disease progression and immunotherapy response. Neoplasma 49:159-166.
11) Maggio, et al., (2002). Chemokines, cytokines and their receptors in Hodgkin's lymphoma cell lines and tissues. Ann Oncol 13 Suppl 1:52-56.
12) Nilsson, K (1992). Burn Cell. 5(1):25-41.
13) Podhorecka, et al., (2002). T type 1/type 2 subsets balance in B-cell chronic lymphocytic leukemia—the three-color flow cytometry analysis. Leuk Res 26:657-660.
14) Pu, Q Q and Bezwoda, W (2000). Anticancer Res. 20(4): 2569-78.
15) Smyth, et al., (2003). Renal cell carcinoma induces prostaglandin E2 and T-helper type 2 cytokine production in peripheral blood mononuclear cells. Ann Surg Oncol 10:455-462.
16) Tatsumi, et al., (2002). Disease-associated bias in T helper type 1 (Th1)/Th2 CD4(+) T cell responses against MAGE-6 in HLA-DRB 1040 (+) patients with renal cell carcinoma or melanoma. J Exp Med 196:619-628.
17) Walls A V et al. (1989). Int. J. Cancer 44846-853.
18) Winter, et al., (2003). Tumour-induced polarization of tumour vaccine-draining lymph node T cells to a type 1 cytokine profile predicts inherent strong immunogenicity of the tumour and correlates with therapeutic efficacy in adoptive transfer studies. Immunology 108:409-419.
19) Cameron, C. M., J. W. Barrett, L. Liu, A. R. Lucas, and G. McFadden. 2005. Myxoma virus M141R expresses a viral CD200 (vOX-2) that is responsible for down-regulation of macrophage and T-cell activation in vivo. J Virol 79:6052.
20) Foster-Cuevas, M., G. J. Wright, M. J. Puklavec, M. H. Brown, and A. N. Barclay. 2004. Human herpesvirus 8 K14 protein mimics CD200 in down-regulating macrophage activation through CD200 receptor. J Virol 78:7667.
21) Nicholas, T. 2003. Human herpesvirus-8-encoded signalling ligands and receptors. J Biomed Sci 10:475.
22) Shiratori, I., M. Yamaguchi, M. Suzukawa, K. Yamamoto, L. L. Lanier, T. Saito, and H. Arase. 2005. Down-regulation of basophil function by human CD200 and human herpesvirus-8 CD200. *J Immunol* 175:4441.
23) Voigt, S., G. R. Sandford, G. S. Hayward, and W. H. Burns. 2005. The English strain of rat cytomegalovirus (CMV) contains a novel captured CD200 (vOX2) gene and a spliced CC chemokine upstream from the major immediate-early region: further evidence for a separate evolutionary lineage from that of rat CMV Maastricht. J Gen Virol 86:263.
24) Zhang, J., J. Wang, C. Wood, D. Xu, and L. Zhang. 2005. Kaposi's sarcoma-associated herpesvirus/human herpesvirus 8 replication and transcription activator regulates viral and cellular genes via interferon-stimulated response elements. *J Virol* 79:5640.

The invention claimed is:

1. A method for treating a patient afflicted with a cancer comprising cancer cells that express CD200, the method comprising administering to the patient an anti-CD200 antibody in an amount effective to treat the cancer, wherein the anti-CD200 antibody:

(i) inhibits the interaction between CD200 and CD200R; and (ii) comprises a variant Fc constant region that has ADCC activity or CDC activity equal to or less than the ADCC activity or CDC activity the anti-CD200 antibody would have if it had a G2/G4 Fc constant region consisting of amino acid residues 137-462 of SEQ ID NO:13.

2. The method of claim 1, wherein the cancer cells overexpress CD200 relative to normal cells of the same histological type as the cells from which the cancer cells are derived.

3. The method of claim 1, wherein the cancer is selected from the group consisting of a neural crest cell cancer, plasma cell cancer, a lymphoma, leukemia, ovarian cancer, skin cancer, lung cancer, renal cancer, breast cancer, prostate cancer, neuroblastoma, and myeloma.

4. The method of claim 1, wherein the anti-CD200 antibody is a murine antibody, a chimeric antibody, a humanized antibody, a deimmunized antibody, or a human antibody.

5. The method of claim 1, wherein the variant Fc constant region is an altered form of a native Fc constant region selected from the group consisting of IgG1, IgG2, IgG3, IgG4, IgM, IgA1, IgA2, IgA, IgD, and IgE.

6. The method of claim 1, wherein the variant Fc constant region comprises at least one amino acid substitution, insertion, or deletion, relative to the corresponding native constant region.

7. The method of claim 1, wherein:
(a) the variant Fc constant region is a G2/G4 constant region;
(b) the variant Fc constant region comprises:
  (i) one or both of: (a) a phenylalanine to alanine substitution at position 234 and (b) a leucine to alanine substitution at position 235;
  (ii) a K322A mutation in the CH2 domain;
  (iii) the CH1 and hinge regions of an IgG2 antibody;
  (iv) the CH2 and CH3 regions of an IgG4 antibody; or
  (v) the CH1 and hinge regions of an IgG2 antibody and the CH2 and CH3 regions of an IgG4 antibody; or
(c) the variant constant region lacks a hinge region.

8. The method of claim 7, wherein the G2/G4 constant region comprises amino acid residues 137-462 of SEQ ID NO:13.

9. The method of claim 1, wherein the anti-CD200 antibody comprises:
(a) a light chain polypeptide comprising:
  (i) amino acid residues 21 to 127 of SEQ ID NO:24; or
  (ii) amino acid residues 21 to 234 of SEQ ID NO:24; and
(b) a heavy chain polypeptide comprising:
  (iii) amino acid residues 21 to 137 of SEQ ID NO:15; or
  (iv) amino acid residues 21 to 463 of SEQ ID NO:15.

10. The method of claim 1, wherein the anti-CD200 antibody comprises:
(a) a light chain polypeptide comprising:
  (i) amino acid residues 21 to 127 of SEQ ID NO:32; or
  (ii) amino acid residues 21 to 234 of SEQ ID NO:32; and
(b) a heavy chain polypeptide comprising:
  (iii) amino acid residues 21 to 142 of SEQ ID NO:20.

11. The method of claim 1, wherein the anti-CD200 antibody comprises:
(a) a light chain polypeptide comprising:
  (i) amino acid residues 23 to 129 of SEQ ID NO:28; or
  (ii) amino acid residues 23 to 236 of SEQ ID NO:28; and
(b) a heavy chain polypeptide comprising:
  (iii) amino acid residues 20 to 136 of SEQ ID NO:13; or
  (iv) amino acid residues 20 to 462 of SEQ ID NO:13.

12. The method of claim 1, further comprising administering to the patient a second agent or therapy.

13. The method of claim 12, wherein the second agent is a chemotherapeutic agent.

14. The method of claim 12, wherein the therapy is a radiation therapy.

15. The method of claim 1, wherein the variant Fc constant region has no ADCC activity or no CDC activity.

16. The method of claim 1, wherein the anti-CD200 antibody comprises:
(a) a heavy chain polypeptide comprising:
  (i) amino acid residues 20 to 136 of SEQ ID NO:11; or
  (ii) amino acid residues 20 to 136 of SEQ ID NO:9; and
(b) a light chain polypeptide comprising amino acid residues 23 to 129 of SEQ ID NO:26.

17. A method for treating a patient afflicted with a cancer comprising cancer cells that express CD200, the method comprising administering to the patient an anti-CD200 antibody in an amount effective to treat the cancer, wherein the anti-CD200 antibody:
(i) inhibits the interaction between CD200 and CD200R; and
(ii) comprises a variant Fc constant region that exhibits decreased effector function relative to the effector function of the native Fc constant region from which the variant Fc constant region was engineered.

18. The method of claim 17, wherein the variant Fc constant region was engineered by: (a) introducing into a native Fc constant region at least one amino acid substitution, insertion, or deletion, wherein the amino acid sequence of the variant Fc constant region is at least 95% identical to the amino acid sequence of the native Fc constant region or (b) altering the glycosylation of a native Fc constant region, wherein the variant Fc constant region has reduced effector function as compared to the native Fc constant region.

19. The method of claim 17, wherein the cancer cells overexpress CD200 relative to normal cells of the same histological type as the cells from which the cancer cells are derived.

20. The method of claim 17, wherein the cancer is selected from the group consisting of a neural crest cell cancer, plasma cell cancer, a lymphoma, leukemia, ovarian cancer, skin cancer, lung cancer, renal cancer, breast cancer, prostate cancer, neuroblastoma, and myeloma.

21. The method of claim 17, wherein the anti-CD200 antibody is a murine antibody, a chimeric antibody, a humanized antibody, a deimmunized antibody, or a human antibody.

22. The method of claim 17, wherein the variant Fc constant region is an altered form of a native Fc constant region selected from the group consisting of IgG1, IgG2, IgG3, IgG4, IgM, IgA1, IgA2, IgA, IgD, and IgE.

23. The method of claim 17, wherein the variant Fc constant region comprises at least one amino acid substitution, insertion, or deletion, relative to the corresponding native constant region.

24. The method of claim 17, wherein:
(a) the variant Fc constant region is a G2/G4 constant region;
(b) the variant Fc constant region comprises:
  (i) altered glycosylation;
  (ii) one or both of: (x) a phenylalanine to alanine substitution at position 234 and (y) a leucine to alanine substitution at position 235;
  (iii) a K322A mutation in the CH2 domain;
  (iv) the CH1 and hinge regions of an IgG2 antibody;
  (v) the CH2 and CH3 regions of an IgG4 antibody; or
  (vi) the CH1 and hinge regions of an IgG2 antibody and the CH2 and CH3 regions of an IgG4 antibody; or
(c) the altered constant region lacks a hinge region.

25. The method of claim 24, wherein the G2/G4 constant region comprises amino acid residues 137-462 of SEQ ID NO:13.

26. The method of claim 24, wherein the variant Fc constant region is a produced in a cell line deficient in glycosylation.

27. The method of claim 24, wherein the altered glycosylation comprises one or more of the following: (i) a change in one or more sugar components; (ii) presence of one or more additional sugar components; and (iii) absence of one or more sugar components.

28. The method of claim 17, wherein the anti-CD200 antibody comprises:
(a) a light chain polypeptide comprising:
  (i) amino acid residues 21 to 127 of SEQ ID NO:24; or
  (ii) amino acid residues 21 to 234 of SEQ ID NO:24; and
(b) a heavy chain polypeptide comprising:
  (iii) amino acid residues 21 to 137 of SEQ ID NO:15; or
  (iv) amino acid residues 21 to 463 of SEQ ID NO:15.

29. The method of claim 17, wherein the anti-CD200 antibody comprises:
(a) a light chain polypeptide comprising:
  (i) amino acid residues 21 to 127 of SEQ ID NO:32; or
  (ii) amino acid residues 21 to 234 of SEQ ID NO:32; and
(b) a heavy chain polypeptide comprising:
  (iii) amino acid residues 21 to 142 of SEQ ID NO:20.

30. The method of claim 17, wherein the anti-CD200 antibody comprises:
(a) a light chain polypeptide comprising:
  (i) amino acid residues 23 to 129 of SEQ ID NO:28; or
  (ii) amino acid residues 23 to 236 of SEQ ID NO:28; and
(b) a heavy chain polypeptide comprising:
  (iii) amino acid residues 20 to 136 of SEQ ID NO:13; or
  (iv) amino acid residues 20 to 462 of SEQ ID NO:13.

31. The method of claim 17, wherein the anti-CD200 antibody comprises:
(a) a heavy chain polypeptide comprising:
  (i) amino acid residues 20 to 136 of SEQ ID NO:11; or
  (ii) amino acid residues 20 to 136 of SEQ ID NO:9; and
(b) a light chain polypeptide comprising amino acid residues 23 to 129 of SEQ ID NO:26.

32. The method of claim 17, wherein the variant Fc constant region has 0 to 20% of the FcR binding of the native Fc constant region.

33. The method of claim 17, wherein the variant Fc constant region has reduced or no ADCC activity or CDC activity relative to the native Fc constant region.

34. The method of claim 17, further comprising administering to the patient a second agent or therapy.

35. The method of claim 34, wherein the second agent is a chemotherapeutic agent.

36. The method of claim 34, wherein the therapy is a radiation therapy.

37. A method for treating a patient afflicted with a cancer comprising cancer cells that express CD200, the method comprising administering to the patient an anti-CD200 antibody in an amount effective to treat the cancer, wherein the anti-CD200 antibody comprises a G2/G4 constant region and inhibits the interaction between CD200 and CD200R.

38. The method of claim 37, wherein the G2/G4 constant region comprises amino acid residues 137-462 of SEQ ID NO:13.

39. The method of claim 37, wherein the anti-CD200 antibody is a murine antibody, a chimeric antibody, a humanized antibody, a deimmunized antibody, or a human antibody.

40. The method of claim 37, wherein the anti-CD200 antibody comprises:
I.
(a) a light chain polypeptide comprising:
  (i) amino acid residues 21 to 127 of SEQ ID NO:24; or
  (ii) amino acid residues 21 to 234 of SEQ ID NO:24; and
(b) a heavy chain polypeptide comprising:
  (iii) amino acid residues 21 to 137 of SEQ ID NO:15; or
  (iv) amino acid residues 21 to 463 of SEQ ID NO:15;
II.
(a) a light chain polypeptide comprising:
  (i) amino acid residues 21 to 127 of SEQ ID NO:32; or
  (ii) amino acid residues 21 to 234 of SEQ ID NO:32; and
(b) a heavy chain polypeptide comprising:
  (iii) amino acid residues 21 to 142 of SEQ ID NO:20;
III.
(a) a light chain polypeptide comprising:
  (i) amino acid residues 23 to 129 of SEQ ID NO:28; or
  (ii) amino acid residues 23 to 236 of SEQ ID NO:28; and
(b) a heavy chain polypeptide comprising:
  (iii) amino acid residues 20 to 136 of SEQ ID NO:13; or
  (iv) amino acid residues 20 to 462 of SEQ ID NO:13; or
IV.
(a) a heavy chain polypeptide comprising:
  (i) amino acid residues 20 to 136 of SEQ ID NO:11; or
  (ii) amino acid residues 20 to 136 of SEQ ID NO:9; and
(b) a light chain polypeptide comprising amino acid residues 23 to 129 of SEQ ID NO:26.

41. The method of claim 37, wherein the cancer cells overexpress CD200 relative to normal cells of the same histological type as the cells from which the cancer cells are derived.

42. The method of claim 37, wherein the cancer is selected from the group consisting of a neural crest cell cancer, plasma cell cancer, a lymphoma, leukemia, ovarian cancer, skin cancer, lung cancer, renal cancer, breast cancer, prostate cancer, neuroblastoma, and myeloma.

* * * * *

SEQUENCE LISTING

<160> NUMBER OF SEQ ID NOS: 51

<210> SEQ ID NO 1
<211> LENGTH: 22
<212> TYPE: DNA
<213> ORGANISM: Artificial Sequence
<220> FEATURE:
<223> OTHER INFORMATION: Primer C7mhHF

<400> SEQUENCE: 1
tcctcagcct ccaccaaggg cc                                           22

<210> SEQ ID NO 2
<211> LENGTH: 20
<212> TYPE: DNA
<213> ORGANISM: Artificial Sequence
<220> FEATURE:
<223> OTHER INFORMATION: Primer Rev Age Pri

<400> SEQUENCE: 2
gggcgcctga gttccacgac                                              20

<210> SEQ ID NO 3

```
<211> LENGTH: 39
<212> TYPE: DNA
<213> ORGANISM: Artificial Sequence
<220> FEATURE:
<223> OTHER INFORMATION: Primer C2aB7 rev

<400> SEQUENCE: 3
ggcccttggt ggaggctgag gaaactgtga gagtggtgc                          39

<210> SEQ ID NO 4
<211> LENGTH: 22
<212> TYPE: DNA
<213> ORGANISM: Artificial Sequence
<220> FEATURE:
<223> OTHER INFORMATION: Primer lacpri

<400> SEQUENCE: 4
gctcccggct cgtatgttgt gt                                            22

<210> SEQ ID NO 5
<211> LENGTH: 24
<212> TYPE: DNA
<213> ORGANISM: Artificial Sequence
<220> FEATURE:
<223> OTHER INFORMATION: Primer LeadVHpAX

<400> SEQUENCE: 5
atatgaaata tctgctgccg accg                                          24

<210> SEQ ID NO 6
<211> LENGTH: 2010
<212> TYPE: DNA
<213> ORGANISM: Artificial Sequence
<220> FEATURE:
<223> OTHER INFORMATION: heavy chain chC2aB7-hG1, genomic sequence hG1

<400> SEQUENCE: 6
atgggatgga gctgtatcat cctcttcttg gtagcaacag ctacaggtgt ccactccctc    60
gaggtccagc tgcaacagtc tggacctgag ctggtgaagc ctggggcttc actgaagatg   120
tcctgcaagg cttctggtta ttcattcact gactacatca tactctgggt gaagcagaac   180
catggaaaga gccttgagtg gattggacat attgatcctt actatggtag ttctaactac   240
aatctgaaat tcaagggcaa ggccacattg actgtagaca atcttccagc acagcctac    300 atgcagctca acagtctgac atctgaggac tctgcagtct attactgtgg aagatctaag   360
agggactact ttgactactg gggccaaggc accactctca cagtttcctc agcctccacc   420
aagggcccat cggtcttccc cctggcaccc tcctccaaga gcacctctgg cggcacagcg   480
gccctgggct gcctggtcaa ggactacttc cccgaaccgg tgacggtgtc gtggaactca   540
ggcgccctga ccagcggcgt gcacaccttc ccggctgtcc tacagtcctc aggactctac   600
tccctcagca gcgtggtgac cgtgccctcc agcagcttgg gcacccagac ctacatctgc   660
aacgtgaatc acaagcccag caacaccaag gtggacaaga gagttggtga gaggccagca   720
cagggaggga gggtgtctgc tggaagccag gctcagcgct cctgcctgga cgcatcccgg   780
ctatgcagtc ccagtccagg gcagcaaggc aggccccgtc tgcctcttca cccggaggcc   840
tctgcccgcc ccactcatgc tcagggagag ggtcttctgg cttttttccc aggctctggg   900
caggcacagg ctaggtgccc ctaacccagg ccctgcacac aaaggggcag gtgctgggct   960
cagacctgcc aagagccata tccggggaga ccctgcccct gacctaagcc caccccaaag  1020
gccaaactct ccactccctc agctcggaca ccttctctcc tcccagattc cagtaactcc  1080
```

```
caatcttctc tctgcagagc ccaaatcttg tgacaaaact cacacatgcc caccgtgccc    1140
aggtaagcca gcccaggcct cgccctccag ctcaaggcgg gacaggtgcc ctagagtagc    1200
ctgcatccag ggacaggccc cagccgggtg ctgacacgtc cacctccatc tcttcctcag    1260
cacctgaact cctgggggga ccgtcagtct tcctcttccc cccaaaaccc aaggacaccc    1320
tcatgatctc ccggacccct gaggtcacat gcgtggtggt ggacgtgagc cacgaagacc    1380
ctgaggtcaa gttcaactgg tacgtggacg gcgtggaggt gcataatgcc aagacaaagc    1440
cgcgggagga gcagtacaac agcacgtacc gtgtggtcag cgtcctcacc gtcctgcacc    1500
aggactggct gaatggcaag gagtacaagt gcaaggtctc caacaaagcc ctcccagccc    1560
ccatcgagaa aaccatctcc aaagccaaag gtgggacccg tggggtgcga gggccacatg    1620
gacagaggcc ggctcggccc accctctgcc ctgagagtga ccgctgtacc aacctctgtc    1680
cctacagggc agccccgaga accacaggtg tacaccctgc ccccatcccg ggaggagatg    1740
accaagaacc aggtcagcct gacctgcctg gtcaaaggct tctatcccag cgacatcgcc    1800
gtggagtggg agagcaatgg gcagccggag aacaactaca agaccacgcc tcccgtgctg    1860
gactccgacg gctccttctt cctctatagc aagctcaccg tggacaagag caggtggcag    1920
caggggaacg tcttctcatg ctccgtgatg catgaggctc tgcacaacca ctacacgcag    1980
aagagcctct ccctgtcccc gggtaaatga                                     2010

<210> SEQ ID NO 7
<211> LENGTH: 467
<212> TYPE: PRT
<213> ORGANISM: Artificial Sequence
<220> FEATURE:
<223> OTHER INFORMATION: heavy chain chC2aB7-hG1

<400> SEQUENCE: 7

Met Gly Trp Ser Cys Ile Ile Leu Phe Leu Val Ala Thr Ala Thr Gly
  1               5                  10                  15

Val His Ser Leu Glu Val Gln Leu Gln Gln Ser Gly Pro Glu Leu Val
                 20                  25                  30

Lys Pro Gly Ala Ser Leu Lys Met Ser Cys Lys Ala Ser Gly Tyr Ser
             35                  40                  45

Phe Thr Asp Tyr Ile Ile Leu Trp Val Lys Gln Asn His Gly Lys Ser
         50                  55                  60

Leu Glu Trp Ile Gly His Ile Asp Pro Tyr Tyr Gly Ser Ser Asn Tyr
 65                  70                  75                  80

Asn Leu Lys Phe Lys Gly Lys Ala Thr Leu Thr Val Asp Lys Ser Ser
                 85                  90                  95

Ser Thr Ala Tyr Met Gln Leu Asn Ser Leu Thr Ser Glu Asp Ser Ala
            100                 105                 110

Val Tyr Tyr Cys Gly Arg Ser Lys Arg Asp Tyr Phe Asp Tyr Trp Gly
        115                 120                 125

Gln Gly Thr Thr Leu Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205
```

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
            245                 250                 255

Gly Pro Ser Val Phe Leu Phe Pro Pro Lys Pro Lys Asp Thr Leu Met
        260                 265                 270

Ile Ser Arg Thr Pro Glu Val Thr Cys Val Val Val Asp Val Ser His
    275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
            325                 330                 335

Lys Glu Tyr Lys Cys Lys Val Ser Asn Lys Ala Leu Pro Ala Pro Ile
        340                 345                 350

Glu Lys Thr Ile Ser Lys Ala Lys Gly Gln Pro Arg Glu Pro Gln Val
    355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Val Leu Asp Ser Asp Gly Ser Phe Phe Leu Tyr Ser Lys Leu Thr Val
        420                 425                 430

Asp Lys Ser Arg Trp Gln Gln Gly Asn Val Phe Ser Cys Ser Val Met
    435                 440                 445

His Glu Ala Leu His Asn His Tyr Thr Gln Lys Ser Leu Ser Leu Ser
450                 455                 460

Pro Gly Lys
465

<210> SEQ ID NO 8
<211> LENGTH: 1401
<212> TYPE: DNA
<213> ORGANISM: Artificial Sequence
<220> FEATURE:
<223> OTHER INFORMATION: hB7V4V1-hG1 Heavy chain (cDNA hG1)

<400> SEQUENCE: 8

| | | | | | |
|---|---|---|---|---|---|
| atgggatgga | gctggatctt | tctctttctc | ctgtcagtaa | ctgcaggtgt | gttctctgag | 60 |
| gtccagctgg | tggagtccgg | acctgaggtg | aagaagcctg | gggcttcagt | gaaggtgtcc | 120 |
| tgcaaggctt | ctggttattc | attcactgac | tacatcatac | tctggatcag | gcagcatagc | 180 |
| ggaaagggcc | ttgagtggat | tggacatatt | gatccttact | atggtagttc | taactacaat | 240 |
| ctgaaattca | agggcagggt | cacaatcact | gcagacaaat | ctaccaggac | aacctacatg | 300 |
| gagctcacca | gtctgacatc | tgaggacact | gcagtctatt | actgtggaag | atctaagagg | 360 |
| gactactttg | actactgggg | ccaaggcacc | actctcacag | tttcctcagc | ctccaccaag | 420 |
| ggcccatcgg | tcttccccct | agcacccctc | tccaagagca | cctctggggg | cacagcggcc | 480 |
| ctgggctgcc | tggtcaagga | ctacttcccc | gaaccggtga | cggtgtcgtg | gaactcaggc | 540 |

```
gccctgacca gcggcgtgca caccttcccg gctgtcctac agtcctcagg actctactcc    600
ctcagcagcg tggtgaccgt gccctccagc agcttgggca cccagaccta catctgcaac    660
gtgaatcaca agcccagcaa caccaaggtg gacaagagag ttgagcccaa atcttgtgac    720
aaaactcaca catgcccacc gtgcccagca cctgaactcc tggggggacc gtcagtcttc    780
ctcttccccc caaaacccaa ggacaccctc atgatctccc ggacccctga ggtcacatgc    840
gtggtggtgg acgtgagcca cgaagaccct gaggtcaagt tcaactggta cgtggacggc    900
gtggaggtgc ataatgccaa gacaaagccg cgggaggagc agtacaacag cacgtaccgt    960
gtggtcagcg tcctcaccgt cctgcaccag gactggctga atggcaagga gtacaagtgc   1020
aaggtctcca acaaagccct cccagccccc atcgagaaaa ccatctccaa agccaaaggg   1080
cagccccgag aaccacaggt gtacaccctg cccccatccc gggaggagat gaccaagaac   1140
caggtcagcc tgacctgcct ggtcaaaggc ttctatccca gcgacatcgc cgtggagtgg   1200
gagagcaatg ggcagccgga gaacaactac aagaccacgc ctcccgtgct ggactccgac   1260
ggctccttct tcctctacag caagctcacc gtggacaaga gcaggtggca gcaggggaac   1320
gtcttctcat gctccgtgat gcatgaggct ctgcacaacc actacacgca gaagagcctc   1380
tccctgtctc cgggtaaatg a                                             1401

<210> SEQ ID NO 9
<211> LENGTH: 466
<212> TYPE: PRT
<213> ORGANISM: Artificial Sequence
<220> FEATURE:
<223> OTHER INFORMATION: hB7V4V1-hG1 Heavy chain

<400> SEQUENCE: 9

Met Gly Trp Ser Trp Ile Phe Leu Phe Leu Ser Val Thr Ala Gly
  1               5                  10                  15

Val Phe Ser Glu Val Gln Leu Val Glu Ser Gly Pro Glu Val Lys Lys
                 20                  25                  30

Pro Gly Ala Ser Val Lys Val Ser Cys Lys Ala Ser Gly Tyr Ser Phe
             35                  40                  45

Thr Asp Tyr Ile Ile Leu Trp Ile Arg Gln His Ser Gly Lys Gly Leu
         50                  55                  60

Glu Trp Ile Gly His Ile Asp Pro Tyr Tyr Gly Ser Ser Asn Tyr Asn
 65                  70                  75                  80

Leu Lys Phe Lys Gly Arg Val Thr Ile Thr Ala Asp Lys Ser Thr Arg
                 85                  90                  95

Thr Thr Tyr Met Glu Leu Thr Ser Leu Thr Ser Glu Asp Thr Ala Val
            100                 105                 110

Tyr Tyr Cys Gly Arg Ser Lys Arg Asp Tyr Phe Asp Tyr Trp Gly Gln
            115                 120                 125

Gly Thr Thr Leu Thr Val Ser Ser Ala Ser Thr Lys Gly Pro Ser Val
        130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
```

```
              210                 215                 220
Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
                260                 265                 270

Ser Arg Thr Pro Glu Val Thr Cys Val Val Val Asp Val Ser His Glu
                275                 280                 285

Asp Pro Glu Val Lys Phe Asn Trp Tyr Val Asp Gly Val Glu Val His
290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
                340                 345                 350

Lys Thr Ile Ser Lys Ala Lys Gly Gln Pro Arg Glu Pro Gln Val Tyr
                355                 360                 365

Thr Leu Pro Pro Ser Arg Glu Glu Met Thr Lys Asn Gln Val Ser Leu
                370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
                420                 425                 430

Lys Ser Arg Trp Gln Gln Gly Asn Val Phe Ser Cys Ser Val Met His
                435                 440                 445

Glu Ala Leu His Asn His Tyr Thr Gln Lys Ser Leu Ser Leu Ser Pro
                450                 455                 460

Gly Lys
465

<210> SEQ ID NO 10
<211> LENGTH: 1401
<212> TYPE: DNA
<213> ORGANISM: Artificial Sequence
<220> FEATURE:
<223> OTHER INFORMATION: hB7V3V1-hG1 Heavy chain (cDNA hG1)

<400> SEQUENCE: 10
atgggatgga gccggatctt tctcttcctc ctgtcaataa ttgcaggtgt ccattgccag      60
gtccagctgc aacagtctgg atctgagctg aagaagcctg ggcttcagt gaagatctcc     120 tgcaaggctt ctggttattc attcactgac tacatcatac tctgggtgag cagaaccct    180 ggaaagggcc ttgagtggat tggacatatt gatccttact atggtagttc taactacaat    240
ctgaaattca aggcagagt gacaataccc gccgaccagt ctaccaccac agcctacatg    300
gagctctcca gtctgagatc tgaggacact gcagtctatt actgtggaag atctaagagg    360
gactactttg actactgggg ccaaggcacc actctcacag tttcctcagc ctccaccaag    420
ggcccatcgg tcttccccgct agcaccctcc tccaagagca cctctggggg cacagcggcc    480
ctgggctgcc tggtcaagga ctacttcccc gaaccggtga cggtgtcgtg gaactcaggc    540
gccctgacca gcggcgtgca caccttcccg gctgtcctac agtcctcagg actctactcc    600
```

```
ctcagcagcg tggtgaccgt gccctccagc agcttgggca cccagaccta catctgcaac    660
gtgaatcaca agcccagcaa caccaaggtg gacaagagag ttgagcccaa atcttgtgac    720
aaaactcaca catgcccacc gtgcccagca cctgaactcc tggggggacc gtcagtcttc    780
ctcttccccc caaaacccaa ggacaccctc atgatctccc ggacccctga ggtcacatgc    840
gtggtggtgg acgtgagcca cgaagaccct gaggtcaagt tcaactggta cgtggacggc    900
gtggaggtgc ataatgccaa gacaaagccg cgggaggagc agtacaacag cacgtaccgt    960
gtggtcagcg tcctcaccgt cctgcaccag gactggctga atggcaagga gtacaagtgc   1020
aaggtctcca acaaagccct cccagccccc atcgagaaaa ccatctccaa agccaaaggg   1080
cagccccgag aaccacaggt gtacaccctg cccccatccc gggaggagat gaccaagaac   1140
caggtcagcc tgacctgcct ggtcaaaggc ttctatccca gcgacatcgc cgtggagtgg   1200
gagagcaatg ggcagccgga gaacaactac aagaccacgc ctcccgtgct ggactccgac   1260
ggctccttct tcctctacag caagctcacc gtggacaaga gcaggtggca gcaggggaac   1320
gtcttctcat gctccgtgat gcatgaggct ctgcacaacc actacacgca gaagagcctc   1380
tccctgtctc cgggtaaatg a                                             1401
```

<210> SEQ ID NO 11
<211> LENGTH: 466
<212> TYPE: PRT
<213> ORGANISM: Artificial Sequence
<220> FEATURE:
<223> OTHER INFORMATION: hB7V3V1-hG1 Heavy chain

<400> SEQUENCE: 11

```
Met Gly Trp Ser Arg Ile Phe Leu Phe Leu Leu Ser Ile Ile Ala Gly
 1               5                  10                  15

Val His Cys Gln Val Gln Leu Gln Gln Ser Gly Ser Glu Leu Lys Lys
             20                  25                  30

Pro Gly Ala Ser Val Lys Ile Ser Cys Lys Ala Ser Gly Tyr Ser Phe
         35                  40                  45

Thr Asp Tyr Ile Ile Leu Trp Val Arg Gln Asn Pro Gly Lys Gly Leu
     50                  55                  60

Glu Trp Ile Gly His Ile Asp Pro Tyr Tyr Gly Ser Ser Asn Tyr Asn
 65                  70                  75                  80

Leu Lys Phe Lys Gly Arg Val Thr Ile Thr Ala Asp Gln Ser Thr Thr
                 85                  90                  95

Thr Ala Tyr Met Glu Leu Ser Ser Leu Arg Ser Glu Asp Thr Ala Val
            100                 105                 110

Tyr Tyr Cys Gly Arg Ser Lys Arg Asp Tyr Phe Asp Tyr Trp Gly Gln
        115                 120                 125

Gly Thr Thr Leu Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220
```

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Leu Leu Gly Gly
            245                 250                 255

Pro Ser Val Phe Leu Phe Pro Pro Lys Pro Lys Asp Thr Leu Met Ile
        260                 265                 270

Ser Arg Thr Pro Glu Val Thr Cys Val Val Val Asp Val Ser His Glu
    275                 280                 285

Asp Pro Glu Val Lys Phe Asn Trp Tyr Val Asp Gly Val Glu Val His
290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

```
<210> SEQ ID NO 12
<211> LENGTH: 2002
<212> TYPE: DNA
<213> ORGANISM: Artificial Sequence
<220> FEATURE:
<223> OTHER INFORMATION: hB7V3V2-hG2G4 Heavy chain (genomic sequence
      hG2G4)

<400> SEQUENCE: 12
atgggatgga gctgtatcat cctcttcttg gtagcaacag ctacaggtgt ccactccctc    60
gaggtccagc tgcaacagtc tggacctgag ctggtgaagc ctggggcttc actgaagatg   120
tcctgcaagg cttctggtta ttcattcact gactacatca tactctgggt gaagcagaac   180
catggaaaga gccttgagtg gattggacat attgatcctt actatggtag ttctaactac   240
aatctgaaat tcaagggcaa ggccacattg actgtagaca atcttccag cacagcctac   300 atgcagctca cagtctgac atctgaggac tctgcagtct attactgtgg aagatctaag   360
agggactact ttgactactg gggccaaggc accactctca cagtttcctc agcctccacc   420
aagggcccat ccgtcttccc cctggcgccc tgctccagga gcacctccga gagcacagcc   480
gccctgggct gcctggtcaa ggactacttc cccgaaccgg tgacggtgtc gtggaactca   540
ggcgccctga ccagcggcgt gcacaccttc ccggctgtcc tacagtcctc aggactctac   600
tccctcagca gcgtggtgac cgtgccctcc agcaacttcg gcacccagac ctacacctgc   660
```

```
aacgtagatc acaagcccag caacaccaag gtggacaaga cagttggtga gaggccagct      720
cagggaggga gggtgtctgc tggaagccag gctcagccct cctgcctgga cgcaccccgg      780
ctgtgcagcc ccagcccagg gcagcaaggc aggcccatc tgtctcctca cccggaggcc       840
tctgcccgcc ccactcatgc tcagggagag ggtcttctgg cttttccac caggctccag       900
gcaggcacag gctgggtgcc cctaccccag gcccttcaca cacaggggca ggtgcttggc      960
tcagacctgc caaaagccat atccgggagg accctgcccc tgacctaagc cgaccccaaa     1020
ggccaaactg tccactccct cagctcggac accttctctc ctcccagatc cgagtaactc     1080
ccaatcttct ctctgcagag cgcaaatgtt gtgtcgagtg cccaccgtgc ccaggtaagc     1140
cagcccaggc ctcgcctcc agctcaaggc gggacaggtg ccctagagta gcctgcatcc      1200
agggacaggc cccagctggg tgctgacacg tccacctcca tctcttcctc agcaccacct     1260
gtggcaggac cgtcagtctt cctcttcccc ccaaaaccca aggacaccct catgatctcc     1320
cggacccctg aggtcacgtg cgtggtggtg gacgtgagcc aggaagaccc cgaggtccag     1380
ttcaactggt acgtggatgg cgtggaggtg cataatgcca agacaaagcc gcgggaggag     1440
cagttcaaca gcacgtaccg tgtggtcagc gtcctcaccg tcctgcacca ggactggctg     1500
aacggcaagg agtacaagtg caaggtctcc aacaaaggcc tcccgtcctc catcgagaaa     1560
accatctcca agccaaaagg tgggacccac ggggtgcgag ggccacatgg acagaggtca     1620
gctcggccca ccctctgccc tgggagtgac cgctgtgcca acctctgtcc ctacagggca     1680
gccccgagag ccacaggtgt acaccctgcc cccatcccag gaggagatga ccaagaacca     1740
ggtcagcctg acctgcctgg tcaaaggctt ctaccccagc gacatcgccg tggagtggga     1800
gagcaatggg cagccggaga acaactacaa gaccacgcct cccgtgctgg actccgacgg     1860
ctccttcttc ctctacagca ggctaaccgt ggacaagagc aggtggcagg aggggaatgt     1920
cttctcatgc tccgtgatgc atgaggctct gcacaaccac tacacacaga gagcctctc      1980
cctgtctctg ggtaaatgat ga                                              2002
```

<210> SEQ ID NO 13
<211> LENGTH: 462
<212> TYPE: PRT
<213> ORGANISM: Artificial Sequence
<220> FEATURE:
<223> OTHER INFORMATION: hB7V3V2-hG2G4 Heavy chain

<400> SEQUENCE: 13

```
Met Gly Trp Ser Arg Ile Phe Leu Phe Leu Leu Ser Ile Ile Ala Gly
 1               5                   10                  15

Val His Cys Gln Val Gln Leu Gln Gln Ser Gly Ser Glu Leu Lys Lys
            20                  25                  30

Pro Gly Ala Ser Val Lys Ile Ser Cys Lys Ala Ser Gly Tyr Ser Phe
        35                  40                  45

Thr Asp Tyr Ile Ile Leu Trp Val Arg Gln Asn Pro Gly Lys Gly Leu
    50                  55                  60

Glu Trp Ile Gly His Ile Asp Pro Tyr Tyr Gly Ser Ser Asn Tyr Asn
65                  70                  75                  80

Leu Lys Phe Lys Gly Arg Val Thr Ile Thr Ala Asp Gln Ser Thr Thr
                85                  90                  95

Thr Ala Tyr Met Glu Leu Ser Ser Leu Arg Ser Glu Asp Thr Ala Val
            100                 105                 110

Tyr Tyr Cys Gly Arg Ser Lys Arg Asp Tyr Phe Asp Tyr Trp Gly Gln
        115                 120                 125
```

Gly Thr Thr Leu Thr Val Ser Ser Ala Ser Thr Lys Gly Pro Ser Val
            130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Asn Phe Gly Thr Gln Thr Tyr Thr Cys Asn Val Asp His Lys
210                 215                 220

Pro Ser Asn Thr Lys Val Asp Lys Thr Val Glu Arg Lys Cys Cys Val
225                 230                 235                 240

Glu Cys Pro Pro Cys Pro Ala Pro Pro Val Ala Gly Pro Ser Val Phe
                245                 250                 255

Leu Phe Pro Pro Lys Pro Lys Asp Thr Leu Met Ile Ser Arg Thr Pro
                260                 265                 270

Glu Val Thr Cys Val Val Val Asp Val Ser Gln Glu Asp Pro Glu Val
            275                 280                 285

Gln Phe Asn Trp Tyr Val Asp Gly Val Glu Val His Asn Ala Lys Thr
290                 295                 300

Lys Pro Arg Glu Glu Gln Phe Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Gly Leu Pro Ser Ser Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Gln Glu Glu Met Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Arg Leu Thr Val Asp Lys Ser Arg Trp
            420                 425                 430

Gln Glu Gly Asn Val Phe Ser Cys Ser Val Met His Glu Ala Leu His
        435                 440                 445

Asn His Tyr Thr Gln Lys Ser Leu Ser Leu Ser Leu Gly Lys
450                 455                 460

<210> SEQ ID NO 14
<211> LENGTH: 1999
<212> TYPE: DNA
<213> ORGANISM: Artificial Sequence
<220> FEATURE:
<223> OTHER INFORMATION: chC2aB7-hG2G4 Heavy chain (genomic sequence
      hG2G4)

<400> SEQUENCE: 14
atgggatgga gctgtatcat cctcttcttg gtagcaacag ctacaggtgt ccactccctc      60
gaggtccagc tgcaacagtc tggacctgag ctggtgaagc ctggggcttc actgaagatg     120
tcctgcaagg cttctggtta ttcattcact gactacatca tactctgggt gaagcagaac     180

```
catggaaaga gccttgagtg gattggacat attgatcctt actatggtag ttctaactac    240
aatctgaaat tcaagggcaa ggccacattg actgtagaca atcttccag cacagcctac    300 atgcagctca acagtctgac atctgaggac tctgcagtct attactgtgg aagatctaag    360
agggactact ttgactactg gggccaaggc accactctca cagtttcctc agcctccacc    420
aagggcccat ccgtcttccc cctggcgccc tgctccagga gcacctccga gagcacagcc    480
gccctgggct gcctggtcaa ggactacttc cccgaaccgg tgacggtgtc gtggaactca    540
ggcgccctga ccagcggcgt gcacaccttc ccggctgtcc tacagtcctc aggactctac    600
tccctcagca gcgtggtgac cgtgccctcc agcaacttcg gcacccagac ctacacctgc    660
aacgtagatc acaagcccag caacaccaag gtggacaaga cagttggtga gaggccagct    720
cagggaggga gggtgtctgc tggaagccag gctcagccct cctgcctgga cgcacccc gg    780 ctgtgcagcc ccagcccagg cagcaaggc  aggcccatc tgtctcctca cccggaggcc    840
tctgcccgcc ccactcatgc tcaggagag  gtcttctgg ctttttccac caggctccag    900
gcaggcacag gctgggtgcc cctaccccag gcccttcaca cagggggca ggtgcttggc    960 tcagacctgc caaaagccat atccggggag accctgcccc tgacctaagc cgaccccaaa   1020
ggccaaactg tccactccct cagctcggac accttctctc ctcccagatc gagtaactc    1080 ccaatcttct ctctgcagag cgcaaatgtt gtgtcgagtg cccaccgtgc ccaggtaagc   1140
cagcccaggc ctcgccctcc agctcaaggc gggacaggtg ccctagagta gcctgcatcc   1200
agggacaggc cccagctggg tgctgacacg tccacctcca tctcttcctc agcaccacct   1260
gtggcaggac cgtcagtctt cctcttcccc ccaaaaccca aggacaccct catgatctcc   1320
cggacccctg aggtcacgtg cgtggtggtg gacgtgagcc aggaagaccc cgaggtccag   1380
ttcaactggt acgtggatgg cgtggaggtg cataatgcca agacaaagcc gcgggaggag   1440
cagttcaaca gcacgtaccg tgtggtcagc gtcctcaccg tcctgcacca ggactggctg   1500
aacggcaagg agtacaagtg caaggtctcc aacaaaggcc tcccgtcctc catcgagaaa   1560
accatctcca aagccaaagg tgggacccac ggggtgcgag ggccacatgg acagaggtca   1620
gctcggccca ccctctgccc tgggagtgac cgctgtgcca acctctgtcc ctacagggca   1680
gccccgagag ccacaggtgt acaccctgcc cccatcccag gaggagatga ccaagaacca   1740
ggtcagcctg acctgcctgg tcaaaggctt ctaccccagc gacatcgccg tggagtggga   1800
gagcaatggg cagccggaga acaactacaa gaccacgcct cccgtgctgg actccgacgg   1860
ctccttcttc ctctacagca ggctaaccgt ggacaagagc aggtggcagg aggggaatgt   1920
cttctcatgc tccgtgatgc atgaggctct gcacaaccac tacacacaga gagcctctc    1980 cctgtctctg ggtaaatga                                                1999
```

<210> SEQ ID NO 15
<211> LENGTH: 463
<212> TYPE: PRT
<213> ORGANISM: Artificial Sequence
<220> FEATURE:
<223> OTHER INFORMATION: chC2aB7-hG2G4 Heavy chain

<400> SEQUENCE: 15

Met Gly Trp Ser Cys Ile Ile Leu Phe Leu Val Ala Thr Ala Thr Gly
1               5                   10                  15

Val His Ser Leu Glu Val Gln Leu Gln Gln Ser Gly Pro Glu Leu Val
            20                  25                  30

Lys Pro Gly Ala Ser Leu Lys Met Ser Cys Lys Ala Ser Gly Tyr Ser

-continued

```
                    35                  40                  45
Phe Thr Asp Tyr Ile Ile Leu Trp Val Lys Gln Asn His Gly Lys Ser
         50                  55                  60
Leu Glu Trp Ile Gly His Ile Asp Pro Tyr Tyr Gly Ser Ser Asn Tyr
 65                  70                  75                  80
Asn Leu Lys Phe Lys Gly Lys Ala Thr Leu Thr Val Asp Lys Ser Ser
                 85                  90                  95
Ser Thr Ala Tyr Met Gln Leu Asn Ser Leu Thr Ser Glu Asp Ser Ala
            100                 105                 110
Val Tyr Tyr Cys Gly Arg Ser Lys Arg Asp Tyr Phe Asp Tyr Trp Gly
        115                 120                 125
Gln Gly Thr Thr Leu Thr Val Ser Ser Ala Ser Thr Lys Gly Pro Ser
130                 135                 140
Val Phe Pro Leu Ala Pro Cys Ser Arg Ser Thr Ser Glu Ser Thr Ala
145                 150                 155                 160
Ala Leu Gly Cys Leu Val Lys Asp Tyr Phe Pro Glu Pro Val Thr Val
                165                 170                 175
Ser Trp Asn Ser Gly Ala Leu Thr Ser Gly Val His Thr Phe Pro Ala
            180                 185                 190
Val Leu Gln Ser Ser Gly Leu Tyr Ser Leu Ser Ser Val Val Thr Val
        195                 200                 205
Pro Ser Ser Asn Phe Gly Thr Gln Thr Tyr Thr Cys Asn Val Asp His
210                 215                 220
Lys Pro Ser Asn Thr Lys Val Asp Lys Thr Val Glu Arg Lys Cys Cys
225                 230                 235                 240
Val Glu Cys Pro Pro Cys Pro Ala Pro Pro Val Ala Gly Pro Ser Val
                245                 250                 255
Phe Leu Phe Pro Pro Lys Pro Lys Asp Thr Leu Met Ile Ser Arg Thr
            260                 265                 270
Pro Glu Val Thr Cys Val Val Val Asp Val Ser Gln Glu Asp Pro Glu
        275                 280                 285
Val Gln Phe Asn Trp Tyr Val Asp Gly Val Glu Val His Asn Ala Lys
290                 295                 300
Thr Lys Pro Arg Glu Glu Gln Phe Asn Ser Thr Tyr Arg Val Val Ser
305                 310                 315                 320
Val Leu Thr Val Leu His Gln Asp Trp Leu Asn Gly Lys Glu Tyr Lys
                325                 330                 335
Cys Lys Val Ser Asn Lys Gly Leu Pro Ser Ser Ile Glu Lys Thr Ile
            340                 345                 350
Ser Lys Ala Lys Gly Gln Pro Arg Glu Pro Gln Val Tyr Thr Leu Pro
        355                 360                 365
Pro Ser Gln Glu Glu Met Thr Lys Asn Gln Val Ser Leu Thr Cys Leu
370                 375                 380
Val Lys Gly Phe Tyr Pro Ser Asp Ile Ala Val Glu Trp Glu Ser Asn
385                 390                 395                 400
Gly Gln Pro Glu Asn Asn Tyr Lys Thr Thr Pro Pro Val Leu Asp Ser
                405                 410                 415
Asp Gly Ser Phe Phe Leu Tyr Ser Arg Leu Thr Val Asp Lys Ser Arg
            420                 425                 430
Trp Gln Glu Gly Asn Val Phe Ser Cys Ser Val Met His Glu Ala Leu
        435                 440                 445
His Asn His Tyr Thr Gln Lys Ser Leu Ser Leu Ser Leu Gly Lys
450                 455                 460
```

<210> SEQ ID NO 16
<211> LENGTH: 1391
<212> TYPE: DNA
<213> ORGANISM: Artificial Sequence
<220> FEATURE:
<223> OTHER INFORMATION: hB7V3V2-cG2G4 Heavy chain (cDNA G2G4)

<400> SEQUENCE: 16

| | | | | | |
|---|---|---|---|---|---|
| atgggatgga | gccggatctt | tctcttcctc | ctgtcaataa | ttgcaggtgt | ccattgccag | 60 |
| gtccagctgc | aacagtctgg | atctgagctg | aagaagcctg | ggcttcagt | gaagatctcc | 120 |
| tgcaaggctt | ctggttattc | attcactgac | tacatcatac | tctgggtgag | gcagaaccct | 180 |
| ggaaagggcc | ttgagtggat | tggacatatt | gatccttact | atggtagttc | taactacaat | 240 |
| ctgaaattca | agggcagagt | gacaatcacc | gccgaccagt | ctaccaccac | agcctacatg | 300 |
| gagctctcca | gtctgagatc | tgaggacact | gcagtctatt | actgtggaag | atctaagagg | 360 |
| gactactttg | actactgggg | ccaaggcacc | actctcacag | tttcctcagc | ctccaccaag | 420 |
| ggcccatccg | tcttccccct | ggcgccctgc | tccaggagca | cctccgagag | cacagccgcc | 480 |
| ctgggctgcc | tggtcaagga | ctacttcccc | gaaccggtga | cggtgtcgtg | gaactcaggc | 540 |
| gccctgacca | gcggcgtgca | caccttcccg | gctgtcctac | agtcctcagg | actctactcc | 600 |
| ctcagcagcg | tggtgaccgt | gccctccagc | aacttcggca | cccagaccta | cacctgcaac | 660 |
| gtagatcaca | agcccagcaa | caccaaggtg | gacaagacag | ttgagcgcaa | atgttgtgtc | 720 |
| gagtgcccac | cgtgcccagc | accacctgtg | gcaggaccgt | cagtcttcct | cttccccccca | 780 |
| aaacccaagg | acaccctcat | gatctcccgg | acccctgagg | tcacgtgcgt | ggtggtggac | 840 |
| gtgagccagg | aagaccccga | ggtccagttc | aactggtacg | tggatggcgt | ggaggtgcat | 900 |
| aatgccaaga | caaagccgcg | ggaggagcag | ttcaacagca | cgtaccgtgt | ggtcagcgtc | 960 |
| ctcaccgtcc | tgcaccagga | ctggctgaac | ggcaaggagt | acaagtgcaa | ggtctccaac | 1020 |
| aaaggcctcc | cgtcctccat | cgagaaaacc | atctccaaag | ccaaagggca | gccccgagag | 1080 |
| ccacaggtgt | acaccctgcc | cccatcccag | gaggagatga | ccaagaacca | ggtcagcctg | 1140 |
| acctgcctgg | tcaaaggctt | ctaccccagc | gacatcgccg | tggagtggga | gagcaatggg | 1200 |
| cagccggaga | acaactacaa | gaccacgcct | cccgtgctgg | actccgacgg | ctccttcttc | 1260 |
| ctctacagca | ggctaaccgt | ggacaagagc | aggtggcagg | aggggaatgt | cttctcatgc | 1320 |
| tccgtgatgc | atgaggctct | gcacaaccac | tacacacaga | agagcctctc | cctgtctctg | 1380 |
| ggtaaatgat | g | | | | | 1391 |

<210> SEQ ID NO 17
<211> LENGTH: 2005
<212> TYPE: DNA
<213> ORGANISM: Artificial Sequence
<220> FEATURE:
<223> OTHER INFORMATION: ChC7-hG2G4 Heavy chain (genomic sequence hG2G4)

<400> SEQUENCE: 17

| | | | | | |
|---|---|---|---|---|---|
| atgggatgga | gctgtatcat | cctcttcttg | gtagcaacag | ctacaggtgt | ccactccctc | 60 |
| gaggtccaac | tgcagcagtc | tggacctgag | ctggagaagc | ctggcgcttc | agtgaagata | 120 |
| tcctgcaagg | cttctggtta | ctcattcact | ggctacaaca | tgaactgggt | gaagcagagc | 180 |
| agtggaaaga | gccttgagtg | gattggaaat | tttgatcctt | actatggtgt | tattacctac | 240 |
| aaccagaagt | tcaagggcaa | ggccacattg | actgtagaca | aatcctccag | cacagcctac | 300 |
| atgcagctca | agagcctgac | atctgaggac | tctgcagtct | attactgtgc | aagaacggct | 360 |

-continued

```
acggctctct atactatgga ctactggggt caaggaacct cagtcaccgt ctcctcagcc     420
tccaccaagg gcccatccgt cttccccctg gcgccctgct ccaggagcac ctccgagagc     480
acagccgccc tgggctgcct ggtcaaggac tacttccccg aaccggtgac ggtgtcgtgg     540
aactcaggcg ccctgaccag cggcgtgcac accttcccgg ctgtcctaca gtcctcagga     600
ctctactccc tcagcagcgt ggtgaccgtg ccctccagca cttcggcacc cagacctac      660
acctgcaacg tagatcacaa gcccagcaac accaaggtgg acaagacagt tggtgagagg     720
ccagctcagg gagggagggt gtctgctgga agccaggctc agccctcctg cctggacgca     780
ccccggctgt gcagcccag cccagggcag caaggcaggc cccatctgtc tcctcacccg      840
gaggcctctg cccgccccac tcatgctcag ggagagggtc ttctggcttt tccaccagg      900
ctccaggcag gcacaggctg ggtgcccta ccccaggccc ttcacacaca ggggcaggtg      960
cttggctcag acctgccaaa agccatatcc gggaggaccc tgcccctgac ctaagccgac    1020
cccaaaggcc aaactgtcca ctccctcagc tcggacacct ctctcctcc cagatccgag     1080
taactcccaa tcttctctct gcagagcgca aatgttgtgt cgagtgccca ccgtgcccag    1140
gtaagccagc ccaggcctcg ccctccagct caaggcggga caggtgccct agagtagcct    1200
gcatccaggg acaggcccca gctgggtgct gacacgtcca cctccatctc ttcctcagca    1260
ccacctgtgg caggaccgtc agtcttcctc ttccccccaa aacccaagga caccctcatg    1320
atctcccgga cccctgaggt cacgtgcgtg gtggtggacg tgagccagga agaccccgag    1380
gtccagttca actggtacgt ggatggcgtg gaggtgcata atgccaagac aaagccgcgg    1440
gaggagcagt tcaacagcac gtaccgtgtg gtcagcgtcc tcaccgtcct gcaccaggac    1500
tggctgaacg gcaaggagta caagtgcaag gtctccaaca aaggcctccc gtcctccatc    1560
gagaaaacca tctccaaagc caaaggtggg acccacgggg tgcgagggcc acatggacag    1620
aggtcagctc ggcccaccct ctgccctggg agtgaccgct gtgccaacct ctgtccctac    1680
agggcagccc cgagagccac aggtgtacac cctgccccca tcccaggagg agatgaccaa    1740
gaaccaggtc agcctgacct gcctggtcaa aggcttctac cccagcgaca tcgccgtgga    1800
gtgggagagc aatgggcagc cggagaacaa ctacaagacc acgcctcccg tgctggactc    1860
cgacggctcc ttcttcctct acagcaggct aaccgtggac aagagcaggt ggcaggaggg    1920
gaatgtcttc tcatgctccg tgatgcatga ggctctgcac aaccactaca cacagaagag    1980
cctctccctg tctctgggta aatga                                         2005
```

<210> SEQ ID NO 18
<211> LENGTH: 468
<212> TYPE: PRT
<213> ORGANISM: Artificial Sequence
<220> FEATURE:
<223> OTHER INFORMATION: ChC7-hG2G4 Heavy chain (genomic sequence hG2G4)

<400> SEQUENCE: 18

```
Met Gly Trp Ser Cys Ile Ile Leu Phe Leu Val Ala Thr Ala Thr Gly
1               5                   10                  15

Val His Ser Leu Glu Val Gln Leu Gln Gln Ser Gly Pro Glu Leu Glu
            20                  25                  30

Lys Pro Gly Ala Ser Val Lys Ile Ser Cys Lys Ala Ser Gly Tyr Ser
        35                  40                  45

Phe Thr Gly Tyr Asn Met Asn Trp Val Lys Gln Ser Ser Gly Lys Ser
    50                  55                  60

Leu Glu Trp Ile Gly Asn Phe Asp Pro Tyr Tyr Gly Val Ile Thr Tyr
65                  70                  75                  80
```

Asn Gln Lys Phe Lys Gly Lys Ala Thr Leu Thr Val Asp Lys Ser Ser
                    85                  90                  95

Ser Thr Ala Tyr Met Gln Leu Lys Ser Leu Thr Ser Glu Asp Ser Ala
                100                 105                 110

Val Tyr Tyr Cys Ala Arg Thr Ala Thr Ala Leu Tyr Thr Met Asp Tyr
                115                 120                 125

Trp Gly Gln Gly Thr Ser Val Thr Val Ser Ser Ala Ser Thr Lys Gly
130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
                180                 185                 190

Pro Ala Val Leu Gln Ser Ser Gly Leu Tyr Ser Leu Ser Ser Val Val
                195                 200                 205

Thr Val Pro Ser Ser Asn Phe Gly Thr Gln Thr Tyr Thr Cys Asn Val
210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Gly Lys Pro Ala Pro Pro Val
                245                 250                 255

Ala Gly Pro Ser Val Phe Leu Phe Pro Pro Lys Pro Lys Asp Thr Leu
                260                 265                 270

Met Ile Ser Arg Thr Pro Glu Val Thr Cys Val Val Val Asp Val Ser
                275                 280                 285

Gln Glu Asp Pro Glu Val Gln Phe Asn Trp Tyr Val Asp Gly Val Glu
                290                 295                 300

Val His Asn Ala Lys Thr Lys Pro Arg Glu Glu Gln Phe Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Gly Leu Pro Ser Ser
                340                 345                 350

Ile Glu Lys Thr Ile Ser Lys Ala Lys Gly Gln Pro Arg Glu Pro Gln
                355                 360                 365

Val Tyr Thr Leu Pro Pro Ser Gln Glu Glu Met Thr Lys Asn Gln Val
                370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Arg Leu Thr
                420                 425                 430

Val Asp Lys Ser Arg Trp Gln Glu Gly Asn Val Phe Ser Cys Ser Val
                435                 440                 445

Met His Glu Ala Leu His Asn His Tyr Thr Gln Lys Ser Leu Ser Leu
450                 455                 460

Ser Leu Gly Lys
465

<210> SEQ ID NO 19
<211> LENGTH: 2025
<212> TYPE: DNA

<213> ORGANISM: Artificial Sequence
<220> FEATURE:
<223> OTHER INFORMATION: D1B5-hG1 Heavy chain (genomic sequence hG1 constant region)

<400> SEQUENCE: 19

| | | | | | |
|---|---|---|---|---|---|
| atgggatgga | gctgtatcat | cctcttcttg | gtagcaacag | ctacaggtgt | ccactccctc | 60 |
| gaggtccaac | tgcagcagcc | tggggcagag | cttgtgaggt | caggggcctc | agtcaagttg | 120 |
| tcctgcaaag | cttctggctt | caacattaaa | gactactata | tacactgggt | gaagcagagg | 180 |
| cctgaacagg | gcctgagtg | gattggatgg | attgatcctg | agattggtgc | tactaaatat | 240 |
| gtcccgaagt | tccagggcaa | ggccactatg | actacagaca | catcctccaa | cacagcctac | 300 |
| ctgcagctca | gcagcctgac | atctgaggac | actgccgtct | attactgtaa | tgccctctat | 360 |
| ggtaactacg | accgttacta | tgctatggac | tactggggtc | aaggaacctc | agtcaccgtc | 420 |
| tcctcagcct | ccaccaaggg | cccatcggtc | ttccccctgg | cacctcctc | caagagcacc | 480 |
| tctgcggca | cagcggccct | gggctgcctg | gtcaaggact | acttccccga | accggtgacg | 540 |
| gtgtcgtgga | actcaggcgc | cctgaccagc | ggcgtgcaca | ccttcccggc | tgtcctacag | 600 |
| tcctcaggac | tctactccct | cagcagcgtg | gtgaccgtgc | cctccagcag | cttgggcacc | 660 |
| cagacctaca | tctgcaacgt | gaatcacaag | cccagcaaca | ccaaggtgga | caagagagtt | 720 |
| ggtgagaggc | cagcacaggg | agggagggtg | tctgctggaa | gccaggctca | gcgctcctgc | 780 |
| ctggacgcat | cccggctatg | cagtcccagt | ccagggcagc | aaggcaggcc | ccgtctgcct | 840 |
| cttcacccgg | aggcctctgc | ccgccccact | catgctcagg | gagagggtct | tctggctttt | 900 |
| tccccaggct | ctgggcaggc | acaggctagg | tgcccctaac | ccaggccctg | cacacaaagg | 960 |
| ggcaggtgct | gggctcagac | ctgccaagag | ccatatccgg | gaggaccctg | cccctgacct | 1020 |
| aagcccaccc | caaaggccaa | actctccact | ccctcagctc | ggacaccttc | tctcctccca | 1080 |
| gattccagta | actcccaatc | ttctctctgc | agagcccaaa | tcttgtgaca | aaactcacac | 1140 |
| atgcccaccg | tgcccaggta | agccagccca | ggcctcgccc | tccagctcaa | ggcgggacag | 1200 |
| gtgccctaga | gtagcctgca | tccagggaca | ggccccagcc | gggtgctgac | acgtccacct | 1260 |
| ccatctcttc | ctcagcacct | gaactcctgg | ggggaccgtc | agtcttcctc | ttccccccaa | 1320 |
| aacccaagga | caccctcatg | atctcccgga | cccctgaggt | cacatgcgtg | gtggtggacg | 1380 |
| tgagccacga | agaccctgag | gtcaagttca | actggtacgt | ggacggcgtg | gaggtgcata | 1440 |
| atgccaagac | aaagccgcgg | gaggagcagt | acaacagcac | gtaccgtgtg | gtcagcgtcc | 1500 |
| tcaccgtcct | gcaccaggac | tggctgaatg | gcaaggagta | caagtgcaag | gtctccaaca | 1560 |
| aagcccctcc | agcccccatc | gagaaaacca | tctccaaagc | caaagtggg | acccgtgggg | 1620 |
| tgcgagggcc | acatggacag | aggccggctc | ggcccaccct | ctgccctgag | agtgaccgct | 1680 |
| gtaccaacct | ctgtccctac | agggcagccc | cgagaaccac | aggtgtacac | cctgccccca | 1740 |
| tcccgggagg | agatgaccaa | gaaccaggtc | agcctgacct | gcctggtcaa | aggcttctat | 1800 |
| cccagcgaca | tcgccgtgga | gtgggagagc | aatgggcagc | cggagaacaa | ctacaagacc | 1860 |
| acgcctcccg | tgctggactc | cgacggctcc | ttcttcctct | atagcaagct | caccgtggac | 1920 |
| aagagcaggt | ggcagcaggg | gaacgtcttc | tcatgctccg | tgatgcatga | ggctctgcac | 1980 |
| aaccactaca | cgcagaagag | cctctccctg | tccccgggta | aatga | | 2025 |

<210> SEQ ID NO 20
<211> LENGTH: 472
<212> TYPE: PRT
<213> ORGANISM: Artificial Sequence -continued
<220> FEATURE:
<223> OTHER INFORMATION: D1B5-hG1 Heavy chain

<400> SEQUENCE: 20

Met Gly Trp Ser Cys Ile Ile Leu Phe Leu Val Ala Thr Ala Thr Gly
1               5                   10                  15

Val His Ser Leu Glu Val Gln Leu Gln Gln Pro Gly Ala Glu Leu Val
            20                  25                  30

Arg Ser Gly Ala Ser Val Lys Leu Ser Cys Lys Ala Ser Gly Phe Asn
        35                  40                  45

Ile Lys Asp Tyr Tyr Ile His Trp Val Lys Gln Arg Pro Glu Gln Gly
    50                  55                  60

Leu Glu Trp Ile Gly Trp Ile Asp Pro Glu Ile Gly Ala Thr Lys Tyr
65                  70                  75                  80

Val Pro Lys Phe Gln Gly Lys Ala Thr Met Thr Thr Asp Thr Ser Ser
                85                  90                  95

Asn Thr Ala Tyr Leu Gln Leu Ser Ser Leu Thr Ser Glu Asp Thr Ala
            100                 105                 110

Val Tyr Tyr Cys Asn Ala Leu Tyr Gly Asn Tyr Asp Arg Tyr Tyr Ala
        115                 120                 125

Met Asp Tyr Trp Gly Gln Gly Thr Ser Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Arg Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Glu Glu Met Thr
    370                 375                 380

Lys Asn Gln Val Ser Leu Thr Cys Leu Val Lys Gly Phe Tyr Pro Ser
385                 390                 395                 400

```
Asp Ile Ala Val Glu Trp Glu Ser Asn Gly Gln Pro Glu Asn Asn Tyr
            405                 410                 415

Lys Thr Thr Pro Pro Val Leu Asp Ser Asp Gly Ser Phe Phe Leu Tyr
        420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys
465                 470

<210> SEQ ID NO 21
<211> LENGTH: 2026
<212> TYPE: DNA
<213> ORGANISM: Artificial Sequence
<220> FEATURE:
<223> OTHER INFORMATION: G2G4 63L1D Heavy chain (genomic sequence hG2G4)

<400> SEQUENCE: 21
atgggatgga gctgtatcat cctcttcttg gtagcaacag ctacaggtgt ccactcccag      60
atgcagctgg tgcagtctgg ggctgaggtg aagaagcctg gtcctcggt gaaggtctcc     120 tgcaaggcct ctggaggcac cttcagcaac tatgctacca gttgggtgcg acaggcccct    180
ggacaaggtc ttgagtggct gggagggatc atccccgtct tcggtactgc aaactacgca    240
cagaagtttc agggcagagt caccattacc gcggacgagt ccacgagcac agcctacatg    300
gagttgaata gtctgacatt tgacgacacg gccgtctatt actgtgcgag aggggggtggg    360 ggatggggag gccggaacta ctactactac tactacatgg acgtctgggg caaagggacc    420
actgtcaccg tctcctcagc ctccaccaag ggcccatccg tcttcccccct ggcgccctgc    480 tccaggagca cctccgagag cacagccgcc ctgggctgcc tggtcaagga ctacttcccc    540
gaaccggtga cggtgtcgtg gaactcaggc gccctgacca gcggcgtgca caccttcccg    600
gctgtcctac agtcctcagg actctactcc ctcagcagcg tggtgaccgt gccctccagc    660
aacttcggca cccagaccta cacctgcaac gtagatcaca agcccagcaa caccaaggtg    720
gacaagacag ttggtgagag gccagctcag ggagggaggg tgtctgctgg aagccaggct    780
cagccctcct gcctggacgc accccggctg tgcagcccca gcccagggca gcaaggcagg    840
ccccatctgt ctcctcaccc ggaggcctct gcccgcccca ctcatgctca gggagagggt    900
cttctggctt tttccaccag gctccaggca ggcacaggct gggtgcccct accccaggcc    960
cttcacacac aggggcaggt gcttggctca gacctgccaa aagccatatc cgggaggacc   1020
ctgcccctga cctaagccga ccccaaaggc caaactgtcc actccctcag ctcggacacc   1080
ttctctcctc ccagatccga gtaactccca atcttctctc tgcagagcgc aaatgttgtg   1140
tcgagtgccc accgtgccca ggtaagccag cccaggcctc gccctccagc tcaaggcggg   1200
acaggtgccc tagagtagcc tgcatccagg acaggcccca gctgggtgc tgacacgtcc    1260 acctccatct cttcctcagc accacctgtg caggaccgt cagtcttcct cttccccccca   1320 aaacccaagg acaccctcat gatctcccgg acccctgagg tcacgtgcgt ggtggtggac   1380
gtgagccagg aagaccccga ggtccagttc aactggtacg tggatggcgt ggaggtgcat   1440
aatgccaaga caaagccgcg ggaggagcag ttcaacagca cgtaccgtgt ggtcagcgtc   1500
ctcaccgtcc tgcaccagga ctggctgaac ggcaaggagt acaagtgcaa ggtctccaac   1560
aaaggcctcc cgtcctccat cgagaaaacc atctccaaag ccaaaggtgg acccacgggg   1620
gtgcgagggc cacatggaca gaggtcagct cggcccaccc tctgccctgg gagtgaccgc   1680
```

```
tgtgccaacc tctgtcccta cagggcagcc ccgagagcca caggtgtaca ccctgccccc    1740
atcccaggag gagatgacca agaaccaggt cagcctgacc tgcctggtca aaggcttcta    1800
ccccagcgac atcgccgtgg agtgggagag caatgggcag ccggagaaca actacaagac    1860
cacgcctccc gtgctggact ccgacggctc cttcttcctc tacagcaggc taaccgtgga    1920
caagagcagg tggcaggagg ggaatgtctt ctcatgctcc gtgatgcatg aggctctgca    1980
caaccactac acacagaaga gcctctccct gtctctgggt aaatga                    2026
```

<210> SEQ ID NO 22
<211> LENGTH: 472
<212> TYPE: PRT
<213> ORGANISM: Artificial Sequence
<220> FEATURE:
<223> OTHER INFORMATION: G2G4 63L1D Heavy chain

<400> SEQUENCE: 22

```
Met Gly Trp Ser Cys Ile Ile Leu Phe Leu Val Ala Thr Ala Thr Gly
 1               5                  10                  15

Val His Ser Gln Met Gln Leu Val Gln Ser Gly Ala Glu Val Lys Lys
            20                  25                  30

Pro Gly Ser Ser Val Lys Val Ser Cys Lys Ala Ser Gly Gly Thr Phe
        35                  40                  45

Ser Asn Tyr Ala Thr Ser Trp Val Arg Gln Ala Pro Gly Gln Gly Leu
    50                  55                  60

Glu Trp Leu Gly Gly Ile Ile Pro Val Phe Gly Thr Ala Asn Tyr Ala
65                  70                  75                  80

Gln Lys Phe Gln Gly Arg Val Thr Ile Thr Ala Asp Glu Ser Thr Ser
                85                  90                  95

Thr Ala Tyr Met Glu Leu Asn Ser Leu Thr Phe Asp Asp Thr Ala Val
            100                 105                 110

Tyr Tyr Cys Ala Arg Gly Gly Gly Gly Trp Gly Gly Arg Asn Tyr Tyr
        115                 120                 125

Tyr Tyr Tyr Tyr Met Asp Val Trp Gly Lys Gly Thr Thr Val Thr Val
    130                 135                 140

Ser Ser Ala Ser Thr Lys Gly Pro Ser Val Phe Pro Leu Ala Pro Cys
145                 150                 155                 160

Ser Arg Ser Thr Ser Glu Ser Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Asn Phe Gly Thr
    210                 215                 220

Gln Thr Tyr Thr Cys Asn Val Asp His Lys Pro Ser Asn Thr Lys Val
225                 230                 235                 240

Asp Lys Thr Val Glu Arg Lys Cys Cys Val Glu Cys Pro Pro Cys Pro
                245                 250                 255

Ala Pro Pro Val Ala Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser Gln Glu Asp Pro Glu Val Gln Phe Asn Trp Tyr Val
    290                 295                 300
```

```
Asp Gly Val Glu Val His Asn Ala Lys Thr Lys Pro Arg Glu Glu Gln
305                 310                 315                 320

Phe Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Gly
            340                 345                 350

Leu Pro Ser Ser Ile Glu Lys Thr Ile Ser Lys Ala Lys Gly Gln Pro
        355                 360                 365

Arg Glu Pro Gln Val Tyr Thr Leu Pro Pro Ser Gln Glu Glu Met Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Arg Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Leu Gly Lys
465                 470
```

<210> SEQ ID NO 23
<211> LENGTH: 705
<212> TYPE: DNA
<213> ORGANISM: Artificial Sequence
<220> FEATURE:
<223> OTHER INFORMATION: Light Chain chC2aB7-hG1, human Ck

<400> SEQUENCE: 23

```
atgggatgga gctgtatcat cctcttcttg gtagcaacag ctacaggtgt ccactctaga      60
gacatccaga tgacacagtc tccatcttcc atgtatgcat ctctaggaga gagagtcact     120
atcacttgca aggcgagtca ggacattaat agctatttaa gctggttcca gcagaaacca     180
gggaaatctc ctaagaccct gatctatcgt gcaaacagat tggtagatgg ggttccatca     240
aggttcagtg gcagtggatc tgggcaagat tattctctca ccatcagcag cctggagtat     300
gaagatatgg gaatttatta ttgtctacag tatgatgagt ttccgtacac gttcggaggg     360
gggaccaagc tggaaataaa acggactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag caccctgacg     600
ctgagcaaag cagactacga gaaacacaaa gtctacgcct gcgaagtcac ccatcagggc     660
ctgagctcgc ccgtcacaaa gagcttcaac agggagagt gttaa                      705
```

<210> SEQ ID NO 24
<211> LENGTH: 234
<212> TYPE: PRT
<213> ORGANISM: Artificial Sequence
<220> FEATURE:
<223> OTHER INFORMATION: Light Chain chC2aB7-hG1, human Ck

<400> SEQUENCE: 24

```
Met Gly Trp Ser Cys Ile Ile Leu Phe Leu Val Ala Thr Ala Thr Gly
1               5                   10                  15
```

```
Val His Ser Arg Asp Ile Gln Met Thr Gln Ser Pro Ser Ser Met Tyr
         20                  25                  30

Ala Ser Leu Gly Glu Arg Val Thr Ile Thr Cys Lys Ala Ser Gln Asp
         35                  40                  45

Ile Asn Ser Tyr Leu Ser Trp Phe Gln Gln Lys Pro Gly Lys Ser Pro
 50                  55                  60

Lys Thr Leu Ile Tyr Arg Ala Asn Arg Leu Val Asp Gly Val Pro Ser
 65                  70                  75                  80

Arg Phe Ser Gly Ser Gly Ser Gly Gln Asp Tyr Ser Leu Thr Ile Ser
                 85                  90                  95

Ser Leu Glu Tyr Glu Asp Met Gly Ile Tyr Tyr Cys Leu Gln Tyr Asp
        100                 105                 110

Glu Phe Pro Tyr Thr Phe Gly Gly Thr Lys Leu Glu Ile Lys Arg
        115                 120                 125

Thr Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
        210                 215                 220

Val Thr Lys Ser Phe Asn Arg Gly Glu Cys
225                 230

<210> SEQ ID NO 25
<211> LENGTH: 711
<212> TYPE: DNA
<213> ORGANISM: Artificial Sequence
<220> FEATURE:
<223> OTHER INFORMATION: hB7V4V1-hG1 light chain

<400> SEQUENCE: 25
atggacatga gggtctctgc tcagctcctg gggctcctgc tgctctggct ctcaggagcc     60
agatgtgaca tccagatgac acagtctcca tcttccctgt ctgcatctat aggagacaga    120
gtcactatca cttgcaaggc gagtcaggac attaatagct atttaagctg gttccagcag    180
aaaccaggga agctcctaa gtccctgatc tatcgtgcaa acagattggt agatggggtt    240
ccatcaaggt tcagtggcag tggatctggg acagattata ctctcaccat cagcagcctg    300
cagcctgaag atttcgcagt ttattattgt ctacagtatg atgagtttcc gtacacgttc    360
ggagggggga ccaagctgga aataaaacgt acggtggctg caccatctgt cttcatcttc    420
ccgccatctg atgagcagtt gaaatctgga actgcctctg ttgtgtgcct gctgaataac    480
ttctatccca gagaggccaa agtacagtgg aaggtggata acgccctcca atcgggtaac    540
tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgtta g             711

<210> SEQ ID NO 26
<211> LENGTH: 236
<212> TYPE: PRT
```

<213> ORGANISM: Artificial Sequence
<220> FEATURE:
<223> OTHER INFORMATION: hB7V4V1-hG1 Light chain (human Ck)

<400> SEQUENCE: 26

```
Met Asp Met Arg Val Ser Ala Gln Leu Leu Gly Leu Leu Leu Trp
 1               5                  10                  15

Leu Ser Gly Ala Arg Cys Asp Ile Gln Met Thr Gln Ser Pro Ser
             20                  25                  30

Leu Ser Ala Ser Ile Gly Asp Arg Val Thr Ile Thr Cys Lys Ala Ser
         35                  40                  45

Gln Asp Ile Asn Ser Tyr Leu Ser Trp Tyr Gln Lys Pro Gly Lys
 50                  55                  60

Ala Pro Lys Ser Leu Ile Tyr Arg Ala Asn Arg Leu Val Asp Gly Val
 65                  70                  75                  80

Pro Ser Arg Phe Ser Gly Ser Gly Ser Gly Thr Asp Tyr Thr Leu Thr
             85                  90                  95

Ile Ser Ser Leu Gln Pro Glu Asp Phe Ala Val Tyr Tyr Cys Leu Gln
             100                 105                 110

Tyr Asp Glu Phe Pro Tyr Thr Phe Gly Gly Gly Thr Lys Leu Glu Ile
             115                 120                 125

Lys Arg Thr Val Ala Ala Pro Ser Val Phe Ile Phe Pro Pro Ser Asp
 130                 135                 140

Glu Gln Leu Lys Ser Gly Thr Ala Ser Val Val Cys Leu Leu Asn Asn
 145             150                 155                 160

Phe Tyr Pro Arg Glu Ala Lys Val Gln Trp Lys Val Asp Asn Ala Leu
             165                 170                 175

Gln Ser Gly Asn Ser Gln Glu Ser Val Thr Glu Gln Asp Ser Lys Asp
             180                 185                 190

Ser Thr Tyr Ser Leu Ser Ser Thr Leu Thr Leu Ser Lys Ala Asp Tyr
             195                 200                 205

Glu Lys His Lys Val Tyr Ala Cys Glu Val Thr His Gln Gly Leu Ser
 210                 215                 220

Ser Pro Val Thr Lys Ser Phe Asn Arg Gly Glu Cys
225                 230                 235
```

<210> SEQ ID NO 27
<211> LENGTH: 711
<212> TYPE: DNA
<213> ORGANISM: Artificial Sequence
<220> FEATURE:
<223> OTHER INFORMATION: hB7V3V2-hG1 Light Chain

<400> SEQUENCE: 27

```
atggacatga gggtctctgc tcagctcctg gggctcctgc tgctctggct ctcaggggcc      60
aggtgtgaca tccagatgac acagtctcca tcttccctgt ctgcatctat aggagacaga     120
gtcactatca cttgcaaggc gagtcaggac attaatagct atttaagctg gttccagcag     180
aaaccaggga agctcctaa gctgctgatc tatcgtgcaa acagattggt agatggggtt      240
ccatcaaggt tcagtggcag tggatctggg acagattata ctctcaccat cagcagcctg     300
cagcctgaag atttcgcagt ttattattgt ctacagtatg atgagtttcc gtacacgttc     360
ggagggggga ccaagctgga aataaaacgt acggtggctg caccatctgt cttcatcttc     420
ccgccatctg atgagcagtt gaaatctgga actgcctctg ttgtgtgcct gctgaataac     480
ttctatccca gagaggccaa agtacagtgg aaggtggata acgccctcca atcgggtaac     540
tcccaggaga gtgtcacaga gcaggacagc aaggacagca cctacagcct cagcagcacc     600
```

```
ctgacgctga gcaaagcaga ctacgagaaa cacaaagtct acgcctgcga agtcacccat      660
cagggcctga gctcgcccgt cacaaagagc ttcaacaggg gagagtgtta g              711
```

<210> SEQ ID NO 28
<211> LENGTH: 236
<212> TYPE: PRT
<213> ORGANISM: Artificial Sequence
<220> FEATURE:
<223> OTHER INFORMATION: hB7V3V2-hG1 Light Chain (human Ck)

<400> SEQUENCE: 28

```
Met Asp Met Arg Val Ser Ala Gln Leu Leu Gly Leu Leu Leu Leu Trp
  1               5                  10                  15

Leu Ser Gly Ala Arg Cys Asp Ile Gln Met Thr Gln Ser Pro Ser Ser
                 20                  25                  30

Leu Ser Ala Ser Ile Gly Asp Arg Val Thr Ile Thr Cys Lys Ala Ser
             35                  40                  45

Gln Asp Ile Asn Ser Tyr Leu Ser Trp Phe Gln Gln Lys Pro Gly Lys
         50                  55                  60

Ala Pro Lys Leu Leu Ile Tyr Arg Ala Asn Arg Leu Val Asp Gly Val
 65                  70                  75                  80

Pro Ser Arg Phe Ser Gly Ser Gly Ser Gly Thr Asp Tyr Thr Leu Thr
                 85                  90                  95

Ile Ser Ser Leu Gln Pro Glu Asp Phe Ala Val Tyr Tyr Cys Leu Gln
                100                 105                 110

Tyr Asp Glu Phe Pro Tyr Thr Phe Gly Gly Gly Thr Lys Leu Glu Ile
            115                 120                 125

Lys Arg Thr Val Ala Ala Pro Ser Val Phe Ile Phe Pro Pro Ser Asp
        130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 29
<211> LENGTH: 708
<212> TYPE: DNA
<213> ORGANISM: Artificial Sequence
<220> FEATURE:
<223> OTHER INFORMATION: ChC7-hG2G4 Light chain

<400> SEQUENCE: 29

```
atgggatgga gctgtatcat cctcttcttg gtagcaacag ctacaggtgt ccactctaga      60
gaaattgtgc tcacccagtc tccagcaatc atgtctgcat ctccagggga aaaggtcacc     120
atgacctgca gggccagctc aagtgtaagt tccagttact tgcactggta ccagcagaag     180
tcaggtgcct cccccaaact ctggatttat agcacatcca acttggcttc tggagtccct     240
gctcgcttca gtggcagtgg gtctgggacc tcttactctc tcacaatcag cagtgtggag     300
```

```
gctgaagatg ctgccactta ttactgccag cagtacagtg gttacccact cacgttcggc    360
tcggggacaa agttggaaat aaaacggact gtggctgcac catctgtctt catcttcccg    420
ccatccgatg agcagttgaa atctggaact gcctctgttg tgtgcctgct gaataacttc    480
tatcccagag aggccaaagt acagtggaag gtggataacg ccctccaatc gggtaactcc    540
caggagagtg tcacagagca ggacagcaag gacagcacct acagcctcag cagcaccctg    600
acgctgagca agcagactac gagaaacac aaagtctacg cctgcgaagt cacccatcag    660
ggcctgagct cgcccgtcac aaagagcttc aacaggggag agtgttaa                 708
```

<210> SEQ ID NO 30
<211> LENGTH: 235
<212> TYPE: PRT
<213> ORGANISM: Artificial Sequence
<220> FEATURE:
<223> OTHER INFORMATION: ChC7-hG2G4 Light chain (human Ck)

<400> SEQUENCE: 30

```
Met Gly Trp Ser Cys Ile Ile Leu Phe Leu Val Ala Thr Ala Thr Gly
  1               5                  10                  15

Val His Ser Arg Glu Ile Val Leu Thr Gln Ser Pro Ala Ile Met Ser
             20                  25                  30

Ala Ser Pro Gly Glu Lys Val Thr Met Thr Cys Arg Ala Ser Ser Ser
         35                  40                  45

Val Ser Ser Ser Tyr Leu His Trp Tyr Gln Gln Lys Ser Gly Ala Ser
     50                  55                  60

Pro Lys Leu Trp Ile Tyr Ser Thr Ser Asn Leu Ala Ser Gly Val Pro
 65                  70                  75                  80

Ala Arg Phe Ser Gly Ser Gly Ser Gly Thr Ser Tyr Ser Leu Thr Ile
             85                  90                  95

Ser Ser Val Glu Ala Glu Asp Ala Ala Thr Tyr Tyr Cys Gln Gln Tyr
            100                 105                 110

Ser Gly Tyr Pro Leu Thr Phe Gly Ser Gly Thr Lys Leu Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

<210> SEQ ID NO 31
<211> LENGTH: 705
<212> TYPE: DNA
<213> ORGANISM: Artificial Sequence
<220> FEATURE:
<223> OTHER INFORMATION: D1B5-hG1 Light chain

<400> SEQUENCE: 31

```
atgggatgga gctgtatcat cctcttcttg gtagcaacag ctacaggtgt ccactctaga     60
```

```
gacattgtga tgacccagtc tcaaaaattc atgtccacat cagtaggaga cagggtcagc    120
atcacctgca aggccagtca gaatgttcgt actgctgtag cctggtatca acagaaacca    180
gggcagtctc ctaaagcact gatttacttg gcatccaacc ggcacactgg agtccctgat    240
cgcttcacag gcagtggatc tgggacagat ttcactctca ccattagcaa tgtgcaatct    300
gaagacctgg cagattattt ctgtctgcaa cattggaatt atcctctcac gttcggtgct    360
gggaccaagc tggagctgaa acggactgtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcaa cacccctgacg    600 ctgagcaaag cagactacga gaaacacaaa gtctacgcct gcgaagtcac ccatcagggc    660
ctgagctcgc ccgtcacaaa gagcttcaac aggggagagt gttaa              705
```

<210> SEQ ID NO 32
<211> LENGTH: 234
<212> TYPE: PRT
<213> ORGANISM: Artificial Sequence
<220> FEATURE:
<223> OTHER INFORMATION: D1B5-hG1 Light chain (human Ck)

<400> SEQUENCE: 32

```
Met Gly Trp Ser Cys Ile Ile Leu Phe Leu Val Ala Thr Ala Thr Gly
  1               5                  10                  15

Val His Ser Arg Asp Ile Val Met Thr Gln Ser Gln Lys Phe Met Ser
             20                  25                  30

Thr Ser Val Gly Asp Arg Val Ser Ile Thr Cys Lys Ala Ser Gln Asn
         35                  40                  45

Val Arg Thr Ala Val Ala Trp Tyr Gln Gln Lys Pro Gly Gln Ser Pro
     50                  55                  60

Lys Ala Leu Ile Tyr Leu Ala Ser Asn Arg His Thr Gly Val Pro Asp
 65                  70                  75                  80

Arg Phe Thr Gly Ser Gly Ser Gly Thr Asp Phe Thr Leu Thr Ile Ser
                 85                  90                  95

Asn Val Gln Ser Glu Asp Leu Ala Asp Tyr Phe Cys Leu Gln His Trp
            100                 105                 110

Asn Tyr Pro Leu Thr Phe Gly Ala Gly Thr Lys Leu Glu Leu Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Asn Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 33

```
<211> LENGTH: 696
<212> TYPE: DNA
<213> ORGANISM: Artificial Sequence
<220> FEATURE:
<223> OTHER INFORMATION: G2G4 63L1D Light chain

<400> SEQUENCE: 33
atgggatgga gctgtatcat cctcttcttg gtagcaacag ctacaggtgt ccactcttcc      60
tatgtgctga ctcagccacc ctcggagtca gtggccccag acagacggc caggatttcc     120 tgtgggggga gcaacattgg aagttacggt gtgcactggt accagcagaa ggcaggacag    180
gcccctgtgc tggtcgtcca tgatgattcc gaccggccct cagggattcc tgagcgattc    240
tctggctcca attctgggaa cacggccacc ctgaccatca gcagtgtcga agccggcgat    300
gaggccgact attactgtca ggtgtgggat aatagtgctg tgatattcgg cggagggacc    360
aaactaaccg tcctaagtca gcccaaggct gccccctcgg tcactctgtt cccgccctcc    420
tctgaggagc ttcaagccaa caaggccaca ctggtgtgtc tcataagtga cttctacccg    480
ggagctgtga cagtggcttg gaaagcagat agcagccccg tcaaggcggg agtggagacc    540
accacaccct ccaaacaaag caacaacaag tacgcggcca gcagctatct gagcctgacg    600
cctgagcagt ggaagtccca cagaagctac agctgccagg tcacgcatga agggagcacc    660
gtggagaaga cagtggcccc tacagaatgt tcataa                              696

<210> SEQ ID NO 34
<211> LENGTH: 231
<212> TYPE: PRT
<213> ORGANISM: Artificial Sequence
<220> FEATURE:
<223> OTHER INFORMATION: G2G4 63L1D Light chain (human CL)

<400> SEQUENCE: 34

Met Gly Trp Ser Cys Ile Ile Leu Phe Leu Val Ala Thr Ala Thr Gly
  1               5                  10                  15

Val His Ser Ser Tyr Val Leu Thr Gln Pro Pro Ser Glu Ser Val Ala
             20                  25                  30

Pro Gly Gln Thr Ala Arg Ile Ser Cys Gly Gly Ser Asn Ile Gly Ser
         35                  40                  45

Tyr Gly Val His Trp Tyr Gln Gln Lys Ala Gly Gln Ala Pro Val Leu
     50                  55                  60

Val Val His Asp Asp Ser Asp Arg Pro Ser Gly Ile Pro Glu Arg Phe
 65                  70                  75                  80

Ser Gly Ser Asn Ser Gly Asn Thr Ala Thr Leu Thr Ile Ser Ser Val
                 85                  90                  95

Glu Ala Gly Asp Glu Ala Asp Tyr Tyr Cys Gln Val Trp Asp Asn Ser
            100                 105                 110

Ala Val Ile Phe Gly Gly Gly Thr Lys Leu Thr Val Leu Ser Gln Pro
        115                 120                 125

Lys Ala Ala Pro Ser Val Thr Leu Phe Pro Pro Ser Ser Glu Glu Leu
    130                 135                 140

Gln Ala Asn Lys Ala Thr Leu Val Cys Leu Ile Ser Asp Phe Tyr Pro
145                 150                 155                 160

Gly Ala Val Thr Val Ala Trp Lys Ala Asp Ser Ser Pro Val Lys Ala
                165                 170                 175

Gly Val Glu Thr Thr Thr Pro Ser Lys Gln Ser Asn Asn Lys Tyr Ala
            180                 185                 190

Ala Ser Ser Tyr Leu Ser Leu Thr Pro Glu Gln Trp Lys Ser His Arg
        195                 200                 205
```

Ser Tyr Ser Cys Gln Val Thr His Glu Gly Ser Thr Val Glu Lys Thr
    210                 215                 220

Val Ala Pro Thr Glu Cys Ser
225                 230

<210> SEQ ID NO 35
<211> LENGTH: 31
<212> TYPE: DNA
<213> ORGANISM: Artificial Sequence
<220> FEATURE:
<223> OTHER INFORMATION: forward primer

<400> SEQUENCE: 35
gacaagcttg caaggatgga gaggctggtg a                              31

<210> SEQ ID NO 36
<211> LENGTH: 33
<212> TYPE: DNA
<213> ORGANISM: Artificial Sequence
<220> FEATURE:
<223> OTHER INFORMATION: reverse primer

<400> SEQUENCE: 36
gacggatccg cccctttttcc tcctgctttt ctc                           33

<210> SEQ ID NO 37
<211> LENGTH: 2160
<212> TYPE: DNA
<213> ORGANISM: Artificial Sequence
<220> FEATURE:
<223> OTHER INFORMATION: chC2aB7-hG1 Heavy chain

<400> SEQUENCE: 37
gcgcgccacc agacataata gctgacagac taacagactg ttccttttcca tgggtctttt    60 ctgcagtcac cgtccttgac acgaggcgcg ccgccaccat gggatggagc tgtatcatcc    120
tcttcttggt agcaacagct acaggtgtcc actccctcga ggtccagctg caacagtctg    180
gacctgagct ggtgaagcct ggggcttcac tgaagatgtc ctgcaaggct tctggttatt    240
cattcactga ctacatcata tctctgggtga agcagaacca tggaaagagc cttgagtgga    300
ttggacatat tgatccttac tatggtagtt ctaactacaa tctgaaattc aagggcaagg    360
ccacattgac tgtagacaaa tcttccagca gcctacat gcagctcaac agtctgacat    420
ctgaggactc tgcagtctat tactgtgaa gatctaagag ggactacttt gactactggg    480
gccaaggcac cactctcaca gtttcctcag cctccaccaa gggcccatcg gtcttccccc    540
tggcaccctc ctccaagagc acctctggcg gcacagcggc cctgggctgc ctggtcaagg    600
actacttccc cgaaccggtg acggtgtcgt ggaactcagg cgccctgacc agcggcgtgc    660
acaccttccc ggctgtccta cagtcctcag gactctactc cctcagcagc gtggtgaccg    720
tgccctccag cagcttgggc acccagacct acatctgcaa cgtgaatcac aagcccagca    780
acaccaaggt ggacaagaga gttggtgaga ggccagcaca gggagggagg gtgtctgctg    840
gaagccaggc tcagcgctcc tgcctggacg catcccggct atgcagtccc agtccagggc    900
agcaaggcag gccccgtctg cctcttcacc cggaggcctc tgcccgcccc actcatgctc    960
agggagaggg tcttctggct ttttcccag gctctgggca ggcacaggct aggtgcccct    1020
aacccaggcc ctgcacacaa aggggcaggt gctgggctca gacctgccaa gagccatatc    1080
cgggaggacc ctgcccctga cctaagccca ccccaaaggc caaactctcc actccctcag    1140
ctcggacacc ttctctcctc ccagattcca gtaactccca atcttctctc tgcagagccc    1200

```
aaatcttgtg acaaaactca cacatgccca ccgtgcccag gtaagccagc ccaggcctcg   1260
ccctccagct caaggcggga caggtgccct agagtagcct gcatccaggg acaggcccca   1320
gccgggtgct gacacgtcca cctccatctc ttcctcagca cctgaactcc tggggggacc   1380
gtcagtcttc ctcttccccc caaaacccaa ggacaccctc atgatctccc ggacccctga   1440
ggtcacatgc gtggtggtgg acgtgagcca cgaagaccct gaggtcaagt tcaactggta   1500
cgtggacggc gtggaggtgc ataatgccaa gacaaagccg cgggaggagc agtacaacag   1560
cacgtaccgt gtggtcagcg tcctcaccgt cctgcaccag gactggctga atggcaagga   1620
gtacaagtgc aaggtctcca acaaagccct cccagccccc atcgagaaaa ccatctccaa   1680
agccaaaggt gggacccgtg gggtgcgagg gccacatgga cagaggccgg ctcggcccac   1740
cctctgccct gagagtgacc gctgtaccaa cctctgtccc tacagggcag ccccgagaac   1800
cacaggtgta caccctgccc ccatcccggg aggagatgac caagaaccag gtcagcctga   1860
cctgcctggt caaaggcttc tatcccagcg acatcgccgt ggagtgggag agcaatgggc   1920
agccggagaa caactacaag accacgcctc ccgtgctgga ctccgacggc tccttcttcc   1980
tctatagcaa gctcaccgtg gacaagagca ggtggcagca ggggaacgtc ttctcatgct   2040
ccgtgatgca tgaggctctg cacaaccact acacgcagaa gagcctctcc ctgtccccgg   2100
gtaaatgagt gcgacggcca gaattcattg atcataatca gccataccac atttgtagag   2160

<210> SEQ ID NO 38
<211> LENGTH: 720
<212> TYPE: DNA
<213> ORGANISM: Artificial Sequence
<220> FEATURE:
<223> OTHER INFORMATION: chC2aB7-hG1 Light chain

<400> SEQUENCE: 38
aagcttgccg ccaccatggg atggagctgt atcatcctct tcttggtagc aacagctaca    60
ggtgtccact ctagagacat ccagatgaca cagtctccat cttccatgta tgcatctcta   120
ggagagagag tcactatcac ttgcaaggcg agtcaggaca ttaatagcta tttaagctgg   180
ttccagcaga accagggaa atctcctaag accctgatct atcgtgcaaa cagattggta   240
gatggggttc catcaaggtt cagtggcagt ggatctgggc aagattattc tctcaccatc   300
agcagcctgg agtatgaaga tatgggaatt tattattgtc tacagtatga tgagtttccg   360
tacacgttcg gagggggac caagctggaa ataaaacgga ctgtggctgc accatctgtc   420
ttcatcttcc cgccatctga tgagcagttg aaatctggaa ctgcctctgt tgtgtgcctg   480
ctgaataact tctatcccag agaggccaaa gtacagtgga aggtggataa cgccctccaa   540
tcgggtaact cccaggagag tgtcacagag caggacagca aggacagcac ctacagcctc   600
agcagcaccc tgacgctgag caaagcagac tacgagaaac acaaagtcta cgcctgcgaa   660
gtcacccatc agggcctgag ctcgcccgtc acaaagagct tcaacagggg agagtgttaa   720

<210> SEQ ID NO 39
<211> LENGTH: 1402
<212> TYPE: DNA
<213> ORGANISM: Artificial Sequence
<220> FEATURE:
<223> OTHER INFORMATION: hB7V4V1-hG1 Heavy chain

<400> SEQUENCE: 39
catgggatgg agctggatct ttctctttct cctgtcagta actgcaggtg tgttctctga    60
ggtccagctg gtggagtccg gacctgaggt gaagaagcct ggggcttcag tgaaggtgtc   120
```

| | |
|---|---|
| ctgcaaggct tctggttatt cattcactga ctacatcata ctctggatca ggcagcatag | 180 |
| cggaaagggc cttgagtgga ttggacatat tgatccttac tatggtagtt ctaactacaa | 240 |
| tctgaaattc aagggcaggg tcacaatcac tgcagacaaa tctaccagga caacctacat | 300 |
| ggagctcacc agtctgacat ctgaggacac tgcagtctat tactgtggaa gatctaagag | 360 |
| ggactacttt gactactggg gccaaggcac cactctcaca gtttcctcag cctccaccaa | 420 |
| gggcccatcg gtcttccccgc tagcaccctc ctccaagagc acctctgggg gcacagcggc | 480 |
| cctgggctgc ctggtcaagg actacttccc cgaaccggtg acggtgtcgt ggaactcagg | 540 |
| cgccctgacc agcggcgtgc acaccttccc ggctgtccta cagtcctcag gactctactc | 600 |
| cctcagcagc gtggtgaccg tgccctccag cagcttgggc acccagacct acatctgcaa | 660 |
| cgtgaatcac aagcccagca acaccaaggt ggacaagaga gttgagccca aatcttgtga | 720 |
| caaaactcac acatgcccac cgtgcccagc acctgaactc ctggggggac cgtcagtctt | 780 |
| cctcttcccc ccaaaaccca aggacaccct catgatctcc cggaccccctg aggtcacatg | 840 |
| cgtggtggtg gacgtgagcc acgaagaccc tgaggtcaag ttcaactggt acgtggacgg | 900 |
| cgtggaggtg cataatgcca agacaaagcc gcggaggag cagtacaaca gcacgtaccg | 960 |
| tgtggtcagc gtcctcaccg tcctgcacca ggactggctg aatggcaagg agtacaagtg | 1020 |
| caaggtctcc aacaaagccc tcccagcccc catcgagaaa accatctcca aagccaaagg | 1080 |
| gcagccccga gaaccacagg tgtacaccct gcccccatcc cgggaggaga tgaccaagaa | 1140 |
| ccaggtcagc ctgacctgcc tggtcaaagg cttctatccc agcgacatcg ccgtggagtg | 1200 |
| ggagagcaat gggcagccgg agaacaacta caagaccacg cctcccgtgc tggactccga | 1260 |
| cggctccttc ttcctctaca gcaagctcac cgtggacaag agcaggtggc agcaggggaa | 1320 |
| cgtcttctca tgctccgtga tgcatgaggc tctgcacaac cactacacgc agaagagcct | 1380 |
| ctccctgtct ccgggtaaat ga | 1402 |

<210> SEQ ID NO 40
<211> LENGTH: 765
<212> TYPE: DNA
<213> ORGANISM: Artificial Sequence
<220> FEATURE:
<223> OTHER INFORMATION: hB7V4V1-hG1 and hB7V3V1-hG1 Light chains

<400> SEQUENCE: 40

| | |
|---|---|
| tttccatggg tctttctgc agtcaccgtc cttgacacga agcttgccgc caccatggac | 60 |
| atgagggtct ctgctcagct cctggggctc ctgctgctct ggctctcagg agccagatgt | 120 |
| gacatccaga tgacacagtc tccatcttcc ctgtctgcat ctataggaga cagagtcact | 180 |
| atcacttgca aggcgagtca ggacattaat agctatttaa gctggtacca gcagaaacca | 240 |
| gggaaagctc ctaagtccct gatctatcgt gcaaacagat ggtagatgg ggttccatca | 300 |
| aggttcagtg gcagtggatc tgggacagat tatactctca ccatcagcag cctgcagcct | 360 |
| gaagatttcg cagtttatta ttgtctacag tatgatgagt tccgtacac gttcggaggg | 420 |
| gggaccaagc tggaaataaa acgtacgtg gctgcaccat ctgtcttcat cttcccgcca | 480 |
| tctgatgagc agttgaaatc tggaactgcc tctgttgtgt gcctgctgaa taacttctat | 540 |
| cccagagagg ccaaagtaca gtggaaggtg gataacgccc tccaatcggg taactcccag | 600 |
| gagagtgtca cagagcagga cagcaaggac agcacctaca gcctcagcag cacccttgacg | 660 |
| ctgagcaaag cagactacga gaaacacaaa gtctacgcct gcgaagtcac ccatcagggc | 720 |
| ctgagctcgc ccgtcacaaa gagcttcaac aggggagagt gttag | 765 |

<210> SEQ ID NO 41
<211> LENGTH: 1402
<212> TYPE: DNA
<213> ORGANISM: Artificial Sequence
<220> FEATURE:
<223> OTHER INFORMATION: hB7V3V1-hG1 and hB7V3V2-hG1 Heavy chains

<400> SEQUENCE: 41

| | |
|---|---|
| catgggatgg agccggatct ttctcttcct cctgtcaata attgcaggtg tccattgcca | 60 |
| ggtccagctg caacagtctg gatctgagct gaagaagcct ggggcttcag tgaagatctc | 120 |
| ctgcaaggct tctggttatt cattcactga ctacatcata ctctgggtga ggcagaaccc | 180 |
| tggaaagggc cttgagtgga ttggacatat tgatccttac tatggtagtt ctaactacaa | 240 |
| tctgaaattc aagggcagag tgacaatcac cgccgaccag tctaccacca cagcctacat | 300 |
| ggagctctcc agtctgagat ctgaggacac tgcagtctat tactgtggaa gatctaagag | 360 |
| ggactacttt gactactggg gccaaggcac cactctcaca gtttcctcag cctccaccaa | 420 |
| gggcccatcg gtcttccccc tagcaccctc ctccaagagc acctctgggg gcacagcggc | 480 |
| cctgggctgc ctggtcaagg actacttccc cgaaccggtg acggtgtcgt ggaactcagg | 540 |
| cgccctgacc agcggcgtgc acaccttccc ggctgtccta cagtcctcag gactctactc | 600 |
| cctcagcagc gtggtgaccg tgccctccag cagcttgggc acccagacct acatctgcaa | 660 |
| cgtgaatcac aagcccagca acaccaaggt ggacaagaga gttgagccca atcttgtga | 720 |
| caaaactcac acatgcccac cgtgcccagc acctgaactc ctggggggac cgtcagtctt | 780 |
| cctcttcccc ccaaaaccca aggacaccct catgatctcc cggacccctg aggtcacatg | 840 |
| cgtggtggtg gacgtgagcc acgaagaccc tgaggtcaag ttcaactggt acgtggacgg | 900 |
| cgtggaggtg cataatgcca agacaaagcc gcgggaggag cagtacaaca gcacgtaccg | 960 |
| tgtggtcagc gtcctcaccg tcctgcacca ggactggctg aatggcaagg agtacaagtg | 1020 |
| caaggtctcc aacaaagccc tcccagcccc catcgagaaa accatctcca agccaaagg | 1080 |
| gcagccccga gaaccacagg tgtacaccct gcccccatcc cgggaggaga tgaccaagaa | 1140 |
| ccaggtcagc ctgacctgcc tggtcaaagg cttctatccc agcgacatcg ccgtggagtg | 1200 |
| ggagagcaat gggcagccgg agaacaacta caagaccacg cctcccgtgc tggactccga | 1260 |
| cggctccttc ttcctctaca gcaagctcac cgtggacaag agcaggtggc agcaggggaa | 1320 |
| cgtcttctca tgctccgtga tgcatgaggc tctgcacaac cactacacgc agaagagcct | 1380 |
| ctccctgtct ccgggtaaat ga | 1402 |

<210> SEQ ID NO 42
<211> LENGTH: 765
<212> TYPE: DNA
<213> ORGANISM: Artificial Sequence
<220> FEATURE:
<223> OTHER INFORMATION: hB7V3V2-hG1 and hB7V3V2-hG2G4 Light chains

<400> SEQUENCE: 42

| | |
|---|---|
| tttccatggg tcttttctgc agtcaccgtc cttgacacga agcttgccgc caccatggac | 60 |
| atgagggtct ctgctcagct cctggggctc ctgctgctct ggctctcagg gccaggtgt | 120 |
| gacatccaga tgacacagtc tccatcttcc ctgtctgcat ctataggaga cagagtcact | 180 |
| atcacttgca aggcgagtca ggacattaat agctatttaa gctggttcca gcagaaacca | 240 |
| gggaaagctc ctaagctgct gatctatcgt gcaaacagat tggtagatgg ggttccatca | 300 |
| aggttcagtg gcagtggatc tgggacagat tatactctca ccatcagcag cctgcagcct | 360 |

```
gaagatttcg cagtttatta ttgtctacag tatgatgagt ttccgtacac gttcggaggg    420
gggaccaagc tggaaataaa acgtacggtg gctgcaccat ctgtcttcat cttcccgcca    480
tctgatgagc agttgaaatc tggaactgcc tctgttgtgt gcctgctgaa taacttctat    540
cccagagagg ccaaagtaca gtggaaggtg gataacgccc tccaatcggg taactcccag    600
gagagtgtca cagagcagga cagcaaggac agcacctaca gcctcagcag caccctgacg    660
ctgagcaaag cagactacga gaaacacaaa gtctacgcct gcgaagtcac ccatcagggc    720
ctgagctcgc ccgtcacaaa gagcttcaac aggggagagt gttag               765
```

```
<210> SEQ ID NO 43
<211> LENGTH: 2159
<212> TYPE: DNA
<213> ORGANISM: Artificial Sequence
<220> FEATURE:
<223> OTHER INFORMATION: hB7V3V2-hG2G4 Heavy chain

<400> SEQUENCE: 43
```

```
ccaccagaca taatagctga cagactaaca gactgttcct ttccatgggt cttttctgca     60
gtcaccgtcc ttgacacgaa gcttgccgcc accatgggga ggagccggat cttctctctt    120
ctcctgtcaa taattgcagg tgtccattgc caggtccagc tgcaacagtc tggatctgag    180
ctgaagaagc ctggggcttc agtgaagatc cctgcaaggg cttctggtta ttcattcact    240
gactacatca tactctgggt gaggcagaac cctggaaagg ccttgagtg gattggacat    300 attgatcctt actatggtag ttctaactac aatctgaaat caagggcag agtgacaatc    360 accgccgacc agtctaccac cacagcctac atggagctct ccagtctgag atctgaggac    420
actgcagtct attactgtgg aagatctaag agggactact tgactactg gggccaaggc    480 accactctca cagtttcctc agcctccacc aagggcccat ccgtcttccc cctggcgccc    540
tgctccagga gcacctccga gagcacagcc gccctgggct gcctggtcaa ggactacttc    600
cccgaaccgg tgacggtgtc gtggaactca ggcgccctga ccagcggcgt gcacaccttc    660
ccggctgtcc tacagtcctc aggactctac tccctcagca gcgtggtgac cgtgccctcc    720
agcaacttcg gcacccagac ctacacctgc aacgtagatc acaagcccag caacaccaag    780
gtggacaaga cagttggtga gaggccagct cagggaggga gggtgtctgc tggaagccag    840
gctcagccct cctgcctgga cgcaccccgg ctgtgcagcc ccagcccagg cagcaaggc    900 aggccccatc tgtctcctca cccggaggcc tctgcccgcc ccactcatgc tcagggagag    960
ggtcttctgg ctttttccac caggctccag gcaggcacag gctgggtgcc cctacccag   1020 gcccttcaca cagggggca ggtgcttggc tcagacctgc caaaagccat atccgggagg   1080
accctgcccc tgacctaagc cgaccccaaa ggccaaactg tccactccct cagctcggac   1140
accttctctc ctcccagatc cgagtaactc ccaatcttct ctctgcagag cgcaaatgtt   1200
gtgtcgagtg cccaccgtgc ccaggtaagc cagcccaggc ctcgccctcc agctcaaggc   1260
gggacaggtg ccctagagta gcctgcatcc agggacaggc cccgctgggt gctgacacgt   1320
ccacctccat ctcttcctca gcaccacctg tggcaggacc gtcagtcttc ctcttccccc   1380
caaaacccaa ggacaccctc atgatctccc ggacccctga ggtcacgtgc gtggtggtgg   1440
acgtgagcca ggaagacccc gaggtccagt tcaactggta cgtggatggc gtggaggtgc   1500
ataatgccaa gacaaagccg cgggaggagc agttcaacag cacgtaccgt gtggtcagcg   1560
tcctcaccgt cctgcaccag gactggctga acggcaagga gtacaagtgc aaggtctcca   1620
acaaaggcct cccgtcctcc atcgagaaaa ccatctccaa agccaaaggt gggacccacg   1680
```

| | |
|---|---:|
| gggtgcgagg gccacatgga cagaggtcag ctcggcccac cctctgccct gggagtgacc | 1740 |
| gctgtgccaa cctctgtccc tacagggcag ccccgagagc acaggtgta cacccctgccc | 1800 |
| ccatcccagg aggagatgac caagaaccag gtcagcctga cctgcctggt caaaggcttc | 1860 |
| taccccagcg acatcgccgt ggagtgggag agcaatgggc agccggagaa caactacaag | 1920 |
| accacgcctc ccgtgctgga ctccgacggc tccttcttcc tctacagcag gctaaccgtg | 1980 |
| gacaagagca ggtggcagga ggggaatgtc ttctcatgct ccgtgatgca tgaggctctg | 2040 |
| cacaaccact acacacagaa gagcctctcc ctgtctctgg gtaaatgatg agaattcatt | 2100 |
| gatcataatc agccatacca catttgtaga ggttttactt gctttaaaaa acctcccac | 2159 |

<210> SEQ ID NO 44
<211> LENGTH: 1600
<212> TYPE: DNA
<213> ORGANISM: Artificial Sequence
<220> FEATURE:
<223> OTHER INFORMATION: chC2aB7-hG2G4 Heavy chain

<400> SEQUENCE: 44

| | |
|---|---:|
| gctgacagac taacagactg ttcctttcca tgggtctttt ctgcagtcac cgtccttgac | 60 |
| acgaggcgcg ccgccaccat gggatggagc tgtatcatcc tcttcttggt agcaacagct | 120 |
| acaggtgtcc actccctcga ggtccagctg caacagtctg acctgagct ggtgaagcct | 180 |
| ggggcttcac tgaagatgtc ctgcaaggct tctggttatt cattcactga ctacatcata | 240 |
| ctctgggtga agcagaacca tggaaagagc cttgagtgga ttggacatat tgatccttac | 300 |
| tatggtagtt ctaactacaa tctgaaattc aagggcaagg ccacattgac tgtagacaaa | 360 |
| tcttccagca cagcctacat gcagctcaac agtctgacat ctgaggactc tgcagtctat | 420 |
| tactgtggaa gatctaagag ggactacttt gactactggg gccaaggcac cactctcaca | 480 |
| gtttcctcag cctccaccaa gggcccatcc gtcttccccc tggcgccctg ctccaggagc | 540 |
| acctccgaga gcacagccgc cctgggctgc ctggtcaagg actacttccc cgaaccggtg | 600 |
| acggtgtcgt ggaactcagg cgccctgacc agcggcgtgc acaccttccc ggctgtccta | 660 |
| cagtcctcag gactctactc cctcagcagc gtggtgaccg tgccctccag caacttcggc | 720 |
| acccagacct acacctgcaa cgtagatcac aagcccagca acaccaaggt ggacaagaca | 780 |
| gttggtgaga ggccagctca gggagggagg gtgtctgctg gaagccaggc tcagccctcc | 840 |
| tgcctggacg caccccggct gtgcagcccc agcccagggc agcaaggcag gccccatctg | 900 |
| tctcctcacc cggaggcctc tgcccgcccc actcatgctc agggagaggg tcttctggct | 960 |
| ttttccacca ggctccaggc aggcacaggc tgggtgcccc tacccaggc ccttcacaca | 1020 |
| caggggcagg tgcttggctc agacctgcca aaagccatat ccggaggac cctgcccctg | 1080 |
| acctaagccg accccaaagg ccaaactgtc cactccctca gctcggacac tttctctcct | 1140 |
| cccagatccg agtaactccc aatcttctct ctgcagagcg caaatgttgt gtcgagtgcc | 1200 |
| caccgtgccc aggtaagcca gcccaggcct cgccctccag ctcaaggcgg gacaggtgcc | 1260 |
| ctagagtagc ctgcatccag ggacaggccc cagctgggtg ctgacgtc cacctccatc | 1320 |
| tcttcctcag caccacctgt ggcaggaccg tcagtcttcc tcttcccccc aaaacccaag | 1380 |
| gacaccctca tgatctcccg gacccctgag gtcacgtgcg tggtggtgga cgtgagccag | 1440 |
| gaagacccccg aggtccagtt caactggtac gtggatggcg tggaggtgca taatgccaag | 1500 |
| acaaagccgc gggaggagca gttcaacagc acgtaccgtg tggtcagcgt cctcaccgtc | 1560 |
| ctgcaccagg actggctgaa cggcaaggag tacaagtgca | 1600 |

<210> SEQ ID NO 45
<211> LENGTH: 337
<212> TYPE: PRT
<213> ORGANISM: Artificial Sequence
<220> FEATURE:
<223> OTHER INFORMATION: chC2aB7-hG2G4 Heavy chain

<400> SEQUENCE: 45

Met Gly Trp Ser Cys Ile Ile Leu Phe Leu Val Ala Thr Ala Thr Gly
1               5                   10                  15

Val His Ser Leu Glu Val Gln Leu Gln Gln Ser Gly Pro Glu Leu Val
            20                  25                  30

Lys Pro Gly Ala Ser Leu Lys Met Ser Cys Lys Ala Ser Gly Tyr Ser
        35                  40                  45

Phe Thr Asp Tyr Ile Ile Leu Trp Val Lys Gln Asn His Gly Lys Ser
    50                  55                  60

Leu Glu Trp Ile Gly His Ile Asp Pro Tyr Tyr Gly Ser Ser Asn Tyr
65                  70                  75                  80

Asn Leu Lys Phe Lys Gly Lys Ala Thr Leu Thr Val Asp Lys Ser Ser
                85                  90                  95

Ser Thr Ala Tyr Met Gln Leu Asn Ser Leu Thr Ser Glu Asp Ser Ala
            100                 105                 110

Val Tyr Tyr Cys Gly Arg Ser Lys Arg Asp Tyr Phe Asp Tyr Trp Gly
        115                 120                 125

Gln Gly Thr Thr Leu Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser Gln Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys

<210> SEQ ID NO 46
<211> LENGTH: 735
<212> TYPE: DNA

<210> SEQ ID NO 46
<211> LENGTH: 735
<212> TYPE: DNA
<213> ORGANISM: Artificial Sequence
<220> FEATURE:
<223> OTHER INFORMATION: chC2aB7-hG2G4 Light chain

<400> SEQUENCE: 46

```
aagcttgccg ccaccatggg atggagctgt atcatcctct tcttggtagc aacagctaca    60
ggtgtccact ctagagacat ccagatgaca cagtctccat cttccatgta tgcatctagg   120
agagagagtc actatcactt gcaaggcgag tcaggacatt aatagctatt aagctggttc   180
cagcagaaac cagggaaatc tcctaagacc ctgatctatc gtgcaaacag attggtagat   240
ggggttccat caaggttcag tggcagtgga tctgggcaag attattctct caccatcagc   300
agcctggagt atgaagatat gggaatttat tattgtctac agtatgatga gtttccgtac   360
acgttcggag gggggaccaa gctggaaata aaacggactg tggctgcacc atctgtcttc   420
atcttcccgc catctgatga gcagttgaaa tctggaactg cctctgttgt gtgcctgctg   480
aataacttct atcccagaga ggccaaagta cagtggaagg tggataacgc cctccaatcg   540
ggtaactccc aggagagtgt cacagagcag gacagcaagg acagcaccta cagcctcagc   600
agcaccctga cgctgagcaa agcagactac gagaaacaca agtctacgc ctgcgaagtc   660
acccatcagg gcctgagctc gcccgtcaca aagagcttca caggggaga gtgttcagcg   720
gccgcaattc attga                                                    735
```

<210> SEQ ID NO 47
<211> LENGTH: 240
<212> TYPE: PRT
<213> ORGANISM: Artificial Sequence
<220> FEATURE:
<223> OTHER INFORMATION: chC2aB7-hG2G4 Light chain

<400> SEQUENCE: 47

```
Met Gly Trp Ser Cys Ile Ile Leu Phe Leu Val Ala Thr Ala Thr Gly
  1               5                  10                  15

Val His Ser Arg Asp Ile Gln Met Thr Gln Ser Pro Ser Ser Met Tyr
                 20                  25                  30

Ala Ser Leu Gly Glu Arg Val Thr Ile Thr Cys Lys Ala Ser Gln Asp
             35                  40                  45

Ile Asn Ser Tyr Leu Ser Trp Phe Gln Gln Lys Pro Gly Lys Ser Pro
         50                  55                  60

Lys Thr Leu Ile Tyr Arg Ala Asn Arg Leu Val Asp Gly Val Pro Ser
 65                  70                  75                  80

Arg Phe Ser Gly Ser Gly Ser Gly Gln Asp Tyr Ser Leu Thr Ile Ser
                 85                  90                  95

Ser Leu Glu Tyr Glu Asp Met Gly Ile Tyr Tyr Cys Leu Gln Tyr Asp
                100                 105                 110

Glu Phe Pro Tyr Thr Phe Gly Gly Gly Thr Lys Leu Glu Ile Lys Arg
            115                 120                 125

Thr Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205
```

His Lys Val Tyr Ala Cys Glu Val Thr His Gln Gly Leu Ser Ser Pro
    210                 215                 220

Val Thr Lys Ser Phe Asn Arg Gly Glu Cys Ser Ala Ala Ala Ile His
225                 230                 235                 240

<210> SEQ ID NO 48
<211> LENGTH: 1560
<212> TYPE: DNA
<213> ORGANISM: Artificial Sequence
<220> FEATURE:
<223> OTHER INFORMATION: hB7V3V2-cG2G4 Heavy chain

<400> SEQUENCE: 48

```
ccaccagaca taatagctga cagactaaca gactgttcct ttccatgggt ctttctgca      60
gtcaccgtcc ttgacacgaa gcttgccgcc accatgggat ggagccggat ctttctcttc     120
ctcctgtcaa taattgcagg tgtccattgc caggtccagc tgcaacagtc tggatctgag     180
ctgaagaagc ctggggcttc agtgaagatc tcctgcaagg cttctggtta ttcattcact     240
gactacatca tactctgggt gaggcagaac cctggaaagg ccttgagtg gattggacat      300
attgatcctt actatggtag ttctaactac aatctgaaat tcaagggcag agtgacaatc     360
accgccgacc agtctaccac cacagcctac atggagctct ccagtctgag atctgaggac     420
actgcagtct attactgtgg aagatctaag agggactact tgactactg gggccaaggc     480
accactctca cagtttcctc agcctccacc aagggcccat ccgtcttccc cctggcgccc     540
tgctccagga gcacctccga gagcacagcc gccctgggct gcctggtcaa ggactacttc     600
cccgaaccgg tgacggtgtc gtggaactca ggcgccctga ccagcggcgt gcacaccttc     660
ccggctgtcc tacagtcctc aggactctac tccctcagca gcgtggtgac cgtgccctcc     720
agcaacttcg gcacccagac ctacacctgc aacgtagatc acaagcccag caacaccaag     780
gtggacaaga cagttgagcg caaatgttgt gtcgagtgcc caccgtgccc agcaccacct     840
gtggcaggac cgtcagtctt cctcttcccc ccaaaaccca aggacaccct catgatctcc     900
cggacccctg aggtcacgtg cgtggtggtg gacgtgagcc aggaagaccc cgaggtccag     960
ttcaactggt acgtggatgg cgtggaggtg cataatgcca agacaaagcc gcgggaggag    1020
cagttcaaca gcacgtaccg tgtggtcagc gtcctcaccg tcctgcacca ggactggctg    1080
aacggcaagg agtacaagtg caaggtctcc aacaaaggcc tcccgtcctc catcgagaaa    1140
accatctcca aagccaaagg gcagccccga gagccacagg tgtacaccct gcccccatcc    1200
caggaggaga tgaccaagaa ccaggtcagc ctgacctgcc tggtcaaagg cttctacccc    1260
agcgacatcg ccgtggagtg ggagagcaat gggcagccgg agaacaacta caagaccacg    1320
cctcccgtgc tggactccga cggctccttc ttcctctaca gcaggctaac cgtggacaag    1380
agcaggtggc aggaggggaa tgtcttctca tgctccgtga tgcatgaggc tctgcacaac    1440
cactacacac agaagagcct ctccctgtct ctgggtaaat gatgagaatt cattgatcat    1500
aatcagccat accacatttg tagaggtttt acttgcttta aaaaacctcc cacacctccc    1560
```

<210> SEQ ID NO 49
<211> LENGTH: 772
<212> TYPE: DNA
<213> ORGANISM: Artificial Sequence
<220> FEATURE:
<223> OTHER INFORMATION: hB7V3V2-cG2G4 Light chain

<400> SEQUENCE: 49

```
ctgttccttt ccatgggtct tttctgcagt caccgtcctt gacacgaagc ttgccgccac      60
```

| | |
|---|---|
| catggacatg agggtctctg ctcagctcct ggggctcctg ctgctctggc tctcaggggc | 120 |
| caggtgtgac atccagatga cacagtctcc atcttccctg tctgcatcta taggagacag | 180 |
| agtcactatc acttgcaagg cgagtcagga cattaatagc tatttaagct ggttccagca | 240 |
| gaaaccaggg aaagctccta agctgctgat ctatcgtgca aacagattgg tagatggggt | 300 |
| tccatcaagg ttcagtggca gtggatctgg gacagattat actctcacca tcagcagcct | 360 |
| gcagcctgaa gatttcgcag tttattattg tctacagtat gatgagtttc cgtacacgtt | 420 |
| cggagggggg accaagctgg aaataaaacg tacggtggct gcaccatctg tcttcatctt | 480 |
| cccgccatct gatgagcagt tgaaatctgg aactgcctct gttgtgtgcc tgctgaataa | 540 |
| cttctatccc agagaggcca agtacagtg aaggtggat aacgccctcc aatcgggtaa | 600 |
| ctcccaggag agtgtcacag agcaggacag caaggacagc acctacagcc tcagcagcac | 660 |
| cctgacgctg agcaaagcag actacgagaa acacaaagtc tacgcctgcg aagtcaccca | 720 |
| tcagggcctg agctcgcccg tcacaaagag cttcaacagg ggagagtgtt ag | 772 |

<210> SEQ ID NO 50
<211> LENGTH: 2158
<212> TYPE: DNA
<213> ORGANISM: Artificial Sequence
<220> FEATURE:
<223> OTHER INFORMATION: DIB5-hG1 Heavy chain

<400> SEQUENCE: 50

| | |
|---|---|
| gcgcgccacc agacataata gctgacagac taacagactg ttcctttcca tgggtctttt | 60 |
| ctgcagtcac cgtccttgac acgaggcgcg ccgccaccat gggatggagc tgtatcatcc | 120 |
| tcttcttggt agcaacagct acaggtgtcc actccctcga ggtccaactg cagcagcctg | 180 |
| gggcagagct tgtgaggtca ggggcctcag tcaagttgtc ctgcaaagct tctggcttca | 240 |
| acattaaaga ctactatata cactgggtga agcagaggcc tgaacagggc tggagtggat | 300 |
| tggatggat tgatcctgag attggtgcta ctaaatatgt cccgaagttc cagggcaagg | 360 |
| ccactatgac tacagacaca tcctccaaca cagcctacct gcagctcagc agcctgacat | 420 |
| ctgaggacac tgccgtctat tactgtaatg ccctctatgg taactacgac cgttactatg | 480 |
| ctatggacta ctggggtcaa ggaacctcag tcaccgtctc ctcagcctcc accaagggcc | 540 |
| catcggtctt ccccctggca ccctcctcca agagcacctc tgggcggcaca gcggccctgg | 600 |
| gctgcctggt caaggactac ttccccgaac cggtgacggt gtcgtggaac tcaggcgccc | 660 |
| tgaccagcgg cgtgcacacc ttcccggctg tcctacagtc ctcaggactc tactccctca | 720 |
| gcagcgtggt gaccgtgccc tccagcagct gggcaccca gacctacatc tgcaacgtga | 780 |
| atcacaagcc cagcaacacc aaggtggaca agagagttgg tgagaggcca gcacagggag | 840 |
| ggagggtgtc tgctggaagc caggctcagc gctcctgcct ggacgcatcc cggctatgca | 900 |
| gtcccagtcc agggcagcaa ggcaggcccc gtctgcctct tcacccggag gcctctgccc | 960 |
| gccccactca tgctcaggga gagggtcttc tggcttttc cccaggctct gggcaggcac | 1020 |
| aggctaggtg cccctaaccc aggccctgca cacaaagggg caggtgctgg gctcagacct | 1080 |
| gccaagagcc atatccggga ggaccctgcc cctgacctaa gcccacccca aggccaaac | 1140 |
| tctccactcc ctcagctcgg acaccttctc tcctcccaga ttccagtaac tcccaatctt | 1200 |
| ctctctgcag agcccaaatc ttgtgacaaa actcacacat gcccaccgtg cccaggtaag | 1260 |
| ccagcccagg cctcgccctc cagctcaagg cgggacaggt gccctagagt agcctgcatc | 1320 |
| cagggacagg ccccagccgg gtgctgacac gtccacctcc atctcttcct cagcacctga | 1380 |

```
actcctgggg ggaccgtcag tcttcctctt ccccccaaaa cccaaggaca ccctcatgat    1440
ctcccggacc cctgaggtca catgcgtggt ggtggacgtg agccacgaag accctgaggt    1500
caagttcaac tggtacgtgg acggcgtgga ggtgcataat gccaagacaa agccgcggga    1560
ggagcagtac aacagcacgt accgtgtggt cagcgtcctc accgtcctgc accaggactg    1620
gctgaatggc aaggagtaca agtgcaaggt ctccaacaaa gccctcccag ccccatcga    1680 gaaaaccatc tccaaagcca aggtgggac ccgtggggtg cgagggccac atggacagag    1740
gccggctcgg cccaccctct gccctgagag tgaccgctgt accaacctct gtccctacag    1800
ggcagccccg agaaccacag gtgtacaccc tgcccccatc ccgggaggag atgaccaaga    1860
accaggtcag cctgacctgc ctggtcaaag gcttctatcc cagcgacatc gccgtggagt    1920
gggagagcaa tgggcagccg gagaacaact acaagaccac gcctcccgtg ctggactccg    1980
acggctcctt cttcctctat agcaagctca ccgtggacaa gagcaggtgg cagcagggga    2040
acgtcttctc atgctccgtg atgcatgagg ctctgcacaa ccactacacg cagaagagcc    2100
tctccctgtc cccgggtaaa tgagtgcgac ggccagaatt cattgatcat aatcagcc     2158

<210> SEQ ID NO 51
<211> LENGTH: 720
<212> TYPE: DNA
<213> ORGANISM: Artificial Sequence
<220> FEATURE:
<223> OTHER INFORMATION: DIB5-hG1 Light chain

<400> SEQUENCE: 51
aagcttgccg ccaccatggg atggagctgt atcatcctct tcttggtagc aacagctaca      60
ggtgtccact ctagagacat tgtgatgacc cagtctcaaa aattcatgtc cacatcagta    120
ggagacaggg tcagcatcac ctgcaaggcc agtcagaatg ttcgtactgc tgtagcctgg    180
tatcaacaga aaccagggca gtctcctaaa gcactgattt acttggcatc caaccggcac    240
actggagtcc ctgatcgctt cacaggcagt ggatctggga cagatttcac tctcaccatt    300
agcaatgtgc aatctgaaga cctggcagat tatttctgtc tgcaacattg gaattatcct    360
ctcacgttcg gtgctgggac caagctggag ctgaaacgga ctgtggctgc accatctgtc    420
ttcatcttcc cgccatctga tgagcagttg aaatctggaa ctgcctctgt tgtgtgcctg    480
ctgaataact tctatcccag agaggccaaa gtacagtgga aggtggataa cgccctccaa    540
tcgggtaact cccaggagag tgtcacagag caggacagca aggacagcac ctacagcctc    600
agcaacaccc tgacgctgag caaagcagac tacgagaaac acaaagtcta cgcctgcgaa    660
gtcacccatc agggcctgag ctcgcccgtc acaaagagct tcaacagggg agagtgttaa    720
```